United States Patent [19]

Kamata et al.

[11] Patent Number: 5,047,540
[45] Date of Patent: Sep. 10, 1991

[54] LIPID DERIVATIVES

[75] Inventors: Susumu Kamata; Tatsuo Tsuri, both of Hyogo; Nobuhiro Haga; Takeaki Matsui, both of Osaka; Morio Kishi; Kimio Takahashi, both of Kyoto; Sanji Hagashita, Nara; Kaoru Seno, Hyogo, all of Japan

[73] Assignee: Shionogi & Co., Ltd., Osaka, Japan

[21] Appl. No.: 284,590

[22] Filed: Nov. 29, 1988

[30] Foreign Application Priority Data

Dec. 17, 1987 [JP] Japan .................... 62-320238

[51] Int. Cl.$^5$ ................ C07D 403/06; C07D 215/10
[52] U.S. Cl. ........................... 546/172; 546/170; 546/168; 546/148
[58] Field of Search ............. 548/170; 546/172, 148

[56] References Cited

U.S. PATENT DOCUMENTS

| | | | |
|---|---|---|---|
| 3,920,739 | 11/1975 | Suda et al. | 260/556 A |
| 4,061,639 | 12/1977 | Goralski | 546/172 |
| 4,097,669 | 6/1978 | Reisdorff | 546/172 |
| 4,267,122 | 5/1981 | Thil et al. | 260/501.12 |
| 4,329,289 | 5/1982 | Fahrenholtz et al. | 549/449 |
| 4,471,116 | 9/1984 | Davidson et al. | 544/43 |
| 4,539,408 | 9/1985 | Kampfer et al. | 546/172 |
| 4,762,848 | 9/1988 | Scheunnemann et al. | 548/170 |

FOREIGN PATENT DOCUMENTS 101199 2/1984 European Pat. Off. .
208961 1/1987 European Pat. Off. .
2094444 2/1972 France .

*Primary Examiner*—David B. Springer
*Attorney, Agent, or Firm*—Wenderoth, Lind & Ponack

[57] ABSTRACT

Lipid derivatives represented by the formula:

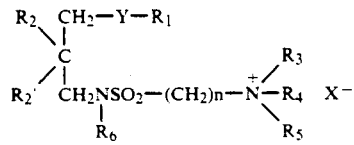

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heoterocyclyloxy; $R_2'$ is hydrogen or $R_2$ and $R_2'$ taken together form $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10, being useful as PAF antagonists, e.g., as antithrombotic, antivasoconstricting, antibronchoconstricting agent or antitumor agent.

19 Claims, No Drawings

LIPID DERIVATIVES

BACKGROUND OF THE INVENTION

1. Field of the Invention

The present invention relates to lipid derivatives which may be used as PAF (Platelet Activating Factor) antagonist or antitumor agent in the field of medicine.

In more detail, the invention relates to the compounds represented by the following formula (I).

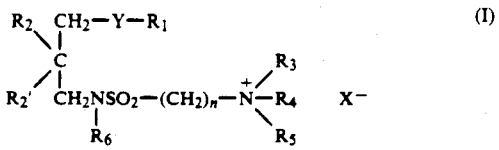

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10.

2. Prior Art

PAF which is represented by the following formula:

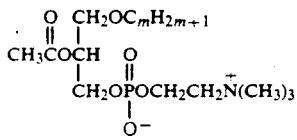

wherein m indicates 16 or 18 is generated from basocyte, neutrophile, acidocyte, macrophage, mast cell, platelet, human leukemia cell, or vascular endothelial cell through various stimulations.

In addition to the platelet activating action, PAF has been known to have the biological activities such as constriction of smooth muscle, decrease of coronary blood flow, inhibition of cardiac effect, increase of vascular permeability or hypotension. It is thought that PAF plays an important role in some physiological and pathological reaction, such as inflammation, asthma, thrombosis, anaphylactic shock, allergy, hypotension, ischemic heart disease, acute transplant rejection, nephritis, and gastric ulcer.

PAF antagonists are being developed as agents for the treatment of those desease. [P. Braquet et al., Pharmacological Reviews, 39, 98–145, (1987)]. Some PAF antagonists which are structurally analogous to PAF are disclosed, for example, in JPN Kokai Nos. 57-67589, 60-243047, and 62-228088.

SUMMARY

Lipid derivatives represented by the formula:

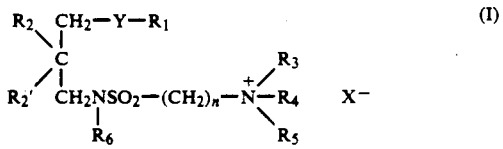

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10.

These compounds may be useful as PAF antagonists, e.g., as antithrombotic, antivasoconstricting, antibronchoconstricting agent or antitumor agent.

DESCRIPTION OF THE PREFERRED EMBODIMENT

Though several PAF antagonists have been developed so far, they still have some problems; e.g., having no specific action to PAF receptor, possession of PAF-like action as well as PAF antagonistic effect, possession of side effect such as hemolysis, their metabolic unstability, and so on. These problems are desired to be solved.

The inventors of the present invention have studied hard to develop useful PAF antagonists or antitumor agents. They found that PAF could be converted into PAF antagonists or antitumor agents if its phosphate moiety would be substituted by sulfonamide. This invention is based on these findings.

The compounds of the present invention are represented by the following formula (I):

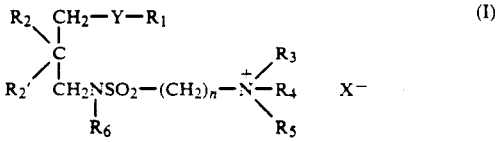

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, heterocyclic group, or heterocyclyloxy; $R_2'$ is hydrogen or taken together with $R_2$ forms $-O(CH_2)_m-$ wherein m is an integer of 1 to 5; $R_3$, $R_4$, and $R_5$ each is hydrogen or lower alkyl or two or three of $R_3$, $R_4$, and $R_5$ taken together with the adjacent nitrogen atom form cyclic ammonio; $R_6$ is hydrogen or lower alkylcarbonyl; $X^-$ is a counter anion; Y is oxygen or sulfur; and n is an integer of 1 to 10.

The following definitions are given for various terms used throughout this specification.

The term "lower alkyl" refers to straight or branched $C_1$ to $C_7$ alkyl, e.g., methyl, ethyl, propyl, isopropyl, butyl, isobutyl, tert-butyl, pentyl, hexyl, heptyl.

The term "alkyl" refers to straight $C_1$ to $C_{35}$ alkyl which may have a doulbe bond or triple bond. Preferably, it refers to $C_{10}$ to $C_{30}$ higher alkyl, e.g., decyl, undecyl, dodecyl, tridecyl, tetradecyl, pentadecyl, hexadecyl, heptadecyl, octadecyl, nanodecyl, icosyl, henicosyl, docosyl, tricosyl, tetracosyl, pentacosyl, hexacosyl, heptacosyl, octacosyl, nonacosyl, triacontyl.

In the term "lower alkyloxy, lower alkylcarbamoyloxy, lower alkylcarbonyl, lower alkylcarbonylamino, lower alkyloxycarbonylamino, lower alkylureido, lower alkyloxymethyl, or lower alkylcarbonylmethyl", the lower alkyl moiety corresponds to the above mentioned lower alkyl.

The term "heterocyclic group" refers to 5- to 7-membered heterocyclic group, which may have one to four heteroatoms such as oxygen, sulfur, and/or nitrogen, optionally substituted by lower alkyl, lower alkyloxy, hydroxy, halogen, or lower alkyloxycarbonyl or a combination thereof. Those substituents on the heterocyclic group are sometimes referred to as "the substituent". Heterocyclic group includes, for example, 1H-pyrrol-1-yl, 2-methyl-1H-pyrrol-1-yl, 3-methyl-1H-pyrrol-1-yl, 1H-imidazol-1-yl, 2-methyl-1H-imidazol-1-yl, 2,4-dimethyl-1H-imidazol-1-yl, 1H-pyrazol-1yl, 5-methyl-1H-pyrazol-1-yl, 3,5-dimethyl-1H-pyrazol-1-yl, 1H-1,2,3-triazol-1-yl, 4-methyl-1H-1,2,3-triazol-1-yl, 4-methyl-2H-1,2,3-triazol-2-yl, 4-methyl-3H-1,2,3-triazol-3-yl, 3-methyl-1H-1,2,4-triazol-1-yl, 3-methyl-2H-1,2,4-triazol-2-yl, 3-methyl-4H-1,2,4-triazol-4-yl, 2H-tetrazol-2-yl, 1H-tetrazol-1-yl, 5-methyl-1H-tetrazol-1-yl, and 5-methyl-2H-tetrazol-2-yl.

The term "heterocyclyloxy" refers to hydroxy substituted by the heterocyclic group and includes, e.g., 3-isoxazolyloxy, 3-isothiazolyloxy, 3-pyrazolyloxy, 3-(4-methylisoxazolyl)oxy, 4-(1,2,3-triazolyl)oxy, and 4-(5-methyl-1,2,3-triazolyl)oxy.

The term "cyclic ammonio" refers to 5 or 6 membered mono-, bi-, or tricyclic ammonion which may contain heteroatoms and optionally be substituted by lower alkyl, carboxyl, lower alkyloxycarbonyl, hydroxy, lower alkyloxy, acyloxy, lower alkylamino, amino, carbamoyl, ureido or the like. Cyclic ammonio includes, e.g., N-methyl-1-pyrrolinio, N-methyl-1-pyrrolidinio, 3-oxazolio, 2-isoxazolio, 3-thiazolio, 4-methyl-3-thiazolio, 5-hydroxyethyl-4-methyl-3-thiazolio, 3-imidazolio, 1-pyridinio, 3-carboxy-1-pyridinio, N-methyl-1-piperidinio, N-methyl-4-morpholio, 1-pyrimidinio, 1-pyrazinio, N-methyl-1-piperazinio, 1-triazinio, 3-benzoxazolio, 3-benzothiazolio, 1-quinolinio, 6-methoxy-1-quinolinio, 5,6,7,8-tetrahydro-1-quinolinio, 2-isoquinolinio, 1-quinoxalinio, azirinio, or the like.

The term "counter anion" refers to a pharmacologically acceptable anion such as halogen anion (e.g., chlorine, bromine, iodine), acetate anion, methylsulfonate anion, sulfate anion, nitrate anion, or phosphate anion. When the substituent on the cyclic ammonio can be an anion, it may form an inner salt with ammonium cation.

In the above definition of $R_1$, $C_{12}$ to $C_{20}$ higher alkyl, e.g., dodecyl, tridecyl, tetradecyl, pentadecyl, hexadecyl, heptadecyl, octadecyl, nonadecyl, and icosyl, are preferable examples for the alkyl and, especially, $C_{16}$ to $C_{18}$ alkyl, e.g., hexadecyl, heptadecyl, octadecyl, and the like are more desirable.

When $R_1$ is alkylcarbamoyl, the alkyl moiety corresponds to the above mentioned alkyl, that is, dodecylcarbamoyl, tridecylcarbamoyl, tetradecylcarbamoyl, pentadecylcarbamoyl, hexadecylcarbamoyl, heptadecylcarbamoyl, octadecylcarbamoyl, nonadecylcarbamoyl, and icosylcarbamoyl are preferable examples for the alkylcarbamoyl and, especially, hexadecylcarbamoyl, heptadecylcarbamoyl, octadecylcarbamoyl, and the like are more desirable.

Especially preferable lower alkyloxy for $R_2$ is methoxy, ethoxy, or propoxy; lower alkylcarbamoyloxy for $R_2$ is methylcarbamoyloxy, ethylcarbamoyloxy, or propylcarbamoyloxy; lower alkylcarbonylamino for $R_2$ is methylcarbonylamino, ethylcarbonylamino, or propylcarbonylamino; lower alkyloxycarbonylamino for $R_2$ is methoxycarbonylamino, ethoxycarbonylamino, or propoxycarbonylamino; lower alkylureido for $R_2$ is methylureido, ethylureido, or propylureido; lower alkyloxymethyl for $R_2$ is methoxymethyl, ethoxymethyl, or propoxymethyl; and lower alkylcarbonylmethyl for $R_2$ is methylcarbonylmethyl, ethylcarbonylmethyl, or propylcarbonylmethyl. Especially preferable heterocyclic group for $R_2$ is N-containing 5 or 6 membered heterocyclic group which may contain oxygen or sulfur and optionally have the substituent, e.g. 3-methyl-2H-1,2,4-triazol-2-yl, 3H-1,2,3,4-tetrazol-3-yl, 5H-1,2,3,4-tetrazol-5-yl, 5-methyl-1H-tetrazol-1-yl, 5-methyl-2H-tetrazol-2-yl. Heterocyclyloxy for $R_2$ refers to hydroxy substituted by the 5 or 6 membered heterocyclic which may contain one to four heteroatoms such as oxygen, sulfur, or nitrogen and optionally have the substituent, e.g., 3-isoxazolyloxy, or 3-(4-methylisoxazolyl)oxy.

The most desirable $R_2$ is methoxy, methylcarbamoyloxy, acetamido, methoxycarbonylamino, methylureido, methoxymethyl, acetylmethyl, cyanomethyl, 3-methyl-2H-1,2,4-triazol-2-yl, 5-methyl-1H-tetrazol-1-yl, 5-methyl-2H-tetrazol-2-yl, or 3-isoxazolyloxy.

$R_2$ and $R_2'$ taken together may form $-O(CH_2)_m-$. Preferable m is an integer of 1 to 5, more desirably m is an integer, 4 or 5, and most desirably an integer, 4.

Especially preferable lower alkyl for $R_3$, $R_4$ and $R_5$ lower alkyl is methyl, ethyl or propyl and the most desirable lower alkyl is methyl.

Especially preferable cyclic ammonio is N-methyl-1-pyrrolinio, N-methyl-1-pyrrolidinio, 3-oxazolio, 2-isoxazolio, 3-thiazolio, 4-methyl-3-thiazolio, 5-hydroxyethyl-4-methyl-3-thiazolio, 1-N-methyl-3-imidazolio, 1-pyridinio, 3-carboxy-1-pyridinio, N-methyl-1-piperidinio, N-methyl-4-morpholio, 1-pyrimidinio, 1-pyrazinio, 1-methyl-1-piperadinio, 1-triazinio, 3-benzoxazolio, 3-benzothiazolio, 1-quinolinio, 6-methoxy-1-quinolinio, 5,6,7,8-tetrahydro-1-quinolinio, 2-isoquinolinio, or 1-quinoxalinio.

Especially preferable alkylcarbonyl for $R_6$ is acetyl, propionyl, or butyryl and the most desirable $R_6$ is acetyl.

Preferable n is an integer of 1 to 10, more desirably n is an integer, 1 to 5, and most desirably an integer, 2 to 4.

The preferable lower alkyl for $R_7$ is above mentioned $C_1$ to $C_7$ alkyl, especially preferable lower alkyl for $R_7$ is methyl or ethyl, or propyl and most desirable lower alkyl for $R_7$ is methyl.

Prot-OH refers to an ordinally used hydroxy protecting group such as benzyl, triarylmethyl, e.g., triphenylmethyl (trityl), trialkylsilyl, e.g., trimethylsilyl, tert-butyldimethylsilyl, tetrahydropyranyl, acetyl, benzoyl, p-nitrobenzoyl, or the like.

Prot-$NH_2$ refers to an amino protecting group such as acetyl, benzoyl, benzoyloxycarbonyl, tert-butoxycarbonyl, trityl, or the like.

Illustrative of the compounds (I) of the invention are:

2-methoxy-1-octadecylcarbamoyloxy-3-(3-trimethylammoniopropylsulfonylamino)propane chloride,
2-methoxy-1-octadecylcarbamoyloxy-3-(3-thiazoliopropylsulfonylamino)propane iodide,
2-methoxy-1-octadecylcarbamoyloxy-3-(3-pyridiniopropylsulfonylamino)propane iodide,
2-methoxy-3-(3-N-methylmorphoriniopropylsulfonylamino)-1-octadecylcarbamoyloxypropane iodide,
2-methoxy-3-[3-(4-methylthiazolinio)propylsulfonylamino]-1-octadecylcarbamoyloxypropane diode,
2-methoxy-1-octadecylcarbamoyloxy-3-(3-pyraziniopropylsulfonylamino)propane iodide,
2-methoxy-1-octadecylcarbamoyloxy-3-(3-quinoliniopropylsulfonylamino)propane iodide,
2-methyoxy-3-[3-(6-methoxyquinolinio)propylsulfonylamino]-1-octadecylcarbamoyloxypropane iodide,
1-hexadecylthio-2-methoxy-3-(3-trimethylammoniopropylsulfonylamino)propane iodide,
1-hexadecylthio-2-methoxy-3-(3-thiazoliopropylsulfonylamino)propane iodide,
1-hexadecyloxy-2-methoxy-3-(3-trimethylammoniopropylsulfonylamino)propane iodide,
1-hexadecyloxy-2-methoxy-3-(3-thiazoliopropylsulfonylamino)propane iodide,
2-methoxy-1-octadecylcarbamoyloxy-3-(2-thiazolioethylsulfonylamino)propane iodide,
2-methoxy-1-octadecylcarbamoyloxy-3-(4-thiazoliobutylsulfonylamino)propane iodide,
2-methoxy-1-octadecylcarbamoyloxy-3-(4-quinoliniobutylsulfonylamino)propane iodide,
3-(4-benzothiazoliobutylsulfonylamino)-2-methoxy-1-octadecylcarbamoyloxypropane iodide,
3-(4-isoquinoliniobutylsulfonylamino)-2-methoxy-1-octadecylcarbamoyloxypropane iodide,
2-methoxy-3-(4-N-methylimidazoliobutylsulfonylamino)-1-octadecylcarbamoyloxypropane iodide,
2-methoxy-1-octadecylcarbamoyloxy-3-(4-quinoliniobutylsulfonylamino)propane chloride,
3-(4-benzothiazoliobutylsulfonylamino)-2-methoxy-1-octadecylcarbamoyloxypropane chloride,
3-(4-isoquinoliniobutylsulfonylamino)-2-methoxy-1-octadecylcarbamoyloxypropane chloride,
3-(4-N-methylimidazoliobutylsulfonylamino)-2-methoxy-1-octadecylcarbamoyloxypropane chloride,
1-hexadecyloxy-2-methoxy-3-[3-(4-methylthiazolio)propylsulfonylamino]propane iodide,
1-hexadecyloxy-2-methoxy-3-(3-pyraziniopropylsulfonylaminno)propane iodide,
2-methoxy-3-(3-N-methylimidazoliopropylsulfonylamino)-1-octadecylcarbamoylthiopropane iodide,
2-methoxy-1-octadecylcarbamoylthio-3-(4-quinoliniopropylsulfonylamino)propane iodide,
2-methoxy-1-octadecylcarbamoylthio-3-(3-thiazoliopropylsulfonylamino)propane iodide,
2-methoxy-1-octadecylcarbamoylthio-3-(4-quinoliniopropylsulfonylamino)propane chloride,
2-methoxy-1-octadecylcarbamoyloxy-3-[4-3-carboxylatepyridinio}butylsulfonylamino]propane,
2-hexadecylthiomethyl-2-(3-trimethylammoniopropylsulfonylaminomethyl)tetrahydrofuran,
2-octadecylcarbamoyloxymethyl-2-(3-quinoliniopropylsulfonylaminomethyl)tetrahydrofuran iodide,
1-hexadecylthio-2-methylcarbamoyloxy-3-(3-quinoliniopropylsulfonylamino)propane iodide,
1-hexadecylthio-2-methylcarbamoyloxy-3-(3-trimethylammoniopropylsulfonylamino)propane iodide,
2-methylcarbamoyloxy-1-octadecylcarbamoyloxy-3-(3-quinoliniopropylsulfonylamino)propane iodide,
2-methylcarbamoyloxy-1-octadecylcarbamoyloxy-3-(3-trimethylammoniopropylsulfonylamino)propane iodide,
1-octadecylcarbamoyloxy-2-methoxycarbonylamino-3-(3-trimethylammoniopropylsulfonylamino)propane iodide,
2-tert-butoxycarbonylamino-1-octadecylcarbamoyloxy-3-(3-trimethylammoniopropylsulfonylamino)propane iodide,
2-acetamido-1-octadecylcarbamoyloxy-3-(3-trimethylammoniopropylsulfonylamino)propane iodide,
1-octadecylcarbamoyloxy-2-(3-methylureido)-3-(3-trimethylammoniopropylsulfonylamino)propane iodide,
1-hexadecylthio-2-methoxycarbonylamino-3-(3-trimethylammoniopropylsulfonylamino)propane iodide,
2-tert-butoxycarbonylamino-1-hexadecylthio-3-(3-trimethylammoniopropylsulfonylamino)propane iodide,
2-acetamido-1-hexadecylthio-3-(3-trimethylammoniopropylsulfonylamino)propane iodide,
1-hexadecylthio-2-(3-methylureido)-3-(3-trimethylammoniopropylamino)propane iodide,
2-acetamido-3-(N-acetyl-3-trimethylammoniopropylsulfonylamino)-1-octadecylcarbamoyloxypropane iodide,
1-octadecylcarbamoyloxy-2-methoxycarbonylamino-3-(3-quinoliniopropylsulfonylamino)propane iodide,
2-butoxycarbonylamino-1-octadecylcarbamoyloxy-3-(3-quinoliniopropylsulfonylamino)propane iodide,
2-acetamido-1-octadecylcarbamoyloxy-3-(3-quinoliniopropylsulfonylamino)propane iodide,
1-octadecylcarbamoyloxy-2-(3-methylureido)-3-(3-quinoliniopropylsulfonylamino)propane iodide,
1-hexadecylthio-2-methoxycarbonylamino-3-(3-quinoliniopropylsulfonylamino)propane iodide,
2-tert-butoxycarbonylamino-1-hexadecylthio-3-(3-quinoliniopropylsulfonylamino)propane iodide,
2-acetamido-1-hexadecylthio-3-(3-quinoliniopropylsulfonylamino)propane iodide,
1-hexadecylthio-2-(3-methylureido)-3-(3-quinoliniopropylamino)propane iodide,
2-acetamido-3-(N-acetyl-3-quinoliniopropylsulfonylamino)-1-octadecylcarbamoyloxypropane iodide,
1-hexadecylthio-2-(3-methyl-2H-1,2,4-triazol-2-yl)-3-(3-trimethylammoniopropylsulfonylamino)propane iodide,
2-(3-methyl-2H-1,2,4-triazol-2-yl)-1-octadecylcarbamoyloxy-3-(3-quinoliniopropylsulfonylamino)propane iodide,
2-(3-methyl-1H-1,2,4-triazol-1-yl)-1-octadecylcarbamoyloxy-3-(3-quinoliniopropylsulfonylamino)propane diode,
2-(5-methyl-1H-tetrazol-1-yl)-1-octadecylcarbamoyloxy-3-(3-trimethylammoniopropylsulfonylamino)propane iodide,
2-(5-methyl-1H-tetrazol-1-yl)-1-octadecylcarbamoyloxy-3-(3-quinoliniopropylsulfonylamino)propane iodide, 1-hexadecylthio-2-(5-methyl-2H-tetrazol-2-yl)-3-(3-trimethylammoniopropylsulfonylamino)propane iodide,
2-(5-methyl-2H-tetrazol-2-yl)-1-octadecylcarbamoyloxy-3-(3-quinoliniopropylsulfonylamino)propane iodide,
2-(3-isoxazolyloxy)-1-hexadecylthio-3-(3-trimethylammoniopropylsulfonylamino)propane iodide,
2-(3-isoxazolyloxy)-1-octadecylcarbamoyloxy-3-(3-trimethylammoniopropylsulfonylamino)propane iodide,
2-(3-isoxazolyloxy)-1-octadecylcarbamoyloxy-3-(3-quinoliniopropylsulfonylamino)propane iodide,
3-(N-acetyl-3-trimethylammoniopropylsulfonylamino)-2-methoxymethyl-1-hexadecyloxypropane iodide,
1-hexadecyloxy-2 methoxymethyl-3-(3-trimethylammoniopropylsulfonylamino)propane iodide,
1-hexadecyloxy-2-methoxymethyl-3-(3-quinoliniopropylsulfonylamino)propane iodide,
1-hexadecylthio-2-methoxymethyl-3-(3-trimethylammoniopropylsulfonylamino)propane iodide,
1-octadecylcarbamoyloxy-2-methoxymethyl-3-(3-quinoliniopropylsulfonylamino)propane iodide,
3-(N-acetyl-3-quinoliniopropylsulfonylamino)-2-methoxymethyl-1-octadecylcarbamoyloxypropane iodide,
1-octadecylcarbamoyloxy-2-(2-oxopropyl)-3-(3-quinoliniopropylsulfonylamino)propane iodide,
2-cyanomethyl-1-hexadecyloxy-3-(3-trimethylammoniopropylsulfonylamino)propane iodide,
2-cyanomethyl-1-hexadecyloxy-3-(3-quinoliniopropylsulfonylamino)propane iodide,
2-cyanomethyl-1-octadecylcarbamoyloxy-3-(3-quinoliniopropylsulfonylamino)propane iodide, and
1-hexadecylthio-2-(2-oxopropyl)-3-(3-trimethylammoniopropylsulfonylamino)propane iodide.

The following abbreviations are used throughout this specification.

Me: methyl,
Et: ethyl,
tBu: tert-butyl,
Ph: phenyl
Tr: triphenylmethyl (trityl),
Ac: acetyl,
DEAD: diethyl azodicarboxylate,
THF: tetrahydrofuran, and
MEK: methyl ethyl ketone.

The compound (I) contains two stereoisomers, i.e., those of R- and S-configuration.

This invention includes each enantiomer, their mixture, and racemate thereof.

The compound (I) of the present invention is prepared by the following process, for example.

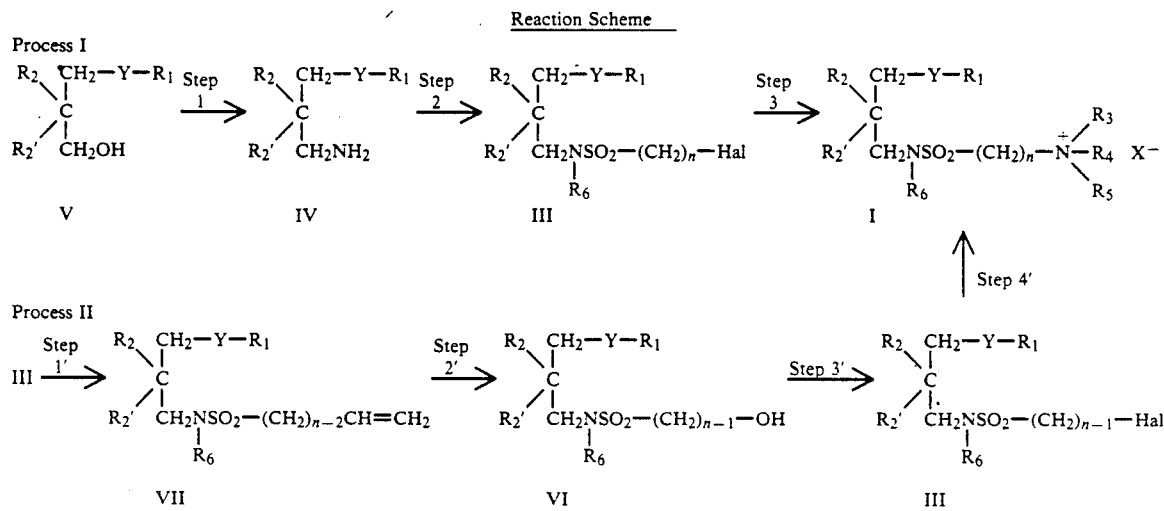

Reaction Scheme

PROCESS I

Step 1

In this step, the hydroxy of the compound V is converted into the amino.

This step can be carried out by hydrolysis of the N-substituted succinimide or N-substituted phthalimide derivative of the compound V.

The reaction to prepare the N-substituted succinimide or N-substituted phthalimide derivatives of the compound V is carried out by reacting succinimide or phthalimide in the presence of triphenylphosphine and diethyl azodicarboxylate in a solvent such as tetrahydrofuran, benzene, or dimethylformamide (DMF) at room temperature for a period of several hours to several tens of hours.

The hydrolysis is carried out in the presence of hydrazine in a solvent such as alcohol (e.g., methanol, ethanol) at room temperature or under reflux condition for several hours.

As an alternative method, the hydroxy of the compound V may be converted into the amino by allowing to react the methanesulfonyloxy or benzenesulfonyloxy derivatives of V with sodium azide or lithium azide, followed by the reduction of the azide-compound with a reduceing agent such as triphenylphosphine.

Step 2

In this step, the compound IV is sulfonylated with a haloalkanesulfonyl halide represented by the formula Hal'—SO$_2$(CH$_2$)n—Hal wherein Hal and Hal' each is halogen, and n is the same as defined above to give the sulfonamide derivative III.

As the said sulfonyl halide, 3-chloropropanesulfonyl chloride, 3-chloropropanesulfonyl bromide, 4-chlorobutansulfonyl chloride, 4-chlorobutanesulfonyl bromide, 5-chloropentanesulfonyl chloride, 6-bromohexanesulfonyl chloride, 7-bromoheptanesulfonyl bromide, 8-chlorooctanesulfonyl chloride, 9- bromononanesulfonyl bromide, 10-chlorodecanesulfonyl chloride, or the like is exemplified.

The reaction is carried out in the presence of a base such as triethylamine, pyridine, sodium hydroxide in a solvent such as chlorinated hydrocarbon (e.g., chloroform, dichloromethane), ether (e.g., ethyl ether, tetrahydrofuran) or aromatic hydrocarbon (e.g., benzene) under cooling or at room temperature for a period of several hours to several tens of hours.

Dimethylaminopyridine may be added as a catalyst, if necessary.

In such a case where the compound prepared by this step is a chloride, it can be further converted into other halides such as bromide or iodide by the treatment with sodium bromide or sodium iodide, respectively, in a usual manner.

When the compound wherein $R_6$ is alkylcarbonyl is required, the compound previously prepared by this step may be allowed to react with an acylating reagent in the presence of a base such as triethylamine, pyridine, N,N-diisopropylethylamine in a chlorinated hydrocarbon, e.g., dichloromethane, chloroform under cooling or at room temperature.

The acylating reagent such as acid halide, e.g., acetyl chloride, propionyl chloride, butyryl chloride, isobutyryl chloride, valeryl chloride, isovaleryl chloride, pivaloyl chloride, pentanoyl chloride, hexanoyl chloride, heptanoyl chloride or acid anhydride, e.g., acetic anhydride, propionic anhydride, butyric anhydride, isobutyric anhydride, valeric anhydride, isovaleric anhydride, pivalic anhydride, hentanoic anhydride, hexanoic anhydride, heptanoic anhydride is exemplified.

Step 3

In this step, the compound III is converted into an ammonium compound to give the compound (I) of the present invention.

As an amine forming an ammonium compound, alkylamine (e.g., trimethylamine, triethylamine) or 5 to 6-membered mono-, bi-, or tricyclic amine which may contain heteroatom and/or have substituent (e.g., N-methylpyrrole, N-methylpyrrolidine, oxazole, isoxazole, thiazole, 4-methylthiazole, N-methylimidazole, pyridine, 3-carboxypyridine, N-methylpiperidine, N-methylmorpholine, pyrimidine, pyrazine, N-methylpiperazine, triazine, benzoxazole, benzothiazole, quinoline, isoquinoline, quinoxaline, azirine) is exemplified.

The reaction is carried out using an amine itself as a solvent or in a solvent such as alcohol (e.g., methanol, ethanol), aromatic hydrocarbon (e.g., benzene, toluene), ether (e.g., ethyl ether, tetrahydrofuran, dioxane) or dimethylformamide at room temperature or under heating for a period of several hours to several tens of hours.

As an alternative method, in such a case where the halogen substituent of the compound III is chloride, the chloride is substituted by bromide or iodide and the resulting compound is allowed to react with several kinds of amines to give an ammonium bromide or iodide which may be further treated with hydrochloric acid to give chloride.

PROCESS II

Step 1'

In this step, a hydrogen halide is eliminated from the compound III to give the compound VII.

This step is carried out by oxidation of the phenylselenide compound or phenylthio compound, which can be prepared by substitution of the halogen of the compound III to phenylselenium anion or phenylthio anion, with a peroxide followed by heating the resulting compound to eliminate benzeneselenic acid or benzenesulfenic acid.

The reaction to prepare the phenylselenyl compound or phenylthio compound is carried out using the reagents obtained by the reduction of diphenyldiselenide or diphenylsulfide with sodium borohydride in a solvent such as an alcohol (e.g., methanol, ethanol, isopropanol), an ether (e.g., ethyl ether, tetrahydrofuran) or dioxane at room temperature or under heating for several hours.

The oxidation is carried out using a peroxide such as an aqueous hydrogen peroxide, m-chloroperbenzoic acid, peracetic acid, tert-butyl hydroperoxide, or the like in a solvent such as an alcohol (e.g., methanol, ethanol) or a chlorinated hydrocarbon (e.g., dichloromethane, chloroform) at room temperature for several hours.

The reaction to eliminate the oxide by heating is carried out in a solvent such as an aromatic hydrocarbone (e.g., benzene, toluene) or a chlorinated hydrocarbon (e.g., dichloromethane, chloroform) under heating.

Step 2'

In this step, the double bond of the compound VII is cleaved oxidatively to give the aldehyde which is then reduced to the compound VI.

The aldehyde is prepared by reductive decomposition of the ozonide which is obtained by the ozonization of the compound VII.

The ozonization is carried out in a solvent such as a chlorinated hydrocarbon (e.g., dichloromethane, chloroform, carbon tetrachloride), an alcohol (e.g., methanol, ethanol), benzene, or ethyl acetate under cooling for several hours; if necessary, the solvent may be used in combination.

The reductive composition of the ozonide is carried out using a reducing agent such as zinc dust in acetic acid, or triphenylphosphite trimethylphosphite, dimethylsulfide, sodium idodide, sulfur dioxide, sodium hydrogensulfite, tin(II) chloride, or iron(II) sulfate, or by catalytic reduction using a catalyst such as platinium, palladium, nickel, palladium on calcium carbonate.

The reduction converting the aldehyde to the alcohol is carried out using reducing agent such as metal hydride (e.g., lithium aluminum hydride, lithium borohydride, sodium borohydride, lithium trimethoxyaluminohydride, lithium tri-tert-butoxyaluminohydride) in a solvent such as an alcohol (e.g., methanol, ethanol) or ether (e.g., ethyl ether, tetrahydrofuran) at room temperature or under heating for several hours.

Step 3'

In this step, the hydroxy of the compound VI is halogenated.

The halogenation is achieved by direct halogenation of the hydroxy using halogenating agent such as phosphorus halide (e.g., phosphorus trichloride, phosphorus pentachloride, phosphorus tribromide, phosphorus pentabromide) or thionyl halide (e.g., thionyl chloride, thionyl bromide) or indirect halogenation through an intermediate to which a leaving group is attached.

The reaction for introducing a leaving group is carried out with a compound forming the leaving group such as a substituted sulfonyl chloride (e.g., methanesulfonyl chloride, benzenesulfonyl chloride, p-toluenesulfonyl chloride) in the presence of a base such as triethylamine, pyridine, or the like in the usual manner. Then, the resulting compound is allowed to react with an alkali metal halide such as lithium chloride, sodium bromide, or sodium idodide.

The reaction is carried out, depending on the property of the halogenating agent, in a solvent such as a chlorinated hydrocarbon (e.g., dichloromethane, chlorofrom, carbon tetrachloride), a ketone (e.g., acetone, methyl ethyl ketone), or dimethylformamide in accordance with the usual manner.

Step 4'

In this step, the halogen of the compound III' is substituted with an amine to give the compound (I) of the present invention. This step may be carried out in accordance with Step 3.

If necessary, the anions of the compounds of the present invention which is prepared in Step 3 or this step may be exchange with other desired anions.

PROCESS (I)

When —Y—$R_1$ is alkylcarbamoylthio, the compound Va can be prepared by the following manner.

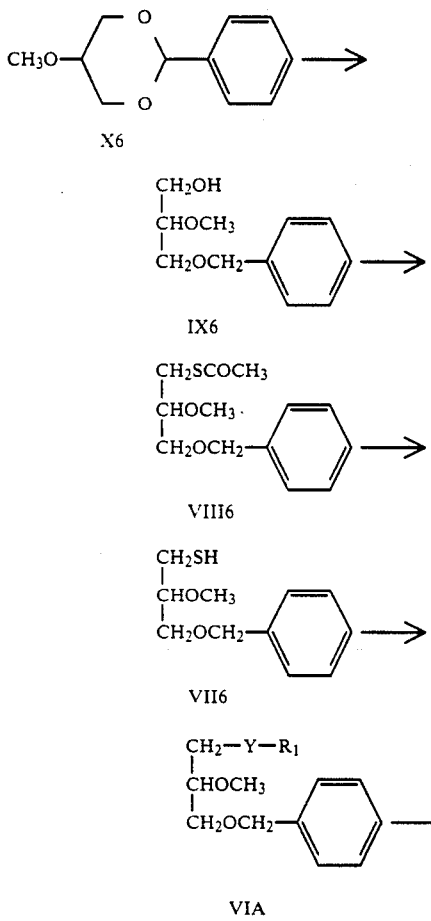

wherein $R_1$ is alkylcarbamoylthio, Y is sulfur.

The compound X6 is reductively cleaved to give the compound IX6 and the hydroxy of the compound IX6 is converted into the mercapto to give the compound VII6 which is then allowed to react with an isocyanate having the desired alkyl to give the compound VIA. The compound VA is prepared by removing the benzyl of the compound VIA.

The reaction to prepare the compound IX6 from the compound X6 is carried out by using lithium aluminium hydride-aluminium chloride as a reducing agent.

The step to prepare the compound VII6 from compound IX6 is achieved as follows.

The hydroxy of the compound IX6 is converted into the leaving group by reaction with a compound which forms a leaving group, such as methanesulfonyl chloride, benzenesulfonyl chloride, p-toluenesulfonyl chloride, or the like in the presence of a base such as triethylamine according to the usual manner prior to the reaction with potassium thioacetate or sodium thioacetate to give the thioacetate VIII6, which is then hydrolyzed with a base to give the mercapto derivative VII6. Then, the prepared compound VII6 is allowed to react with an isocyanate having a desired $C_{12}$ to $C_{20}$ alkyl such as dodecylisocyanate, hexadecylisocyanate, or octadecylisocyanate in a solvent such as pyridine to give the compound VIA.

The compound VA is prepared by cleaving the benzyl ether of the compound VIA with trimethylsilyl iodide or aluminium chloridesodium iodide in acetonitrile under a neutral condition at temperatures of 0° C. to room temperature.

PROCESS (II)

When $R_2$ is alkylcarbamoyloxy, the compound Vc can be prepared by the following manner.

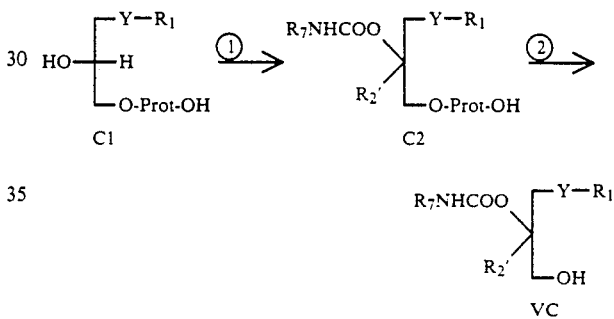

wherein $R_7$ is lower alkyl, Prot-OH is hydroxy protecting group, and $R_1$, $R_2'$, and Y each has the same meaning as defined before.

① In this step, an alcohol Cl is attached to an alkylisocyanate.

As the alkylisocyanate, methyl isocyanate, ethyl isocyanate, propyl isocyanate, isopropyl isocyanate, butyl isocyanate, tert-butyl isocyanate, or the like is exemplified.

The reaction is carried out in a solvent such as chlorinated hydrocarbon, e.g., dichloromethane, chloroform or dimethylformamide at room temperature or under heating for a period of several hours to several hours.

A catalyst such as an acid, e.g., boron trifluoride etherate, hydrochloric acid, aluminum chloride or a base, e.g., triethylamine, pyridine, 4-dimethylaminopyridine, 4-methylpiperidine may be used, if necessary.

② In this step, the 3-hydroxy protecting group is removed.

The deprotection, of which condition depends on the protecting group, is carried out in the presence of an acid, e.g., (1) trifluoroacetic acid, (2) acetic acid, (3) hydrogen bromide/acetic acid, (4) hydrochloric acid/chloroform. The reaction may be carried out by catalytic hydrogenolysis in the presence of a palladium catalyst.

PROCESS (III)

When —Y—R$_1$ is alkylcarbamoyloxy and R$_2$ is alkoxycarbonylamino, the compound VE can be prepared by the following manner.

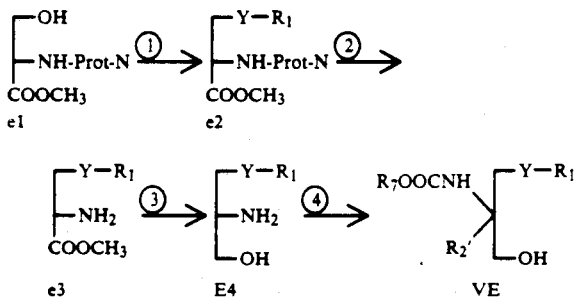

wherein R$_1$ is alkylcarbamoyl, Y is oxygen, and Prot-N is amino protecting group, and R$_2'$, R$_7$ each has the same meaning as defined before.

① In this step, a C$_{12}$-C$_{20}$ alkyl isocyanate is condensed to the alcohol E1.

As the alkyl isocyanate used for this step, dodecyl isocyanate, tridecyl isocyanate, tetradecyl isocyanate, pentadecyl isocyanate, hexadecyl isocyanate, heptadecyl isocyanate, octadecyl isocyanate, nonadecyl isocyanate, icosanyl isocyanate or the like is exemplified. The reaction is carried out in the same manner as described in Process (ii)-①.

② In this step, the amino protecting group is removed.

The deprotection, the condition of which depend on the protecting group, is carried out in the usual manner such as by catalytic hydrogenolysis (with palladium catalyst under atmospheric hydrogen at room temperature in methanol, methanol-acetic acid, or glacial acetic acid) or by mild acid treatment (aqueous acetic acid at 30° C. or aqueous trifluoroacetic acid at −5° C.).

③ In this step, the methoxycarbonyl of the compound E3 is reduced into the hydroxymethyl. As a reducing agent, an metal hydride complex, e.g., lithium aluminumhydride, lithium borohydride, sodium borohydride, lithium trimethoxyaluminohydride, lithium tri-tert-butoxyaluminohydride, calcium borohydride resulted from calcium chloride and sodium borohydride is exemplified.

The reaction is carried out in a solvent such as alcohol, e.g., methanol, ethanol, propanol or ether, e.g., ethyl ether, tetrahydrofuran, glyme, diglyme under cooling for several hours.

④ In this step, the amino of the compound E4 is converted into the alkyloxycarbonylamino.

The reagent for alkyloxycarbonylaminolation such as alkyl haloformate, e.g., methyl chloroformate, methyl bromoformate, ethyl chloroformate, propylchloroformate, isopropyl chloroformate, butyl chloroformate, isobutyl bromoformate, tert-butyl chloroformate, pentyl chloroformate, hexyl chloroformate, heptyl chloroformate or dialkyl dicarbonate, e.g., dimethyl dicarbonate, diethyl dicarbonate, dipropyl dicarbonate, diisopropyl dicarbonate, dibutyl dicarbonate, di-tert-butyl dicarbonate, dipentyl dicarbonate, dihexyl dicarbonate, diheptyl dicarbonate is exemplified.

The reaction is carried out in a solvent such as ether, e.g., ethyl ether, tetrahydrofuran or ketone, e.g., acetone at room temperature for several hours.

PROCESS (IV)

When —Y—R$_1$ is alkylthio and R$_2$ is alkoxycarbonylamino, the compound IVE2 can be prepared by the following manner.

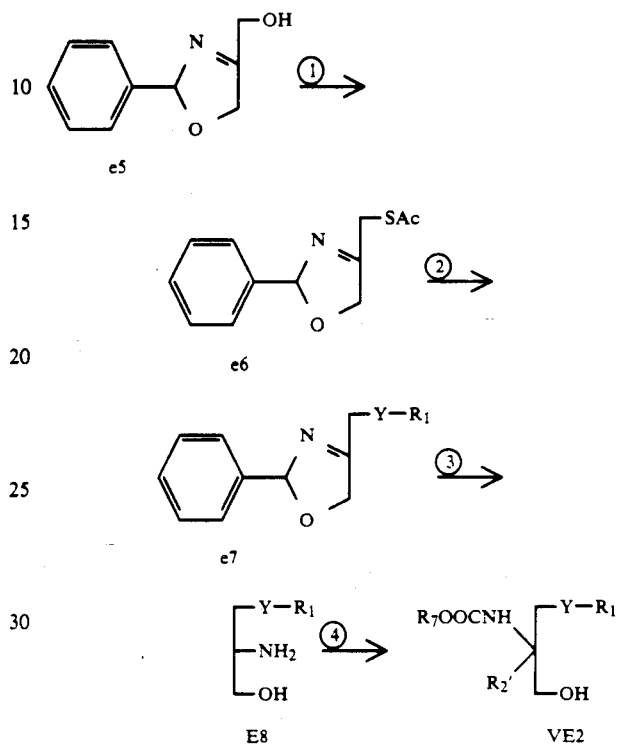

wherein R$_1$ is alkyl, Y is oxygen, and R$_2'$ and R$_7$ each has the same meaning as defined before.

① In this step, the alcohol e5 is converted into the thioacetate e6.

This step can be carried out by the same procedure to prepare the compound VII6 from the compound IX6 in Process (i), that is, the alcohol e5 is converted into a sulfonate or halide which is then converted into the thioacetate with potassium thioacetate or sodium thioacetate.

② In this step, acetyl of the compound e6 is converted into the desired alkyl.

The thioacetate e6 is hydrolyzed with a base to give the thiol which is treated with sodium hydroxide to give the thiolate anion which is allowed to react with C$_{12}$-C$_{20}$ alkyl halide, e.g., dodecyl bromide, tridecyl bromide, tetradecyl bromide, pentadecyl bromide, pentadecyl chloride, hexadecyl bromide, pentadecyl bromide, heptadecyl bromide, octadecyl bromide, octadecyl chloride, nonadecyl bromide, icosanyl bromide to give the compound E7.

This step can be carried out by using C$_{12}$-C$_{20}$ alkylisocyanate in the same manner as described in Process (i).

③ In this step, the amino and hydroxy protecting group of the compound E7 is removed.

The reaction is carried out in the presence of an acid such as dilute hydrochloric acid or dilute sulfuric acid.

④ In this step, the amino of the compound E8 is converted into the alkyloxycarbonylamino.

This step can be carried out in the same manner as described in Process (iii)-④.

PROCESS (V)

When $R_2$ is alkylureido or alkanoylamino, the compound IIIF or IIIG is prepared by the following manner.

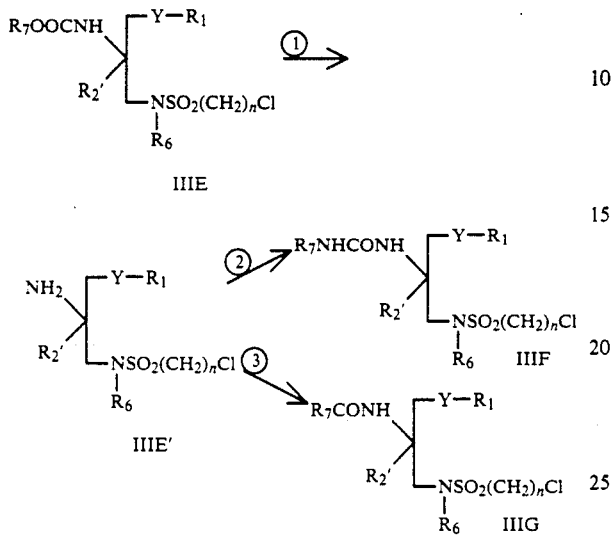

wherein $R_1$, $R_2'$, $R_6$, $R_7$, Y, and n each has the same meaning as defined before.

①  In this step, the alkoxycarbonyl of the compound IIIE which is prepared from compound VE1 or VE2 by allowing reaction in the same manner described in Process I, Steps 1 and 2 is cleaved to give the compound IIIE'.

This step is carried out in the usual manner for removing the urethane type amino protecting group, for example, hydrogen bromide or hydrochloric acid treatment in acetic acid, hydrochloric acid treatment in ethyl ether, ethyl acetate or nitromethane, or trifluoroacetic acid treatment.

②  In this step, the compound IIIF is prepared by the addition of an alkylisocyanate to the amine IIIE'.

The reaction is carried out using the $C_1$-$C_7$ alkylisocyanate, e.g., methyl isocyanate, ethyl isocyanate, propyl isocyanate, isopropyl isocyanate, butyl isocyanate, tert-butyl isocyanate, pentyl isocyanate, hexyl isocyanate, heptyl isocyanate in an inactive solvent such as aromatic hydrocarbon, e.g., benzene, toluene, chlorobenzene, chlorinated hydrocarbon, e.g., chloroform, dichloromethane, ether, e.g., tetrahydrofuran, or acetone.

③  In this step, the amine IIIE' is converted into the acid amide IIIG.

The acylating reagent such as acid halide, e.g., acetyl chloride, propionyl chloride, butyryl chloride, isobutyryl chloride, valeryl chloride, isovaleryl chloride, pivaloyl chloride, pentanoyl chloride, hexanoyl chloride, heptanoyl chloride or acid anhydride. e.g., acetic anhydride, propionic anhydride, butyric anhydride, isobutyric anhydride, valeric anhydride, isovaleric anhydride. pivalic anhydride, pentanoic anhydride, hexanoic anhydride, heptanoic anhydride is exemplified.

The reaction is carried out by heating without solvent or in an inactive solvent such as ethyl ether, benzene or the like. A base such as pyridine or an acid such as sulfuric acid may be added, if necessary.

PROCESS (VI)

When $R_2$ is heterocyclic group or heterocyclyloxy, the compound VHIJ can be prepared by the following manner.

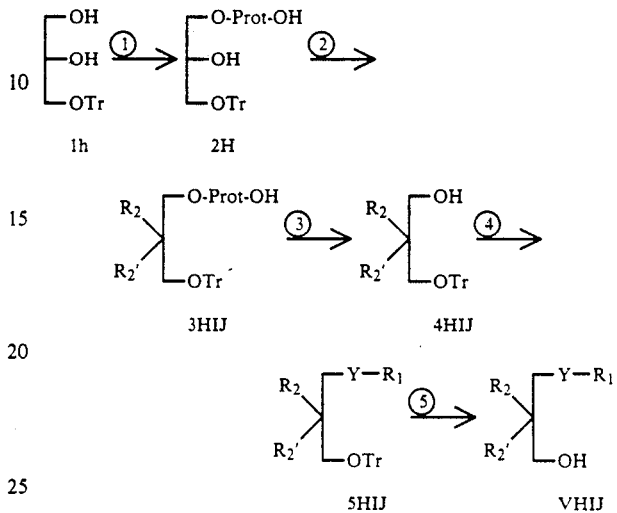

wherein $R_2$ is heterocyclic group or heterocyclyloxy and $R_1$, $R_2'$, Y and Prot-OH each has the same meaning as defined before.

①  In this step, the hydroxy at 1 position is selectively protected.

The protecting group selectively attached to the primary hydroxy such as tert-butyldimethylsilyl is used. The reaction is carried out using tert-butyldimethylchlorosilane in the presence of a base such as imidazole.

②  In this step, the desired heterocyclic group or heterocyclyloxy is introduced to 2H to give the compound 3HIJ.

The reaction is achieved according to the manner described in O. Mitsunobu, SYNTHESIS, 1, (1981).

The reaction is carried out using the desired heterocycle such as pyrrole, 2-methylpyrrole, 3-methylpyrrole, imidazole, 2-methylimidazole, 2,4-dimethylimidazole, pyrazole, 5-methylpyrazole, 3,5-dimethylpyrazole, 1,2,3-triazole, 4-methyl-1,2,3-triazole. 3-methyl-1,2,4-triazole, 3,5-dimethyl-1,2,4-triazole, tetrazole, or 5-methyltetrazole or 3-hydroxyisoxazole, 3-hydroxyisothiazole, 3-hydroxypyrazole, 3-hydroxy-4-methylisoxazole, 4-hydroxy-1,2,3-triazole or 4-hydroxy-5-methyl-1,2,3-triazole in the presence of triphenylphosphine and diethyl azodicarboxylate in a dry ether solvent such as ethyl ether, tetrahydrofuran, or benzene.

③  In this step, the hydroxy protecting group at 1 position is removed selectively.

The deprotection is carried out in the usual manner such as the acetic acid treatment at room temperature or tetra-n-butylammonium fluoride treatment in tetrahydrofuran.

④  In this step, the hydroxy of the compound 4HIJ is converted into the desired side chain.

This step can be carried out in the same manner as described in Processes (i), (ii)-①, or (iv)-①, ②.

⑤  In this step, the hydroxy protecting group at 3 position of the compound 5HIJ is removed.

The deprotection is carried out in the usual manner using an agent such as acetic acid, hydrochloric acid/- chloroform, hydrobromic acid/acetic acid, p-toluenesulfonic acid or the like.

PROCESS (VII)

When $R_2$ is alkaloylmethyl, the compound IIIM can be prepared by the following manner.

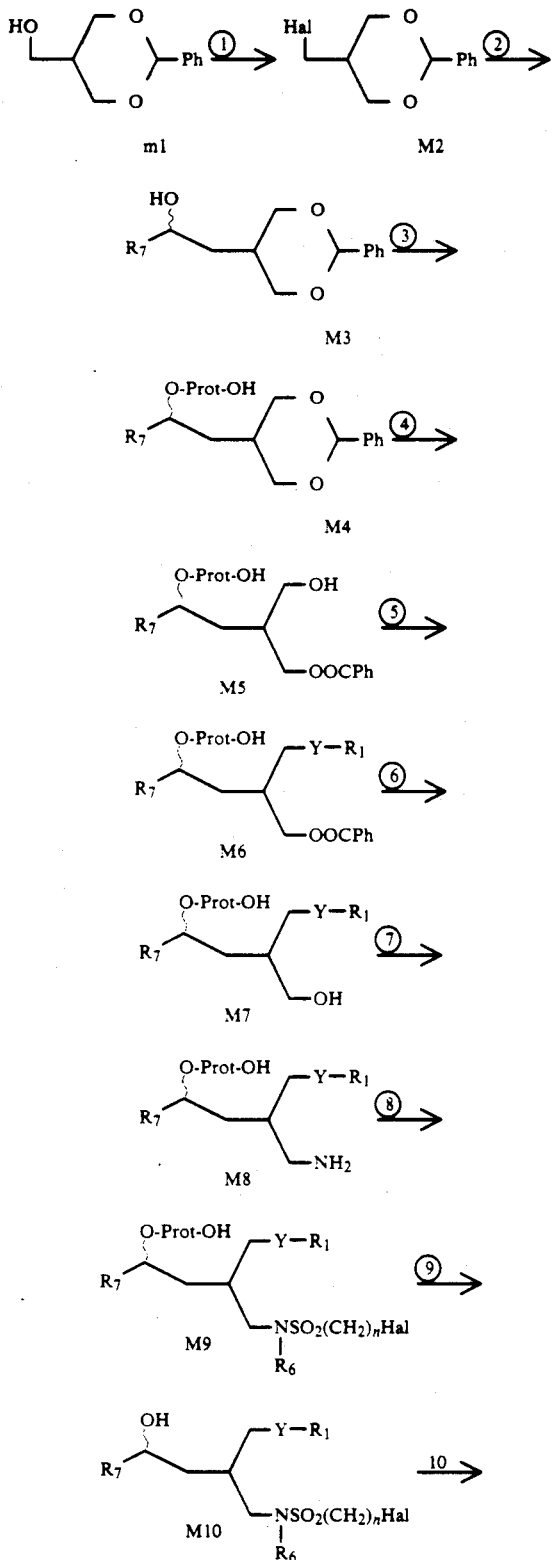

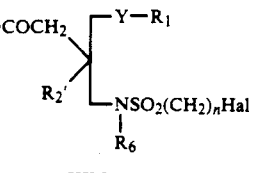

IIIM wherein $R_1$, $R_2'$, $R_6$, $R_7$, Y, n, Hal, and Prot-OH each has the same meaning as defined before.

① In this step, the hydroxy of the compound m1 is halogenated.

This step can be carried out in the same manner as described in Process II, Step 3'.

② In this step, an aldehyde is condensed additionally to the compound M2 to give the compound M3.

This step can be carried out in the usual manner of Grignard reaction.

The aldehyde such as $C_2$–$C_8$ aldehyde, e.g., acetoaldehyde, propionaldehyde, butyraldehyde, isobutyraldehyde, valeraldehyde, isovaleraldehyde, pivaloaldehyde, hexanol, heptanol, octanol is exemplified.

③ In this step, the hydroxy of the compound M3 is prottected.

The ordinally used hydroxy protecting group can be used.

In the case when triarylmethyl (e.g., trityl) or aroyl (e.g., benzoyl) is introduced, the corresponding halide such as trityl chloride, trityl bromide, or benzoyl chloride is allowed to react in the presence of base such as pyridine, triethylamine.

In the case when trialkylsilyl (e.g., trimethylsilyl, tert-butyldimethylsilyl) is introduced, trialkylsilane such as trimethylchlorosilane or tert-butyldimethylchlorosilane is allowed to react in the presence of base such as imidazole.

④ In this step, the compound M4 is cleaved to the compound M5.

The reaction is carried out by treatment with an aqueous suspension of N-bromosuccinimide containing a trace of hydrobromic acid.

⑤ In this step, the hydroxy of the compound M5 is converted into the desired side chain.

This step is carried out in the same manner as described in Processes (i), (ii)-①, or (iv)-①, ②.

⑥ In this step, the compound M6 is hydrolyzed with a base to give the compound M7.

The reaction is carried out in the usual manner with a base such as sodium hydroxide, potassium hydroxide, barium hydroxide, or the like in water or in an alcohol (e.g., methanol, ethanol).

⑦ In this step, the hydroxy of the compound M7 is converted into the amino.

This step can be carried in the same manner as described in Process I Step 1.

⑧ In this step, the compound M8 is sulfonylated to give the sulfonamide derivative M9.

This step can be carried out in the same manner as described in Process I Step 2.

⑨ In this step, the hydroxy protecting group of the compound M9 is removed.

The deprotection is carried out as follows.

When protecting group is triarylmethyl, it is cleaved by treatment with acid, when protecting group is trialylsilyl, it is cleaved by treatment with acetic acid or with tetra-n-butylammonium fluoride in tetrahydrofuran, and when protecting group is aroyl, it is cleaved by hydrolysis with a base such as sodium methoxide.

10 In this step, the hydroxy of the compound M10 is oxidized into the carbonyl.

As an oxidizing agent, chromate-type agent such as Jones' reagent, Collins' reagent, pyridinium chlorochromate or pyridinium dichromate, or dimethylsulfoxide combined with sulfur trioxide, trifluoroacetic anhydride, methanesulfonic anhydride, thionyl chloride or oxalyl chloride or the like may be used. In a case where dimethylsulfoxide is used as an oxidizing agent, a tertiary amine such as triethylamine or pyridine may be used as a decomposing agent. As a solvent, according to the property of the agent a chlorinated hydrocarbon such as chloroform or dichloromethane, ether such as diethyl ether, tetrahydrofuran, or dimethylsulfoxide may be used. The reaction may be carried out under cooling or at room temperature within several hours.

PROCESS (VIII)

When $R_2$ is cyanomethyl, the compound VN can be prepared in the following manner.

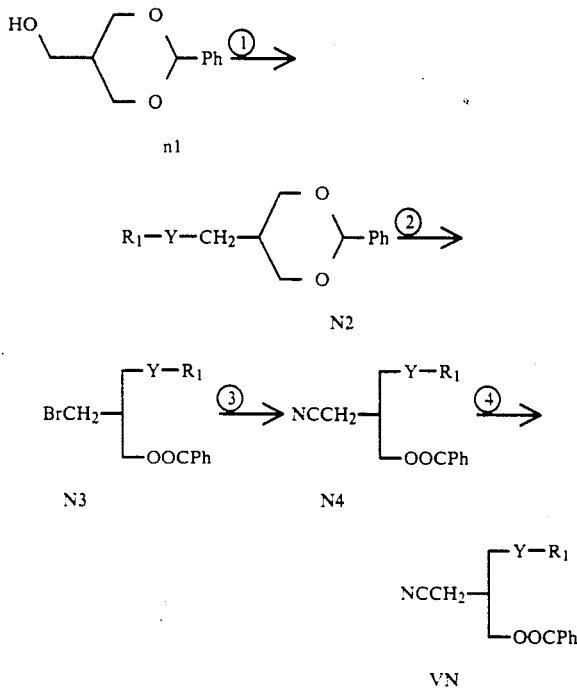

wherein $R_1$ and Y each has the same meaning as defined before.

① In this step, the hydroxy of the compound n1 is converted to the desired side chain.

This step can be carried out in the same manner as described in Process (i), (ii)-①, or (iv)-①, ②.

② In this step, the acetal N2 is cleaved into the compound N3.

This step is carried out by using N-bromosuccinimide in a solvent such as chlorinated hydrocarbon (e.g., carbon tetrachloride, chloroform, dichloromethane) by heating for several hours.

③ In this step, the compound N3 is cyanolated to give the compound N4.

This step can be carried out using metal cyanine such as sodium cyanide, potassium cyanide, copper(I) cyanide or the like in a solvent such as acetone, acetonitrile, pyridine, ethyl ether, benzene, dimethylsulfoxide, dimethylformamide under heating. A phase transfer catalyst such as crown ether, e.g., 18-crown-6 or tetraethylammonium cyanide may be used, if necessary.

④ In this step, the benzoate N4 is hydrolyzed to the alcohol.

This step can be carried out in the same manner, the usual manner of the hydrolysis with a base, as described in Process (vii)-⑥.

The following examples are included to explain the embodiments of the present invention in more detail, but these are not intended to limit the scope of the invention.

The following compounds may be used as starting materials.

2-Methoxy-3-octadecylcarbamoyloxtpropylamine (Japan Kokai No. 85-243047), 3-hexadecylthio-2-methoxypropanol (Ger. Offen. DE 3,204,735), 3-hexadecyloxy-2-methoxypropanol [Shimazu et al., Chem. Pharm. Bull., 30, 3260, (1982)], β-methyl-αγ-benzylidenglycol [P. E. Verkade, et al., Recl. Trav. Chim. Pays,-Bas., 61, 831, (1942)], 2-hexadecylthiomethyl-2-hydroxymethyltetrahydrofuran (U.S. Pat. No. 792,095), 2-hydroxymethyl-2-octadecylcarbamoylmethyltetrahydrofuran (U.S. Pat. No. 792,095), 1-hexadecylthio-3-trityloxy-2-propanol [J. Med. Chem., 31, 410 (1988)], 1-octadecylcarbamoyloxy-3-trityloxy-2-propanol, [J. Med. Chem., 31, 410 (1988)], N-tritylserine methyl ester [Tetrahedron Letters. 22, 491, (1981)], 4-hydroxymethyl-2-phenyl-2-oxazoline [J. Org. Chem., 48, 1197 (1983)], 3-trityloxy-1,2-propandiol [Chem. Ber., 94, 812, (1961)], 3-hexadecyloxy-2-methoxymethylpropanol [JP Kokai Pub. No. 83-10592], 3-hexadecylthio-2-methoxymethylpropylamine [JP Kokai Pub. No. 82-98291], 2-methoxymethyl-3-octadecylcarbamoyloxypropanol [JP Kokai Pub. No. 83-10592] and 5-hydroxymethyl-2-phenyl-1,3-dioxane [Lipids, 22(11), 947–951 (1987)].

(1) Preparation of 3-(3-chloropropylsulfonylamino)-2-methoxy-1-octadecylcarbamoyloxypropane IIIa1

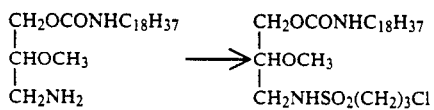

```
CH2OCONHC18H37          CH2OCONHC18H37
|                       |
CHOCH3          ——>     CHOCH3
|                       |
CH2NH2                  CH2NHSO2(CH2)3Cl

IVa1                    IIIa1
```

To a solution of 1.2 g (3 mM) of 2-methoxy-3-octadecylcarbamoyloxypropylamine IVa1 (described in JP Kokai No. 60-243047) in 24 ml of dichloromethane and 0.54 ml (3.9 mM) of triethylamine is added 0.401 ml (3.3 mM) of 3-chloropropanesulfonyl chloride with ice-cooling and the mixture is stirred at room temperature overnight. The product is isolated by dichloromethane extraction and dichloromethane layer is washed with saturated aqueous sodium hydrogencarbonate and saturated aqueous sodium chloride, dried over anhydrous magnesium sulfate, and evaporated. The residue is purified by the column chromatography on silica gel with a n-hexane-ethyl acetate (3:2) mixture as an eluent. The product is recrystallized from chloroform-n-hexane mixture to give 1.386 g (2.56 mM) of 3-(3-chloropropylsulfonylamino)-2-methoxy-1-octadecylcarbamoyloxypropane IIIa1 as colorless crystals in 85% yield.

NMR: δppm (CDCl₃) 0.86 (t, 3H), 1.24 (s, 30H), 1.58(m, 2H), 2.1~2.5 (m, 2H), 2.9~3.6 (m, 7H), 3.44 (s, 3H), 3.67 (t, 2H, J=6.0 Hz), 4.18 (m, 2H), 4.87 (m, 1H), 5.10 (m, 1H).

IR: νmax (CHCl₃) 3445, 2920, 2850, 1715, 1510, 1460, 1330, 1220, 1145 cm⁻¹.

Anal. Calcd. (%) for C₂₆H₅₃O₅N₂SCl: C 57.70, H 9.87, N 5.18, S 5.92, Cl 6.55, Found (%) C 57.51, H 9.84, N 5.34, S 5.95, Cl 6.82.

MS: 540 (M+, Cl³⁵).

Mp.: 64.5°~66° C.

(2) Preparation of 3-(3-iodopropylsulfonylamino)-2-methoxy-1-octadecylcarbamoyloxypropane IIa1

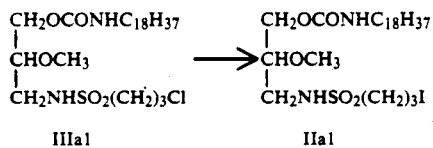

To a solution of 972 mg (1.8 mM) of 3-(3-chloropropylsulfonylamino)-2-methoxy-1-octadecylcarbamoyloxypropane IIIa1 in 10 ml of methyl ethyl ketone is added 500 mg (3.38 mM) of sodium iodide and the mixture is refluxed for 3 hours with stirring. After the solvent is evaporated, the residue is purified by the column chromatography on silica gel with a n-hexane-ethyl acetate (1:1) mixture as an eluent. The product is recrystallized from chloroform-n-hexane to give 972 mg (1.54 mM) of 3-(3-iodopropylsulfonylamino)-2-methoxy-1-octadecylcarbamoyloxypropane IIa1 in 86% yield.

NMR: δppm (CDCl₃) 0.88 (t, 3H), 1.26 (s, 30H), 1.5 (m, 2H), 2.25~2.40 (m, 2H), 3.1~3.3 (m, 4H), 3.31 (t, 2H, J=6.6 Hz), 3.46 (s, 3H), 3.50 (m, 1H), 4.05~4.30 (m, 2H), 4.83 (m, 1H), 5.00 (t, 1H, J=6 Hz).

IR: νmax (CHCl₃) 3450, 2940, 2855, 1725, 1510, 1470, 1335, 1230, 1145 cm⁻¹.

Anal. Calcd. (%) for C₂₆H₅₃O₅N₂SI: C 49.12, H 8.44, N 4.56, S 5.34, I 20.08, Found (%) C 49.36, H 8.44, N 4.43, S 5.07, I 20.10.

MS: 505 (M-I)+.

mp.: 61.5°~62.5° C.

EXAMPLE 1

Preparation of 2-methoxy-1-octadecylcarbamoyloxy-3-(3-trimethylammoniosulfonylamino)propane chloride Ia1

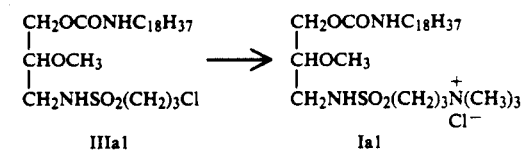

A solution of 420 mg (0.776 mM) of 3-(3-chloropropylsulfonylamino)-2-methoxy-1-octadecylcarbamoyloxypropane IIIa1 in 10 ml mixture of trimethylamine-toluene (10 ml/25 ml) is heated at 120° C. in a sealed tube for 24 hours. The solvent is evaporated and the residue which is washed with acetone-ether several times is purified by column chromatography on HP-20 to give 50 mg of 2-methoxy-1-octadecylcarbamoyloxy-3-(3-trimethylammoniosulfonylamino)propane chloride Ia1 in 11% yield.

NMR: δppm (CDCl₃) 0.86 (t, 3H), 1.25 (s, 30H), 1.4~1.6 (m, 2H), 2.0~2.5 (m, 2H), 3.20 (s, 3H), 3.0~3.4 (m, 6H), 3.46 (s, 3H), 3.4~3.8 (m, 3H), 4.15 (m, 2H).

IR: νmax (CHCl₃) 3450, 2925, 2850, 1710, 1460, 1320, 1220, 1140 cm⁻¹.

Anal. Calcd. (%) for C₂₉H₆₂O₅N₃SCl.1.5H₂O: C 55.52, H 10.44, N 6.70, S 5.11, Cl 5.65, Found (%) C 55.49, H 10.42, N 6.78, S 4.85, Cl 5.78.

mp.: 60°~62° C.

EXAMPLE 2

Preparation of 2-methoxy-1-octadecylcarbamoyloxy-3-(3-thiazoliopropylsulfonylamino)propane iodide Ia2

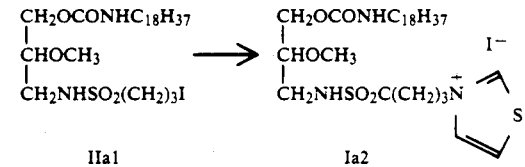

A solution of 240 mg (0.38 mM) of 3-(3-iodopropylsulfonylamino)-2-methoxy-1-octadecylcarbamoyloxypropane in 2 ml of thiazole is stirred at 50° C. overnight. After thiazole is evaporated, the residue is recrystalized from dichloromethane-acetone to give 150 mg (0.209 mM) of 2-methoxy-1-octadecylcarbamoyloxy-3-(3-thiazoliopropylsulfonylamino)propane iodide Ia2 in 55% yield.

NMR: δppm (d₆DMSO) 0.86 (t, 3H), 1.24 (s, 30H), 1.36 (m, 2H), 2.2~2.4 (m, 2H), 2.9~3.2 (m, 6H), 3.32 (s, 3H), 3.3~3.45 (m, 1H), 3.80~4.15 (m, 2H), 4.67 (t, 2H, J=7.2 Hz), 7.15 (t, 1H, J=5.6 Hz), 7.33 (t, 1H, J=5.8 Hz), 8.35~8.42 (m, 1H), 8.60 (d, 1H, J=3.8 Hz), 10.20 (s, 1H).

IR: νmax (KBr) 3360, 2925, 2855, 1685, 1565, 1470, 1310, 1280, 1145, 1130 cm⁻¹.

Anal. Calcd. (%) for C₂₉H₅₆O₅N₃S₂I.0.2H₂O: C 48.28, H 7.88, N 5.82, S 8.89, I 17.59, Found (%) C 48.37, H 7.88, N 6.00, S 9.22, I 17.38.

mp.: 116°~118° C. (Decompose).

EXAMPLES 3 TO 7

The compounds shown in Table 1 are prepared from the compound IIa1 by the same procedure as described in Example 2.

In Example 4, the residue resulting from evaporating an amine is washed with n-hexane and in Examples 5 and 6, the said residue is washed with ethyl ether.

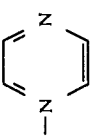

TABLE 1-continued $$\underset{\text{IIa1}}{\overset{\text{CH}_2\text{OCONHC}_{18}\text{H}_{37}}{\underset{\text{CH}_2\text{NHSO}_2(\text{CH}_2)_3\text{I}}{\overset{|}{\text{CH}_3\text{OCH}}}}} \longrightarrow \underset{\text{Ia}}{\overset{\text{CH}_2\text{OCONHC}_{18}\text{H}_{37}}{\underset{\text{CH}_2\text{NHSO}_2(\text{CH}_2)_3\overset{+}{\text{N}}\underset{\text{R}_6}{\overset{\text{R}_5}{\diagdown}}\text{R}_4}{\overset{|}{\text{CH}_3\text{OCH}}}}} \quad \text{I}^-$$

| Ex. No. | Cpd. No. | S.M. II 1 [mg] | Amine | Reaction Tempt. | Reaction Time | Purification | Yd. [mg] [%] | NMR: δ ppm | IRvmax; [cm$^{-1}$] mp. [°C.] | Analysis Calcd. (%) Found (%) |
|---|---|---|---|---|---|---|---|---|---|---|
| 7 | Ia 7 | 1300 | Quinoline (2 ml) 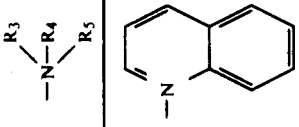 | 60° C. | overnight | recryst. Et$_2$O | 850 54% | (CDCl$_3$) 0.88(t, 3H), 1.25 (s, 30H), 1.5(m, 2H), 2.60~ 2.85(m, 2H), 3.0~3.2(m, 2H), 3.2~3.44(m, 2H), 3.5~3.7(m, 3H), 3.41(s, 3H), 4.0~4.2(m, 2H), 5.32(t, 1H, J=6Hz), 5.60(t, 2H, J=8.1Hz), 6.06(t, 1H, J=6Hz), 7.97(t, 1H, J=8Hz), 8.1~8.44(m, 3H), 8.71(d, 1H, J=9.2Hz), 9.03(d, 1H, J=8.2Hz), 10.27 (d, 1H, J=5.4Hz). | (CHCl$_3$) 3445, 2920, 2850, 1710, 1520, 1460, 1320, 1230, 1140. 56.5~58 (dec.) | (C$_{35}$H$_{60}$O$_5$N$_3$SI.0.75H$_2$O) C 54.22, H 7.99 N 5.42 S 4.13, I 16.37. C 54.28, H 7.92, N 5.50, S 4.26, I 16.65 |

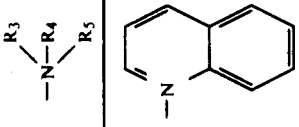

(3) Preparation of
3-hexadecylthio-2-methoxypropylamine IVA2

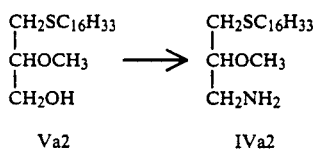

To a solution of 4.356 g (12.57 mM) of 3-hexadecylthio-2-methoxypropanol Va2 (described in Ger. Offen. DE 3,204,735), 3.7 g (25.14 mM) of phthalimide, and 6.59 g (25.14 mM) of triphenylphosphine in 150 ml of tetrahydrofuran is added dropwise 4.37 g (25.14 mM) of diethyl azodicarboxylate with ice-cooling and the mixture is stirred at room temperature for 3 days. After the solvent is evaporated, the residue is purified by column chromatography on silica gel with a n-hexane-ethyl acetate-chloroform (9:1:1) mixture as an eluent. The product is recrystallized from dichloromethane-n-hexane to give 4.9 g (10.23 mM) of the phthalimide compound in 82% yield.

To a solution of 4.678 g (9.83 mM) of the phthalimide compound in 100 ml of methanol is added 0.54 g (10.79 mM) of hydrazine monohydrate and the mixture is stirred for 5 hours under refluxing. After the solvent is evaporated, the residue is dissolved in chloroform and filtered through Celit to remove the insoluble material. The filtered is evaporated and the residue is purified by the column chromatography on silica gel with a chloroform-methanol (20:1 to 9:1) (0.2% triethylamine) mixture as an eluent to give 2.98 g (8.622 mM) of 3-hexadecylthio-2-methoxypropylamine IVa2 in 88% yield.

NMR: δppm (CDCl$_3$) 0.88 (t, 3H), 1.26 (s, 26H), 1.6 (m, 2H), 2.5~3.0 (m, 6H), 3.30 (m, 1H), 3.43 (s, 3H).

IR: νmax (CHCl$_3$) 3380, 2930, 2850, 1465, 1380, 1230, 1110 cm$^{-1}$.

MS: 346 (MH$^+$).

(4) Preparation of
3-(3-chloropropylsulfonylamino)-1-hexadecylthio-2-methoxypropane IIIa2

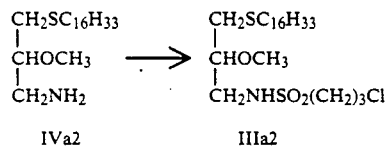

To a solution of 1.018 g (2.95 mM) of 3-hexadecylthio-2-methoxypropylamine IVa2 in 15 ml of dichloromethane and 0.534 ml (3.83 mM) of triethylamine is added 0.563 mg (3.24 mM) of 3-chloropropanesulfonyl chloride with ice-cooling and the mixture is stirred at 0° C. for 3 hours. After the solvent is evaporated, the residue is purified by the column chromatography on silica gel with a n-hexane-ethyl acetate (4:1) mixture as an eluent. The product is recrystallized from chloroform-n-hexane to give 1.275 g (2.62 mM) of 3-(3-chloropropylsulfonylamino)-1-hexadecylthio-2-methoxypropane IIIa2 as a colorless powder in 89% yield.

NMR: δppm (CDCl$_3$) 0.88 (t, 3H), 1.26 (s, 26H), 1.6 (m, 2H), 2.2~2.4 (m, 2H), 2.55 (t, 2H, J=7.4 Hz), 2.53~2.80 (m, 2H), 3.10~3.30 (m, 3H), 3.42 (s, 3H), 3.4~3.6 (m, 2H), 3.69 (t, 2H, J=6.2 Hz), 4.70 (t, 1H, J=6 Hz).

IR: νmax (CHCl$_3$) 3380, 2930, 2850, 1470, 1410, 1330, 1150, 1095 cm$^{-1}$.

Anal. Calcd. (%) for C$_{23}$H$_{48}$O$_3$NS$_2$Cl: C 56.82, H 9.95, N 2.88, S 13.19, Cl 7.29, Found (%): C 56.76, H 9.89, N 3.18, S 12.94, Cl 7.18.

MS: 485 (M$^+$, Cl$^{35}$).

mp.: 49°~50° C.

(5) Preparation of
1-hexadecylthio-3-(3-iodopropylsulfonylamino)-2-methoxypropane IIa2

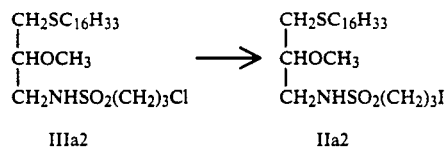

To a solution of 1.03 g (2.12 mM) of 3-(3-chloropropylsulfonylamino)-1-hexadecylthio-2-methoxypropane IIIa2 in 20 ml of methyl ethyl ketone is added 636 mg (4.24 mM) of sodium iodide and the mixture is refluxed or 3 hours with stirring. After the solvent is evaporated, the residue is purified by the column chromatography on silica gel with a n-hexane-ethyl acetate (4:1) mixture as an eluent to give 1.06 g (1.835 mM) of 1-hexadecylthio-3-(3-iodopropylsulfonylamino)-2-methoxypropane IIa2 as an oil in 87% yield.

NMR: δppm (CDCl$_3$) 0.88 (t, 3H), 1.26 (s, 26H), 1.6 (m, 2H), 2.22~2.40 (m, 2H), 2.55 (t, 2H, J=7.4 Hz), 2.53~2.81 (m, 2H), 3.11~3.26 (m, 3H), 3.31 (t, 2H, J=6.6 Hz), 3.43 (s, 3H), 3.41~3.56 (m, 1H), 4.65 (t, 1H, J=6 Hz).

IR: νmax (CHCl$_3$) 3370, 2920, 2850, 1460, 1405, 1325, 1145, 1090 cm$^{-1}$.

Anal. Calcd. (%) for C$_{23}$H$_{48}$O$_3$NS$_2$I: C 47.82, H 8.38, N 2.42, S 11.10, I 21.97, Found (%): C 47.62, H 8.28, N 2.50, S 11.09, I 22.18.

MS: 577 (M$^+$).

EXAMPLE 8

Preparation of
1-hexadecylthio-2-methoxy-3-(3-trimethylammoniopropylsulfonylamino)propane iodide Ia8

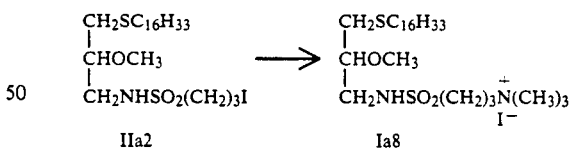

A solution of 500 mg (0.866 mM) of 1-hexadecylthio-3-(3-iodopropylsulfonylamino)-2-methoxypropane IIa2 in 10 ml of mixture of trimethylamine-toluene (10 ml/25 ml) is allowed to react at room temperature in a sealed tube for 24 hours. After the solvent is evaporated, the residue is purified by the column chromatography on silica gel with a chloroform-methanol (5:1 to 3:1) mixture as an eluent. The product is recrystallized from dichloromethane-n-hexane to give 330 mg (0.518 mM) of 1-hexadecylthio-3-(3-trimethylammoniopropylsulfonylamino)-2-methoxypropane Ia8 in 60% yield.

NMR: δppm (CDCl$_3$) 0.88 (t, 3H), 1.26 (s, 26H), 1.58 (m, 2H), 2.3~2.5 (m, 2H), 2.56 (t, 2H, J=7.2 Hz), 2.72 (d, 2H, J=5.8 Hz), 3.20~3.65 (m, 5H), 3.43 (s, 9H), 3.45 (s, 3H), 3.85~3.93 (m, 2H), 6.20 (t, 1H, J=6 Hz).

IR: νmax (CHCl₃) 3375, 2925, 2850, 1470, 1330, 1230, 1150, 1090, 1055, 1030 cm⁻¹.

mp.: 69°~71° C.

Anal. Calcd. for C₂₆H₅₇O₃N₂S₂I.0.4H₂O: C 48.49, H 9.05, N 4.35, S 9.96, I 19.71, Found (%): C 48.66, H 8.85, N 4.47, S 10.19, I 19.47.

EXAMPLE 9

Preparation of 1-hexadecylthio-2-methoxy-3-(3-thiazoliopropylsulfonylamino)propane iodide Ia9

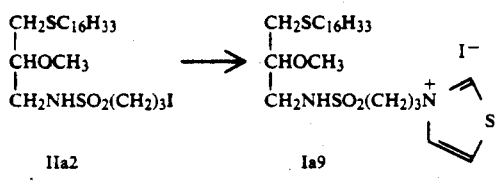

A solution of 600 mg (1.04 mM) of 1-hexadecylthio-3-(3-iodopropylsulfonylamino)-2-methoxypropane IIa2 in 5 ml of thiazole is stirred at 60° C. for 6 hours. After thiazole is evaporated, the residue is washed with ether and recrystallized from acetone to give 387 mg (0.584 mM) of 1-hexadecylthio-2-methoxy-3-(3-thiazoliopropylsulfonylamino)propane iodide Ia9 in 56% yield.

NMR: δppm (CDCl₃) 0.88 (t, 3H), 1.26 (s, 26H), 1.58 (m, 2H), 2.55 (t, 2H, J=7.3 Hz), 2.70 (d, 2H, J=5.6 Hz), 2.5~2.7 (m, 2H), 3.1~3.5 (m, 4H), 3.43 (s, 3H), 3.55 (m, 1H), 5.04 (t, 2H, J=7.4 Hz), 6.26 (t, 1H, J=6 Hz), 8.29~8.32 (m, 1H), 8.72~8.75 (m, 1H), 10.59~10.60 (m, 1H).

IR: νmax (CHCl₃) 3375, 2930, 2850, 1460, 1325, 1220, 1140, 1090 cm⁻¹.

Anal. Calcd. (%) for C₂₆H₅₁O₃N₃S₃I.0.1H₂O: C 46.99, H 7.76, N 4.21, S 14.47, I 19.10, Found (%): C 46.79, H 7.71, N 4.25, S 14.42, I 19.01.

mp.: 70°-73° C.

(6) Preparation of 3-hexadecyloxy-2-methoxypropylamine IVa3

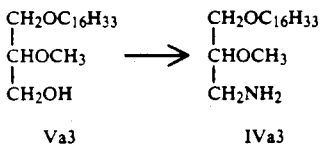

To a solution of 8.26 g (25 mM) of 3-hexadecyloxy-2-methoxypropanol Va3 [described in Shimazu et al., Chem. Pharm. Bull. 30, 3260, (1982)], 7.35 g (50 mM) of phthalimide, and 13.1 g (50 mM) of triphenylphosphine in 300 ml of tetrahydrofuran is added dropwise 8.7 g (50 mM) of diethyl azodicarboxylate with ice-cooling, and the mixture is stirred at room temperature for 3 days. After the solvent is evaporated, the residue is purified by the column chromatography on silica gel with a n-hexane-ethyl acetate-chloroform (9:1:1) mixture as an eluent. The product is recrystallized from n-hexane to give 10.142 g (22.06 mM) of the phthalimide compound in 88% yield.

To a solution of 10.142 g (22.06 mM) of the phthalimide compound in 200 ml of methanol is added 1.47 g (29.4 mM) of hydrazine monohydrate and the mixture is refluxed for 5 hours with stirring. After the solvent is evaporated, the residue to which is added chloroform is passed through Celite to remove the insoluble material. The filtrate is evaporated and the residue is purified by column chromatography on silica gel with a chloroform-methanol (5:1) (0.2% triethylamine) as an eluent to give 5.523 g (16.76 mM) of 3-hexadecyloxy-2-methoxypropylamine IVa3 in 76% yield.

NMR: δppm (CDCl₃) 0.88 (t, 3H), 1.26 (s, 26H), 1.58 (m, 2H), 2.70~2.96 (m, 6H), 3.33 (m, 1H), 3.45 (s, 3H), 3.40~3.60 (m, 6H).

IR: νmax (CHCl₃) 3380, 2920, 2845, 1580, 1465, 1360, 1240, 1115, 860 cm⁻¹.

MS: 330 (MH+).

(7) Preparation of 3-(3-chloropropylsulfonylamino)-1-hexadecyloxy-2-methoxypropane IIIa3

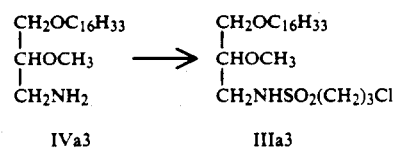

To a solution of 3.368 g (10.22 mM) of 3-hexadecyloxy-2-methoxypropylamine IVa3 in 35 ml of dichloromethane and 1.85 ml (13.29 mM) of triethylamine is added 1.99 g (11.24 mM) of 3-chloropropanesulfonyl chloride with ice-cooling and the mixture is stirred at room temperature for 4 hours and then heated for 30 minutes with stirring. After the solvent is evaporated, the residue is purified by the column chromatography on silica gel with a n-hexane-ethyl acetate (3:1) mixture as an eluent. The product is recrystallized form methanol to give 4.15 g (8.827 mM) of 3-(3-chloropropylsulfonylamino)-1-hexadecyloxy-2-methoxypropane IIIa3 as a colorless powder in 86% yield.

NMR: δppm (CDCl₃) 0.88 (t, 3H), 1.26 (s, 26H), 1.56 (m, 2H), 2.20~2.38 (m, 2H), 3.15~3.60 (m, 9H), 3.44 (s, 3H), 3.68 (t, 2H, J=6.2 Hz), 4.79 (t, 1H, J=6 Hz).

IR: νmax (CHCl₃) 3375, 2920, 2845, 1465, 1335, 1410, 1265, 1145 cm⁻¹.

mp.: 49°~50° C.

Anal. Calcd. (%) for C₂₃H₄₈O₄NSCl: C 58.76, H 10.29, N 2.98, S 6.82, Cl 7.54, Found (%) C 58.63, H 10.20, N 3.00, S 6.72, Cl 7.47.

MS: 469 (M+, Cl³⁵).

(8) Preparation of 1-hexadecyloxy-3-(3-iodopropylsulfonylamino)-2-methoxypropane IIa3

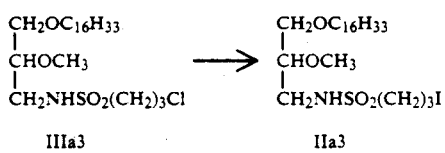

To a solution of 3.845 (8.18 mM) of 3-(3-chloropropylsulfonylamino)-1-hexadecyloxy-2-methoxypropane IIIa3 in 30 ml of methyl ethyl ketone is added 2.45 g (16.36 mM) of sodium iodide and the mixture is refluxed for 3 hours with stirring. After the solvent is evaporated, the residue is purified by the column chromatography on silica gel with a n-hexane-ethyl acetate (4:1) mixture as an eluent. The product is recrystallied from methanol to give 3.556 g (6.332 mM) of 1-hexadecyloxy-3-(3-iodopropylsulfonylamino)-2-methoxypropane IIa3 in 77% yield.

NMR: δppm (CDCl₃) 0.88 (t, 3H), 1.26 (s, 26H), 1.58 (m, 2H), 2.25~2.40 (m, 2H), 3.10~3.60 (m, 9H), 3.30 (t, 2H, J=6.6 Hz), 3.44 (s, 3H), 4.81 (t, 1H, J=6 Hz).

IR: νmax (CHCl₃) 3380, 2930, 2855, 1470, 1410, 1335, 1270, 1150 cm⁻¹.

Anal. Calcd. (%) for $C_{23}H_{48}O_4NSI$: C 49.19, H 8.61, N 2.49, S 5.71, I 22.60, Found (%) C 49.11, H 8.54, N 2.53, S 6.00, I 22.48.

MS: 562 (M+).

mp.: 46°~47° C.

EXAMPLE 10

Preparation of 1-hexadecyloxy-2-methoxy-3-(3-trimethylammonio-propylsulfonylamino)propane iodide Ia10

$$\begin{array}{c}CH_2OC_{16}H_{33}\\|\\CHOCH_3\\|\\CH_2NHSO_2(CH_2)_3I\end{array} \longrightarrow \begin{array}{c}CH_2OC_{16}H_{33}\\|\\CHOCH_3\\|\\CH_2NHSO_2(CH_2)_3\overset{+}{N}(CH_3)_3\\ \quad I^-\end{array}$$

IIa3　　Ia10

A solution of 600 mg (1.068 mM) of 1-hexadecyloxy-3-(3-iodopropylsulfonylamino)-2-methoxypropane IIa3 in 10 ml of trimethylamine-toluene (10 ml/25 ml) mixture is allowed to react at room temperature in a sealed tube for 24 hours. After the solvent is evaporated, the residue is washed with ether to give 577 mg of 1-hexadecyloxy-2-methoxy-3-(3-trimethylammoniopropylsulfonyamino)propane iodide Ia10 in 87% yield.

NMR: δppm (CDCl₃) 0.88 (t, 3H), 1.26 (s, 26H), 1.58 (m, 2H), 2.3~2.5 (m, 2H), 3.15~3.65 (m, 9H), 3.42 (s, 9H), 3.47 (s, 3H), 3.80~3.95 (m, 2H), 6.3 (t, 1H, J=6 Hz).

IR: νmax (CHCl₃) 3380, 2925, 2850, 1470, 1325, 1230, 1145 cm⁻¹.

Anal. Calcd. (%) for $C_{26}H_{57}O_3N_2SI$: C 50.31, H 9.26, N 4.51, S 5.17, I 20.44, Found (%): C 50.20, H 9.25, N 4.63, S 5.29, I 20.48.

mp.: 80.5°~82.5° C.

EXAMPLE 11

Preparation of 1-hexadecyloxy-2-methoxy-3-(3-thiazoliopropylsulfonylamino)propane iodide Ia11

$$\begin{array}{c}CH_2OC_{16}H_{33}\\|\\CHOCH_3\\|\\CH_2NHSO_2(CH_2)_3I\end{array} \longrightarrow \begin{array}{c}CH_2OC_{16}H_{33}\\|\\CHOCH_3\\|\\CH_2NHSO_2(CH_2)_3\overset{+}{N}\!\!\diagdown\!\!\diagup\!\!S\end{array} I^-$$

IIa3　　Ia11

A solution of 600 mg (1.07 mM) of 1-hexadecyloxy-3-(3-iodopropylsulfonylamino)-2-methoxypropane in 5 ml of thiazole is stirred at 50° C. for 6 hours. After thiazole is evaporated, the residue is purified by the column chromatography on silica gel with a chloroform-methanol (5:1 to 3:1) mixture as an eluent. The product is recrystallized from ether-dichloromethane to give 450 mg (0.70 mM) of 1-hexadecyloxy-2-methoxy-3-(3-thiazoliopropylsulfonylamino)propane iodide Ia11 in 66% yield.

NMR: δppm (DMSO) 0.85 (t, 3H), 1.24 (s, 26H), 1.48 (m, 2H), 2.2~2.4 (m, 2H), 3.31 (s, 3H), 2.9~3.5 (m, 9H), 4.65 (t, 2H, J=7 Hz), 7.26 (t, 1H), J=6 Hz), 8.36~8.39 (m, 1H), 8.57~8.60 (m, 1H), 10.17~10.20 (m, 1H).

IR: νmax (CHCl₃) 3400, 2930, 2850, 1460, 1320, 1220, 1140 cm⁻¹.

mp.: 52°~53° C.

(9) Preparation of 2-methoxy-1-octadecylcarbamoyloxy-3-(3-phenylselenylpropylsulfonylamino)propane IIa1'

$$\begin{array}{c}CH_2OCONHC_{18}H_{37}\\|\\CHOCH_3\\|\\CH_2NHSO_2(CH_2)_3I\end{array} \longrightarrow \begin{array}{c}CH_2OCONHC_{18}H_{37}\\|\\CHOCH_3\\|\\CH_2NHSO_2(CH_2)_3SePh\end{array}$$

IIa1　　IIa'1

To a solution of 1.52 g (4.9 mM) of diphenyl diselenide in 25 ml of dry ethanol is added 370 mg (9.78 mM) of sodium borohydride with ice-cooling and the mixture is stirred for 30 minutes. To the above mixture are added 0.56 ml (9.78 mM) of acetic acid and a solution of 1.03 g (1.63 mM) of 3-(3-iodopropylsulfonylamino)-2-methoxy-1-octadecylcarbamoyloxypropane in 10 ml of tetrahydrofuran and the mixture is stirred at room temperature for 1.5 hours. The product is extracted with ethyl acetate, and the organic layer is washed with 1N-hydrochloric acid, saturated aqueous sodium hydrogencarbonate, and saturated aqueous sodium chloride, dried over anhydrous magnesium sulfate, and evaporated. The residue is purified by the column chromatography on silica gel with a n-hexane-ethyl acetate (2:1) eluent to give 1.06 g (1.60 mM) of 2-methoxy-1-octadecylcarbamoyloxy-3-(3-phenylselenylpropylsulfonylamino)propane IIa1' as a colorless powder in 98% yield.

NMR: δppm (CDCl₃) 0.88 (t, 3H), 1.26 (s, 30H), 1.5 (m, 2H), 2.1~2.24 (m, 2H), 3.01 (t, 2H, J=7 Hz), 3.08~3.32 (m, 6H), 3.42 (s, 3H), 3.46 (m, 1H), 4.00~4.28 (m, 2H), 4.73~4.90 (m, 2H), 7.24~7.34 (m, 3H), 7.45~7.57 (m, 2H).

IR: νmax (CHCl₃) 3450, 2930, 2850, 1720, 1515, 1460, 1330, 1220, 1145 cm⁻¹.

MS: M+ 662 (Se⁸⁰).

(10) Preparation of 2-methoxy-1-octadecylcarbamoyloxy-3-(3-propensulfonylamino)propane VIIa4

$$\begin{array}{c}CH_2OCONHC_{18}H_{37}\\|\\CHOCH_3\\|\\CH_2NHSO_2(CH_2)_3SePh\end{array} \longrightarrow \begin{array}{c}CH_2OCONHC_{18}H_{37}\\|\\CHOCH_3\\|\\CH_2NHSO_2\!\!\diagup\!\!\diagdown\!\!=\end{array}$$

IIa'1　　VIIa4

To a solution of 1.028 g (1.553 mM) of 2-methoxy-1-octadecylcarbamoyloxy-3-(3-phenylselenylpropylsulfonylamino)propane in 30 ml of mixture of methanol-dichloromethane (5:1) are added 0.25 ml (3.16 mM) of pyridine and 2 ml of 30% hydrogen peroxide with ice-cooling and the mixture is warmed to room temperature and stirred for 5 hours. The product is isolated by ethyl acetate extraction and the organic layer is washed with an aqueous sodium chloride, dried over anhydrous magnesium sulfate, and evaporated. To the residue are added 30 ml of benzene and 0.25 ml of pyridine and the mixture is heated at 45° C. to 50° C. for an hour. After the solvent is evaporated, the residue is purified by the column chromatography on silica gel with a n-hexane-ethyl acetate (2:1 to 1:1) mixture as an eluent. The product is recrystallized from dichloromethane-n-hexane to give 624 mg (1.24 mM) of 2-methoxy-1-octadecylcarbamoyloxy-3-(3-propenesulfonylamino)propane VIIa4 as colorless crystals in 80% yield.

NMR: δppm (CDCl$_3$) 0.88 (t, 3H), 1.26 (s, 30H), 1.5 (m, 2H), 3.1~3.4 (m, 4H), 3.74~3.82 (m, 2H), 3.45 (s, 3H), 3.50 (m, 1H), 4.05~4.30 (m, 2H), 4.8 (m, 1H), 4.93 (t, 1H, J=6 Hz), 5.35~5.50 (m, 2H), 5.82~6.04 (m, 1H).

IR: νmax (CHCl$_3$) 3460, 2930, 2850, 1725, 1520, 1475, 1340, 1240, 1150 cm$^{-1}$.

Anal. Calcd. (%) for C$_{26}$H$_{52}$O$_5$N$_2$S: C 61.87, H 10.38, N 5.55, S 6.35, Found (%): C 61.68, H 10.34, N 5.73, S 6.20.

mp.: 74°~75.5° C.

(11) Preparation of 2-methoxy-1-octadecylcarbamoyloxy-3-(2-hydroxyethylsulfonylamino)propane VIa4

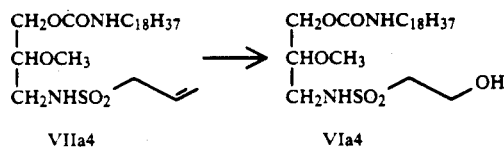

A solution of 600 mg (1.19 mM) of 2-methoxy-1-octadecylcarbamoyloxy-3-(3-propenesulfonylamino)propane VIIa4 in 22 ml of methanol-dichloromethane (1:10) mixture is ionized at −78° C. The resulting ozonide is decomposed with 0.5 ml of dimethylsulfide. After the solvent is evaporated, 300 mg (7.93 mM) of sodium borohydride is added with ice-cooling to the residue in methanol. The mixture is warmed up to room temperature and stirred for 2 hours. The product is isolated by ethyl acetate extraction and the organic layer is washed with an aqueous solution of sodium chloride, dried over anhydrous magnesium sulfate, and evaporated. The residue is purified by the column chromatography on silica gel with a n-hexane-ethyl acetate mixture as an eluent to give 300 mg (0.59 mM) of 2-methoxy-1-octadecylcarbamoyloxy-3-(2-hydroxyethylsulfonylamino)propane VIa4 as a colorless powder in 50% yield.

NMR: δppm (CDCl$_3$) 0.88 (t, 3H), 1.26 (s, 30H), 1.5 (m, 2H), 2.05 (br., 1H), 3.05~3.35 (m, 6H), 3.45 (s, 3H), 3.51 (m, 1H), 4.02~4.12 (m, 2H), 4.12~4.27 (m, 2H), 4.89 (m, 1H), 5.19 (m, 1H).

IR: νmax (CHCl$_3$) 3450, 2920, 2850, 1710, 1510, 1465, 1330, 1220, 1135 cm$^{-1}$.

MS: 509 (MH$^+$).

(12) Preparation of 2-methoxy-1-octadecylcarbamoyloxy-3-(2-methanesulfonyloxyethylsulfonylamino)propane VIa4'

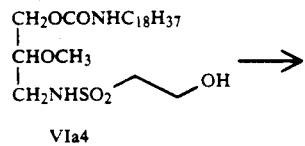

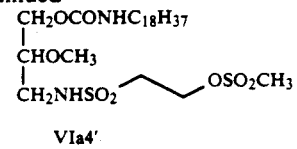

To a solution of 298 mg (0.586 mM) of 2-methoxy-1-octadecylcarbamoyloxy-3-(2-hydroxyethylsulfonylamino)propane VIa4 in 6 ml of dichloromethane and 2 ml of tetrahydrofuran are added 50 μl (0.645 mM) of methanesulfonyl chloride and 0.106 ml of triethylamine with ice-cooling and the mixture is stirred at room temperature for 2 hours. After the solvent is evaporated, the residue is purified by the column chromatography on silica gel with a n-hexane-ethyl acetate (1:1 to 1:2) mixture as an eluent to give 287 mg (0.489 mM) of 2-methoxy-1-octadecylcarbamoyloxy-3-(2-methanesulfonylamino)propane VIa4' as an colorless powder in 83% yield.

NMR: δppm (CDCl$_3$) 0.88 (t, 3H), 1.26 (s, 30H), 1.5 (m, 2H), 3.11 (s, 3H), 3.10~3.42 (m, 4H), 3.45 (s, 3H), 3.50 (t, 2H, J=6 Hz), 4.15~4.28 (m, 2H), 4.61 (t, 2H, J=6 Hz), 4.91 (m, 1H), 5.19 (t, 1H, J=6.2 Hz).

IR: νmax (CHCl$_3$) 3460, 2930, 2850, 1725, 1520, 1470, 1345, 1235, 1180, 1155, 1000, 970 cm$^{-1}$.

(13) Preparation of 3-(2-iodoethylsulfonylamino)-2-methoxy-1-octadecylcarbamoyloxypropane IIa4

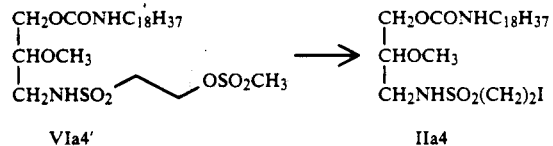

To a solution of 200 mg (0.341 mM) of 2-methoxy-1-octadecylcarbamoyloxy-3-(2-methanesulfonyloxyethylsulfonylamino)propane VIa4' in 5 ml of acetone is added 200 mg (1.33 mM) of sodium iodide and the mixture is refluxed with stirring for 5 hours. After the solvent is evaporated, the residue is purified by the column chromatography on silica gel with a n-hexane-ethyl acetate (2:1) mixture as an eluent to give 188 mg (0.296 mM) of 3-(2-iodoethylsulfonylamino)-2-methoxy-1-octadecylcarbamoyloxypropane IIa4 in 87% yield.

NMR: δppm (CDCl$_3$) 0.88 (t, 3H), 1.26 (s, 30H), 1.5 (m, 2H), 3.10~3.30 (m, 4H), 3.46 (s, 3H), 3.30~3.60 (m, 5H), 4.1~4.3 (m, 2H), 4.83 (m, 1H), 5.10 (t, 1H, J=6.3 Hz).

IR: νmax (CHCl$_3$) 3450, 2935, 2855, 1720, 1515, 1460, 1410, 1335, 1220, 1145, 1090, 1050 cm$^{-1}$.

EXAMPLE 12

Preparation of 2-methoxy-1-octadecylcarbamoyloxy-3-(2-thiazolioethylsulfonylamino)propane iodide Ia12

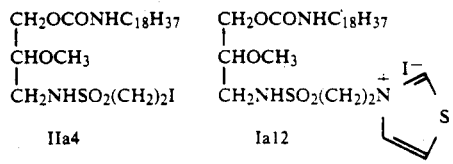

A solution of 188 mg (0.296 mM) of 3-(2-iodoethylsulfonylamino)-2-methoxy-1-octadecylcarbamoyloxypropane in 2 ml of thiazole is stirred at 60° C. for 12 hours. After thiazole is evaporated, the residue is purified by the column chromatography on silica gel with a chloroform-methanol (5:1) mixture as an eluent. The product is recrystallized from ether-dichloromethane-acetone to give 30 mg (0.043 mM) of 2-methoxy-1-octadecylcarbamoyloxy-3-(2-thazolioethylsulfonylamino)propane iodide Ia12 in 14% yield.

NMR: δppm (CDCl$_3$+CD$_3$OD) 0.88 (t, 3H), 1.25 (s, 30H), 1.5 (m, 2H), 3.05~3.20 (m, 2H), 3.20~3.40 (m, 2H), 3.46 (s, 3H), 3.60 (m, 1H), 3.94 (m, 2H), 4.0~4.3 (m, 2H), 5.2~5.4 (m, 2H), 5.55 (m, 1H), 6.82 (m, 1H), 8.17 (d, 1H, J=3.8 Hz), 8.70 (d, 1H, J=3.8 Hz), 10.60~10.65 (m, 1H).

IR: νmax (KBr) 3360, 2920, 2850, 1700, 1535, 1460, 1335, 1255, 1150 cm$^{-1}$.

(14) Preparation of 3-(4-chlorobutylsulfonylamino)-2-methoxy-1-octadecylcarbamoyloxypropane IIIa5

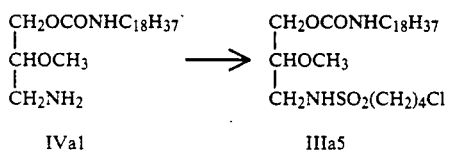

IVa1     IIIa5

To a solution of 1.2 g (3 mM) of 2-methoxy-3-octadecylcarbamoyloxypropylamine IVa1 in 24 ml of dichloromethane and 0.5 ml (3.6 mM) of triethylamine is added 0.75 g (3.93 mM) of 4-chlorobutanesulfonyl chloride with ice-cooling and the mixture is stirred at room temperature overnight. The product is isolated with dichloromethane extraction and dichloromethane layer is washed with saturated aqueous sodium hydrogencarbonate and saturated aqueous sodium chloride, dried over anhydrous magnesium sulfate, and evaporated. The residue is purified by the column chromatography on silica gel with a n-hexane-ethyl acetate (3:2) mixture as an eluent. The product is recrystallized from dichloromethane-n-hexane to give 1.28 g (2.305 mM) of 3-(4-chlorobutylsulfonylamino)-2-methoxy-1-octadecylcarbamoyloxypropane IIIa5 as colorless crystals in 77% yield.

NMR: δppm (CDCl$_3$) 0.88 (t, 3H), 1.25 (s, 30H), 1.48 (m, 2H), 1.8~2.1 (m, 4H), 3.0~3.4 (m, 6H), 3.45 (s, 3H), 3.4~3.55 (m, 1H), 3.58 (t, 2H, J=6.0 Hz), 4.05~4.3 (m, 2H), 4.8 (br, 1H), 4.94 (t, 1H, J=6 Hz).

IR: νmax (CHCl$_3$) 3450, 2930, 2850, 1720, 1510, 1330, 1225, 1140, 1040 cm$^{-1}$.

Anal. Calcd. (%) for C$_{27}$H$_{55}$O$_5$N$_2$SCl: C 58.41, H 9.98, N 5.05, S 5.77, Cl 6.38, Found (%) C 58.15, H 9.91, N 5.16, S 5.89, Cl 6.71.

MS: 554 (M$^+$, Cl$^{35}$).

mp.: 57.5°~58.5° C.

(15) Preparation of 3-(4-iodobutylsulfonylamino)-2-methoxy-1-octadecylcarbamoyloxypropane IIa5

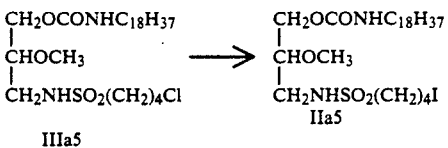

IIIa5     IIa5

To a solution of 1.23 g (2.22 mM) of 3-(4-chlorobutylsulfonylamino)-2-methoxy-1-octadecylcarbamoyloxypropane IIIa5 in 20 ml of methyl ethyl ketone is added 0.67 g (4.44 mM) of sodium iodide and the mixture is heated for 3 hours with stirring. After the solvent is evaporated, the residue is purified by the column chromatography on silica gel with a n-hexane-ethyl acetate (1:1) mixture as an eluent. The product is recrystallized from chloroform-n-hexane to give 1.16 g (1.79 mM) of 3-(4-iodobutylsulfonylamino)-2-methoxy-1-octadecylcarbamoyloxypropane IIa5 in 81% yield.

NMR: δppm (CDCl$_3$) 0.88 (t, 3H), 1.26 (s, 30H), 1.5 (m, 2H), 1.9~2.0 (m, 4H), 3.0~3.4 (m, 10H), 3.46 (s, 3H), 3.50 (m, 1H), 4.1~4.3 (m, 2H), 4.7 (br, 1H), 4.87 (t, 1H, J=6.6 Hz).

IR: νmax (CHCl$_3$) 3450, 2925, 2850, 1720, 1510, 1330, 1230, 1140 cm$^{-1}$.

mp.: 71°~72° C.

Anal. Calcd. (%) for C$_{27}$H$_{55}$O$_5$N$_2$SI: C 50.15, H 8.57, N 4.33, S 4.96, I 19.62, Found (%) C 50.09, H 8.45, N 4.41, S 5.26, I 19.33.

MS: 647 (M$^+$).

EXAMPLE 13

Preparation of 2-methoxy-1-octadecylcarbamoyloxy-3-(4-thiazoliobutylsulfonylamino)propane iodide Ia13

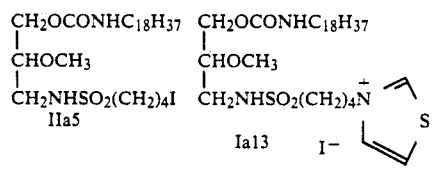

IIa5     Ia13   I$^-$

A solution of 300 mg (0.464 mM) of 3-(4-iodobutylsulfonylamino)-2-methoxy-1-octadecylcarbamoyloxypropane in 3 ml of thiazole is stirred at 60° C. for 6 hours. After thiazole is evaporated, the residue is washed with ether and recrystallized from ether-dichloromethane to give 140 mg (0.191 mM) of 2-methoxy-1-octadecylcarbamoyloxy-3-(4-thiazoliobutylsulfonylamino)propane iodide Ia13 in 41% yield.

NMR: δppm (CDCl$_3$) 0.88 (t, 3H), 1.25 (s, 30H), 1.5 (m, 2H), 1.8~2.05 (m, 2H), 2.05~2.40 (m, 2H), 3.00~3.40 (m, 6H), 3.44 (s, 3H), 3.60 (m, 1H), 4.0~4.3 (m, 2H), 4.85 (m, 2H), 5.38 (br, 1H), 6.16 (br, 1H), 8.3~8.4 (m, 1H), 8.6~8.7 (m, 1H), 10.55 (s, 1H).

IR: νmax (CHCl$_3$) 3400, 2930, 2850, 1715, 1465, 1430, 1320, 1235, 1140 cm$^{-1}$.

Anal. Calcd. (%) for C$_{30}$H$_{58}$O$_5$N$_3$S$_2$I.0.5H$_2$O: C 48.64, H 8.03, N 5.67, S 8.66, I 17.13, Found (%) C 48.46, H 7.99, N 5.77, S 8.87, I 17.02.

mp.: 59.5°~61.5° C.

EXAMPLES 14 TO 17

The compounds of the present invention shown in the following Table 2 are prepared from the compound IIa5 by the same procedure as described in Example 2.

TABLE 2

$$\begin{array}{c}CH_2OCONHC_{18}H_{37}\\|\\CH_3OCH\\|\\CH_2NHSO_2(CH_2)_4I\end{array} \longrightarrow \begin{array}{c}CH_2OCONHC_{18}H_{37}\\|\\CH_3OCH\\|\\CH_2NHSO_2(CH_2)_4\overset{+}{N}\begin{array}{c}R_5\\|\\|\\R_6\end{array}R_4\ I^-\end{array}$$

IIa5 → Ia

| Ex. No. | Cpd. No. | S.M. II 5 [mg] | $-N\begin{array}{c}R_3\\|\\R_4\end{array}R_5$ | Amine | Reaction Tempt. | Reaction Time | Purification | Yd. [mg] [%] | NMR: δppm | IRνmax [cm⁻¹] mp. [°C.] | Analysis Calcd. (%) Found (%) |
|---|---|---|---|---|---|---|---|---|---|---|---|
| 14 | Ia 14 | 650 | quinolinium | Quinoline (3 ml) | 45° C. | 2 Days | The product dissolved in chloroform-methanol is washed with 5.7% HI and water. The solvent is evaporated and the residue is recrystallized from acetone. | 490 63% | (CDCl₃) 0.88(t, 3H), 1.25(s, 30H), 1.48(m, 2H), 2.0~2.5(m, 4H), 3.0~3.2(m, 2H), 3.2~3.4 (m, 4H), 3.42(s, 3H), 3.54(m, 1H, =5.5Hz), 5.28(t, 1H, =5.5Hz), 5.46 (t, 2H, J=7.6 Hz), 5.85(t, 1H, J=6Hz), 7.97 (t, 1H, J=8.0Hz), 8.05~8.40(m, 3H), 8.68(d, 1H, J=9.6Hz), 9.01(d, 1H, J=8.2Hz), 10.25(d, 1H, J=5.4Hz). | (CHCl₃) 3450, 2925, 2850, 1715, 1520, 1460, 1325, 1220, 1140. 56.0~59.0 | (C₃₆H₆₂O₅N₃SI.0.5H₂O) C 55.09, H 8.09, N 5.35 S 4.08, I 16.17 C 54.88, H 7.95, N 5.41 S 4.33, I 16.25. |
| 15 | Ia 15 | 688 | benzothiazolium | Benzothiazole (2 ml) | 60° C. | Overnight | The product obtained by trituration with ether is recrystallized from acetone-ether. | 555 67% | (CDCl₃) 0.88(t, 3H), 1.25(s, 30H), 1.48(m, 2H), 2.0~2.25 (m, 2H), 2.25~2.50(m, 2H), 3.0 ~3.2(m, 2H), 3.2~3.4(m, 4H), 3.40(s, 3H), 3.57(m, 1H), 4.0~ 4.3(m, 2H), 5.10~5.35(m, 3H), 5.98(t, 1H, J=6Hz), 7.8~8.0(m, 2H), 8.3~8.45(m, 2H), 11.35(s, 1H). | (CHCl₃) 3450, 2930, 2850, 1715, 1510, 1460, 1430, 1330, 1220, 1140. 59.0~61.0 | (C₃₄H₆₀O₅N₃S₂I.0.5H₂O) C 51.63, H 7.77, N 5.31 S 8.10, I 16.05, C 51.43, H 7.83, N 5.38 S 8.39, I 16.02. |
| 16 | Ia 16 | 600 | isoquinolinium | Isoquinoline (2 ml) | 60° C. | Overnight | (1) Column chromatography on silica gel (Eluent: chloroform-methanol = 5:1) (2) Recrystallization (Acetone-ether) | 542 75% | (CDCl₃) 0.88(t, 3H), 1.25 (s, 30H), 1.48(m, 2H), 1.95~ 2.15(m, 2H), 2.30~2.50(m, 2H), 3.0~3.2(m, 2H), 3.2~3.4(m, 4H), 3.41(s, 3H), 3.57(m, 1H), 4.0~4.3(m, 2H), 5.13(t, 2H, J= 7.6Hz), 5.32(t, 1H, J=5Hz), 5.90(t, 1H, J=6Hz), 7.9~8.1(m, 1H), 8.1~8.2(m, 2H), 8.37(d, 1H, J=6.8Hz), 8.65(d, 1H, J=8.4 Hz), 8.86~8.98(m, 1H), 10.69 (s, 1H). | (CHCl₃) 3450, 2930, 2850, 1715, 1460, 1320, 1220, 1140. 59.0~60.0 (Decompose) | (C₃₆H₆₂O₆N₃SI.0.1H₂O) C 55.60, H 8.06, N 5.40 S 4.12, I 16.32, C 55.35, H 8.04, N 5.58 S 4.47, I 16.16. |

TABLE 2-continued $$\text{CH}_3\text{OCH} \begin{array}{c} \text{CH}_2\text{OCONHC}_{18}\text{H}_{37} \\ | \\ \text{CH}_2\text{NHSO}_2(\text{CH}_2)_4\text{I} \end{array} \longrightarrow \text{CH}_3\text{OCH} \begin{array}{c} \text{CH}_2\text{OCONHC}_{18}\text{H}_{37} \\ | \\ \text{CH}_2\text{NHSO}_2(\text{CH}_2)_4\overset{+}{\text{N}}\diagdown\begin{array}{c}\text{R}_5\\\text{R}_4\\\text{R}_6\end{array}\quad \text{I}^- \end{array}$$

IIa5 → Ia

| Ex. No. | Cpd. No. | S.M. IIa5 [mg] | Amine | $-\text{N}\diagdown\begin{array}{c}\text{R}_3\\\text{R}_4\\\text{R}_5\end{array}$ | Reaction Tempt. | Reaction Time | Purification | Yd. [mg] [%] | NMR: δppm | IRυmax [cm$^{-1}$] mp. [°C.] | Analysis Calcd. (%) Found (%) |
|---|---|---|---|---|---|---|---|---|---|---|---|
| 17 | Ia 17 | 650 | N-methylimidazole (1.5 ml) | $-\text{N}\diagup\diagdown\overset{\text{N}}{\underset{\text{H}_3\text{C}}{}}$ | 25° C. | Overnight | After precipitated from acetone as a powder, the product is washed with ether. | 501 69% | (CDCl$_3$) 0.88(t, 3H), 1.25 (s, 30H), 1.49(m, 2H), 1.75~2.00(m, 2H), 2.0~2.2(m, 2H), 3.0~3.5(m, 6H), 3.44(s, 3H), 3.59(m, 1H), 4.06(s, 3H), 4.0~4.3(m, 2H), 4.47(t, 2H, J=6.7Hz), 5.21(t, 1H, J=6Hz), 5.93(t, 1H, J=6Hz), 7.38(s, 1H), 7.62(s, 1H), 9.71(s, 1H). | (CHCl$_3$) 3450, 2920, 2850, 1715, 1460, 1325, 1220, 1140. | (C$_{31}$H$_{62}$O$_5$N$_4$SI) C 51.09, H 8.44, N 7.69 S 4.40, I 17.41, C 50.79, H 8.36, N 7.67 S 4.71, I 17.41. |

EXAMPLE 18

Preparation of 2-methoxy-1-octadecylcarbamoyloxy-3-(4-quinoliobutylsulfonylamino)propane chloride Ia18

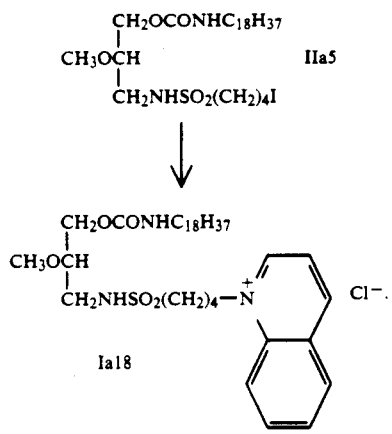

A solution of 1.57 g (2.43 mM) of 3-(4-iodobutylsulfonylamino)-2-methoxy-1-octadecylcarbamoyloxypropane in 3 ml of quinoline is stirred at 40° C. for 3 days. The product is isolated by extraction with a chloroform-methanol mixture and the organic layer is washed with 1N-hydrochloric acid twice. After the solvent is evaporated, the residue is recrystallized from acetone to give 1.07 g (1.56 mM) of 2-methoxy-1-octadecylcarbamoyloxy-3-(4-quinoliobutylsulfonylamino)propane chloride Ia18 in 64% yield.

NMR: δppm (CDCl$_3$) 0.88 (t, 3H), 1.25 (s, 30H), 1.48 (m, 2H), 2.0~2.3 (m, 2H), 2.3~2.5 (m, 2H), 3.0~3.2 (m, 2H), 3.2~3.4 (m, 4H), 3.39 (s, 3H), 3.58 (m, 1H), 4.0~4.3 (m, 2H), 5.40~5.65 (m, 3H), 6.85 (t, 1H, J=7 Hz), 7.93 (t, 1H, J=7.2 Hz), 8.0~8.4 (m, 3H), 8.65 (d, 1H, J=9 Hz), 9.01 (d, 1H, J=8.2 Hz), 10.35 (d, 1H, J=5.2 Hz).

IR: νmax (CHCl$_3$) 3450, 2925, 2850, 1715, 1520, 1465, 1320, 1220, 1140.

mp.: 57.0°~59.0° C.

Anal. Calcd. (%) for C$_{36}$H$_{62}$O$_5$N$_3$SCl.1.5H$_2$O: C 60.78, H 9.21, N 5.91, S 4.51, Cl 4.98, Found (%): C 60.94, H 9.02, N 5.91, S 4.78, Cl 4.58.

mp.: 57° C. to 59° C.

EXAMPLE 19

Preparation of 3-(4-benzothiazoliobutylsulfonylamino)-2-methoxy-1-octadecylcarbamoyloxypropane chloride Ia19

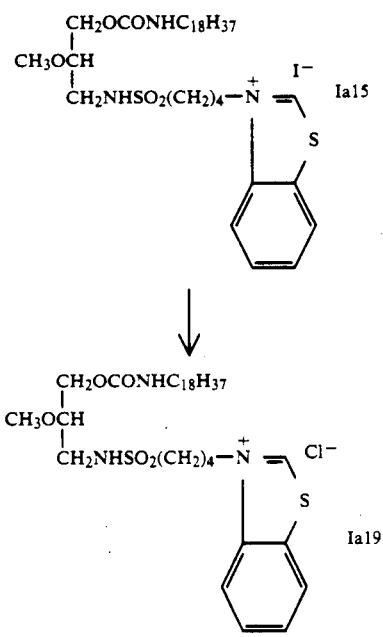

A solution of 300 mg (0.384 mM) of 3-(4-benzothiazoliobutylsulfonylamino)-2-methoxy-1-octadecylcarbamoyloxypropane iodide Ia15 in a chloroform-methanol mixture is washed with aqueous 1N-hydrochloric acid twice and with water once and the solvent is evaporated. The residue is recrystallized from dichloromethane-acetone acetone to give 65 mg (0.0941 mM) of 3-(4-benzothiazoliobutylsulfonylamino)-2-methoxy-1-octadecylcarbamoyloxypropane chloride Ia19 in 25% yield.

NMR: 67 ppm (CDCl$_3$): 0.88 (t, 3H), 1.25 (s, 30H), 1.48 (m, 2H), 2.0~2.2 (m, 2H), 2.2~2.4 (m, 2H), 3.0~3.2 (m, 2H), 3.2~3.4 (m, 4H), 3.38 (s, 3H), 3.55 (m, 1H), 4.0~4.3 (m, 2H), 5.25 (m, 2H), 5.52 (br, 1H), 6.80 (br, 1H), 7.70~7.95 (m, 2H), 8.2~8.4 (m, 2H), 11.80 (s, 1H).

IR: νmax (CHCl$_3$): 3450, 2940, 2855, 1715, 1515, 1465, 1435, 1330, 1220, 1140 cm$^{-1}$.

mp.: 57.0°~59.0° C.

Anal. Calcd. (%) for C$_{36}$H$_{62}$O$_5$N$_3$SCl.1.5H$_2$O: C 56.92, H 8.85, N 5.86, S 8.94, Cl 4.94, Found (%) C 56.72, H 8.71, N 6.05, S 8.97, Cl 4.68.

EXAMPLES 20 TO 21

The compounds shown in Table 3 are prepared in the same manner as in Example 19.

TABLE 3

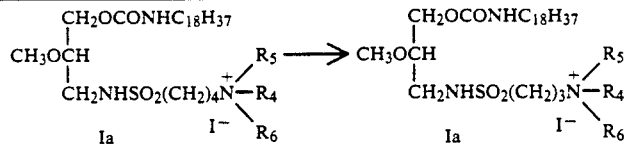

| Ex. No. | Cpd. No. | −N(R3)(R4)(R5) | Yd. | NMR: δppm | IRνmax [cm$^{-1}$] mp. [°C.] | Analysis Calcd. (%) Found (%) |
|---|---|---|---|---|---|---|
| 20 | Ia 20 | 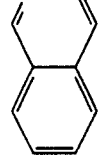 | 59% | (CDCl$_3$) 0.88(t, 3H), 1.25 (s, 30H), 1.46(m, 2H), 1.95~2.15(m, 2H), 2.25~2.45(m, 2H), 3.0~3.2(m, 2H), 3.2~3.4(m, 4H), 3.37(s, 3H), 3.55(m, 1H), 4.0~4.3(m, 2H), 5.16(t, 2H, J=7.5Hz), 5.63(br, 1H), 6.9(br, 1H), 7.85~8.0(m, 1H), 8.0~8.16(m, 2H), 8.30(d, 1H, J=6.8 Hz), 8.64(d, 1H, J=7.8Hz), 8.94(d, 1H, J=6.8Hz), 10.76 (s, 1H). | (CHCl$_3$) 3450, 2920, 2845, 1710, 1510, 1460, 1320, 1220, 1135. 56.0~57.0 | (C$_{36}$H$_{62}$O$_5$N$_3$SCl.1.5H$_2$O) C 60.78, H 9.21, N 5.91, S 4.51, Cl 4.98, C 60.80, H 9.11, N 5.99, S 4.51, Cl 4.98. |
| 21 | Ia 21 |  | 43% | (CDCl$_3$) 0.88(t, 3H), 1.25 (s, 30H), 1.48(m, 2H), 1.8~2.0(m, 2H), 2.0~2.2(m, 2H), 3.0~3.3(m, 6H), 3.42(s, 3H), 3.59(m, 1H), 4.04(s, 3H), 4.0~4.28(m, 2H), 4.45(t, 2H, J=6.6 Hz), 5.50(t, 1H, J=6Hz), 6.96 (t, 1H, J=7Hz), 7.41(s, 1H), 7.61(s, 1H), 10.01(s, 1H). | (CHCl$_3$) 3450, 2920, 2850, 1710, 1460, 1320, 1220, 1135. 58.5~59.5 | (C$_{31}$H$_{62}$O$_5$N$_4$SCl.2.3H$_2$O) C 54.85, H 9.74, N 8.25, S 4.72, Cl 5.22, C 54.67, H 9.50, N 8.28, S 5.01, Cl 5.47. |

EXAMPLES 22 TO 23

The compounds shown in Table 4 are prepared by the same procedure as described in Example 9.

(16) Preparation of 3-benzyloxy-1-hydroxy-2-methoxypropane IX6

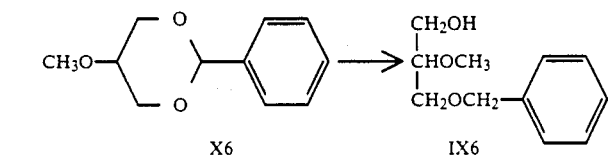

TABLE 4

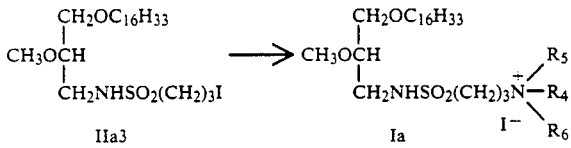

| Ex. No. | Cpd. No. | −N(R3)(R4)(R5) | Amine | NMR: δppm | IRνmax [cm$^{-1}$] |
|---|---|---|---|---|---|
| 22 | Ia 22 | 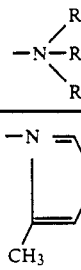 | | (CDCl$_3$) 0.88(t, 3H), 1.26 (s, 26H), 1.55(m, 2H), 2.45~2.65(m, 2H), 2.70(s, 3H), 3.15~3.60(m, 9H), 3.45 (s, 3H), 4.92(t, 2H, J=8.0Hz), 5.88(t, 1H, J=6Hz), 7.78~7.82 (m, 1H), 10.90(d, 1H, J=2.8Hz). | (CHCl$_3$) 3370 2925, 2850, 1465, 1440, 1325, 1210, 1140. |
| 23 | Ia 23 | 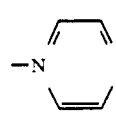 | | (CDCl$_3$) 0.88(t, 3H), 1.26 (s, 26H), 1.56(m, 2H), 2.55~2.80(m, 2H), 3.0~3.6(m, 9H), 3.44(s, 3H), 5.18(t, 2H, J=7.6 Hz), 6.26(t, 1H, J=6Hz), 9.54 (s, 4H). | (CHCl$_3$) 2925, 2850, 1440, 1320, 1210, 1135, 720. |

To a suspension of 18.98 g (0.5 mol) of lithium aluminum-hydride in 400 ml of ether is added dropwise a solution of 66.69 g (0.5 mol) of aluminium chloride in 250 ml of ether at −40° C. and the mixture is stirred at −20° C. for 30 minutes. To the reaction mixture is added a solution of β-methyl-αγ-benzilideneglycol X6 [described in P. E. Verkade, et al., Recl. Trav. Chim. Pays, Bas., 61, 831, (1942)] in 200 ml of dichloromethane at such a rate that the reaction temperature is kept below −20° C. After warming up to room temperature gradually, the mixture is stirred for 2 hours. A saturated aqueous solution of sodium sulfate is added to the reaction mixture with ice-cooling and the resulting white percipitate is removed by the filtration. The filtrate is concentrated under reduced pressure and the residue is distilled under reduced pressure to give 47.1 g of the titled compound IX6 in 96% yield as a distilate at 133° C. (2 to 3 mmHg).

NMR: δppm (CDCl$_3$) 2.44 (s, 1H), 3.38~3.52 (m, 1H), 3.45 (s, 3H), 3.53~3.83 (m, 4H), 4.53 (s, 2H), 7.32 (s, 5H).

(17) Preparation of 1-acetylthio-3-benzlyoxy-2-methoxypropane VII6

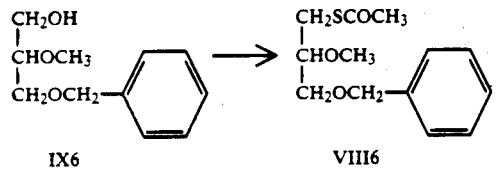

IX6         VIII6

To a solution of 14.7 g (75 mM) of dl-3-benzyloxy-2-methoxypropylalcohol IX6 and 12.53 ml (90 mM) of triethylamine in 150 ml of dichloromethane is added 6.08 ml (78.75 mM) of methanesulfonyl chloride with ice-cooling and the mixture is stirred at room temperature for an hour. The product is isolated by dichloromethane extraction and the dichloromethane layer is washed with water, dried, and evaporated to give the crude mesylate IX6'. To a solution of the above crude mesylate IX6' in 200 ml of acetonitrile is added 8.994 g (78.75 mM) of potassium thioacetate and the mixture is heated under reflux for 15 hours. After cooling, the reaction mixture is poured into water and the product is isolated by ethyl acetate extraction. The ethyl acetate layer is washed with water, dried, and evaporated. The oily residue is distilled under reduced pressure to give 16.92 g (67 mM) of the title compound, 1-acetylthio-3-benzyloxy-2-methoxypropane VIII6 as a distillates of bp. 130° C. to 137° C. (2 mmHg) in 89% yield.

NMR: δppm (CDCl$_3$): 2.34 (s, 3H), 3.13 (d, 2H, J=5.6 Hz), 3.43~3.58 (m, 3H), 4.55 (s, 2H), 7.33 (s, 5H).

IR: νmax (CHCl$_3$): 3000, 2930, 2850, 2820, 1685, 1450, 1355, 1100 cm$^{-1}$.

(18) Preparation of 3-benzyloxy-2-methoxypropylthioalcohol VII6

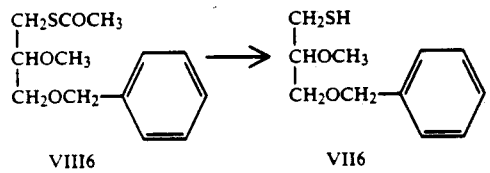

VIII6         VII6

To a solution of 14.028 g (55 mM) of acetylthio-3-benzyloxy-2-methoxypropane VIII6 in 300 ml of methanol is added dropwise 11.24 ml (58.3 mM) of 28 weight % solution of sodium methoxide in methanol at −10° C. After the mixture is stirred at −10° C. to 0° C. for 2 hours, 3.58 ml of methanesulfonic acid is added. The reaction mixture is poured into water and the product is isolated by ethyl acetate extraction. The ethyl acetate layer is washed with water, dried, and evaporated. The oily residue is purified by column chromatography on silica gel using an ether-n-hexane (3:97) mixture as an eluent to give 8.85 g (41.7 mM) of the titled compound, 3-benzyloxy-2-methoxypropylthioalcohol VII6 as an oil.

NMR: δppm (CDCl$_3$): 1.49 (t, 1H, J=8.5 Hz), 2.58~2.87 (m, 2H), 3.40~3.53 (m, 1H), 3.44 (s, 3H), 3.56~3.63 (m, 2H), 4.55 (s, 2H), 7.34 (s, 5H).

IR: νmax (CHCl$_3$): 3000, 2940, 2860, 2820, 1455, 1365, 1100 cm$^{-1}$.

(19) Preparation of 3-benzyloxy-2-methoxy-1-octadecylcarbamoylthiopropane VI6

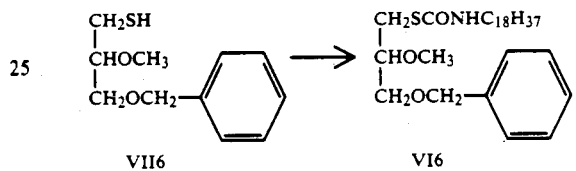

VII6         VI6

A solution of 7.258 g (34.2 mM) of 3-benzyloxy-2-methoxypropylthioalcohol VII6 and 11.65 g (39.4 mM) of octadecylisocyanate in 100 ml of pyridine is heated under reflux for 1 hour. The reaction mixture is concentrated and the residue is purified by column chromatography on silica gel using a toluene-ethyl acetate (9:1 to 4:1) mixture as an eluent to give 17.027 g (33.6 mM) of the titled compound, 3-benzyloxy-2-methoxy-1-octadecylcarbamoylthiopropane VI6 as a solid in 98% yield.

NMR: δppm (CDCl$_3$): 0.88 (t, 3H), 1.25 (s, 30H), 1.40~1.60 (m, 2H), 3.10~3.19 (m, 2H), 3.19~3.34 (m, 2H), 3.46 (s, 3H), 3.50~3.62 (m, 3H), 4.56 (s, 2H), 5.37~5.50 (broad, 1H), 7.33 (s, 5H).

mp.: 40°~41° C.

Anal. Calcd. (%) for C$_{30}$H$_{53}$O$_3$NS: C 70.96, H 10.52, N 2.76, S 6.31, Found (%): C 70.90, H 10.50, N 2.91, S 5.99.

(20) Preparation of 3-octadecylcarbamoylthio-2-methoxypropylalcohol Va6

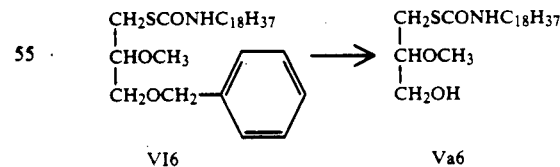

VI6         Va6

To a solution of 1.02 g (2 mM) of 3-benzyloxy-2-methoxy-1-octadcylcarbamoylthiopropane VIa6 in 80 ml of acetonitrile is added 0.4 ml (2.81 mM) of trimethylsilyl iodide with ice-cooling and the mixture is allowed to stand at room temperature for 15 hours. To the reaction mixture is added 50 ml of 10% aqueous solution of sodium thiosulfate and the product is isolated with dichloromethane extraction. The dichloromethane layer is washed with water, dried, and evaporated. The residue is purified by column chromatography on silica gel using a n-hexane-ethyl acetate (2:1) mixture as an eluent to give 480 mg (1.15 mM) of the titled compound, 3-octadecylcarbamoylthio-2-methoxypropylalcohol Va6 as a solid in 57% yield.

NMR: δppm (CDCl$_3$): 0.88 (t, 3H), 1.26 (s, 30H), 1.42~1.60 (m, 2H), 2.75~2.97 (broad, 1H), 2.98~3.38 (m, 1H), 3.44 (s, 3H), 3.38~3.52 (m, 1H), 3.52~3.75 (m, 2H), 5.42~5.63 (broad, 1H).

mp.: 62°~63° C.

IR: νmax (CHCl$_3$) 3430, 2920, 2850, 1655, 1500, 1465, 1190, 1100, 1045 cm$^{-1}$.

Anal. Calcd. (%) for $C_{23}H_{47}NSO_3$: C 66.14, H 11.34, N 3.35, S 7.68, Found (%): C 65.78, H 11.34, N 3.31, S 7.50.

(21) Preparation of 2-methoxy-3-octadecylcarbamoylthiopropylamine IVa6

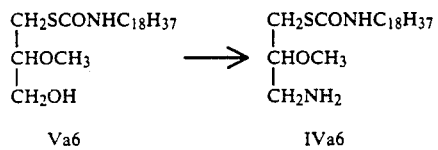

Va6    IVa6

To a solution of 417.7 mg (1 mM) of 2-methoxy-3-octadecylcarbamoylthiopropylalcohol Va6, 229.2 mg (1.5 mM) of phthalimide, and 408.6 mg (1.5 mM) of triphenylphophine in 15 ml of tetrahydrofuran, which is cooled to −30° C., is added dropwise 271.2 mg (1.5 mM) of diethyl azodicarboxylate and the mixture is stirred for 30 minutes, and at room temperature for additional 2 hours. After the solvent is evaporated, the residue is purified by the column chromatography on silica gel with a benzene-ethyl acetate (9:1) mixture as an eluent to give 400 mg (0.732 mM) of the phthalimide-compound in 73% yield.

To a solution of 1.091 g (1.864 mM) of the phthalimide-compound in 30 ml of ethanol and 10 ml of tetrahydrofuran is added 2.5 ml of hydrazine monohydrate and the mixture is stirred at room temperature for 3 hours. After the solvent is evaporated, the residue is purified by the column chromatography on silica gel with a chloroform-methanol (5:1) mixture as an (0.2% triethylamine) eluent to give 418.3 mg (1.003 mM) of 2-methoxy-3-octadecylcarbamoylthiopropylamine IVa6 in 54% yield.

NMR: δppm (CDCl$_3$+CD$_3$OD): 0.88 (t, 3H), 1.26 (s, 30H), 1.40~1.62 (m, 2H), 2.65~2.94 (m, 2H), 2.95~3.17 (m, 1H), 3.17~3.30 (m, 2H), 3.30~3.42 (m, 1H), 3.45 (s, 3H).

IR: νmax (CHCl$_3$): 3425, 2930, 2850, 1665, 1500, 1190, 1100 cm$^{-1}$.

(22) Preparation of 3-(3-chloropropylsulfonylamino)-2-methoxy-1-octadecylcarbamoylthiopropane IIIa6

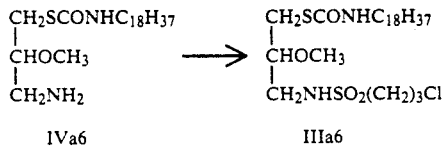

IVa6    IIIa6

To a solution of 93 mg (0.223 mM) of 2-methoxy-3-octadecylcarbamoylthiopropylamine IVa6 and 40.4 μl (3.9 mM) of triethylamine in 5 ml of dichloromethane and 2 ml of tetrahydrofuran is added 29.8 μl (3.3 mM) of 3-chloropropanesulfonyl chloride with ice-cooling, and the mixture is stirred for 2 hours and at room temperature for an additional 30 minutes. The product is isolated by dichloromethane extraction and the dichloromethane layer is washed with an aqueous sodium hydrogencarbonate and a saturated aqueous solution of sodium chloride, dried over anhydrous magnesium sulfate, and evaporated. The residue is purified by the column chromatography on silica gel with a benzene-ethyl acetate (4:1) mixture as an eluent to give 83 mg (0.149 mM) of 3-(3-chloropropylsulfonylamino)-2-methoxy-1-octadecylcarbamoylthiopropane IIIa6 as a colorless powder in 67% yield.

NMR: δppm (CDCl$_3$) 0.88 (t, 3H), 1.26 (s, 30H), 1.40~1.60 (m, 2H), 2.20~2.37 (m, 2H), 2.93~3.40 (m, 8H), 3.40~3.55 (m, 1H), 3.43 (s, 3H), 3.69 (t, J=5.3 Hz, 2H), 5.17~5.35 (broad, 1H), 5.37~5.54 (broad, 1H).

IR: νmax (CHCl$_3$) 3420, 2930, 2850, 1670, 1495, 1460, 1335, 1185, 1150, 1090 cm$^{-1}$.

(23) Preparation of 3-(3-iodopropylsulfonylamino)-2-methoxy-1-octadecylcarbamoylthiopropane IIa6

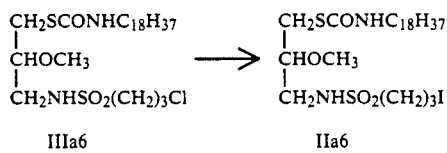

IIIa6    IIa6

To a solution of 197 mg (0.354 mM) of 3-(3-chloropropylsulfonylamino)-2-methoxy-1-octadecylcarbamoylthiopropane IIIa6 in 7 ml of methyl ethyl ketone is added 265 mg (1.77 mM) of sodium iodide and the mixture is heated under refluxing for 3 hours with stirring. After the solvent is evaporated, the residue is purified by the column chromatography on silica gel with a n-hexane-ethyl acetate (3:1) mixture as an eluent to give 197 mg (0.304 mM) of 3-(3-iodopropylsulfonylamino)-2-methoxy-1-octadecylcarbamoylthiopropane IIa6 in 86% yield.

NMR: δppm (CDCl$_3$) 0.88 (t, 3H), 1.26 (s, 30H), 1.42~1.62 (m, 2H), 2.25~2.42 (m, 2H), 2.95~3.50 (m, 8H), 3.44 (s, 3H), 3.50~3.58 (m, 1H), 5.18~5.34 (broad, 1H), 5.38~5.57 (broad, 1H).

IR: νmax (CHCl$_3$) 3425, 2925, 2850, 1670, 1500, 1460, 1325, 1185, 1140, 1100 cm$^{-1}$.

EXAMPLE 24

Preparation of 2-methoxy-1-octadecylcarbamoylthio-3-(3-N-methylimidazoliniopropylsulfonylamino)propane iodide Ia24

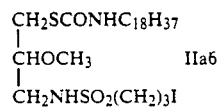

-continued

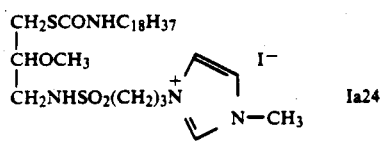 Ia24

A solution of 100 mg of 3-(3-iodopropylsulfonylamino)-2-methoxy-1-octadecylcarbamoylthiopropane IIa6 in 0.3 ml of N-methylimidazole is stirred at 25° C. overnight. After the solvent is evaporated, the residue is washed with water to give 102 mg of 2-methoxy-1-octadecylcarbamoylthio-3-(3-N-methylimidazoliniopropylsulfonylamino)propane iodide Ia24 in 91% yield.

NMR: δppm (CDCl$_3$) 0.88 (t, 3H), 1.26 (s, 30H), 1.45~1.65 (m, 2H), 2.40~2.63 (m, 2H), 2.93~3.40 (m, 8H), 3.43 (s, 3H), 3.45~3.60 (m, 1H), 4.06 (s, 3H), 4.63 (m, 2H), 5.96~6.24 (broad, 2H), 7.38 (s, 1H), 7.71 (s, 1H), 9.66 (s, 1H).

IR: νmax (CHCl$_3$) 3430, 3150, 2920, 2850, 1670, 1495, 1460, 1320, 1140, 1095 cm$^{-1}$.

EXAMPLE 25

Preparation of 2-methoxy-1-octadecylcarbamoylthio-3-(3-quinoliniopropylsulfonylamino)propane iodide Ia25

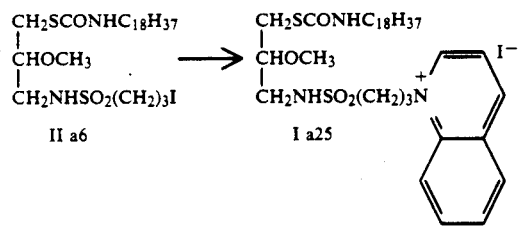

A solution of 88 mg (0.136 mM) of 3-(3-iodopropylsulfonylamino)-2-methoxy-1-octadecylcarbamoylthiopropane IIa6 in 1 ml of quinoline is stirred at 45° C. for 2 days and the product is isolated by extraction with a mixture of chloroform-methanol and the organic layer is washed with 5.7% hydroiodic acid twice and with water once and the solvent is evaporated. The residue is recrystallized from acetone to give 2-methoxy-1-octadecylcarbamoylthio-3-(3-quinoliniopropylsulfonylamino)propane iodide Ia25.

NMR: δppm: (CDCl$_3$) 0.88 (t, 3H), 1.25 (s, 30H), 1.40~1.62 (m, 2H), 2.62~2.85 (m, 2H), 2.90~3.65 (m, 9H), 3.39 (s, 3H), 5.56 (t, 2H, J=8.1 Hz), 5.80~6.25 (broad, 2H), 7.99 (t, 1H, J=7.4 Hz), 8.13~8.37 (m, 3H), 8.67 (d, 1H, J=8.8 Hz), 9.07 (d, 1H, J=8.2 Hz), 10.14 (d, 1H, J=5.2 Hz).

IR: νmax (CHCl$_3$) 3430, 2930, 2855, 1670, 1500, 1465, 1330, 1150 cm$^{-1}$.

EXAMPLE 26

Preparation of 2-methoxy-1-octadecylcarbamoylthio-3-(3-thiazoliniopropylsulfonylamino)propane iodide Ia26

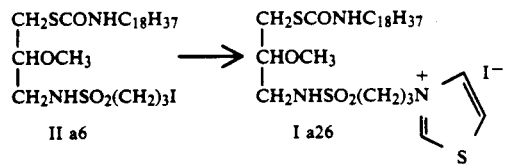

A solution of 76 mg of 3-(3-iodopropylsulfonylamino)-2-methoxy-1-octadecylcarbamoylthiopropane IIa6 in 1 ml of thiazole is heated at 60° C. for 6 hours. After the solvent is evaporated, the residue is washed with ether and subsequently with acetonitrile to give 32 mg of 2-methoxy-1-octadecylcarbamoylthio-3-(3-thiazoliniopropylsulfonylamino)propane iodide Ia26 in 37% yield.

NMR: δppm (CDCl$_3$) 0.88 (t, 3H), 1.25 (s, 30H), 1.40~1.62 (2H), 2.50~2.75 (m, 2H), 2.95~3.60 (m, 9H), 3.42 (s, 3H), 4.95~5.20 (m, 2H), 6.07~6.29 (m, 2H), 8.20~8.30 (m, 1H), 9.70~9.80 (m, 1H), 10.20~10.32 (m, 1H).

IR: νmax (CHCl$_3$) 3420, 2925, 2850, 1670, 1500, 1465, 1330, 1150 cm$^{-1}$.

EXAMPLE 27

Preparation of 2-methoxy-1-octadecylcarbamoylthio-3-(4-quinoliniopropylsulfonyamino)propane chloride Ia27

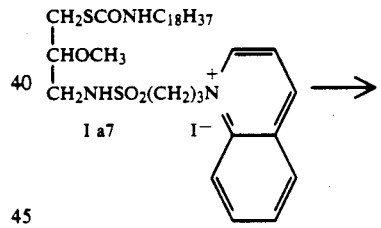

The titled compound is prepared in by the same procedure as described in Example 19.

NMR: δppm (CDCl$_3$) 0.88 (t, 3H), 1.25 (s, 30H), 1.48 (m, 2H), 2.15~2.35 (m, 2H), 3.0~3.2 (m, 2H), 3.2~3.35 (m, 2H), 3.37 (s, 3H), 3.35~3.50 (m, 1H), 3.50~3.70 (m, 2H), 4.00~4.30 (m, 2H), 5.55~5.80 (m, 3H), 7.75 (t, 1H, J=6 Hz), 7.94 (t, 1H, J=7.6 Hz), 8.15~8.40 (m, 3H), 8.74 (d, 1H, J=9.0 Hz), 8.97 (d, 1H, J=8.2 Hz), 10.48 (d, 1H, J=5.6 Hz).

IR: νmax (CHCl$_3$) 3455, 2930, 2855, 1715, 1530, 1470, 1325, 1220, 1140 cm$^{-1}$.

mp.: 57°~59° C.

Anal. Calcd. (%) for $C_{35}H_{60}O_5N_3SCl \cdot 1.2H_2O$: C 60.75, H 9.09, N 6.07, S 4.63, Cl 5.12, Found (%): C 60.66, H 9.09, N 6.23, S 4.51, Cl 4.89.

EXAMPLE 28

Preparation of 1-(N-n-octadecylcarbamoyloxy)-2-methoxy-3-[4-[3-carboxylatepyridinio]butylsulfonylamino]propane Ia28

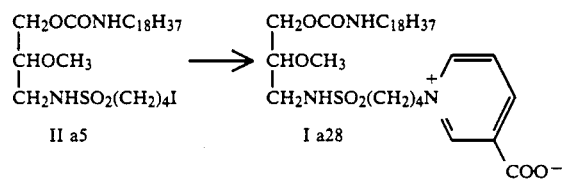

A solution of 600 mg (0.928 mmol) of 3-(4-iodobutylsulfonylamino)-2-methoxy-1-octadecylcarbamoyloxypropane and 230 mg (1.87 mmol) of nicotinic acid in 10 ml of dimethylsulfoxide is heated at 80° C. for 3 days. The product is isolated by dichloromethane extraction and dichloromethane layer is washed once with a 1N-hydrochloric acid, saturated aqueous solution of sodium hydrogencarbonate, and saturated aqueous solution of sodium chloride and evaporated. The residue is recrystallized from dichloromethane-acetone mixture to give 279 mg (0.435 mmol) of 1-(N-n-octadecylcarbamoyloxy)-2-methoxy-3-[4-[carboxylatepyridinio]butylsulfonylamino]propane Ia28 in 47% yield.

NMR: δppm (CDCl$_3$) 0.88 (t, 3H), 1.25 (s, 30H), 1.48 (m, 2H), 1.65~1.95 (m, 2H), 1.95~2.25 (m, 2H), 2.9~3.3 (m, 6H), 3.36 (s, 3H), 3.50 (m, 1H), 3.9~4.3 (m, 2H), 4.6~4.9 (m, 2H), 5.65~5.80 (m, 1H), 7.20~7.50 (m, 1H), 7.90~8.10 (m, 1H), 8.70~8.90 (m, 1H), 8.90~9.10 (m, 1H), 9.25~9.50 (m, 1H).

IR: νmax (CHCl$_3$) 3450, 2920, 2850, 1710, 1640, 1615, 1510, 1460, 1360, 1210, 1135 cm$^{-1}$.

Anal. Calcd. (%) for $C_{33}H_{59}O_7N_3S \cdot 1.2H_2O$: C 59.74, H 9.33, N 6.33, S 4.83, Found (%): C 59.61, H 9.36, N 6.26, S 4.63.

(23) Preparation of 2-aminomethyl-2-hexadecylthiomethyltetrahydrofuran IVb1

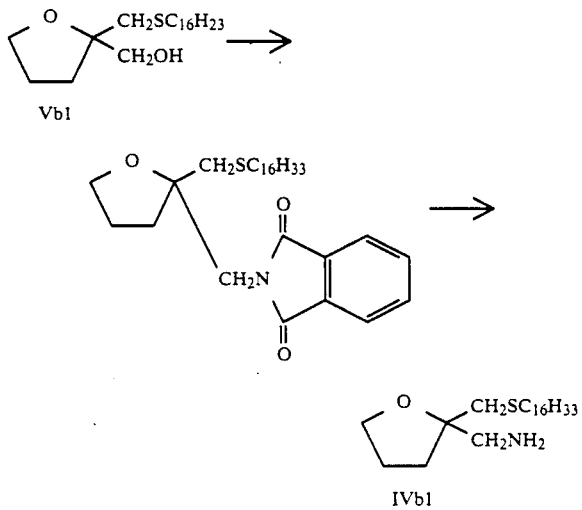

2-Hexadecylthiomethyl-2-hydroxymethyltetrahydrofuran IVb1 is allowed to react and worked by the same procedure as described in (3), the summary of the experimental condition and the physical data of the prodcut are listed in the Tables 5 and 6.

(24) Preparation of 2-(3-chloropropylsulfonylaminomethyl)-2-hexadecylthiomethyltetrahydrofuran IIIb1

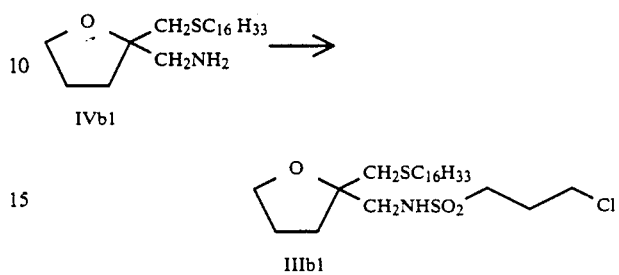

2-Aminomethyl-2-hexadecylthiomethyltetrahydrofuran IVb1 is allowed to react and worked by the same procedure as described in (4). m.p. 44.5° to 45.5° C. The summary of the experimental condition and the physical data of the prodcut are listed in the Table 7.

(25) Preparation of 2-hexadecylthiomethyl-2-(iodopropylsulfonylmethyl)-tetrahydrofuran IIb1

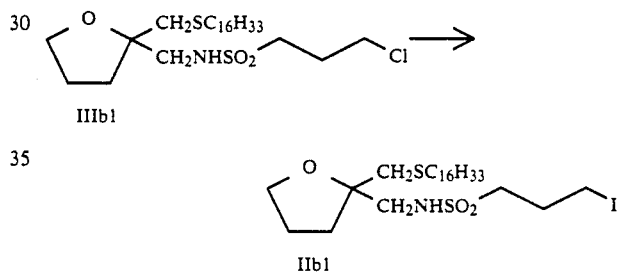

2-(3-Chloropropylsulfonylaminomethyl)-2-hexadecylthiomethyltetrahydrofuran IIIb1 is allowed to react and worked by the same procedure as described in (5). m.p. 36° to 37° C. The summary of the experimental condition and the physical data of the prodcut are listed in the Table 8.

EXAMPLE 29

Preparation of 2-hexadecylthiomethyl-2-(3-trimethylammoniopropylsulfonylaminomethyl)tetrahydrofuran Ib1

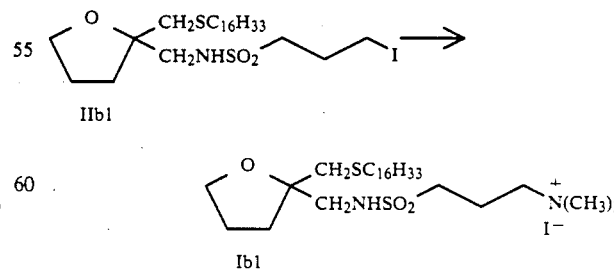

2-hexadecylthiomethyl-2-(3-iodopropylsulfonylaminomethyl)tetrahydrofuran is allowed to react and worked by the same procedure as described in Example 8. The summary of the experimental condition and the physical data of the prodcut are listed in the Table 9.

(26) Preparation of 2-aminomethyl-2-octadecylcarbamoyloxymethyltetrafuran IVb2

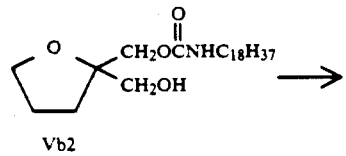

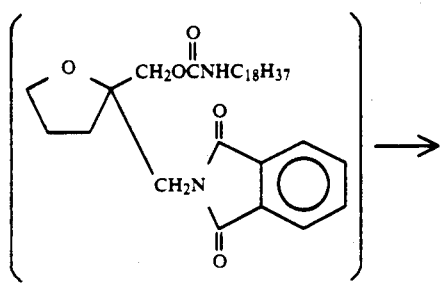

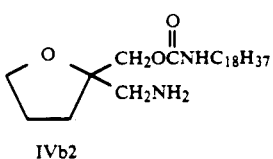

2-Hydroxymethyl-2-octadecylcarbamoyloxymethyltetrahydrofuran is allowed to react and worked by the same procedure as described in (3). m.p. (The phthalimido compound) 91° to 92° C. The summary of the experimental condition and the physical data of the product are listed in the Tables 5 and 6.

(27) Preparation of 2-(3-chloropropylsulfonylaminomethyl)-2-octadecylcarbamoyloxymethyltetrahydrofuran IIIb2

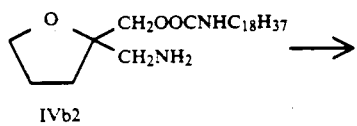

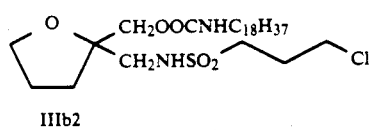

2-Aminomethyl-2-octadecylcarbamoyloxymethyltetrahydrofuran IVb2 is allowed to react and worked by the same procedure as described in (4). The summary of the experimental condition and the physical data of the prodcut are listed in the Table 7.

(28) Preparation of 2-(3-iodopropylsulfonylaminomethyl)-2-octadecylcarbamoyloxymethyltetrahydrofuran IIb2

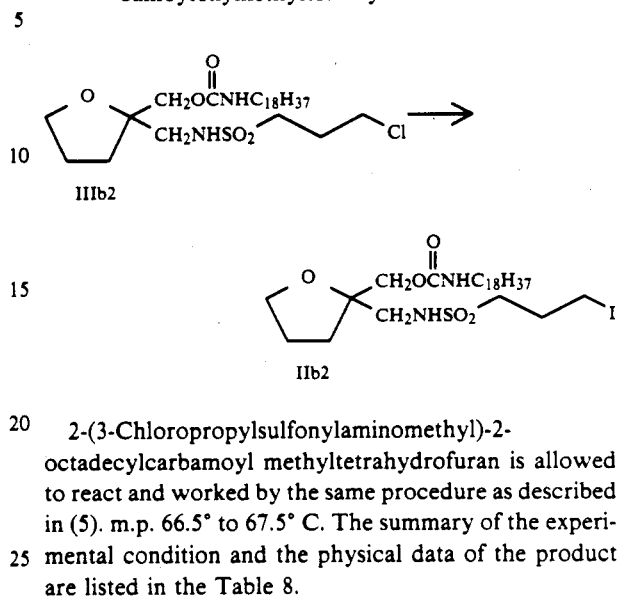

2-(3-Chloropropylsulfonylaminomethyl)-2-octadecylcarbamoyl methyltetrahydrofuran is allowed to react and worked by the same procedure as described in (5). m.p. 66.5° to 67.5° C. The summary of the experimental condition and the physical data of the product are listed in the Table 8.

EXAMPLE 30

Preparation of 2-octadecylcarbamoyloxymethyl-2-(3-quinoliniopropylsulfonylaminomethyl)tetrahydrofuran iodido Ib2

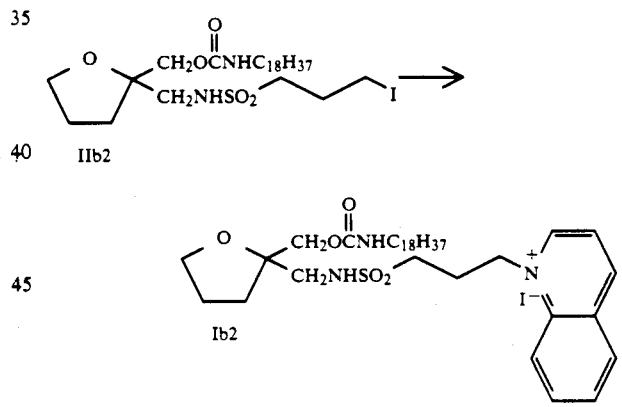

2-(3-iodopropylsulfonylaminomethyl)-2-octadecylcarbamoyloxymethyltetrahydrofuran IIb2 is allowed to react and worked by the same procedure as described in Example 25. The summary of the experimental condition and the physical data of the product are listed in the Table 10.

(29) Preparation of 3-hexadecylthio-2-methylcarbamoyloxypropanol Vc1

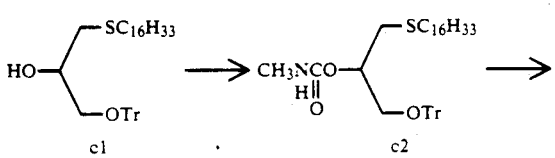

-continued

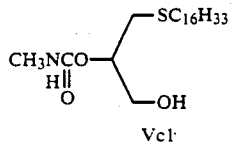
Vc1

To a solution of 1-hexadecylthio-3-trityloxy-2-propanol c1 4.6 g (8.0 mmol) in dichloromethane 100 ml are added 4-dimethylaminopyridine 1.17 g (9.6 mmol) and methyl isocyanate 4.72 ml (80 mmol). The solution is allowed to stand at room temperature for 72 hr and concentrated. The residue is chromatographed on $SiO_2$ (46 g) and eluted with ethyl acetate:hexane (1:5) to give 1-hexadecylthio-2-methylcarbamoyloxy-3-trityloxypropane c2 as a crude oil (5.6 g). The oil is dissolved in dichloromethane 100 ml and boron trifluoride-methanol complex 1.68 ml (15.5 mmol) is added under cooling. The resulting yellow solution is stirred at 0° C. for 15 min and then at room temperature for 1 hr. Sodium carbonate aq solution is added to neutralize the reaction mixture and an organic layer is separated. The organic layer is subjected to $SiO_2$ (80 g) column chromatography and eluted with ethyl acetate:hexane (1:1) to afford crude crystals 2.07 g. The crystals are triturated and washed with pentane to yield the titled compound Vc1 1.205 g. The mother liqour is purified by Lobar column chromatography with the same solvent as described above to give additional Vc1 0.321 g (49% total yield), mp. 53°–55° C.

NMR: δ ($CDCl_3$) 0.80~1.70 (m, 31H), 2.22 (br. s, 1H), 2.50~2.75 (m, 4H), 2.80 (d, J=5 Hz, 3H), 3.82 (m, 2H), 4.85 (br. m, 2H).

(30) Preparation of 3-hexadecylthio-2-methylcarbamoyloxypropylamine IVc1

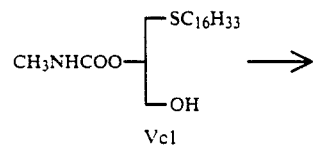

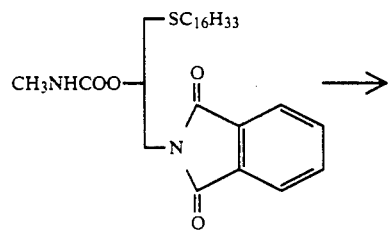

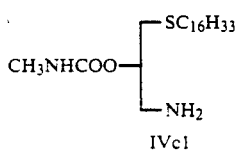

3-Hexadecylthio-2-methylcarbamoyloxypropanol is allowed to react and worked up by the same procedure as described in (3). The summary of the experimental condition and the physical data of the prodcut are listed in the Tables 5 and 6.

The crude phthalimide compound is recrystallizied from methanol-dichloromethane (10:1).

(31) Preparation of 3-(3-chloropropylsulfonylamino)-1-hexadecylthio-2-methylcarbamoyloxypropane IIIc1

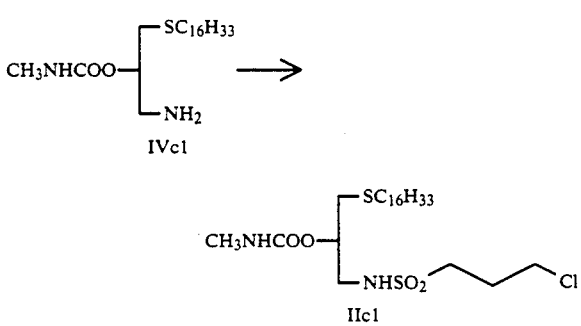

3-Hexadecylthio-2-methylcarbamoyloxypropylamine IVc1 is allowed to react and worked up by the same procedure as described in (4). m.p. 84.5°–85.5° C. The summary of the experimental condition and the physical data of the prodcut are listed in the Table 7.

(32) Preparation of 1-hexadecylthio-3-(3-iodopropylsulfonylamino)-2-methylcarbamoyloxypropane IIc1

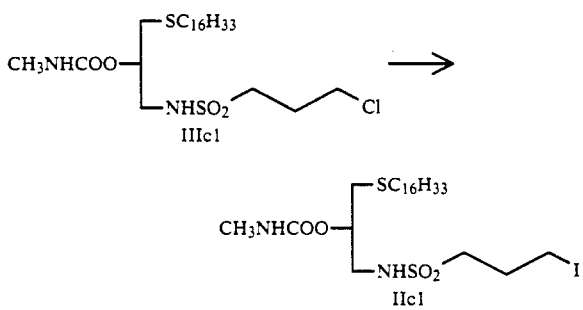

3-(3-Chloropropylsulfonylamino)-1-hexadecylthio-2-methylcarbamoyloxypropan IIIc1 is allowed to react and worked up by the same procedure as described in (5). The summary of the experimental condition and the physical data of the prodcut are listed in the Table 8.

EXAMPLE 31

Preparation of 1-hexadecylthio-2-methylcarbamoyloxy-3-(3-quinoliniopropylsulfonylamino)propane iodide Ic1

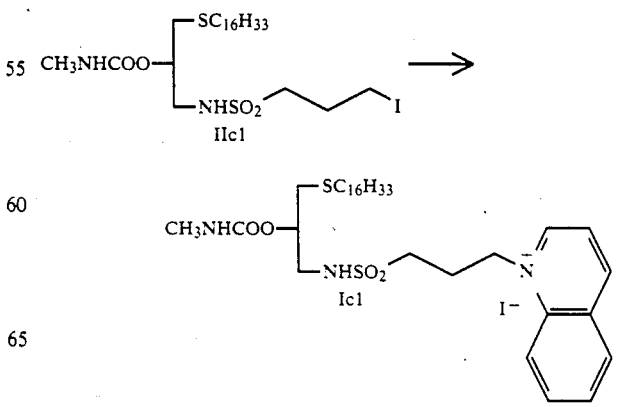

1-Hexadecylthio-3-(3-iodopropylsulfonylamino)-2-methylcarbamoyloxypropane IIc1 is allowed to react and worked up by the same procedure as described in Example 25. The summary of the experimental condition and the physical data of the product are listed in the Table 10.

EXAMPLE 32

Preparation of 1-hexadecylthio-2-methylcarbamoyloxy-3-(3-trimethylammoniopropylsulfonylamino)propane iodide Ic2

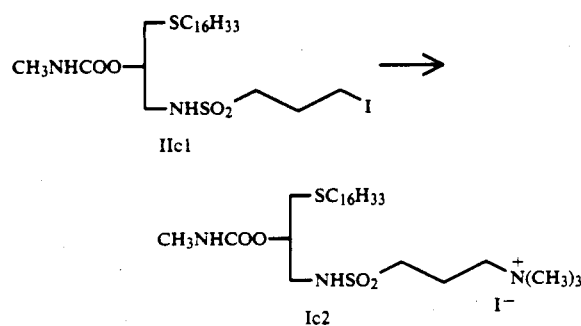

1-Hexadecylthio-3-(3-iodopropylsulfonylamino)-2-methylcarbamoyloxypropane IIc1 is allowed to react and worked up by the same procedure as described in Example 8. The summary of the experimental condition and the physical data of the prodcut are listed in the Table 9.

(33) Preparation of 2-methylcarbamoyloxy-1-octadecylcarbamoyloxy-3-trityloxypropane c4

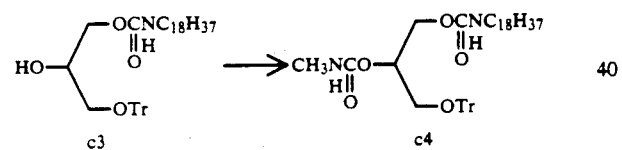

1-octadecylcarbamoyloxy-3-trityloxy-2-propanol c3 1.26 g (2.0 mmol) obtained above is dissolved in dichloromethane 20 ml and 4-dimethylaminopyridine 0.293 g (2.4 mmol) and methylisocyanate 1.18 ml (20 mmol) are added. The solution is stirred at room temperature for 24 hr and evaporated. The residue is purified by $SiO_2$ column chromatography with ethyl acetate:hexane (1:1) to yield the titled compound c4 0.789 g (59% yield). mp. 89°–91° C.

NMR: δ (CDCl$_3$) 0.86 (t, J=6 Hz, 3H), 1.28 (br. s, 32H), 2.74 (d, J=6 Hz, 3H), 2.90~3.45 (m, 4H), 4.24 (d, J=6 Hz, 2H), 4.70 (m, 2H), 5.10 (m, 1H), 7.15~7.65 (m, 15H).

(34) Preparation of 2-methylcarbamoyloxy-3-octadecylcarbamoyloxypropanol Vc2

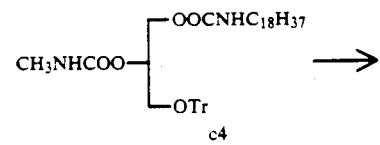

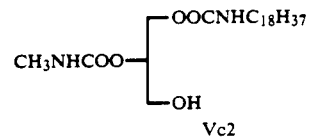

The compound c4 4.5 g (6.68 mmol) obtained above is dissolved in dichloromethane 45 ml and boron trifluoride-methanol complex 1.08 ml (9.96 mmol) is added at 0° C. The solution is stirred at room temperature for 4 hr and washed with sodium hydrogen carbonate aq solution. The organic layer is dried over anhydrous sodium sulfate and evaporated. The residual crystals are recrystallized from methanol-ether to yield the titled compound Vc2 2.04 g (69% yield). mp. 92°–93° C.

NMR: δ (CDCl$_3$) 0.86 (t, J=6 Hz, 3H), 1.26 (br. s, 32H), 2.75 (d, J=6 Hz, 3H), 2.80~3.45 (m, 3H), 3.68 (m, 2H), 4.25 (d, J=6 Hz, 2H), 4.75~5.25 (m, 3H).

IR: νmax (Nujol) 3340, 3290, 1685, 1520, 1375, 1285, 1150, 1065 cm$^{-1}$.

(35) Preparation of 2-methylcarbamoyloxy-3-octadecylcarbamoyloxypropylamine IVc2

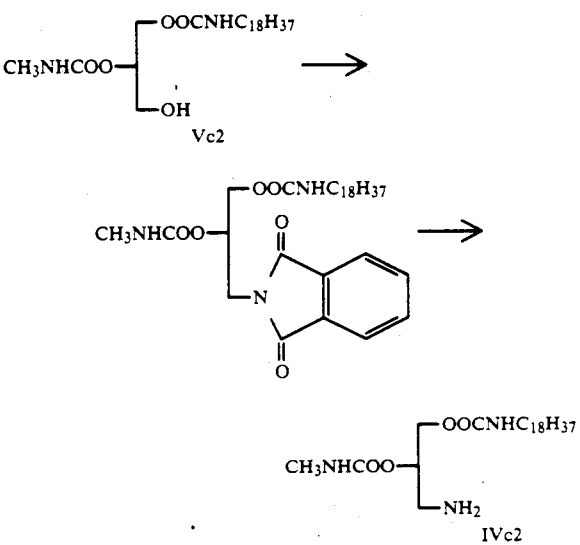

2-Methylcarbamoyloxy-3-octadecylcarbamoyloxypropanol Vc2 is allowed to react and worked up by the same procedure as described in (3) to give an amine IVc2 of m.p. 91°–92° C. The summary of the experimental condition and the physical data of the product are listed in the Table 5 and 6.

(36) Preparation of 3-(3-chloropropylsulfonylamino)-2-methylcarbamoyloxy-1-octadecylcarbamoyloxypropane IIIc2

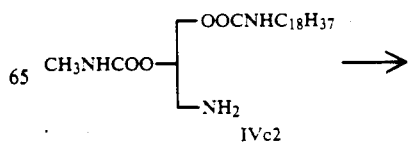

-continued

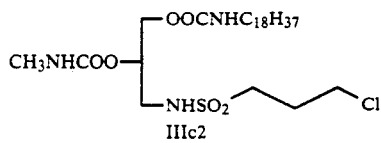

2-Methylcarbamoyloxy-3-octadecylcarbamoyloxy-propylamine IVc2 is allowed to react and worked up by the same procedure as described in (4). m.p. 102°–104° C. The summary of the experimental condition and the physical data of the product are listed in the Table 7.

(37) Preparation of 3-(3-iodopropylsulfonylamino)-2-methylcarbamoyloxy-1-octadecylcarbamoyloxypropane IIc2

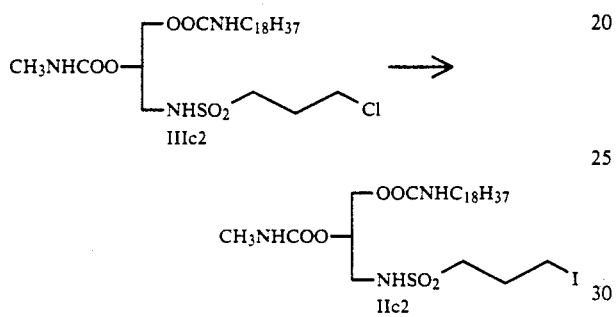

3-(3-Chloropropylsulfonylamino)-2-methylcarbamoyloxy-1-octadecylcarbamoyloxypropane IIIc2 is allowed to react and worked up by the same procedure as described in (5). m.p. 97°–99° C. The summary of the experimental condition and the physical data of the prodcut are listed in the Table 8.

EXAMPLE 33

Preparation of 2-methylcarbamoyloxy-1-octadecylcarbamoyloxy-3-(3-quinoliniopropylsulfonylamino)propane iodide Ic3

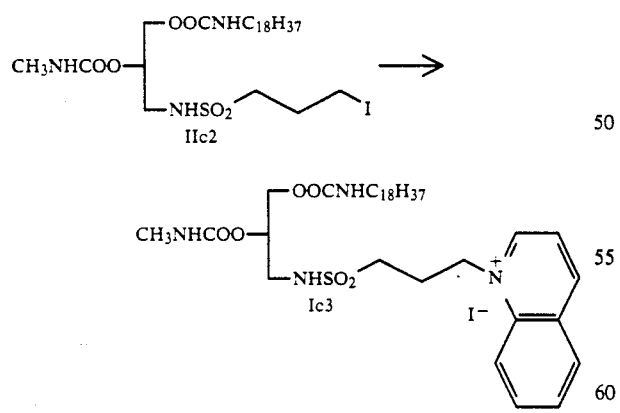

3-(3-Iodopropylsulfonylamino)-2-methylcarbamoyloxy-1-octadecylcarbamoyloxypropane IIc2 is allowed to react and worked up by the same procedure as described in Example 25. The summary of the experimental condition and the physical data of the prodcut are listed in the Table 10.

EXAMPLE 34

Preparation of 2-methylcarbamoyloxy-1-octadecylcarbamoyloxy-3-(3-trimethylammoniopropylsulfonylamino)propane iodide Ic4

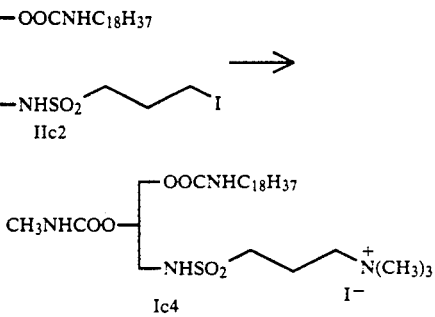

3-(3-Iodopropylsulfonylamino)-2-methylcarbamoyloxy-1-octadecylcarbamoyloxypropane IIc2 is allowed to react and worked up by the same procedure as described in Example 8. The summary of the experimental condition and the physical data of the prodcut are listed in the Table 9.

(38) Preparation of O-octadecylcarbamoyl-N-triphenylmethylserine methyl ester e2

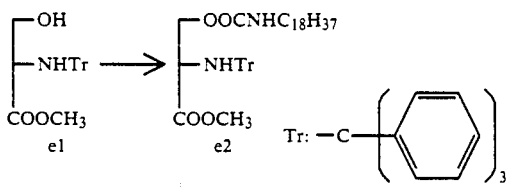

A solution of 1.67 g of N-triphenylmethylserine methyl ester and 2.0 g of stearylisocyanate in 10 ml of N,N-dimethyl-formamide is heated at 85° C. for 16 h, poured to ice-water and extracted with ethyl acetate. The extracts are washed with water, dried over anhydrous sodium sulfate and concentrated under reduced pressure. The residue is subjected to flash chromatography on silica gel in hexane:ethyl acetate (3:2) to give 2.46 g (82.6% yield) of the titled compound e2.

NMR (CDCl$_3$) δppm: 0.88 (3H, t, J=7 Hz), 1.25 (30H, s), 1.46 (2H, m), 2.78 (1H, d, J=10 Hz), 3.16 (2H, m), 3.19 (3H, s), 3.58 (1H, m), 4.21 (1H, dd, J=11.6 Hz), 4.37 (1H, dd, J=11.5 Hz), 4.69 (1H, t, J=11 Hz), 7.1–7.3 (9H, m), 7.45–7.6 (6H, m).

(39) Preparation of O-octadecylcarbamoylserine methyl ester e3

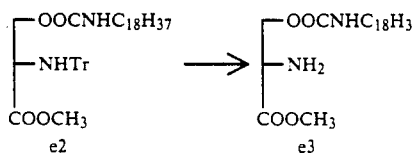

To a solution of 573 mg of e2 in 15 ml of acetone is added 5 ml of 10% hydrochloric acid. The mixture is allowed to stand at room temperature overnight made alkaline with aqueous sodium carbonate and extracted with ethyl acetate. The extracts are washed with water dried over anhydrous sodium sulfate and concentrated under reduced pressure. The residue is subjected to flash chromatography on silica gel in ethyl acetate:methanol (9:1) and recrystallized from ethyl acetate-hexane to give 276 mg (74.9% yield) of the titled compound 3e. mp. 70°-71° C.

NMR: (CDCl₃) δppm 0.89 (3H, t, J=6 Hz), 1.26 (30H, s), 1.49 (2H, m), 1.78 (2H, s), 3.16 (2H, m), 3.73 (1H, m), 3.76 (3H, s), 4.31 (2H, d, J=5 Hz), 4.76 (1H, s).

(40) Preparation of 2-amino-3-octadecylcarbamoyloxypropanol e4

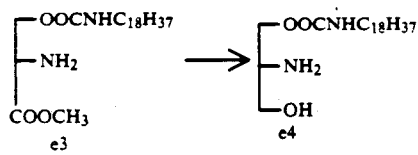

To a mixture of 760 mg of sodium borohydride in 30 ml of ethanol is added 1.11 g of calcium chloride at −40° C. The mixture is stirred at −20° C. for 1 h. A solution of 2.08 g of e3 in 50 ml of ethanol is added dropwise to the mixture at −20° C. The mixture is stirred at −20° C. for 3 h. Water is added. The mixture is extracted with ethyl acetate. The extracts are washed with water, dried over anhydrous sodium sulfate and concentrated under reduced pressure. The residue is subjected to flash chromatography on silica gel in chloroform:methanol (9:1) and then recrystallized from hexane to give 1.57 g (80.9% yield) of the titled compound e4. mp. 103°-105° C.

NMR: (CDCl₃) δppm 0.88 (3H, t, J=6 Hz), 1.26 (30H, s), 1.49 (2H, m), 1.73 (3H, s), 3.06 (1H, m), 3.17 (2H, m), 3.51 (2H, m), 4.08 (2H, d, J=5 Hz), 4.75 (1H, s).

(41) Preparation of 2-methoxycarbonylamino-3-octadecylcarbamoyloxypropanol Ve1

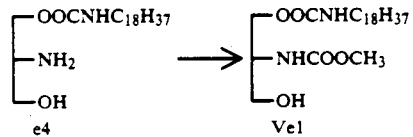

A solution of 117 mg of methyl chloroformate in 8 ml of acetone is added dropwise to a suspension of 120 mg of e4 in 3 ml of 3.3% aqueous sodium carbonate. The mixture is stirred for 6 h and extracted with ethyl acetate. The extracts are washed with water, dried over anhydrous sodium sulfate and concentrated under reduced pressure. The residue is subjected to flash chromatography on silica gel in ethyl acetate and recrystallized from hexane to give 115 mg (82.3% yield) of the titled compound Vel. mp. 84°-85° C.

NMR (CDCl₃) δppm 0.89 (3H, t, J=6 Hz), 1.26 (30H, s), 1.50 (2H, m), 1.61 (1H, s), 3.07 (1H, br. s), 3.18 (2H, m), 3.69 (3H, s), 3.86 (1H, br. s), 4.20 (2H, d, J=5 Hz), 4.83 (1H, s), 5.23 (1H, d, J=7 Hz).

(42) Preparation of 2-tert-butoxycarbonylamino-3-octadecylcarbamoyloxypropanol Ve2

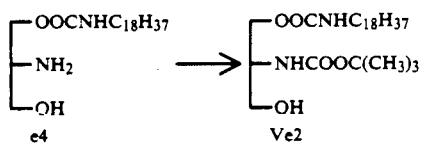

2-tert-Butoxycarbonylamino-3-octadecylcarbamoyloxypropanol Ve2 is prepared by the same manner as described in (41) by using tert-butyldicarbonate instead of methyl chloroformate.

Yield 93.4%. mp. 73°-75° C.

NMR: (CDCl₃) δppm 0.87 (3H, t, J=5 Hz), 1.26 (30H, s), 1.44 (9H, s), 1.56 (2H, m), 3.18 (2H, m), 3.63 (2H, m), 3.81 (1H, br. s), 4.18 (2H, d, J=5 Hz), 4.78 (1H, br. s), 5.20 (1H, br. s).

(43) Preparation of 2-methoxycarbonylamino-3-octadecylcarbamoyloxypropylamine IVe1

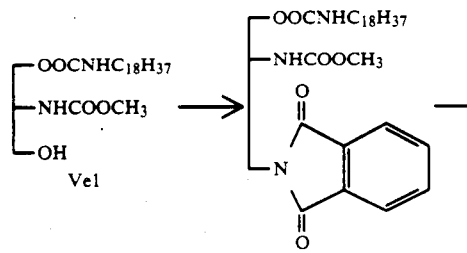

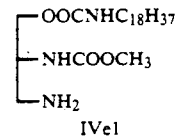

2-Methoxycarbamoyl-3-octadecylcarbamoyloxypropanol Ve1 is allowed to react and worked up by the same procdure as described in (3). The phthalimide derivative: m.p. 128°-129° C., the amine derivative: 85°-86° C. The summary of the experimental condition and the physical data of the product are listed in Tables 5 and 6.

(44) Preparation of 2-tert-butyoxycarbonylamino-3-octadecylcarbonyloxypropylamine IVe2

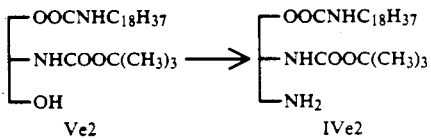

2-tert-Butoxycarbonylamino-3-octadecylcarbamoyloxypropane Ve2 is allowed to react and worked up by the same procdure as described in (3). The phthalimide compound; m.p. 127°-129° C. The amino compound IVe2 69°-70° C. The summary of the experimental condition and the physical data of the product are listed in Tables 5 and 6.

(45) Preparation of 4-acetylthiomethyl-2-phenyl-2-oxazoline e6

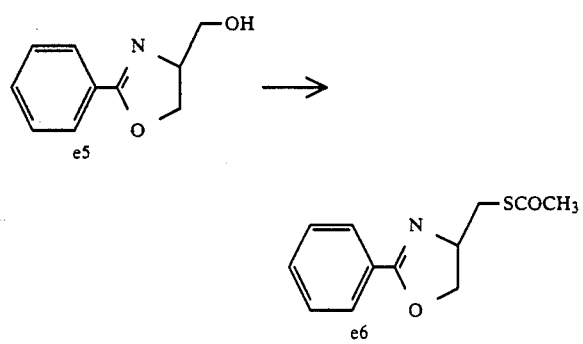

4-Hydroxymethyl-2-phenyl-2-oxazoline e5 is allowed to react by the same procedure as described in (17). The extract is purified by the flash chromatography on silica gel eluted with hexane:ethyl acetate 2:1. The product is recrystallized from hexane to give the titled compound e6 as needle crystals. mp. 59°–60° C.

NMR (CDCl$_3$) δppm 2.37 (3H, s), 3.23 (2H, m), 4.11 (1H, m), 4.33–4.62 (2H), 7.36–7.55 (3H), 7.95 (2H, m).

(46) Preparation of 4-hexadecylthiomethyl-2-phenyl-2-oxazoline e7

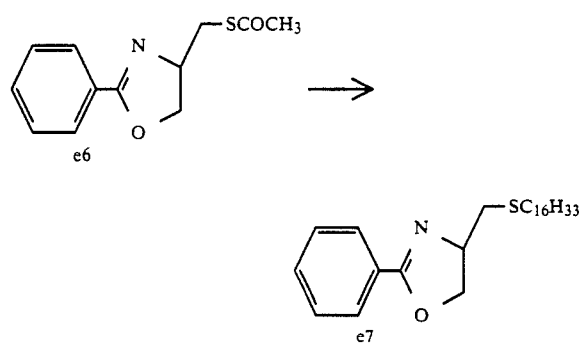

To a solution of 13.28 g of the thiolester e6 in 70 ml of methanol is added 60 ml of 10% aqueous sodium hydroxide at 0° C. The solution is stirred at room temperature for 2 h. Water is added. The mixture is extracted with ether. The extracts are washed with water, dried over anhydrous sodium sulfate and concentrated under reduced pressure to give 7.68 g (70.4% yield) of the crude thiol.

To a solution of the residue in 40 ml of dry tetrahydrofuran is added 1.6 g of 60% sodium hydride in small portions at room temperature. The mixture is stirred for 30 min. A solution of 12.22 g of 1-bromohexadecane in 10 ml of dry tetrahydrofuran is added. The mixture is stirred at room temperature overnight. Ether is added. The mixture is washed with water, dried over anhydrous sodium sulfate and concentrated under reduced pressure. The residue is subjected to flash chromatography on silica gel in hexane:ethyl acetate (4:1) and then recrystallized from hexane to give 14.68 g (62.3% yield) of the titled compound e7. mp. 39°–41° C.

NMR (CDCl$_3$) δppm 0.88 (3H, t, J=6.5 Hz), 1.25 (26H, s), 1.59 (2H, m), 2.53–2.67 (3H, m), 2.99 (1H, m), 4.30 (1H, m), 4.43–4.59 (2H), 7.36–7.54 (3H), 7.95 (2H, m).

(47) Preparation of 2-amino-3-hexadecylthiopropanol e8

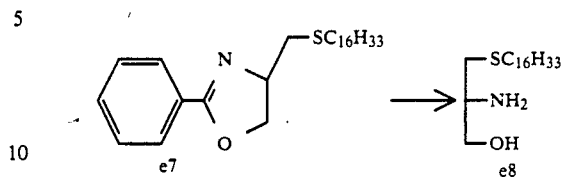

A suspension of 15.0 g of the oxazoline e7 in 55 ml of 6N-sulfuric acid is stirred at 105° C. for 24 h, made alkaline with 10% of aqueous sodium hydroxide and extracted with ethyl acetate. The extracts are washed with water, dried over anhydrous sodium sulfate and concentrated under reduced pressure. The residue is subjected to flash chromatography on silica gel in chloroform and then chloroform:methanol (10:1) and recrystallized from dichloromethane-hexane to give 11.16 g (93.7% yield) of the titled compound e8 as plates. mp. 70°–71° C.

NMR (CDCl$_3$) δppm 0.88 (3H, t, J=6.5 Hz), 1.26 (26H, s), 1.58 (2H, m), 1.85 (3H, s), 2.46 (1H, dd, J=8.2, 13.3 Hz), 2.52 (2H, t, J=7.3 Hz), 2.66 (1H, dd, J=4.8, 13.3 Hz), 3.02 (1H, m), 3.42 (1H, dd, J=6.5, 10.7 Hz), 3.67 (1H, dd, J=4.1, 10.7 Hz).

(48) Preparation of 3-hexadecylthio-2-methoxycarbonylaminopropanol e9

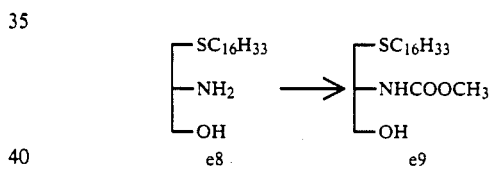

The compound e8 is allowed to react by the same procedure as described in (41). Yield 94.6%, m.p. 55°–56° C.

NMR (CDCl$_3$) δppm: 0.88 (3H, t, J=6.4 Hz), 1.26 (26H, s), 1.58 (2H, m), 2.55 (2H, t, J=7.2 Hz), 2.73 (2H, d, J=5.7 Hz), 3.69 (3H, s), 3.67–3.88 (3H), 5.21 (br. s).

(49) Preparation of 3-hexadecylthio-2-tert-butoxycarbonylaminopropanol 12b

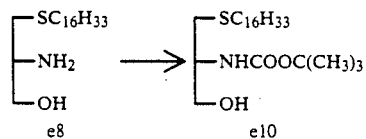

The compound e8 is allowed to react by the same procedure as described in (42). Yield 95.9%, m.p. 48°–50° C.

NMR (CDCl$_3$) δppm: 0.88 (3H, t, J=6.4 Hz), 1.26 (26H, s), 1.45 (9H, s), 1.58 (2H, m), 1.96 (1H, s), 2.55 (2H, t, J=7.0 Hz), 2.71 (2H, d, J=4.0 Hz), 3.69–3.82 (3H), 5.02 (1H, br. s).

(50) Preparation of 1-hexadecylthio-3-methanesulfonyloxy-2-methoxycarbonylaminopropane e11

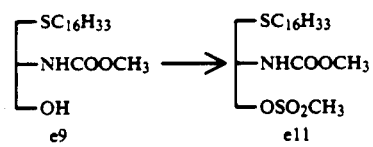

A solution of 0.96 g of methanesulfonyl chloride in 5 ml of dichloromethane is added dropwise to a solution of 2.727 g of the alcohol e9 in 35 ml of dichloromethane and 4 ml of triethylamine at $-10°$ C. The mixture is stirred at $-10°$ C. for 2 h. Ether is added. The mixture is washed with water, 10% hydrochloric acid, aqueous sodium hydrogencarbonate and water, dried over anhydrous sodium sulfate and concentrated under reduced pressure. The residue is recrystallized from benzene-hexane to give 3.133 g (95.7% yield) of the titled compound e11 as a powder. mp. 82°–83° C.

NMR (CDCl$_3$) δppm: 0.88 (3H, t, J=6.5 Hz), 1.26 (26H, s), 1.58 (2H, m), 2.55 (2H, t, J=7.2 Hz), 2.68 (1H, dd, J=7.3, 13.5 Hz), 2.78 (1H, dd, J=5.2, 13.5 Hz), 3.05 (3H, s), 3.70 (3H, s), 4.05 (1H, m), 4.34 (1H, dd, J=4.3, 10.2 Hz), 4.45 (1H, dd, J=4.2, 10.2 Hz), 5.10 (1H, d, J=8.0 Hz).

(51) Preparation of 2-tert-butoxycarbonylamino-1-hexadecylthio-3-methanesulfoxypropane e12

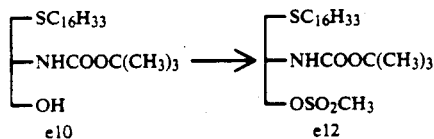

The compound e10 is allowed to react by the same procedure as in (50). Yield: 97.9%. mp. 90°–91° C.

NMR (CDCl$_3$) δppm 0.88 (3H, t, J=6.4 Hz), 1.26 (26H, s), 1.45 (9H, s), 1.58 (2H, m), 2.55 (2H, t, J=7.1 Hz), 2.67 (1H, dd, J=7.2, 13.5 Hz), 2.76 (1H, dd, J=5.6, 13.5 Hz), 3.05 (3H, s), 4.00 (1H, m), 4.32 (1H, dd, J=4.3, 10.2 Hz), 4.45 (1H, dd, J=4.1, 10.2 Hz), 4.90 (1H, d, J=7.8 Hz).

(52) Preparation of 3-azido-1-hexadecylthio-2-methoxycarbonylaminopropane e13

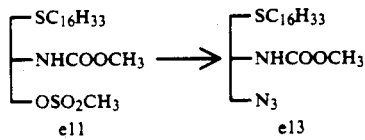

A mixture of 4.677 g of the mesylate e11 and 1 g of sodium azide in 25 ml of hexamethylphosphoric triamide is stirred at 50° C. for 4 h. Ether is added. The mixture is washed with water, dried over anhydrous sodium sulfate and concentrated under reduced pressure. The residue is subjected to flash chromatography on silica gel in hexane:ethyl acetate (8:1) and then recrystallized from hexane to give 3.925 g (94.6% yield) of the titled compound e13 as needles. mp. 44.5°–45.5° C.

NMR (CDCl$_3$) δppm 0.88 (3H, t, J=6.5 Hz), 1.26 (26H, s), 1.58 (2H, m), 2.54 (2H, t, J=7.3 Hz), 2.64 (1H, dd, J=7.3, 13.9 Hz), 2.73 (1H, dd, J=6.0, 13.9 Hz), 3.52 (1H, dd, J=5.0, 12.3 Hz), 3.65 (1H, dd, J=4.5, 12.3 Hz), 3.69 (3H, s), 3.91 (1H, m), 4.98 (1H, d, J=6.5 Hz).

(53) Preparation of 3-azido-2-tert-butoxycarbonylamino-1-hexadecylthiopropane e14

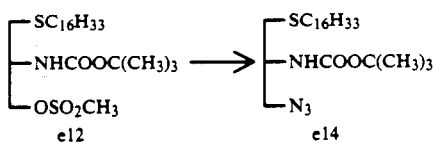

The compound e12 is allowed to react by the same procedure as described in (52). Yield: 93.6%, mp. 63°–64° C.

NMR (CDCl$_3$) δppm 0.88 (3H, t, J=6.4 Hz), 1.26 (26H, s), 1.45 (9H, s), 1.58 (2H, m), 2.54 (2H, t, J=7.3 Hz), 2.63 (1H, dd, J=7.4, 14.0 Hz), 2.71 (1H, dd, J=6.1, 14.0 Hz), 3.50 (1H, dd, J=5.1, 12.2 Hz), 3.64 (1H, dd, J=4.2, 12.2 Hz), 3.86 (1H, m), 4.81 (1H, d, J=6.5 Hz).

(54) Prepration of 3-hexadecylthio-2-methoxycarbonylaminopropylamine IVe3

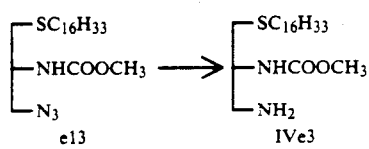

A solution of 3.875 g of the azide e13 and 3.19 g of triphenylphosphine in 40 ml of tetrahydrofuran is stirred for 20 h and 10 ml of water is added. The mixture is heated under reflux for 30 min. Ether is added. The mixture is washed with water, dried over anhydrous sodium sulfate and concentrated under reduced pressure. The residue is subjected to flash chromatography on silica gel in chloroform and then chloroform:methanol (25:2) and then recrystallized from hexane to give 3.532 g (97.2% yield) of the titled compound IVe3 as crystalline powders. mp. 49°–50.5° C.

NMR (CDCl$_3$) δppm 0.88 (3H, t, J=6.4 Hz), 1.26 (26H, s), 1.45 (2H, s), 1.58 (2H, m), 2.54 (2H, t, J=7.3 Hz), 2.62 (1H, dd, J=6.9, 13.2 Hz), 2.74 (1H, dd, J=5.7, 13.2 Hz), 2.87 (2H, d, J=5.5 Hz), 3.68 (3H, s), 3.76 (1H, m), 5.14 (1H, d, J=7.6 Hz).

(55) Preparation of 3-hexadecylthio-2-tert-butoxycarbonylaminopropylamine IVe4

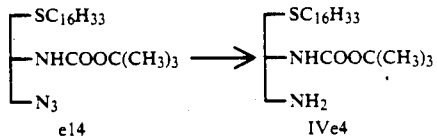

The compound e14 is allowed to react by the same manner as described in (54). Yield: 95.3%. mp. 46°–47° C.

NMR (CDCl$_3$) δppm 0.88 (3H, t, J=6.4 Hz), 1.26 (26H, s), 1.45 (9H, s), 1.50–1.66 (4H), 2.54 (2H, t, J=7.3

Hz), 2.62 (1H, dd, J=6.7, 13.1 Hz), 2.72 (1H, dd, J=5.5, 13.1 Hz), 2.86 (2H, d, J=5.1 Hz), 3.71 (1H, m), 4.94 (1H, d, J=7.5 Hz).

(56) Preparation of 3-(3-chloropropylsulfonylamino)-2-methoxycarbonylamino-1-octadecylcarbamoyloxypropane IIIe1

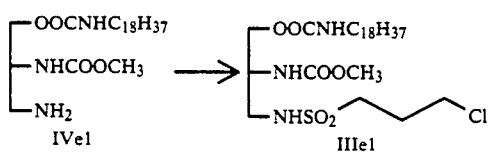

2-Methoxycarbonylamino-3-octadecylcarbamoyloxypropylamine IVe1 is allowed to react and worked up by the same procedure as described in (4). m.p. 99°–101° C. The summary of the experimental condition and the physical data of the product are listed in Table 7.

(57) Preparation of 2-tert-butoxycarbonylamino-3-(3-chloropropylsulfonylamino)-1-octadecylcarbamoyloxypropane IIIe2

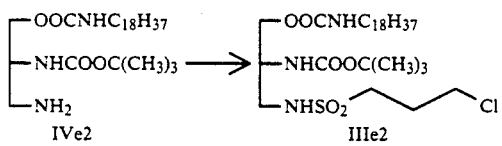

2-tert-Butoxycarbonylamino-3-octadecylcarbamoyloxypropylamine IVe2 is allowed to react by the same procedure as described in (4). m.p. 112°–115° C. The summary of the experimental condition and the physical data of the product are listed in Table 7.

(58) Preparation of 3-(3-chloropropylsulfonylamino)-1-hexadecylthio-2-methoxycarbonylaminopropane IIIe3

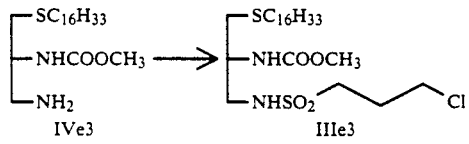

3-Hexadecylthio-2-methoxycarbonylaminopropylamine IVe3 is allowed to react and worked up by the same procedure as described in (4). m.p. 67°–69° C. The summary of the experimental condition and the physical data of the product are listed in Table 7.

(59) Preparation of 2-tert-butoxycarbonylamino-3-(3-chloropropylsulfonylamino)-1-hexadecylthiopropane IIIe4

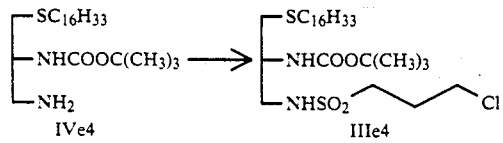

3-Hexadecylthio-2-tert-butoxycarbonylaminopropylamine IVe4 is allowed to react and worked up by the same procedure as described in (4). m.p. 100.5°–101.5° C. The summary of the experimental condition and the physical data of the product are listed in Table 7.

(60) Preparation of 2-amino-3-(3-chloropropylsulfonylamino)-1-octadecylcarbamoyloxypropane IIIe1'

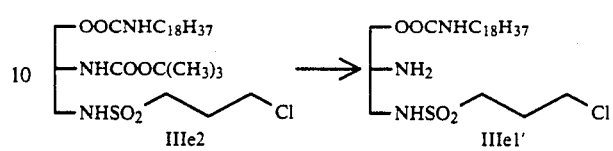

A solution of 0.5 ml of trifluoroacetic acid in 2 ml of dichloromethane is added dropwise to a suspension of 252 mg of the BOC derivative IIIe2 in 5 ml dichloromethane at room temperature. The mixture is stirred at room temperature for 2 h and made alkaline with aqueous sodium hydrogencarbonate. The organic phase is separated and the aqueous phase is extracted with dichloromethane. The combined organic phases are washed with water, dried over anhydrous sodium sulfate and concentrated under reduced pressure. The residue is subjected to flash chromatography on silica gel in chloroform:methane (9:1) and recrystallized from ethyl acetate-hexane to give 190 mg (89.7% yield) of the titled compound IIIe1' as crystalline powders. mp. 86°–88° C.

NMR (CDCl$_3$) δppm 0.88 (3H, t, J=5 Hz), 1.26 (30H, s), 1.50 (2H, m), 2.20 (2H, br. s), 2.30 (2H, m), 3.16 (6H, m), 3.69 (2H, t, J=6 Hz), 4.09 (3H, br. s), 4.88 (1H, br. s).

(61) Preparation of 2-amino-3-(3-chloropropylsulfonylamino)-1-hexadecylthiopropane IIIe2'

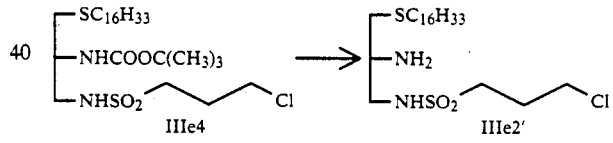

The compound IIIe4 is allowed to react by the same manner as described in (60). Yield 98.4%. m.p. 76°–77° C.

NMR (CDCl$_3$) δppm 0.88 (3H, t, J=6.4 Hz), 1.26 (26H, s), 1.58 (2H, m), 2.20 (3H, br. s), 2.30 (2H, m), 2.44–2.55 (3H), 2.65 (1H, dd, J=5.0, 13.3 Hz), 2.97 (1H, dd, J=7.5, 11.8 Hz), 3.07 (1H, m), 3.19–3.33 (3H), 3.70 (2H, t, J=6.2 Hz).

(62) Preparation of 2-acetamido-3-(3-chloropropylsulfonylamino)-1-octadecylcarbamoyloxypropane IIIg1

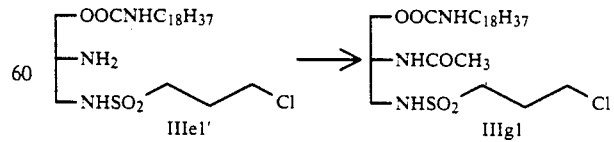

A solution of 0.77 ml of pyridine in 2 ml of dichloromethane is added to a solution of 501 mg of the amine IIIe1' and 194 mg of acetic anhydride in 15 ml of dichloromethane. The mixture is stirred at room temperature for 2 h, washed with dilute hydrochloric acid, aqueous

(63) Preparation of 3-(3-chloropropylsulfonylamino)-2-(3-methylureido)-1-octadecylcarbamoyloxypropane IIIf1

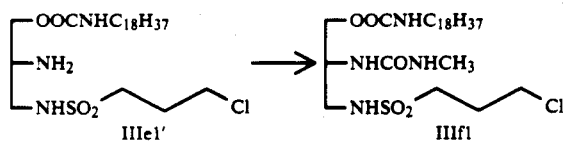

To a solution of 480 mg of the amine IIIe1' in 5 ml of N,N-dimethylformamide is added 0.2 ml of methylisocyanate. The mixture is stirred at room temperature for 1 h, poured to water and extracted with ethyl acetate. The extracts are dried over anhydrous sodium sulfate and concentrated under reduced pressure. The residue is subjected to flash chromatography on silica gel in chloroform:methanol (9:1) and recrystallized from ethyl acetate to give 469 mg (88.0% yield) of the titled compound. mp. 87°–90° C.

NMR (CDCl$_3$) δppm 0.88 (3H, t, J=6 Hz), 1.26 (30H, s), 1.50 (2H, m), 2.28 (2H, m), 2.77 (3H, s), 3.1–3.3 (6H), 3.68 (2H, t, J=7 Hz), 4.05 (1H, br. s), 4.15 (2H, m), 5.04 (1H, br. s), 5.51 (1H, br. s), 6.11 (1H, br. s).

(64) Preparation of 2-acetamido-3-(3-chloropropylsulfonylamino)-1-hexadecylthiopropane IIIg2

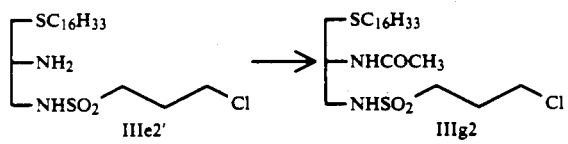

A solution of 161.5 mg (2.042 mmol) of the amine IIIe2' in 2 ml of dichloromethane is added dropwise to a solution of 962 mg (2.042 mmol) of the amine IIIe2' and 0.5 ml of acetic anhydride in 20 ml of dichloromethane at room temperature. The mixture stirred for 1 h. The volatile materials are removed by distillation under reduced pressure and the residue is subjected to flash chromatography on silica gel in chloroform and then chloroform:methanol (20:1) and recrystallized from hexane to give 924 mg (88.2% yield) of the titled compound IIIg2. mp. 86°–88° C.

NMR (CDCl$_3$) δppm 0.88 (3H, t, J=6.5 Hz), 1.26 (26H, s), 1.58 (2H, m), 2.03 (3H, s), 2.28 (2H, m), 2.54 (2H, t, J=7.3 Hz), 2.65 (1H, dd, J=7.0, 13.5 Hz), 2.76 (1H, dd, J=5.9, 13.5 Hz), 3.18–3.37 (4H), 3.69 (2H, t, J=6.2 Hz), 4.13 (1H, m), 5.36 (1H, t, J=6.1 Hz), 6.23 (1H, d, J=7.9 Hz).

(65) Preparation of 3-(3-chloropropylsulfonylamino)-1-hexadecylthio-2-(3-methylureido)-propane IIIf2

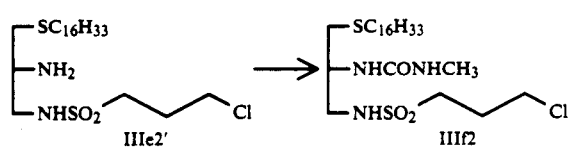

A solution of 0.2 ml of methyl isocyanate in 2 ml of N,N-dimethylformamide is added to a solution of 1.01 g (2.143 mmol) of the amine IIIe2' in 20 ml of N,N-dimethylformamide. The solution is stirred at room temperature for 3 h and ethyl acetate is added. The mixture is washed with water, dried over anhydrous sodium sulfate and concentrated under reduced pressure. The residue is recrystallized from hexane to give 1.107 g (97.8% yield) of the titled compound IIIf2. mp. 79°–80° C.

NMR (CDCl$_3$) δppm: 0.88 (3H, t, J=6.4 Hz), 1.26 (26H, s), 1.57 (2H, m), 1.88 (1H, br. s), 2.28 (2H, m), 2.54 (2H, t, J=7.0 Hz), 2.70 (2H, m), 2.78 (3H, s), 3.17–3.41 (4H), 3.68 (2H, t, J=6.2 Hz), 3.99 (1H, m), 5.12 (1H, br. s), 5.78 (1H. br. s).

(66) Preparation of 3-(N-acetyl-3-chloropropylsulfonylamino)-2-acetamido-1-octadecylcarbamoyloxypropane IIIg3

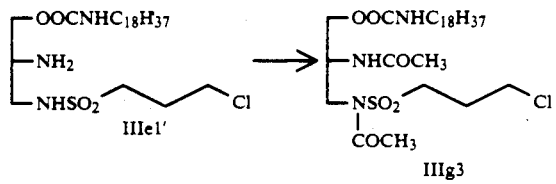

A solution of 0.5 ml of acetic anhydride in 2 ml of dichloromethane is added to a solution of 361 mg of the amine IIIe1' in 2 ml of triethylamine and 10 ml of dichloromethane. The mixture is allowed to stand at room temperature overnight, washed with dilute hydrochloric acid, aqueous sodium hydrogencarbonate and water dried over anhydrous sodium sulfate and concentrated under reduced pressure. The residue is subjected to flash chromatography on silica gel in chloroform:methanol (20:1) and recrystallized from ethyl acetate to give 342 mg (81.7% yield) of the titled compound IIIg3. mp. 116°–117° C.

NMR (CDCl$_3$) δppm 0.88 (3H, t, J=5 Hz), 1.26 (30H, s), 1.50 (2H, m), 1.99 (3H, s), 2.33 (2H, m), 2.46 (3H, s), 3.17 (2H, m), 3.58 (2H, t, J=7 Hz), 3.69 (2H, t, J=7 Hz), 3.90 (2H, m), 4.10 (1H, dd, J=12.5 Hz), 4.22 (1H, dd, J=12.5 Hz), 4.47 (1H, m), 4.81 (1H, t, J=5 Hz), 6.08 (1H, d, J=7 Hz).

(67) Preparation of 3-(3-iodopropylsulfonylamino)-2-methoxycarbonylamino-1-octadecylcarbamoyloxypropane IIe1

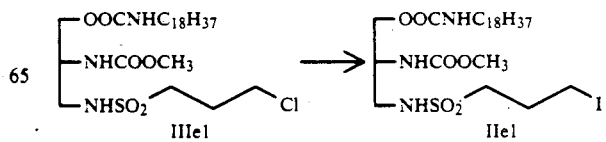

3-(3-Chloropropylsulfonylamino)-2-methoxycarbonylamino-1-octadecylcarbamoyloxypropane IIIe1 is allowed to react and worked up by the same procedure as described in (5). m.p. 97° C. The summary of the experimental condition and the physical data of the product are listed in Table 8.

(68) Preparation of
2-butoxycarbonylamino-3-(3-iodopropylsulfonylamino)-1-octadecylcarbamoyloxypropane IIe2

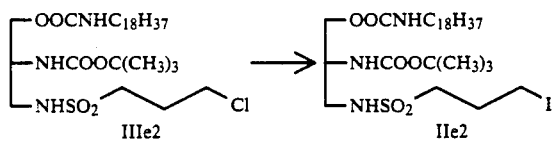

2-Butoxycarbonylamino-3-(3-chloropropylsulfonylamino)-1-octadecylcarbamoyloxypropane IIIe2 is allowed to react and worked up by the same procedure as described in (5). m.p. 96°-98° C. The summary of the experimental condition and the physical data of the product are listed in Table 8.

(69) Preparation of
2-acetamido-3-(3-iodopropylsulfonylamino)-1-octadecylcarbamoyloxypropane IIg1

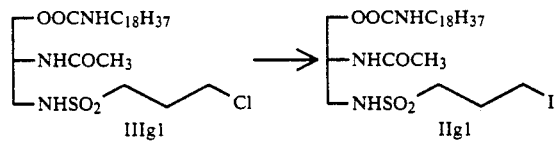

2-acetamido-3-(3-chloropropylsulfonylamino)-1-octadecylcarbamoyloxypropane IIIg1 is allowed to react and worked up by the same procedure as described in (5). m.p. 101°-102° C. The summary of the experimental condition and the physical data of the product are listed in Table 8.

(70) Preparation of
3-(3-iodopropylsulfonylamino)-2-(3-methylureido)-1-octadecylcarbamoyloxypropane IIf1

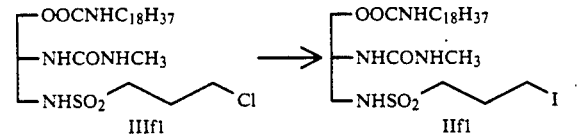

3-(3-chloropropylsulfonylamino)-2-(3-methylureido)-1-octadecylcarbamoyloxypropane IIIf1 is allowed to react and worked up by the same procedure as described in (5). m.p. 87°-89° C. The summary of the experimental condition and the physical data of the product are listed in Table 8.

(71) Preparation of
1-hexadecylthio-3-(3-iodopropylsulfonylamino)-2-methoxycarbonylaminopropane IIe3

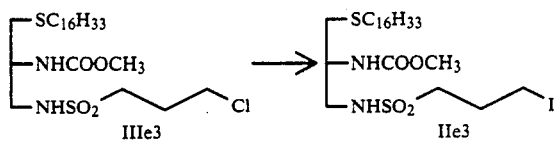

3-(3-Chloropropylsulfonylamino)-1-hexadecylthio-2-methoxycarbonylaminopropane IIIe3 is allowed to react and worked up by the same procedure as described in (5). m.p. 79°-81° C. The summary of the experimental condition and the physical data of the product are listed in Table 8.

(72) Preparation of
2-butoxycarbonylamino-1-hexadecylthio-3-(3-iodopropylsulfonylamino)propane IIe4

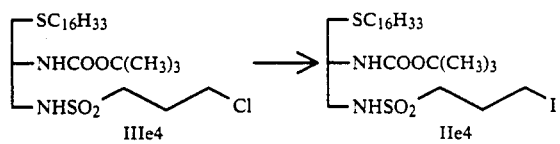

2-Butoxycarbonylamino-3-(3-chloropropylsulfonylamino)-1-hexadecylthiopropane IIIe4 is allowed to react and worked up by the same procedure as described in (5). m.p. 82°-83° C. The summary of the experimental condition and the physical data of the product are listed in Table 8.

(73) Preparation of
2-acetamido-1-hexadecylthio-3-(3-iodopropylsulfonylamino)propane IIg2

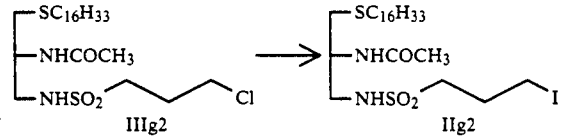

2-Acetamido-3-(3-chloropropylsulfonylamino)-1-hexadecylthiopropane IIIg2 is allowed to react and worked up by the same procedure as described in (5). m.p. 75°-76° C. The summary of the experimental condition and the physical data of the product are listed in Table 8.

(74) Preparation of
1-hexadecylthio-3-(3-iodopropylsulfonylamino)-2-(3-methylureido)propane IIf2

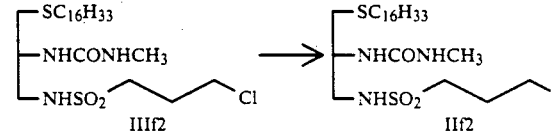

3-(3-Chloropropylsulfonylamino)-1-hexadecylthio-2-(3-methylureido)propane IIIf2 is allowed to react and worked up by the same procedure as described in (5). m.p. 70°-71° C. The summary of the experimental condition and the physical data of the product are listed in Table 8.

(75) Preparation of
3-(N-acetyl-3-iodopropylsulfonylamino)-2-acetamido-
1-octadecylcarbamoyloxypropane IIg3

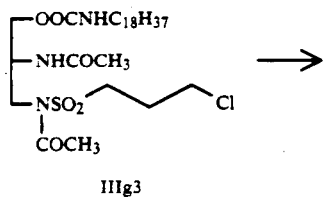

IIIg3

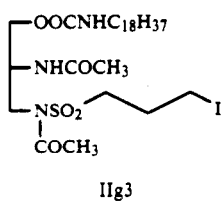

IIg3

3-(N-Acetyl-3-iodopropylsulfonylamino)-2-acetamido-1-octadecylcarbamoyloxypropane IIIg3 is allowed to react and worked up by the same procedure as described in (5). m.p. 118°–119° C. The summary of the experimental condition and the physical data of the product are listed in Table 8.

EXAMPLE 35

Preparation of
1-octadecylcarbamoyloxy-2-methoxycarbonylamino-3-(3-trimethylammoniopropylsulfonylamino)propane iodide Ie1

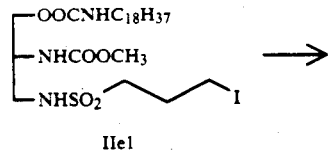

IIe1

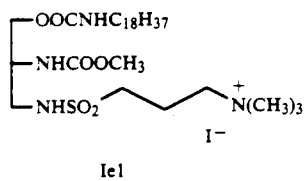

Ie1

3-(3-Iodopropylsulfonylamino)-2-methoxycarbonylamino-1-octadecylcarbamoyloxypropane IIe1 is allowed to react and worked up by the same procedure as described in Example 8. The summary of the experimental condition and the physical data of the product are listed in Table 9.

EXAMPLE 36

2-tert-butoxycarbonylamino-1-octadecylcarbamoyloxy-3-(3-trimethylammoniopropylsulfonylamino)propane iodide Ie2

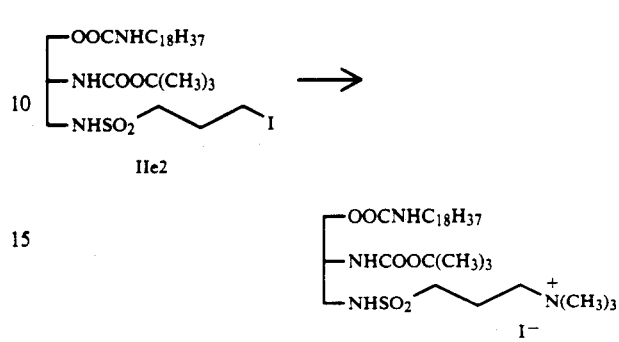

2-tert-Butoxycarbonylamino-3-(3-iodopropylsulfonylamino)-1-octadecylcarbamoyloxypropane IIe2 is allowed to react and worked up by the same procedure as described in Example 8. The summary of the experimental condition and the physical data of the product are listed in Table 9.

EXAMPLE 37

Preparation of
2-acetamido-1-octadecylcarbamoyloxy-3-(3-trimethylammoniopropylsulfonylamino)propane iodide Ig1

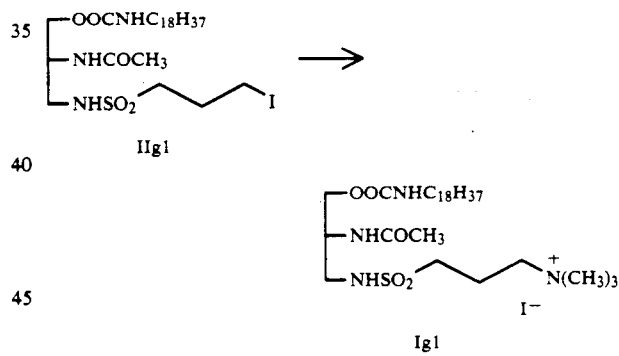

2-Acetamido-3-(3-iodopropylsulfonylamino)-1-octadecylcarbamoyloxypropane IIg1 is allowed to react and worked up by the same procedure as described in Example 8. The summary of the experimental condition and the physical data of the product are listed in Table 9.

EXAMPLE 38

Preparation of
1-octadecylcarbamoyloxy-2-(3-methylureido)-3-(3-trimethylammoniopropylsulfonylamino)propane iodide If1

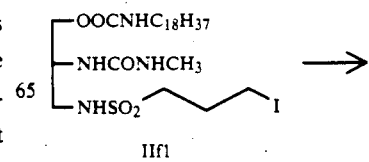

IIf1

-continued

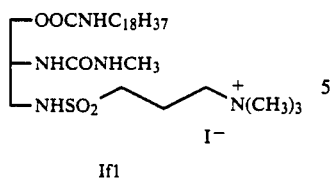

If1

3-(3-Iodopropylsulfonylamino)-2-(3-methylureido)-1-octadecylcarbamoyloxypropane IIf1 is allowed to react and worked up by the same procedure as described in Example 8. The summary of the experimental condition and the physical data of the product are listed in Table 9.

EXAMPLE 39

Preparation of 1-hexadecylthio-2-methoxycarbonylamino-3-(3-trimethylammoniopropylsulfonylamino)propane iodide Ie3

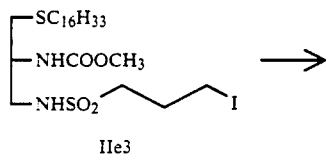

IIe3

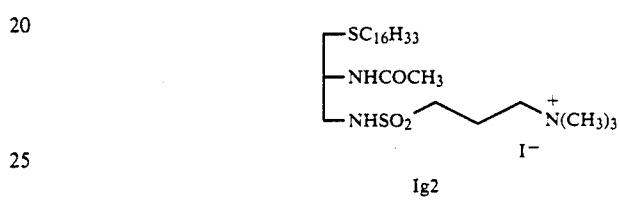

Ie3

1-Hexadecylthio-3-(3-iodopropylsulfonylamino)-2-methoxycarbonylamino propane IIe3 is allowed to react and worked up by the same procedure as described in Example 8. The summary of the experimental condition and the physical data of the product are listed in Table 9.

EXAMPLE 40

Preparation of 2-tert-butoxycarbonylamino-1-hexadecylthio-3-(3-trimethylammoniopropylsulfonylamino)propane iodide Ie4

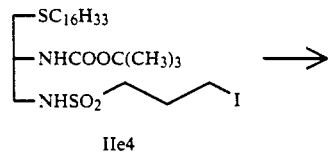

IIe4

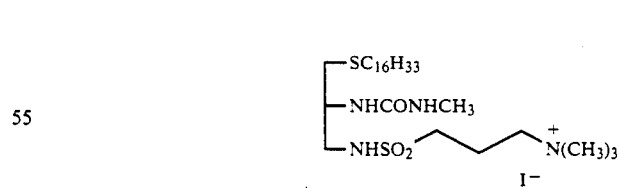

Ie4

2-tert-Butoxycarbonylamino-1-hexadecylthio-3-(3-iodopropylsulfonylamino)propane IIe4 is allowed to react and worked up by the same procedure as described in Example 8. The summary of the experimental condition and the physical data of the product are listed in Table 9.

EXAMPLE 41

Preparation of 2-acetamido-1-hexadecylthio-3-(3-trimethylammoniopropylsulfonylamino)propane iodide Ig2

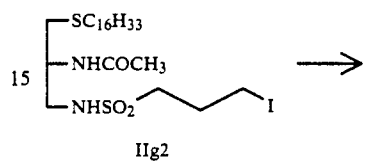

IIg2

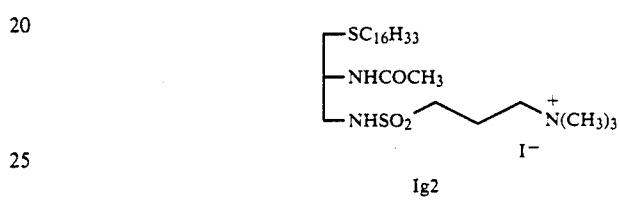

Ig2

2-Acetamido-1-hexadecylthio-3-(3-iodopropylsulfonylamino)propane IIg2 is allowed to react and worked up by the same procedure as described in Example 8. The summary of the experimental condition and the physical data of the product are listed in Table 9.

EXAMPLE 42

Preparation of 1-hexadecylthio-2-(3-methylureido)-3-(3-trimethylammoniopropylamino)propane iodide If2

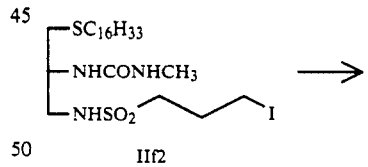

IIf2

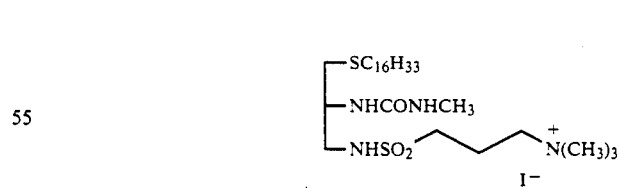

If2

1-Hexadecylthio-3-(3-iodopropylsulfonylamino)-2-(3-methylureido)propane IIf2 is allowed to react and worked up by the same procedure as described in Example 8. The summary of the experimental condition and the physical data of the product are listed in Table 9.

EXAMPLE 43

Preparation of 3-(N-acetyl-3-trimethylammoniopropylsulfonylamino)-2-acetamido-1-octadecylcarbamoyloxypropane iodide Ig3

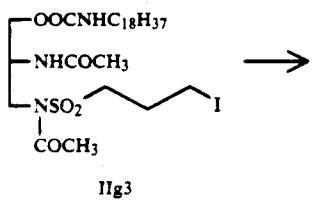

IIg3

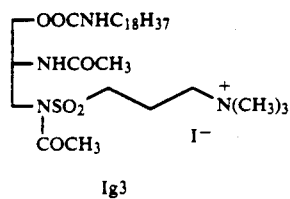

Ig3

3-(N-Acetyl-3-iodopropylsulfonylamino)-2-acetamido-1-octadecylcarbamoyloxypropane IIg3 is allowed to react and worked up by the same procedure as described in Example 8. The summary of the experimental condition and the physical data of the product are listed in Table 9.

EXAMPLE 44

Preparation of 1-octadecylcarbamoyloxy-2-methoxycarbonylamino-3-(3-quinoliniopropylsulfonylamino)propane iodide Ie5

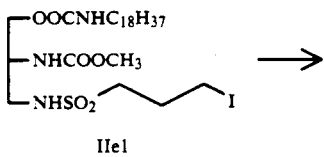

IIe1

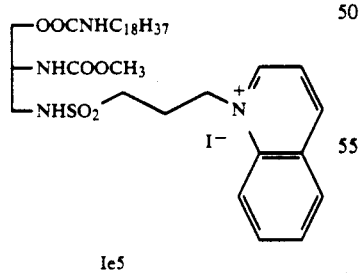

Ie5

3-(3-Iodopropylsulfonylamino)-2-methoxycarbonylamino-1-octadecylcarbamoyloxypropane IIe1 is allowed to react and worked up by the same procedure as described in Example 25. The summary of the experimental condition and the physical data of the product are listed in Table 10.

EXAMPLE 45

Preparation of 2-tert-butoxycarbonylamino-1-octadecylcarbamoyloxy-3-(3-quinoliniopropylsulfonylamino)propane iodide Ie6

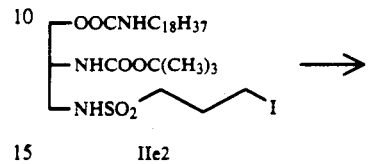

IIe2

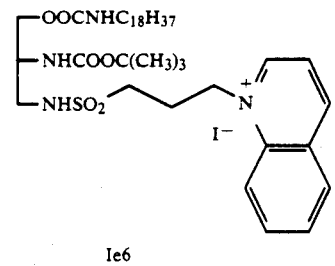

Ie6

2-tert-Butoxycarbonylamino-3-(3-iodopropylsulfonylamino)-1-octadecylcarbamoyloxypropane IIe2 is allowed to react and worked up by the same procedure as described in Example 25. The summary of the experimental condition and the physical data of the product are listed in Table 10.

EXAMPLE 46

Preparation of 2-acetamido-1-octadecylcarbamoyloxy-3-(3-quinoliniopropylsulfonylamino)propane iodide Ig4

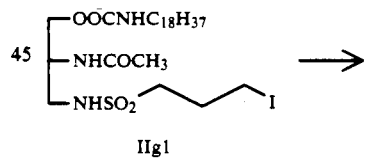

IIg1

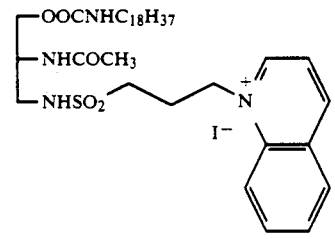

Ig4

2-Acetamido-3-(3-iodopropylsulfonylamino)-1-octadecylcarbamoyloxy propane IIg1 is allowed to react and worked up by the same procedure as described in Example 25. The summary of the experimental condition and the physical data of the product are listed in Table 10.

EXAMPLE 47

Preparation of
1-octadecylcarbamoyloxy-2-(3-methylureido)-3-(3-quinoliniopropylsulfonylamino)propane iodide If3

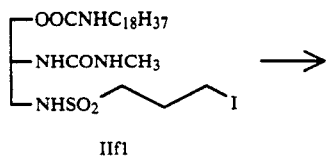

IIf1

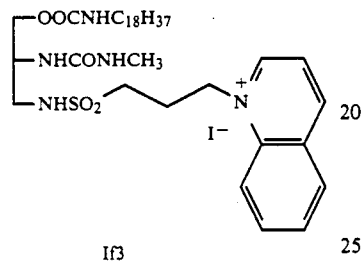

If3

3-(3-Iodopropylsulfonylamino)-2-(3-methylureido)-1-octadecylcarbamoyloxypropane IIf1 is allowed to react and worked up by the same procedure as described in Example 25. The summary of the experimental condition and the physical data of the product are listed in Table 10.

EXAMPLE 48

Preparation of
1-hexadecylthio-2-methoxycarbonylamino-3-(3-quuinoliniopropylsulfonylamino)propane iodide Ie7

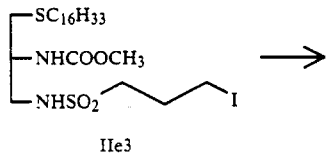

IIe3

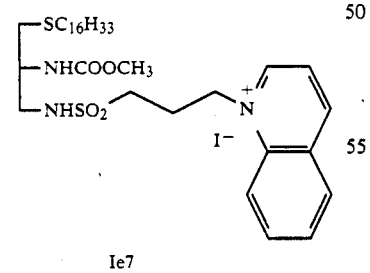

Ie7

1-Hexadecylthio-3-(3-iodopropylsulfonylamino)-2-methoxycarbonylaminopropane IIe3 is allowed to react and worked up by the same procedure as described in Example 25. The summary of the experimental condition and the physical data of the product are listed in Table 10.

EXAMPLE 49

Preparation of
2-tert-butoxycarbonylamino-1-hexadecylthio-3-(3-quinoliniopropylsulfonylamino)propane iodide Ie8

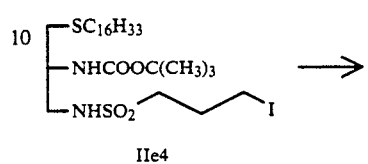

IIe4

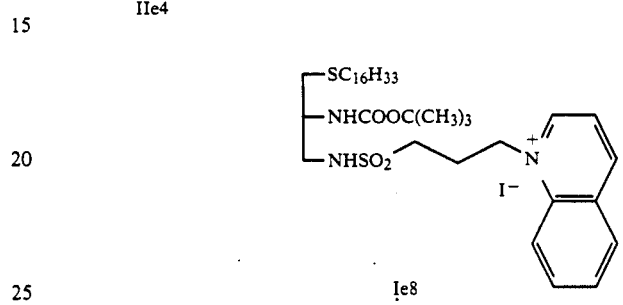

Ie8

2-tert-Butoxycarbonylamino-1-hexadecylthio-3-(3-iodopropylsulfonylamino)propane IIe4 is allowed to react and worked up by the same procedure as described in Example 25. The summary of the experimental condition and the physical data of the product are listed in Table 10.

EXAMPLE 50

Preparation of
2-acetamido-1-hexadecylthio-3-(3-quinoliniopropylsulfonylamino)propane iodide Ig5

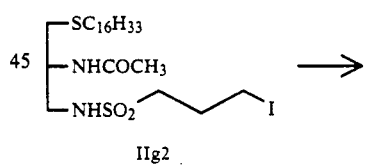

IIg2

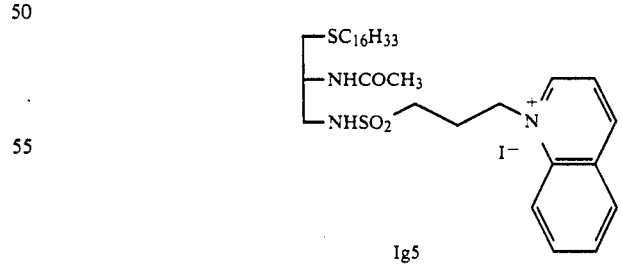

Ig5

2-Acetamido-1-hexadecylthio-3-(3-iodopropylsulfonylamino)propane IIg2 is allowed to react and worked up by the same procedure as described in Example 25. The summary of the experimental condition and the physical data of the product are listed in Table 10.

EXAMPLE 51

Preparation of
1-hexadecylthio-2-(3-methylureido)-3-(3-quinolinio-propylamino)propane iodide If4

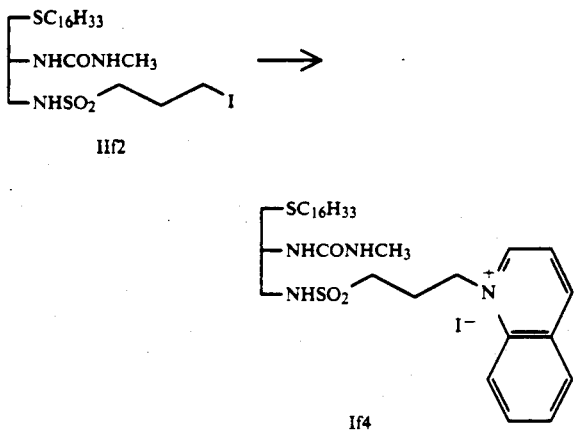

1-Hexadecylthio-3-(3-iodopropylsulfonylamino)-2-(3-methylureido)propane IIf2 is allowed to react and worked up by the same procedure as described in Example 25. The summary of the experimental condition and the physical data of the product are listed in Table 10.

EXAMPLE 52

Preparation of
3-(N-acetyl-3-quinoliniopropylsulfonylamino)-2-acetamido-1-octadecylcarbamoyloxypropane iodide Ig6

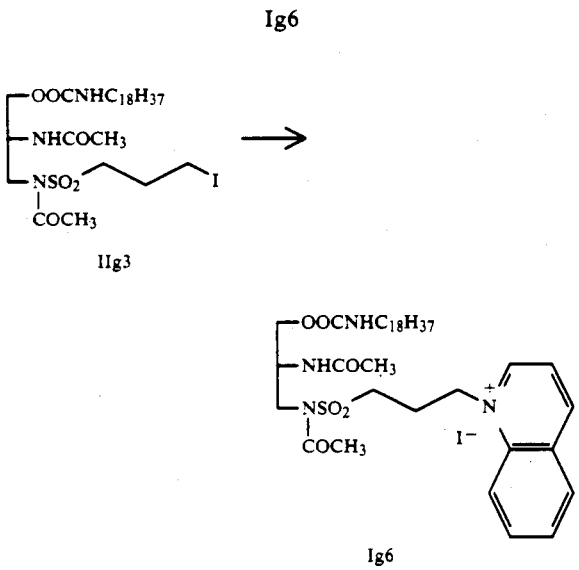

3-(N-Acetyl-3-iodopropylsulfonylamino)-2-acetamido-1-octadecylcarbamoyloxypropane IIg3 is allowed to react and worked up by the same procedure as described in Example 25. The summary of the experimental condition and the physical data of the product are listed in Table 10.

(76) Preparation of
1-tert-butyldimethylsilyloxy-3-triphenylmethoxypropan-2-ol 2h

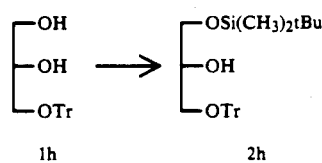

A solution of 14.2 g (94 mM) of tert-butyldimethylsilyl chloride and 12.8 g (198 mM) of imidazole in 200 ml of dimethylformamide is stirred at room temperature for 30 minutes. To this solution is added a solution of 31.45 g (94 mM) of 3-triphenylmethoxy-1,2-propanediol 1 h in 100 ml of dimethylformamide dropwise and the mixture is stirred at room temperature for another 2 hr. The mixture is poured into ice-water and the product is isolated by dichloromethane extraction. The dichloromethane layer is washed with water (twice) and saturated aqueous sodium chloride, dried over anhydrous magnesium sulfate and evaporated. The residue is purified by column silica gel chromatography using toluene:ethyl acetate (9:1) mixture as an eluent and 40.7 g (90% yield) of title compound 2h is obtained.

NMR: δ(CDCl$_3$) 0.02 & 0.03 (s, each 3H), 0.84 (s, 9H), 2.46 (d, J=5 Hz, 1H), 3.14 (ABX, J=9.2 & 5.84 Hz, 1H), 3.22 (ABX, J=9.2 & 5.76 Hz, 1H), 3.67 (ABX, J=9.40 & 4.91 Hz, 1H), 3.70 (ABX, J=9.40 & 3.09 Hz, 1H), 3.75–3.9 (m, 1H), 7.1–7.5 (m, 15H).

(77) Preparation of
1-tert-butyldimethylsilyloxy-2-(5-methyl-2H-tetrazol-2-yl)-3-triphenylmethoxypropane 3h and
1-tert-butyldimethylsilyloxy-2-(5-methyl-1H-tetrazol-1-yl)-3-triphenylmethoxypropane 3i

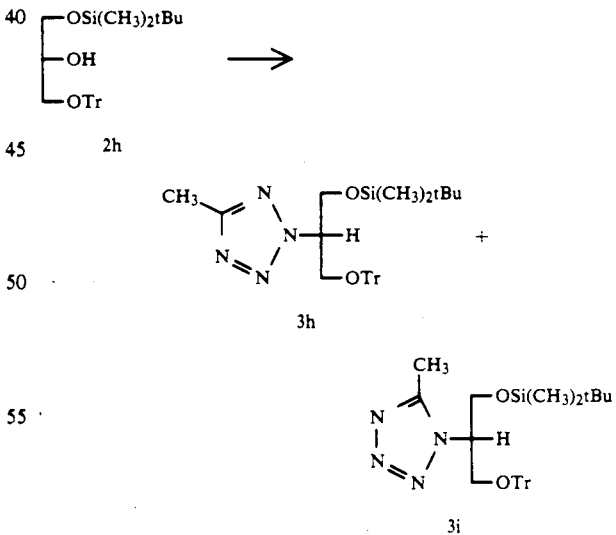

To a stirred solution of 1.0 g (2.23 mM) of 1-tert-butyldimethylsilyloxy-3-triphenylmethoxypropan-2-ol 2h, 877 mg (3.35 mM) of triphenylphosphine, and 0.53 ml (3.35 mM) of diethyl azodicarboxylate in 30 ml of tetrahydrofuran at 0° C., is added 281 mg (3.35 mM) of 5-methyltetrazole dropwise and the mixture is stirred at room temperature for 15 hr. The product is isolated by dichloromethane extraction. The dichloromethane layer is washed with saturated aqueous sodium bicarbonate, dried and evaporated. The residue is separated by column silica gel chromatography using n-hexane:toluene (1:1) and toluene:ethyl acetate (9:1) mixture as an eluent and 0.74 g (64% yield) of the title compounds 3h and 0.36 g (31% yield) of 3i are obtained.

Compound 3g: Oil,
NMR: δppm (CDCl₃) −0.10 (s, 3H), −0.08 (s, 3H), 0.74 (s, 9H), 2.54 (s, 3H), 3.57 (ABX, J=9.8 & 4.6 Hz, 1H), 3.63 (ABX, J=9.8 & 7.6 Hz, 1H), 4.0-4.15 (m, 2H), 4.95-5.15 (m, 1H), 7.1-7.35 (m, 15H).

Compound 3i: Oil,
NMR: δppm (CDCl₃) −0.16 (s, 3H), −0.09 (s, 3H), 0.73 (s, 9H), 2.56 (s, 3H), 3.59 (ABX, J=9.8 & 5.6 Hz, 1H), 3.67 (ABX, J=9.8 & 9.4 Hz, 1H), 3.91 (ABX, J=10.4 & 9.9 Hz, 1H), 3.97 (ABX, J=10.4 & 5.9 Hz, 1H), 4.35-4.5 (m, 1H), 7.15-7.4 (m, 15H).

(78) Preparation of 2-(5-methyl-2H-tetrazol-2-yl)-3-triphenylmethoxypropanol 4h

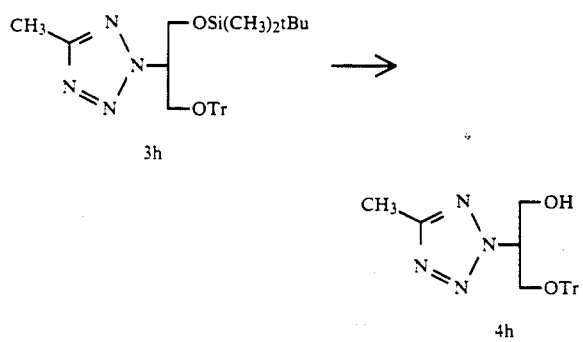

To a solution of 17.2 g (33.4 mM) of 1-tert-butyldimethylsilyloxy-2-(5-methyl-2H-tetrazol-2-yl)-3-triphenylmethoxypropane 3h in 300 ml of tetrahydrofuran is added a solution of 36.8 ml (36.8 mM) of 1M tetra-b-butylammonium fluoride in tetrahydrofuran and the mixture is stirred at room temperature for 10 minutes. The product is isolated by dichloromethane extraction. The dichloromethane layer is washed with water and saturated aqueous sodium chloride, dried over anhydrous magnesium sulfate and evaporated. The residue is purified by column silica gel chromatography using toluene:ethyl acetate (9:1) mixture as an eluent and 12.8 g (96% yield) of the title compound 4h is obtained. mp. 126°-127° C. (Recryastallized from dichloromethane-methanol).

NMR: δppm (CDCl₃) 2.49 (s, 3H), 2.94 (t, J=6.5 Hz, 1H), 3.6-3.75 (m, 2H), 3.95-4.3 (m, 2H), 4.9-5.1 (m, 1H), 7.15-7.45 (m, 15H).

(79) Preparation of 2-(5-methyl-1H-tetrazol-1-yl)-3-triphenylmethoxypropanol 4i

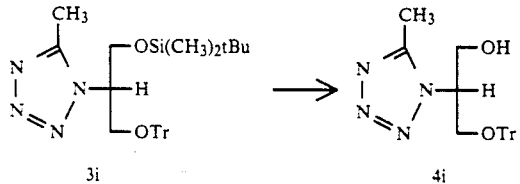

A solution of 5.92 g (12 mM) of 1-1-tert-butyldimethylsilyloxy-2-(5-methyl-1H-tetrazol-1-yl)-3-triphenyl methoxypropane 3i in 100 ml of tetrahydrofuran is allowed to react with 12.7 ml (12.7 mM) of tetra-n-butylammonium fluoride in 100 ml of tetrahydrofuran and the resulting mixture is worked up by the same procedure as described in (78) to give 4.17 g of the titled compound 4i. (Yield 91%).

NMR: δppm (CDCl₃) 2.49 (s, 3H), 3.5-3.65 (m, 3H), 3.9-4.2 (m, 3H), 4.35-4.5 (m, 1H), 7.1-7.35 (m, 15H).

(80) Preparation of 1-hexadecylthio-2-(5-methyl-1H-tetrazol-1-yl)-3-triphenylmethoxypropane 5i

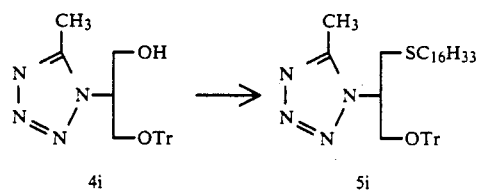

To a stirred solution of 1.86 g (4.6 mM) 2-(5-methyl-1H-tetrazol-1-yl)-3-triphenylmethoxypropanol 4i and 0.71 ml (5.1 mM) of triethylamine in 50 ml of dichloromethane at 0° C., is added 0.38 ml (4.8 mM) of methanesulfonyl chloride dropwise and the mixture is stirred at room temperature for overnight. The product is isolated by dichloromethane extraction. The dichloromethane layer is washed with water (twice) and saturated aqueous sodium chloride, dried over anhydrous magnesium sulfate and evaporated to obtain crude methane sulfonate product. A mixture of 204 mg (5.1 mM) of 60% sodium hydride in oil, 1.75 ml (5.5 mM) of n-hexadecyl mercaptane (98% purity) in 20 ml of benzene is allowed to react at 70° C. for 30 min and to the resulting mixture after cooling is added a solution of the methane sulfonate product obtained above in 20 ml of benzene and 100 mg of dicyclohexyl-18-crown-6 and the mixture is stirred at room temperature for 4 hr. The mixture is pured into ice-water and the product is isolated by ethyl acetate extraction. The ethyl acetate layer is washed with water and saturated aqueous sodium chloride, dried over magnesium sulfate and evaporated. The residue is purified by column silica gel chromatography using toluene:ethyl acetate (9:1) mixture as an eluent and 2.97 g (100% yield) of the title compound 5i is obtained.

NMR: δppm (CDCl₃) 0.88 (t, J=6 Hz, 3H), 2.21 (t, J=7.5 Hz, 2H), 2.56 (s, 3H), 2.99 (d, J=7.2 Hz, 2H), 3.62 (ABX, J=10 & 4.9 Hz, 1H), 3.68 (ABX, J=10 & 8.2 Hz, 1H), 4.2-4.4 (m, 1H), 7.1-7.4 (m, 15H).

(81) Preparation of 3-hexadecylthio-2-(5-methyl-1H-tetrazol-1-yl)propanol Vi1

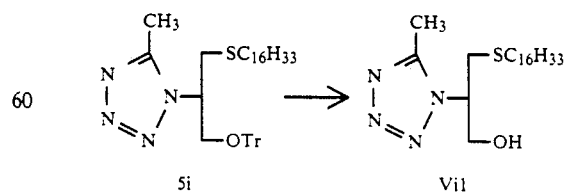

A mixture of 2.90 g (4.5 mM) of 1-hexadecylthio-2-(5-methyl-1H-tetrazol-1-yl)-3-triphenylmethoxypropane and 170 mg (0.9 mM) of p-toluenesulfonic acid monohydrate in 60 ml of methanol-tetrahydrofuran (1:1) mixture is stirred at room temperature for overnight. The mixture was poured into ice-water containing 151 mg (1.8 mM) of sodium bicarbonate and the product is isolated by ethyl acetate extraction. The ethyl acetate layer is washed with saturated aqueous sodium chloride, dried over anhydrous magnesium sulfate and evaporated. The residue is purified by column silica gel chromatography using toluene:ethyl acetate (4:1–1:1) mixture as an eluent and 1.46 g (81% yield) of the title compound Vi1 is obtained. mp. 77°–78° C.

NMR: δppm (CDCl$_3$) 0.88 (t, J=7 Hz, 3H), 1.4–1.6 (m, 2H), 2.34 (t, J=7.4 Hz, 2H), 2.59 (s, 3H), 3.03 (ABX, J=14.4 & 10.1 Hz, 1H), 3.07 (ABX, J=14.4 & 5.9 Hz, 1H), 4.08 (ABX, J=10.8 & 3.2 Hz, 1H), 4.15 (ABX, J=10.8 & 7.6 Hz, 1H), 4.35–4.55 (m, 1H).

(82) Preparation of 2-(5-methyl-1H-tetrazol-1-yl)-3-octadecylcarbamoyloxypropanol Vi2

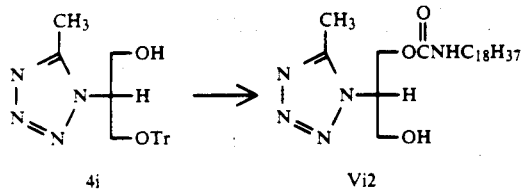

A mixture of 1.9 g (4.7 mM) of 2-(5-methyl-1H-tetrazol-1-yl)-3-triphenylmethoxypropane-1-ol and 20 ml (5.6 mM) of n-octadecyl isocyanate in 40 ml of pyridine is allowed to react at room temperature of 60 hr. and at 60° C. for 2 hr. The mixture is isolated by dichloromethane extraction. The dichloromethane layer is washed with water and saturated aqueous sodium chloride, dried over anhydrous magnesium sulfate and evaporated. The residue is purified by column silica gel chromatography using toluene:ethyl acetate (9:1–2:1) mixture as an eluent to obatin 1.84 g of crude 1-n-octadecylcarbamate derivative. A mixture of 1.84 g of the crude 1-n-octadecylcarbamate derivative obatined above and 150 mg (0.79 mM) of p-toluenesulfonic acid monohydrate in 50 ml of methanol-tetrahydrofuran (1:1) mixture is stirred at room temperature for overnight. The mixture is poured into ice-water containing 132 mg (1.6 mM) of sodium bicarbonate and the product is isolated by dichloromethane extraction. The dichloromethane layer is washed with saturated aqueous sodium chloride, dried over magnesium sulfate and evaporated. The residue is purified by column silica gel chromatography using toluene-ethyl acetate (2:1–1:1) mixture and ethyl acetate as an eluent and 1.05 g (49% from 4i) of the title compound Vi2 is obtained. mp. 80°–83° C.

NMR: δppm (CDCl$_3$) 0.88 (t, J=6.4 Hz, 3H), 1.4–1.6 (m, 2H), 2.54 (s, 3H), 3.13 (quartet, J=6.4 Hz, 2H), 4.0–4.25 (m, 2H), 4.38 (ABX, J=11.8 & 8.3 Hz, 1H), 4.56 (ABX, J=11.8 & 4.5 Hz, 1H), 4.65–4.8 (m, 1H), 5.01 (t, J=5.7 Hz, 1H).

(83) Preparation of 1-hexadecylthio-2-(5-methyl-2H-tetrazol-2-yl)-3-triphenylmethoxypropane 5h

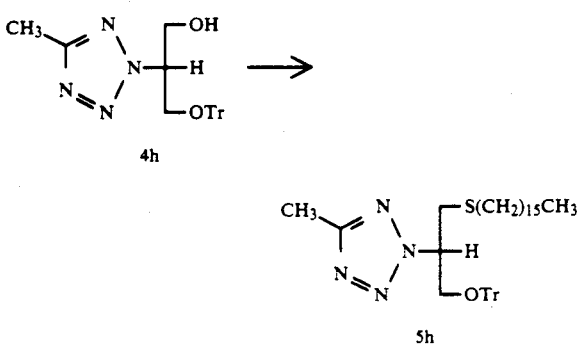

Using 2.5 ml (18 mM) of triethylamine and 1.3 ml (17 mM) of methanesulfonyl chloride in 150 ml of dichloromethane, 6.50 g (16 mM) of 2-(5-methyl-2H-tetrazol-2-yl)-3-triphenylmethoxypropanol 4h is converted to methanesulfonate derivative by the same procedure as descrived in example 80. Using 0.71 g (18 mM) of 60% sodium hydride in oil, 4.70 g (18 mM) of n-hexadecyl mercaptane (98% purity), and the crude methane sulfonate derivative obtained above in 150 ml of benzene is converted to the title compound 5h by the same procedure as described in (80). The product is used for the next reaction without further purification.

NMR: δppm (CDCl$_3$) 0.88 (t, J=7 Hz, 3H), 2.34 (t, J=7.5 Hz, 2H), 2.55 (s, 3H), 3.05 (d, J=7.2 Hz, 2H), 3.60 (ABX, J=10 & 5.0 Hz, 1H), 3.66 (ABX, J=10 & 7.3 Hz, 1H), 4.9–5.1 (m, 1H), 7.15–7.5 (m, 15H).

(84) Preparation of 3-hexadecylthio-2-(5-methyl-2H-tetrazol-2-yl)propanol Vh1

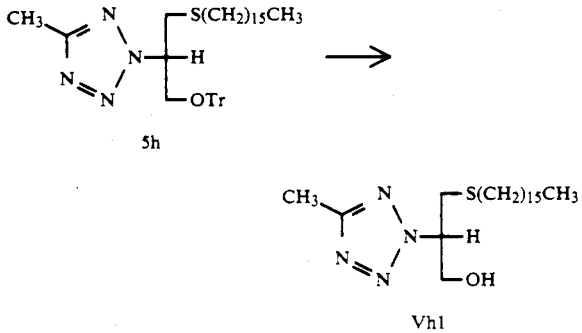

Using 10.2 g of crude 1-hexadecylthio-2-(5-methyl-2H-tetrazol-2-yl)-3-triphenylmethoxypropane 5h and 500 mg (2.6 mM) of p-toluene sulfonic acid monohydrate in 200 ml of methanol-tetrahydrofurane (1:1) mixture is converted to 3.17 g (49% from the compound 4h) of the title compound Vh1 by the same procedure as described in (81).

NMR δppm (CDCl$_3$) 0.88 (t, J=7 Hz, 3H), 1.45–1.65 (m, 2H), 2.48 (t, J=7.4 Hz, 2H), 2.52 (s, 3H), 3.08 (ABX, J=14.6 & 7.6 Hz, 1H), 3.12 (ABX, J=14.6 & 7.4 Hz, 1H), 4.16 (ABX, J=12.4 & 4.3 Hz, 1H), 4.19 (ABX, J=12.4 & 7.7 Hz, 1H), 4.9–5.1 (m, 1H).

(85) Preparation of 2-(5-methyl-2H-tetrazol-2-yl)-3-octadecylcarbamoyloxypropanol Vh2

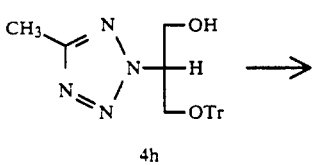

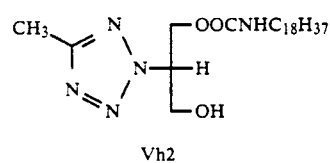

Using 5.71 g (14 mM) of 2-(5-methyl-2H-tetrazol-2-yl)-3-triphenylmethoxypropanol 4h and 5.9 ml (17 mM) of n-octadecyl isocyanate in 120 ml of pyridine is converted to the crude carbamate derivative by the same procedure as described in (82). Using 5.74 g of the crude carbamate derivative obtained above and 400 mg (2.1 mM) of p-toluenesulfonic acid monohydrate in 150 ml of methanol-tetrahydrofuran (1:1) mixture is converted to 3.39 g (52% from the compound 4h) of the title compound Vh2 by the same procedure as descrived in (82). mp. 76°–77° C.

NMR: δppm (CDCl$_3$) 0.88 (t, J=7 Hz, 3H), 1.35–1.55 (m, 2H), 2.54 (s, 3H), 3.14 (quartet, J=6.5 Hz, 2H), 4.14 (d, J=5.8 Hz, 2H), 4.55–4.7 (m, 2H), 4.8–4.95 (m, 1H), 5.0–5.2 (m, 1H).

(86) Preparation of 3-hexadecylthio-2-(5-methyl-1H-tetrazol-1-yl)propylamine IVi1

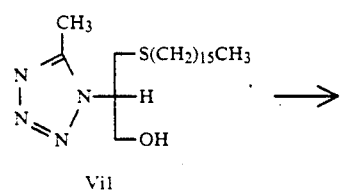

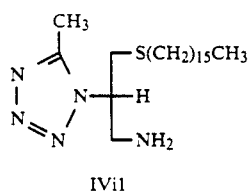

3-Hexadecylthio-2-(5-methyl-1H-tetrazol-1-yl)propanol Vi1 is allowed to react and worked up by the same procedure as described in (3). The summary of the experimental condition and the physical data of the product are listed in Tables 5 and 6.

The prepared phthalimide is used for the next reaction without further purification.

(87) Preparation of 3-(3-chloropropylsulfonylamino)-1-hexadecylthio-2-(5-methyl-1H-tetrazol-1-yl)propane IIIi1

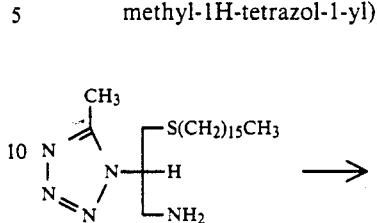

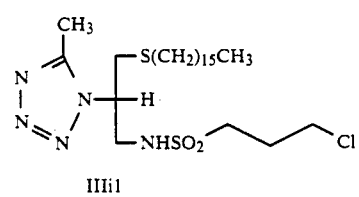

3-Hexadecylthio-2-(5-methyl-1H-tetrazol-1-yl)propylamine IVi1 is allowed to react and worked up by the same procedure as described in (4). m.p. 62°–62.5° C. The summary of the experimental condition and the physical data of the product are listed in Table 7.

The yield is calculated from the 3-hydroxy compound 5i.

(88) Preparation of 1-hexadecylthio-3-(3-iodopropylsulfonylamino)-2-(5-methyl-1H-tetrazol-1-yl)propane IIi1

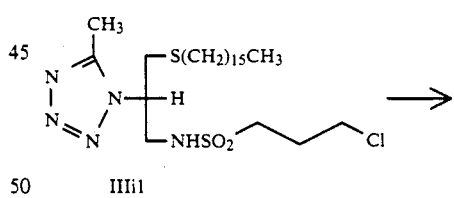

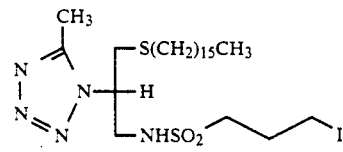

3-(3-Chloropropylsulfonylamino)-1-hexadecylthio-2-(5-methyl-1H-tetrazol-1-yl)propane IIIi1 is allowed to react and worked up by the same procedure as described in (5). m.p. 63.5°–65.5° C. The summary of the experimental condition and the physical data of the product are listed in Table 8.

EXAMPLE 53

Preparation of 1-n-hexadecylthio-2-(5-methyl-1H-tetrazol-1-yl)-3-(3-trimethylammoniopropylsulfonylamino)propane iodide Ii1

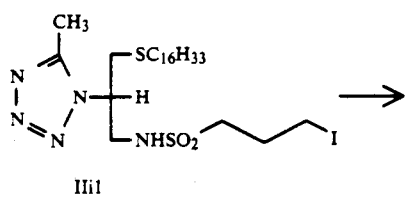

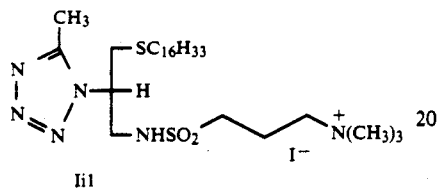

1-Hexadecylthio-3-(3-iodopropylsulfonylamino)-2-(5-methyl-1H-tetrazol-1-yl)propane IIi1 is allowed to react and worked up by the same procedure as described in Example 8. The summary of the experimental condition and the physical data of the product are listed in Table 9.

(89) Preparation of 2-(5-methyl-1H-tetrazol-1-yl)-3-octadecylcarbamoyloxypropylamine IVi2

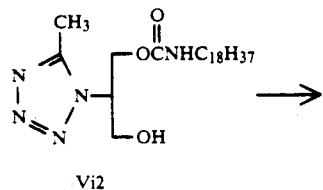

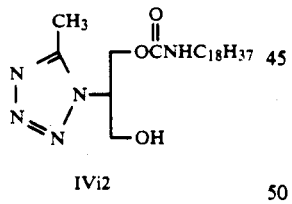

To a stirred solution of 1.02 g (2.25 mM) of 2-(5-methyl-1H-tetrazol-1-yl)-3-octadecylcarbamoyloxypropanol Vi2, 885 mg (3.38 mM) of triphenylphosphine, and 1.9 ml (3.38 mM) of 1.8 mM benzene solution of hydrazoic acid in 50 ml of tetrahydrofurane at −50° C. is added 0.53 ml (3.38 mM) of diethyl azodicarboxylate dropwise and the mixture is raised to room temperature during 2 hr. Subsequently, 150 mg of 10% palladium carbon is added to the mixture which is stirred under hydrogen gas for 30 minutes. After 10% palldium carbon filtered off, the solvent is evaporated. The residue obtained is purified by column silica gel chromatography using ethyl acetate-choroform/methanol (9/1) mixture as an eluent and 0.82 g (81% yield) of the title compound is obtained.

NMR: δppm (CDCl$_3$) 0.88 (t, J=7 Hz, 3H), 2.52 (s, 3H), 3.13 (quartet, J=6.6 Hz, 2H), 3.15–3.45 (m, 2H), 4.23 (ABX, J=12.6 & 9.8 Hz, 1H), 4.52 (ABX, J=12.6 & 4.2 Hz, 1H), 4.5–4.65 (m, 1H), 5.07 (t, J=6 Hz, 1H).

(90) Preparation of 3-(3-chloropropylsulfonylamino)-2-(5-methyl-1H-tetrazol-1-yl)-1-octadecylcarbamoyloxypropane IIIi2

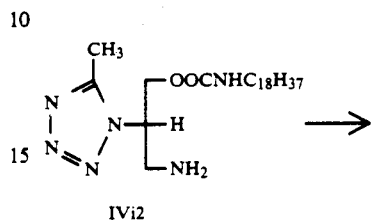

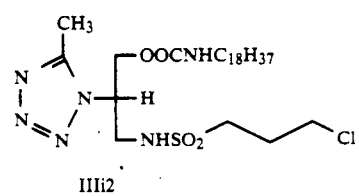

2-(5-Methyl-1H-tetrazol-1-yl)-3-octadecylcarbamoyloxypropylamine IVi2 is allowed to react and worked up by the same procedure as described in (4). m.p. 74°–77° C. The summary of the experimental condition and the physical data of the product are listed in Table 7.

(91) Preparation of 3-(3-iodopropylsulfonylamino)-2-(5-methyl-1H-tetrazol-1-yl)-1-octadecylcarbamoyloxypropane IIi2

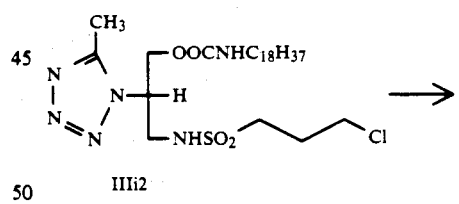

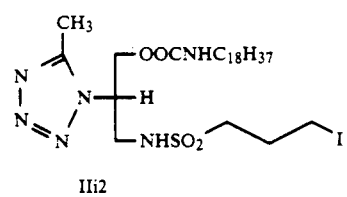

3-(3-Iodopropylsulfonylamino)-2-(5-methyl-1H-tetrazol-1-yl)-1-octadecylcarbamoyloxypropane IIIi2 is allowed to react and worked up by the same procedure as described in (5). m.p. 82.5°–83.5° C. The summary of the experimental condition and the physical data of the product are listed in Table 8.

EXAMPLE 54

Preparation of 2-(5-methyl-1H-tetrazol-1-yl)-1-octadecylcarbamoyloxy-3-(3-quinoliniopropylsulfonylamino)propane iodide Ii3

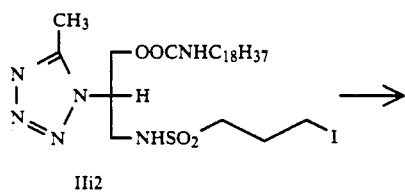

IIi2

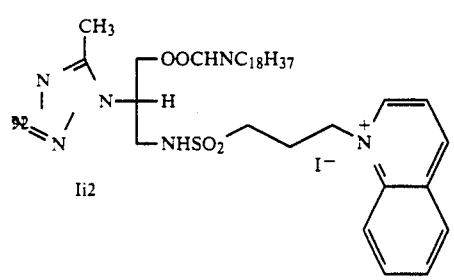

Ii2

3-(3-Iodopropylsulfonylamino)-2-(5-methyl-1H-tetrazol-1-yl)-1-octadecylcarbamoyloxypropane IIi2 is allowed to react and worked up by the same procedure as described in Example 25. The summary of the experimental condition and the physical data of the product are listed in Table 10.

(92) Preparation of 3-hexadecylthio-2-(5-methyl-2H-tetrazol-2-yl)propylamine IVh1

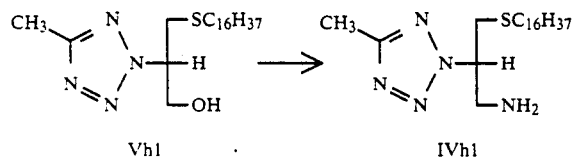

Vh1   IVh1

3-hexadecylthio-2-(5-methyl-2H-tetrazol-2-yl)propanol Vh1 is allowed to react and worked up by the same procedure as described in (3). The phthalimide compound: m.p. 82°–83° C. The summary of the experimental condition and the physical data of the product are listed in Tables 5 and 6.

(93) Preparation of 3-(3-chloropropylsulfonylamino)-1-hexadecylthio-2-(5-methyl-2H-tetrazol-2-yl)propane IIIh1

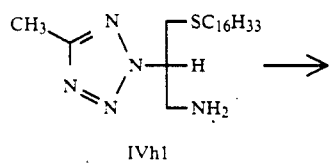

IVh1

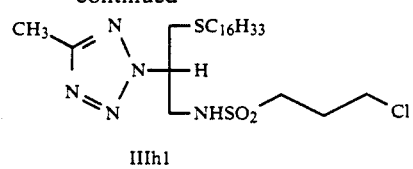

IIIh1

3-Hexadecylthio-2-(5-methyl-2H-tetrazol-2-yl)propylamine IVh1 is allowed to react and worked up by the same procedure as described in (4). The summary of the experimental condition and the physical data of the product are listed in Table 7.

(94) Preparation of 1-hexadecylthio-3-(3-iodopropylsulfonylamino)-2-(5-methyl-2H-tetrazol-2-yl)propane IIh1

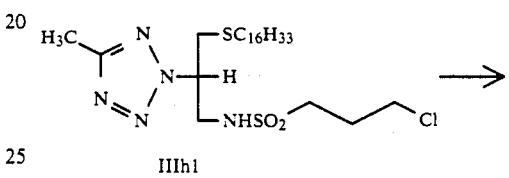

IIIh1

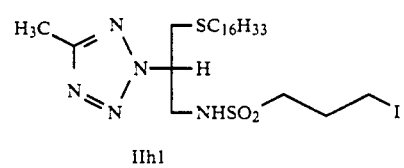

IIh1

3-(3-Chloropropylsulfonylamino)-1-hexadecylthio-2-(5-methyl-2H-tetrazol-2-yl)propane IIIh1 is allowed to react and worked up by the same procedure as described in (5). m.p. 50°–51° C. The summary of the experimental condition and the physical data of the product are listed in Table 8.

EXAMPLE 55

Preparation of 1-hexadecylthio-2-(5-methyl-2H-tetrazol-2-yl)-3-(3-trimethylammoniopropylsulfonylamino)propane iodide Ih1

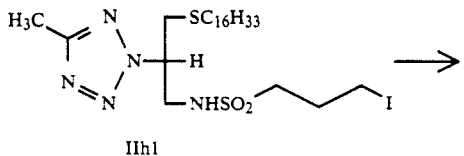

IIh1

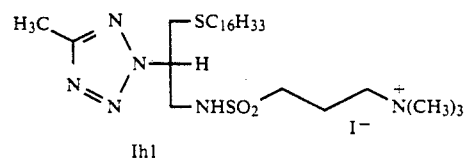

Ih1

1-Hexadecylthio-3-(3-iodopropylsulfonylamino)-2-(5-methyl-2H-tetrazol-2-yl)propane IIh1 is allowed to react and worked up by the same procedure as described in Example 8. The summary of the experimental condition and the physical data of the product are listed in Table 9.

(95) Preparation of 2-(5-methyl-2H-tetrazol-2-yl)-3-octadecylcarbamoyloxypropylamine VIh2

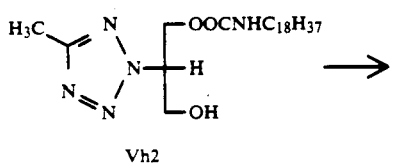

Vh2

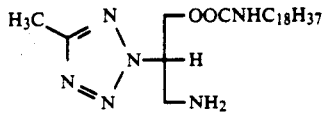

IVh2

Using 2.57 g (5.7 mM) of 2-(5-methyl-2H-tetrazoyl-2-yl)-3-octadecylcarbamoyloxypropanol Vh2, 2.23 g (8.6 mM) of triphenylphosphine, 4.7 ml (8.6 mM) of 1.8 mM benzene solution of hydrazoic acid, and 1.44 g (8.6 mM) of diethyl azodicarboxylate in tetrahydrofurane is converted to azido derivative by the sme procedure as described in (89). Using the azido derivative obtained above and 350 mg of 10% palladium carbon is converted to the title compound by the same procedure as described in (89). The crude product containing a trace of impurity can be purified at the next step.

NMR: δppm (CDCl$_3$) 0.88 (t, J=6.5 Hz, 3H), 1.4-1.65 (m, 2H), 2.55 (s, 3H), 3.12 (quartet, J=6.6 Hz, 2H), 3.25-3.35 (m, 2H), 4.47 (ABX, J=11.6 & 8.0 Hz, 1H), 4.59 (ABX, J=11.6 & 4.1 Hz, 1H), 4.8-4.95 (m, 1H), 4.95-5.1 (m, 1H).

(96) Preparation of 3-(3-chloropropylsulfonylamino)-2-(5-methyl-2H-tetrazol-2-yl)-1-octadecylcarbamoyloxypropane IIIh2

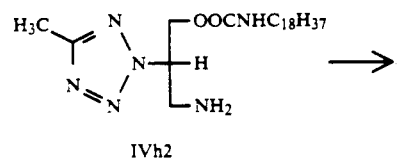

IVh2

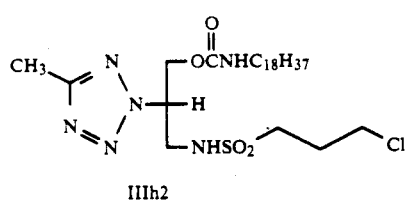

IIIh2

2-(5-Methyl-2H-tetrazol-2-yl)-1-octadecylcarbamoyloxypropylamine IVh2 is allowed to react and worked up by the same procedure as described in (4). m.p. 70°-70.5° C. The summary of the experimental condition and the physical data of the product are listed in Table 7.

The yield is calculated from the hydroxy compound Vh2.

(97) Preparation of 3-(3-iodopropylsulfonylamino)-2-(5-methyl-2H-tetrazol-2-yl)-1-octadecylcarbamoyloxypropane IIh2

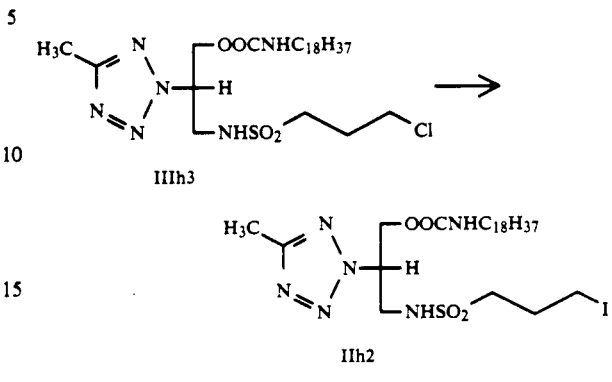

3-(3-Chloropropylsulfonylamino)-2-(5-methyl-2H-tetrazol-2-yl)-1-octadecylcarbamoyloxypropane IIIh3 is allowed to react and worked up by the same procedure as described in (5). m.p. 53.5°-54° C. The summary of the experimental condition and the physical data of the product are listed in Table 8.

EXAMPLE 56

Preparation of 2-(5-methyl-2H-tetrazol-2-yl)-1-octadecylcarbamoyloxy-3-(3-quinoliniopropylsulfonylamino)propane iodide Ih3

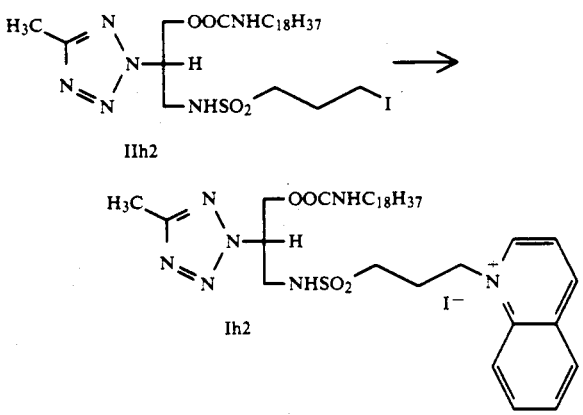

3-(3-Iodopropylsulfonylamino)-2-(5-methyl-2H-tetrazol-2-yl)-1-octadecylcarbamoyloxypropane IIh2 is allowed to react and worked up by the same procedure as described in Example 25. The summary of the experimental condition and the physical data of the product are listed in Table 10.

(98) Preparation of 1-tert-butyldimethylsilyloxy-2-(3-isoxazolyloxy)-3-triphenylmethoxypropane 3j

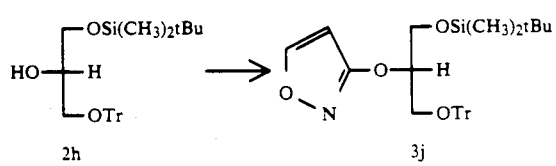

A mixture of 6.72 g (15 mM) of 1-tert-butyldimethylsilyloxy-3-triphenylmethoxypropane-2-ol 2h, 1.53 g (18 mM) of 3-hydroxyisoxazole, 4.71 g (18 mM) of triphenylphosphine, and 3.10 g of diethyl azodicarboxylate in 100 ml of tetrahydrofuran is allowed to react by the same procedure as described in (77) to give 7.24 g of the titled compound 3j (94% yield).

NMR: δppm (CDCl₃) 0 & 0.01 (s, each 3H), 0.82 (s, 9H), 3.36 (ABX, J=10.2 & 5.31 Hz, 1H), 3.47 (ABX, J=10.2 & 4.09, 1H), 3.96 (d, J=5.2 Hz, 2H), 4.85-5.0 (m, 1H), 6.01 (d, J=1.6 Hz, 1H), 7.15-7.6 (m, 15H), 8.13 (d, J=1.6 Hz, 1H).

(99) Preparation of 2-(3-isoxazolyloxy)-3-triphenylmethoxypropanol 4j

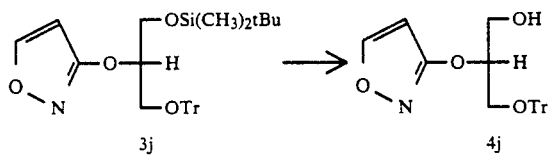

A mixture of 7.24 g (1.4 mM) of 1-tert-butyldimethylsilyloxy-2-(3-isoxazolyloxy)-3-triphenylmethoxypropane 3j, and 15.4 ml (15 mM) of 1M tetra-n-butylammonium fluoride in tetrahydrofuran in 100 ml of tetrahydrofuran is allowed to react by the same procedure as described in (78) to give 5.37 g of the titled compound 4j (95% yield).

NMR: δppm (CDCl₃) 2.31 (t, J=6 Hz, 1H), 3.40 (ABX, J=10.2 & 4.89 Hz, 1H), 3.50 (ABX, J=10.2 & 4.51 Hz, 1H), 3.94 (quartet, J=4.6 Hz, 1H), 3.96 (quartet, J=4.6 Hz, 1H), 4.85-4.95 (m, 1H), 6.01 (d, J=1.8 Hz, 1H), 7.15-7.55 (m, 15H), 8.12 (d, J=1.81 Hz, 1H).

(100) Preparation of 1-hexadecylthio-2-(3-isoxazolyloxy)-3-triphenylmethoxypropane 5j

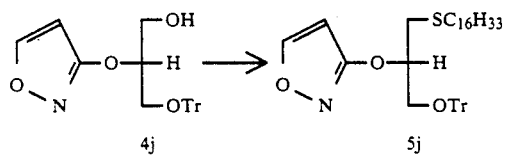

A mixture of 0.17 g (0.42 mM) of 2-(3-isoxazolyloxy)-3-triphenylmethoxypropanol 4j, 65 μl (0.46 mM) of triethylamine, and 34 μl (0.44 mM) of methanesulfonyl chloride in 4 ml is allowed to react by the same procedure as descerebed in (80) to give the methanesulfonate which is then allowed to react with 18 mg (0.46 mM) of 60% suspension of sodium hydride in mineral oil and 0.12 g (0.46 mM) of n-hexadecyl mercaptan (purity 98%) in 6 ml of benzene by the same procedure as described in (80) to give 0.19 g of the titled compound 5j (70% yield).

m.p. 41°-44° C.

NMR: δppm (CDCl₃) 0.88 (t, J=7 Hz, 3H), 2.48 (t, J=7.3 Hz, 2H), 2.96 (d, J=7.8 Hz, 2H), 3.38 (ABX, J=10.2 & 4.78 Hz, 1H), 3.52 (ABX, J=10.2 & 3.98 Hz, 1H), 4.9-5.05 (m, 1H), 6.00 (d, J=1.8 Hz, 1H), 7.15-7.5 (m, 15H), 8.11 (d, J=1.8 Hz, 1H).

(101) Preparation of 3-hexadecylthio-2-(3-isoxazolyloxy)propanol Vj1

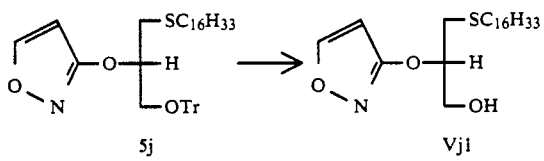

A mixture of 7.30 g (11 mM) of 1-hexadecylthio-2-(3-isoxazolyloxy)-3-triphenylmethoxypropane 5j and 433 mg (2.3 mM) of p-toluenesulfonic acid monohydrate in 150 ml of methanol-tetrahydrofuran (1:1) mixture by the same procedure as described in (81) to give 4.25 g of the titled compound Vj1 (94% yield).

NMR: δppm (CDCl₃) 0.88 (t, J=6.2 Hz, 3H), 1.45-1.7 (m, 2H), 2.5 (broad, 1H), 2.60 (t, J=7.4 Hz), 2.87 (ABX, J=12.8 & 6.48 Hz, 1H), 2.95 (ABX, J=12.8 & 3.52 Hz, 1H), 3.92 (ABX, J=13.0 & 4.8 Hz, 1H), 4.01 (ABX, J=13.0 & 3.2 Hz, 1H), 4.8-4.9 (m, 1H), 5.99 (d, J=1.8 Hz, 1H), 8.13 (d, J=1.8 Hz, 1H).

(102) Preparation of 3-hexadecylthio-2-(3-isoxazolyloxy)propylamine IVj1

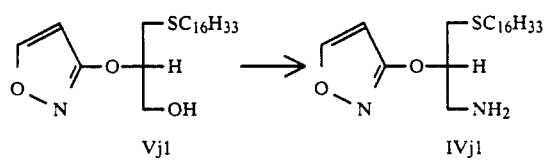

3-Hexadecylthio-2-(3-isoxazolyloxy)propanol Vj1 is allowed to react and worked up by the same procedure as described in (3). The phthalimide compound: m.p. 73°-74° C. The summary of the experimental condition and the physical data of the product are listed in Tables 5 and 6.

(103) Preparation of 3-(3-chloropropylsulfonylamino-1-hexadecylthio-2-(3-isoxazolyloxy)propane IIIj1

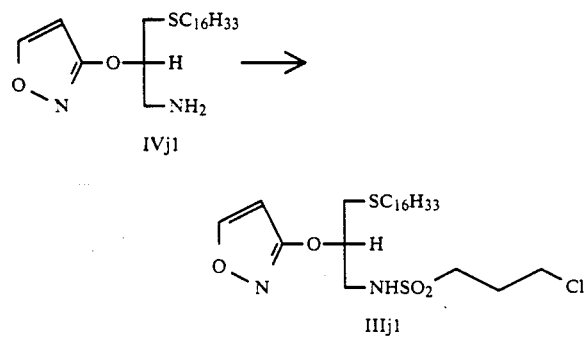

3-Hexadecylthio-2-(3-isoxazolyloxy)propylamine IVJ1 is allowed to react and worked up by the same procedure as described in (4). The summary of the experimental condition and the physical data of the product are listed in Table 7.

(104) Preparation of 1-hexadecylthio-3-(3-iodopropylsulfonylamino)-2-(3-isoxazolyloxy)propane IIj1

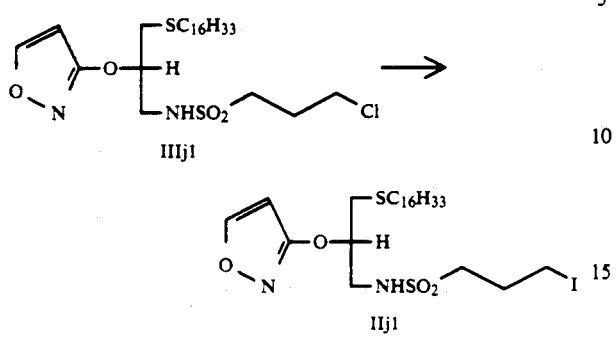

3-(3-Chloropropylsulfonylamino)-1-hexadecylthio-2-(3-isoxazolyloxy)propane IIIj1 is allowed to react and worked up by the same procedure as described in (5). The summary of the experimental condition and the physical data of the product are listed in Table 8.

EXAMPLE 57

Preparation of 1-hexadecylthio-2-(3-isoxazolyloxy)-3-(3-trimethylammoniopropylsulfonylamino)propane iodide Ij1

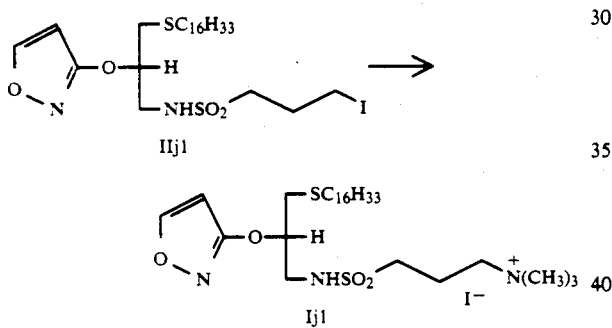

1-Hexadecylthio-3-(3-iodopropylsulfonylamino)-2-(3-isoxazolyloxy)propane IIj1 is allowed to react and worked up by the same procedure as described in Example 8. The summary of the experimental condition and the physical data of the product are listed in Table 9.

(105) Preparation of 3-(3-chloropropylsulfonylamino)-2-(3-isoxazolyloxy)-1-octadecylcarbamoyloxypropane IIIj2

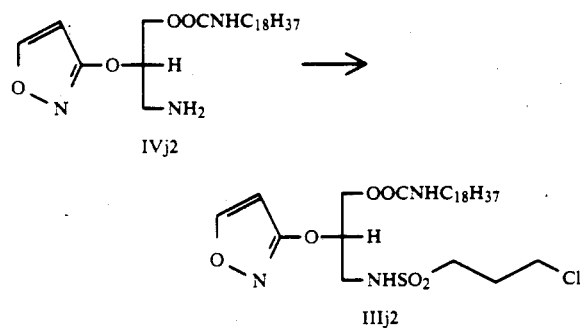

2-(3-Isoxazolyloxy)-1-octadecylcarbamoyloxypropylamine IVj2 is allowed to react and worked up by the same procedure as described in (4). m.p. 63.5°–65° C. The summary of the experimental condition and the physical data of the product are listed in Table 7.

(106) Preparation of 3-(3-iodopropylsulfonylamino)-2-(3-isoxazolyloxy)-1-octadecylcarbamoyloxypropane IIj2

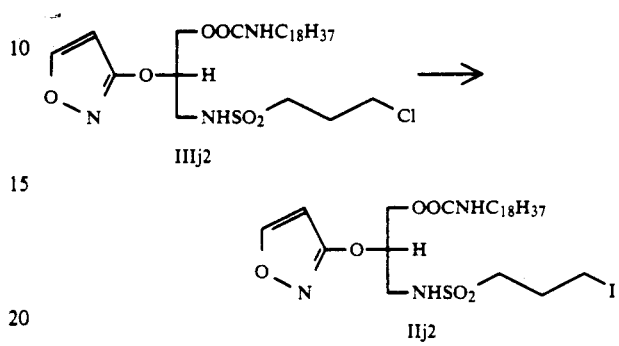

3-(3-Chloropropylsulfonylamino)-2-(3-isoxazolyloxy)-1-octadecylcarbamoyloxypropane IIIj2 is allowed to react and worked up by the same procedure as described in (5). m.p. 69°–71.5° C. The summary of the experimental condition and the physical data of the product are listed in Table 8.

EXAMPLE 58

Preparation of 2-(3-isoxazolyloxy)-1-octadecylcarbamoyloxy-3-(3-trimethylammoniopropylsulfonylamino)propane iodide Ij2

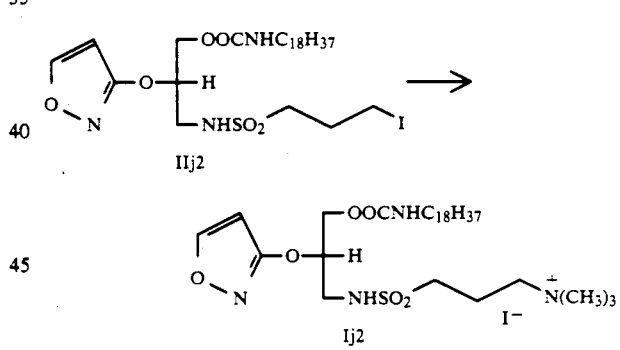

3-(3-Iodopropylsulfonylamino)-2-(3-isoxazolyloxy)-1-octadecylcarbamoyloxypropane IIj2 is allowed to react and worked up by the same procedure as described in Example 8. The summary of the experimental condition and the physical data of the product are listed in Table 9.

EXAMPLE 59

Preparation of 2-(3-isoxazolyloxy)-1-octadecylcarbamoyloxy-3-(3-quinoliniopropylsulfonylamino)propane iodide Ij3

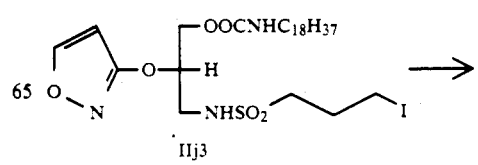

-continued

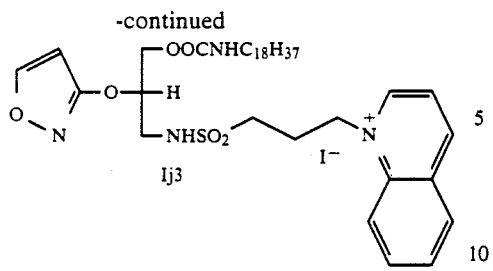

3-(3-Iodopropylsulfonylamino)-2-(3-isoxazolyloxy)-1-octadecylcarbamoyloxypropane IIj3 is allowed to react and worked up by the same procedure as described in Example 25. The summary of the experimental condition and the physical data of the product are listed in Table 10.

(107) Preparation of
3-hexadecyloxy-2-methoxymethylpropylamine IVk1

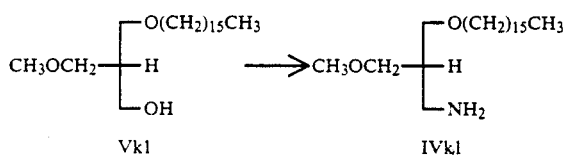

3-Hexadecyloxy-2-methoxymethylpropanol Vk1 is allowed to react and worked up by the same procedure as described in (3). The phthalimide compound: m.p. 49°–51° C. The summary of the experimental condition and the physical data of the product are listed in Tables 5 and 6.

(108) Preparation of
3-(3-chloropropylsulfonylamino)-1-hexadecyloxy-2-methoxymethylpropane IIIk1

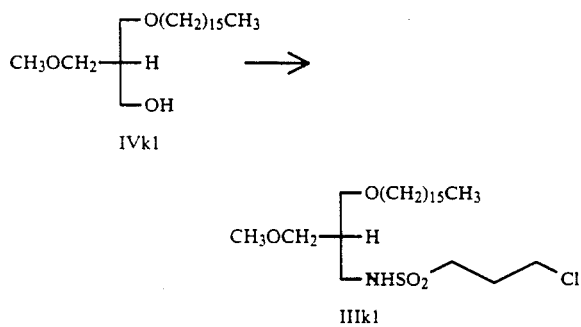

3-Hexadecyloxy-2-methoxymethylpropylamine IVk1 is allowed to react and worked up by the same procedure as described in (4). m.p. 44°–46.5° C. The summary of the experimental condition and the physical data of the product are listed in Table 7.

(109) Preparation of
1-hexadecyloxy-3-(3-iodopropylsulfonylamino-2-methoxymethylpropane IIk1

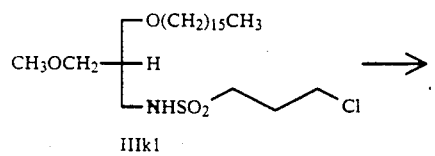

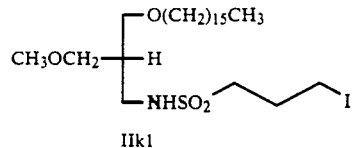

3-(3-Chloropropylsulfonylamino)-1-hexadecyloxy-2-methoxymethylpropane IIIk1 is allowed to react and worked up by the same procedure as described in (5). m.p. 42.5°–44° C. The summary of the experimental condition and the physical data of the product are listed in Table 8.

(110) Preparation of
3-(N-acetyl-3-iodopropylsulfonylamino)-1-hexadecyloxy-2-methoxymethylpropane IIk1'

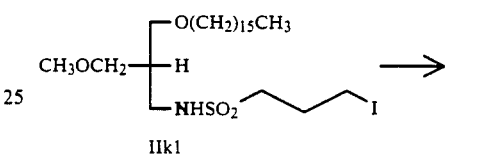

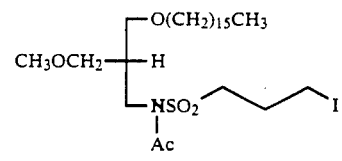

To a cooled mixture of 0.76 g (1.3 mM) of 1-hexadecyloxy-3-(3-iodopropylsulfonylamino)-2-methoxymethylpropane IIk1 and 0.14 ml (2.0 mM) of acetyl chloride in 10 ml of dichloromethane at 0° C., is added 0.39 ml (2.2 mM) of diisopropylamine and the mixture is stirred at 0° C., for 3 hours. The mixture is poured into ice-water and the product is isolated by dichloromethane extraction. The dichloromethane layer is washed with saturated aqueous sodium chloride, dried over anhydrous magnesium sulfate and evaporated. The residue is purified by column silica gel chromatography using toluene-ethyl acetate (9:1) mixture and 0.81 g (99% yield) of the titled compound IIk1' is obtained.

NMR δppm (CDCl$_3$): 0.88 (t, J=6 Hz, 3H), 1.95–2.15 (m, 1H), 2.2–2.45 (m, 2H), 2.38 (s, 3H), 3.29 (t, J=5 Hz, 2H), 3.32 (s, 3H), 3.59 (t, J=8 Hz, 2H), 3.82 (d, J=6 Hz, 2H).

EXAMPLE 60

Preparation of
3-(N-acetyl-3-trimethylammoniopropylsulfonylamino)-1-hexadecyloxy-2-methoxymethylpropane iodide Ik1

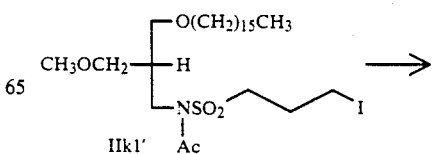

-continued

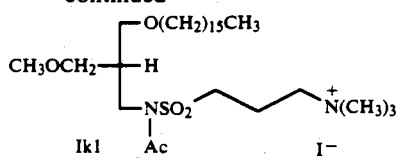

3-(N-Acetyl-3-iodopropylsulfonylamino-1-hexadecyloxy-2-methoxymethylpropane IIk1' is allowed to react and worked up by the same procedure as described in Example 8. The summary of the experimental condition and the physical data of the product are listed in Table 8.

EXAMPLE 61

Preparation of 1-hexadecyloxy-2-methoxymethyl-3-(3-trimethylammoniopropylsulfonylamino)propane iodide Ik2

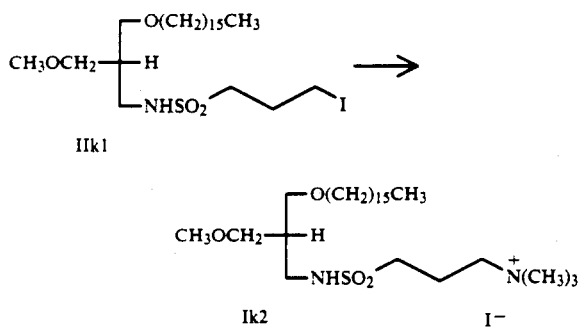

1-Hexadecyloxy-3-(3-iodopropylsulfonylamino)-2-methoxymethylpropane IIk1 is allowed to react and worked up by the same procedure as described in Example 8. The summary of the experimental condition and the physical data of the product are listed in Table 9.

EXAMPLE 62

Preparation of 1-hexadecyloxy-2-methoxymethyl-3-(3-quinoliniopropylsulfonylamino)propane iodide Ik3

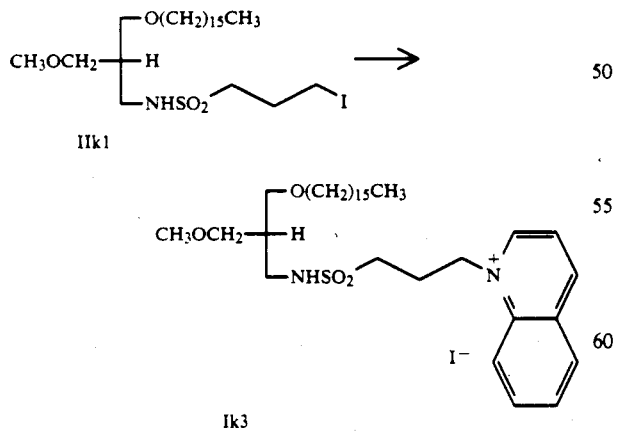

1-Hexadecyloxy-3-(3-iodopropylsulfonylamino)-2-methoxymethylpropane IIk1 is allowed to react and worked up by the same procedure as described in Example 25. The summary of the experimental condition and the physical data of the product are listed in Table 10.

(111) Preparation of 3-hexadecylthio-2-methoxymethylpropylamine IVk3

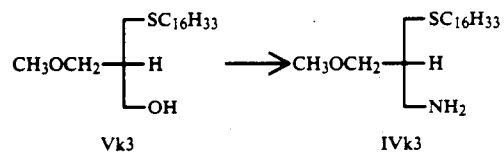

3-Hexadecylthio-2-methoxymethylpropanol IVk3 is allowed to react and worked up by the same procedure as described in (4). The phthalimide compound m.p. 45° C. The summary of the experimental condition and the physical data of the product are listed in Tables 5 and 6.

(112) Preparation of 3-(3-chloropropylsulfonylamino)-1-hexadecylthio-2-methoxymethylpropane IVk3

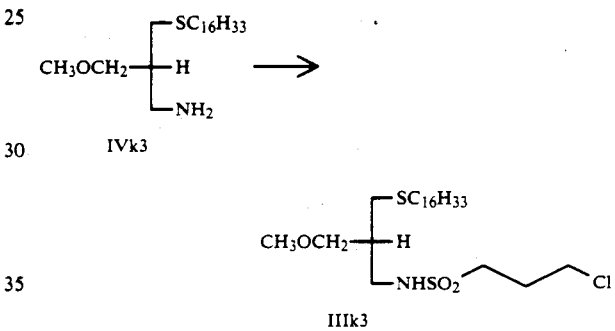

3-Hexadecylthio-2-methoxymethylpropylamine IVk3 is allowed to react and worked up by the same procedure as described in (4). m.p. 41.5°–43° C. The summary of the experimental and the physical data of the product are listed in Table 7.

(113) Preparation of 1-hexadecylthio-3-(3-iodopropylsulfonylamino)-2-methoxymethylpropane IIk3

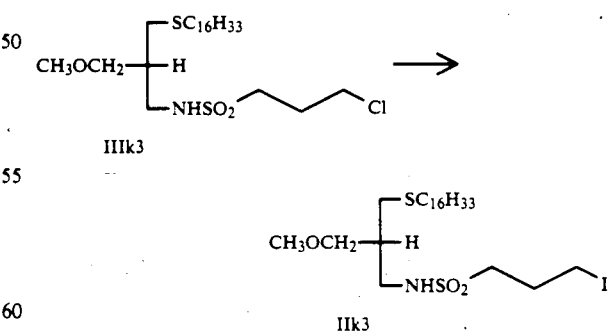

3-(3-Chloropropylsulfonylamino)-1 3-(3-Chloropropylsulfonylamino)-1-hexadecylthio-2-methoxymethylpropane IIIk3 is allowed to react and worked up by the same procedure as described in (5). The summary of the experimental condition and the physical data of the product are listed in Table 8.

EXAMPLE 63

Preparation of 1-hexadecylthio-2-methoxymethyl-3-(3-trimethylammoniopropylsulfonylamino)propane iodide Ik4

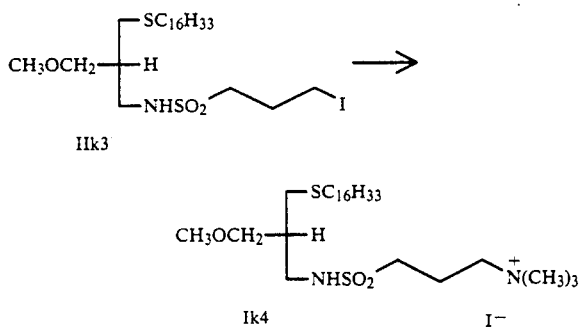

1-Hexadecylthio-3-(3-iodopropylsulfonylamino)-2-methoxymethylpropane IIk3 is allowed to react and worked up by the same procedure as described in Example 8. The summary of the experimental condition and the physical data of the product are listed in Table 9.

(114) Preparation of 2-methoxymethyl-3-octadecylcarbamoyloxypropylamine IVk2

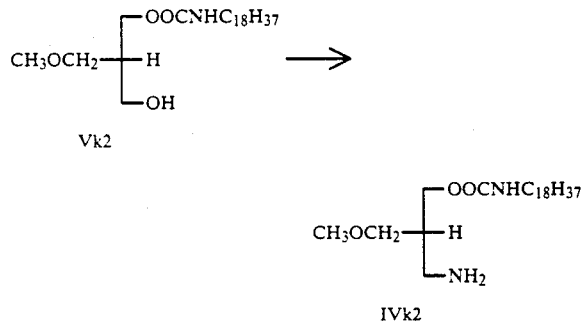

2-Methoxymethyl-3-octadecylcarbamoyloxypropanol Vk2 is allowed to react and worked up by the same procedure as described in (4). The phthalimide compound: m.p. 84°-85° C. The summary of the experimental condition and the physical data of the product are listed in Table 6.

(115) Preparation of 3-(3-chloropropylsulfonylamino)-2-methoxymethyl-1-octadecylcarbamoyloxypropane IIIk2

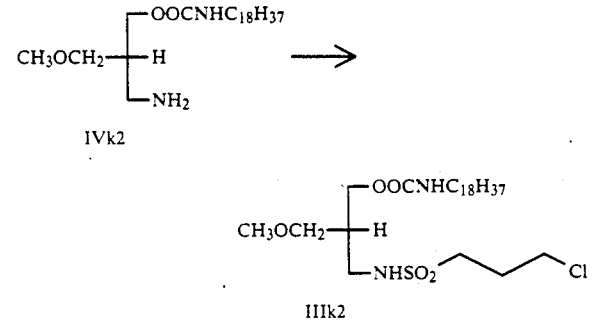

2-Methoxymethyl-3-octadecylcarbamoyloxypropylamine IVk2 is allowed to react and worked up by the same procedure as described in (4). m.p. 72°-73° C. The summary of the experimental condition and the physical data of the product are listed in Table 7.

(116) Preparation of 3-(3-iodopropylsulfonylamino)-2-methoxymethyl-1-octadecylcarbamoyloxypropane IIk2

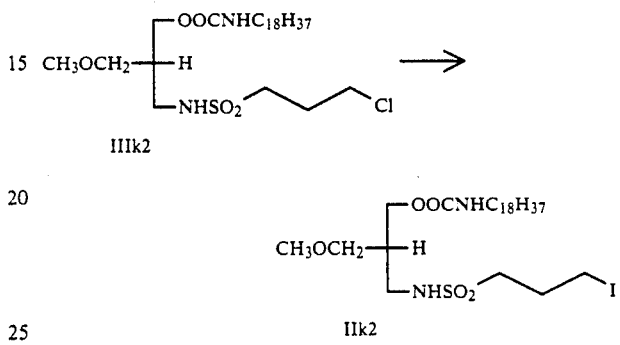

3-(3-(Chloropropylsulfonylamino)-2-methoxymethyl-1-octadecylcarbamoyl oxypropane IIIk2 is allowed to react and worked up by the same procedure as described in (5). m.p. 69°-70° C. The summary of the experimental condition and the physical data of the product are listed in Table 8.

(117) Preparation of 3-(N-acetyl-3-iodopropylsulfonylamino)-2-methoxymethyl-1-octadecylcarbamoyloxypropane IIk2'

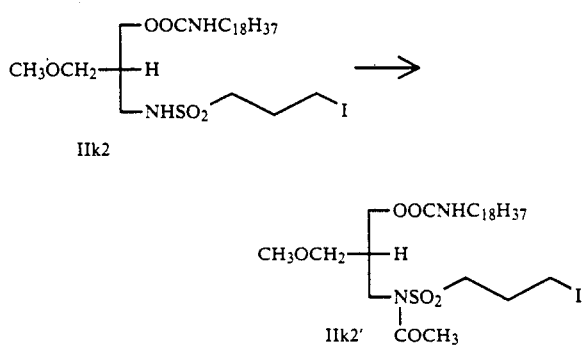

A mixture of 0.72 g (1.1 mM) of 3-(3-iodopropylsulfonylamino)-2-methoxymethyl-1-octadecylcarbamoyloxypropane IIk2, 88 μl (1.2 mM) of acetyl chloride and 0.25 ml (1.4 mM) of N,N-diisopropylethylamine is allowed to react by the same procedure as described in (110) and 0.65 g (85% yield) of the title compound IIk2' is obtained. m.p. 71°-72° C.

NMR: δppm (CDCl$_3$) 0.88 (t, J=6 Hz, 3H), 1.4–1.6 (m, 2H), 2.25–2.5 (m, 3H), 2.40 (s, 3H), 3.15 (q, J=6 Hz, 2H), 3.30 (t, J=7 Hz, 3H), 3.32 (s, 3H), 3.35–3.5 (m, 2H), 3.56 (t, J=8 Hz, 2H), 3.84 (d, J=7 Hz, 2H), 4–4.2 (m, 2H), 4.79 (t, J=6 Hz, 1H).

EXAMPLE 64

Preparation of 2-methoxymethyl-1-octadecylcarbamoyloxy-3-(3-quinoliniopropylsulfonylamino)propane iodide Ik5

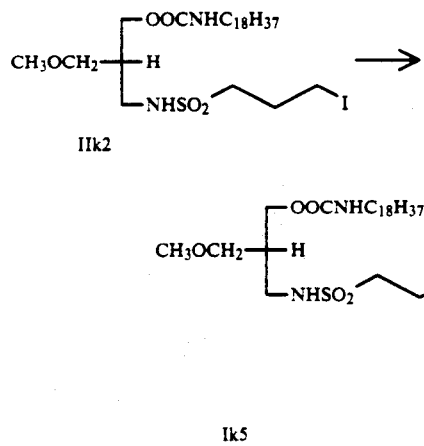

3-(3-Iodopropylsulfonylamino)-2-methoxymethyl-1-octadecylcarbamoyloxypropane IIk2 is allowed to react and worked up by the same procedure as described in Example 25. The summary of the experimental condition and the physical data of the product are listed in Table 10.

EXAMPLE 65

Preparation of 3-(N-acetyl-3-quinoliniopropylsulfonylamino)-2-methoxymethyl-1-octadecylcarbamoyloxypropane iodide Ik6

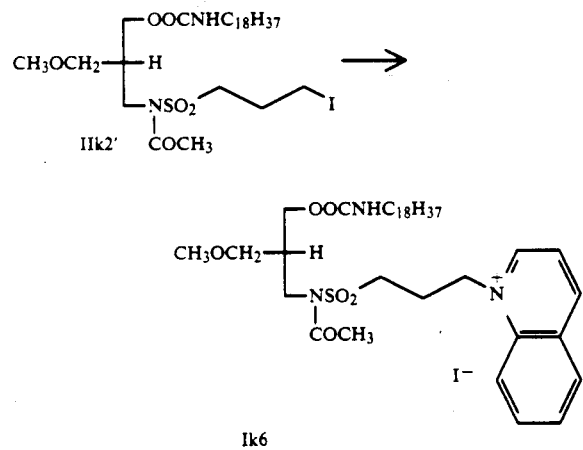

3-(N-Acetyl-3-iodopropylsulfonylamino)-2-methoxymethyl-1-octadecylcarbamoyloxypropane IIk2' is allowed to react and worked up by the same procedure as described in Example 25. The summary of the experimental condition and the physical data of the product are listed in Table 10.

(118) Preparation of 5-bromomethyl-2-phenyl-1,3-dioxane m2

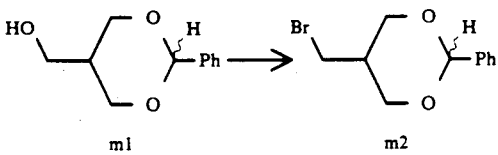

To a vigorously stirred solution of 19.4 g (0.1M) of 5-hydroxymethyl-2-phenyl-1,3-dioxane m1 and 33.1 g (0.1M) of tetrabromomethane in 60 ml of anhydrous benzene at 70° C., is added 26.2 g (0.1M) of triphenylphosphine in 45 minutes. After stirring at 70° C. for an another 30 minutes, the solvent is evaporated. To the residue is added 200 ml of ether and ether insoluble triphenylphosphine oxide is removed by filtration. After repeating this procedure twice, the solvent of the filtrated is evaporated. Distillation of the residual product gives 19.391 g (75.4% yield) of the titled compound m2.

B.P. 145°~158° C. (1 mmHg).

(119) Preparation of 5-(2-hydroxypropan-1-yl)-2-phenyl-1,3-dioxane m3

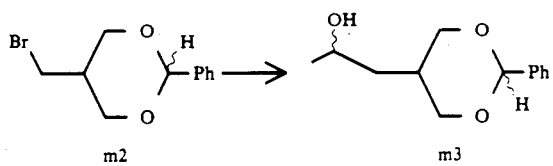

To a solution of 19.39 g (75.4 mM) of 5-bromomethyl-2-phenyl-1,3-dioxane m2 in 200 ml of tetrahydrofuran is added 1.923 g (79.17 mM) of magnesium and the mixture is allowed to react for 7 hours under ultrasonic bibration. The mixture is cooled to −70° C. and 21.27 ml (377 mM) of acetaldehyde is added and then the mixture is stirred at 0° C. for 15 hours. The mixture is poured into an ice-cooled saturated aqueous ammonium chloride solution and the product is isolated by ethyl acetate extraction. The ethyl acetate layer is washed with saturated aqueous sodium chloride, dried over anhydrous magnesium sulfate and evaporated. By eliminating the polar impurity by passing short column of silica gel, 11.353 g of the crude titled compound m3 is obtained which is used to the next reaction without further purification.

IR: νmax (CHCl$_3$) 3620~3150 cm$^{-1}$ (broad).

(120) Preparation of 5-(2-benzoyloxypropan-1-yl)-2-phenyl-1,3-dioxane m4

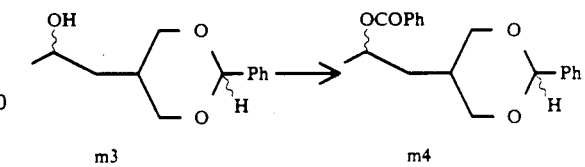

To a solution of 10.829 g of crude 5-(2-hydroxypropan-1-yl)-2-phenyl-1,3-dioxane m3 in 200 ml of dichloromethane at 0° C., is added 11.3 ml (97.4 mM) of benzoyl chloride and 20.5 ml (146.1 mM) of triethylamine and 100 mg of 4-dimethylaminopyridine. After stirring at room temperature for 15 hours, the mixture is poured into 2N aqueous hydrochloric acid and the product is isolated by dichloromethane extraction. The dichloromethane layer is washed with saturated aqueous sodium bicarbonate and saturated aqueous sodium chloride, dried over anhydrous magnesium sulfate and evaporated. By eliminating the polar by-product by passing a short column of silica gel using n-hexane-ethyl acetate (4:1) mixture, as an eluent 17.125 g of the crude product of the titled compound m4 is obtained.

IR: νmax (CHCl₃) 1715 cm⁻¹.

(121) Preparation of 2-(2-benzoyloxypropan-1-yl)-3-hydroxypropyl benzoate m5

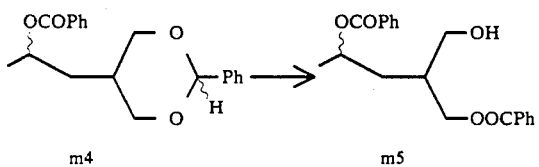

To a stirred and ice cooled suspension of 9.344 g (52.5 mM) of N-bromosuccinimide in 250 ml of water are added a drop of conc. hydrobromic acid and 17.125 g of the crude 5-(2-benzoyloxypropan-1-yl)-2-phenyl-1,3-dioxane m4 obtained in the previous reaction dropwise. After standing at 0° C. for another 1 hour, 22 g (260 mM) of sodium bicarbonate is added to the reaction mixture and the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (1:1) as an eluent gives 7.401 g (29.7% yield from the compound m2) of the titled compound m5 as an oily product.

IR: νmax (CHCl₃) 3600~3250 (broad), 1700 cm⁻¹.
NRM: δppm (CDCl₃) 1.40 (d, J=2.6 Hz, 1.5H), 1.43 (d, J=2.6 Hz, 1.5H), 1.67-1.99 (m, 2H), 2.01-2.24 (m, 1H), 2.51-1.52 (br. 1H), 3.57-3.82 (m, 2H), 4.32-4.60 (m, 2H), 5.26-5.47 (m, 1H), 7.37-7.67 (m, 6H), 7.93-8.13 (m, 4H).

(122) Preparation of 2-(2-benzoyloxypropan-1-yl)-3-octadecylcarbamoyloxypropyl benzoate m6

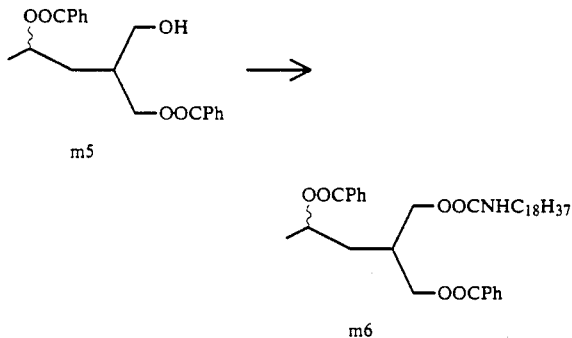

A mixture of 3.70 g (11.2 mM) of 2-(2-benzoyloxypropan-1-yl)-3-hydroxypropyl benzoate m5 and 4.964 g (16.8 mM) of octadecyl isocyanate in 74 ml of pyridine is heated at 70° C. for 15 hours and the solvent is evaporated. To the residue with cooling, is added 2N aqueous hydrochloric acid and the product is isolated by ethyl acetate extraction. The ethyl acetate layer is washed with saturated aqueous sodium bicarbonate and saturated aqueous sodium chloride, dried over anhydrous magnesium sulfate and evaporated. Purification of the product by column silica gel chromatography using n-hexane-ethyl acetate (1:1) as an eluent gives 6.28 g (87.8% yield) of the titled compound m6.

IR: νmax (CHCl₃) 3440, 1705 cm⁻¹.
NMR: δppm (CDCl₃) 0.88 (t, J=6.4 Hz, 3H), 1.10-1.35 (m, 30H), 1.36-1.55 (m, 5H), 1.68-2.07 (m, 2H), 2.22-2.45 (m, 1H), 2.97-3.21 (m, 2H), 4.10-4.27 (m, 2H), 4.27-4.45 (m, 2H), 4.62-4.83 (br., 1H), 5.28-5.50 (m, 1H), 7.38-7.64 (m, 6H), 7.97-8.13 (m, 4H).

(123) Preparation of 2-(2-benzoyloxypropan-1-yl)-3-methanesulfonyloxypropyl benzoate m11'

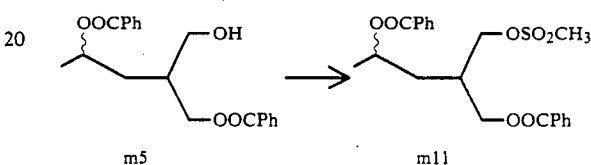

To an ice cooled solution of 1.85 g (5.60 mM) of 2-(2-benzoyloxypropan-1-yl)-3-hydroxy-propyl benzoate m5 in 40 ml of dichloromethane are added 0.607 ml (7.84 mM) of methanesulfonyl chloride and 1.34 ml (9.52 mM) of triethylamine. After stirring at 0° C. for 30 minutes, the mixture is poured into an ice cooled 2N aqueous hydrochloric acid and the product is isolated by dichloromethane extraction. The dichloromethane layer is washed with saturated aqueous sodium bicarbonate and saturated aqueous sodium chloride, dried over anhydrous magnesium sulfate. Evaporation of the solvent gives the crude product of the titled compound m11'.

NMR: δppm (CDCl₃) 1.43 (d, J=6.2 Hz, 3H), 1.74-2.08 (m, 2H), 2.27-2.53 (m, 1H), 3.01 (s, 3H), 4.25-4.54 (m, 4H), 5.27-5.47 (m, 1H), 7.37-7.65 (m, 6H), 7.95-8.11 (m, 4H).

(124) Preparation of 2-(2-benzoyloxypropan-1-yl)-3-hexadecylthiopropyl benzoate m11

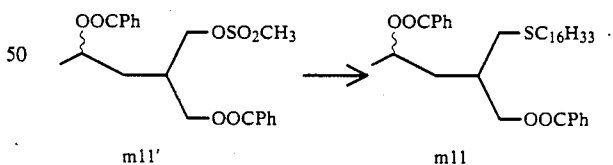

A mixture of 3.858 g (14.92 mM) of n-hexadecyl mercaptane and 554 mg (13.86 mM) of 60% sodium hydride in oil in 100 ml of benzene is heated at 50° C. for 1 hour and a solution of the crude 2-(2-benzoyloxypropan-1-yl)-3-methanesulfonyloxypropyl benzoate m11' in 5 ml of benzene is added. After heating the mixture at 50° C. for another 1 hour, the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (95:5) as an eluent gives 4.416 g (71.1% yield) of the titled compound m11.

NMR: δppm (CDCl₃) 0.88 (t, J=6.4 Hz, 3H), 1.12-1.38 (m, 26H), 1.40 (d, J=6.2 Hz, 3H), 1.45-1.65 (m, 2H), 1.67-2.31 (m, 3H), 2.49-2.53 (m, 2H), 2.57-2.82 (m, 2H), 4.29-4.55 (m, 2H), 5.26-5.45 (m, 1H), 7.36-7.63 (m, 6H), 7.97-8.11 (m, 4H).

(125) Preparation of 2-(2-benzoyloxypropan-1-yl)-3-octadecylcarbamoyloxypropanol m7

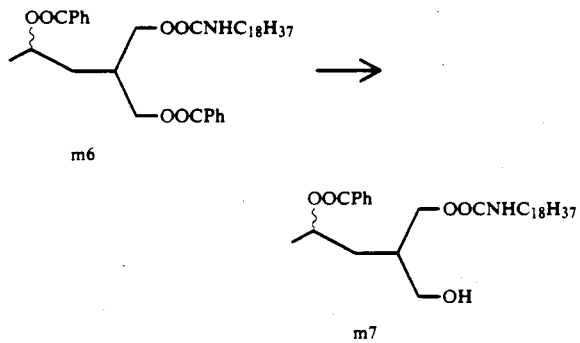

To an ice cooled solution of 2.879 g (4.51 mM) of 2-(2-benzoyloxypropan-1-yl)-3-octadecylcarbamoyloxypropyl benzoate m6 in 25 ml of methanol and 25 ml of tetrahydrofuran, is added 4.51 ml (9.02 mM) of 2N aqueous sodium hydroxide and the mixture is stirred at 0° C. for 2 hours. The mixture is poured into ice-water and the product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (2:1) as an eluent gives 1.72 g (71.4% yield) of the titled compound m7.

NMR: δppm (CDCl₃) 0.88 (t, J=6.4 Hz, 3H), 1.10-1.39 (m, 30H), 1.37 (d, J=6.2 Hz, 3H), 1.38-1.53 (m, 2H), 1.60-1.81 (m, 2H), 1.85-2.02 (m, 1H), 2.92-3.24 (m, 2H), 3.39-3.70 (m, 2H), 4.05-4.32 (m, 2H), 4.68-4.88 (m, 1H), 5.20-5.40 (m, 1H), 7.35-7.66 (m, 3H), 8.04 (d, J=6.8 Hz, 2H).

(126) Preparation of 2-(2-benzoyloxypropan-1-yl)-3-hexadecylthiopropanol m12

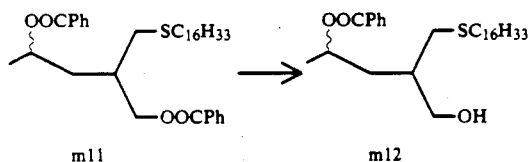

Using 6.89 ml (13.78 mM) of 2N aqueous sodium hydroxide, 4.017 g (6.89 mM) of 2-(2-benzoyloxypropan-1-yl)-3-hexadecylthiopropyl benzoate m11 in 38 ml of methanol and 43 ml of tetrahydrofuan is converted to 2.071 g (62.8% yield) of the titled compound m12 by the same procedure as described in (125).

NMRR: δppm (CDCl₃) 0.88 (t, J=6.4 Hz, 3H), 1.12-1.38 (m, 26H), 1.38 (d, J=6.2 Hz, 3H), 1.45-1.63 (m, 2H), 1.63-2.01 (m, 3H), 2.47 (t, J=7.0 Hz, 2H), 2.51-2.75 (m, 2H), 3.62-3.82 (m, 2H), 5.15-5.42 (m, 1H), 7.39-7.61 (m, 3H), 8.04 (d, J=7.2 Hz, 2H).

(127) Preparation of 2-(2-benzoyloxypropan-1-yl)-3-octadecylcarbamoyloxyproyl methanesulfonate m7a

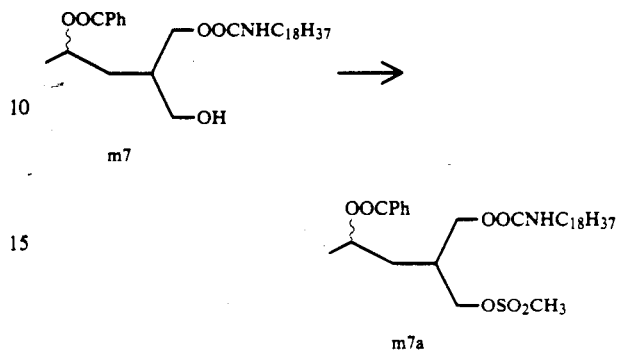

Using 0.358 ml (4.63 mM) of methanesulfonyl chloride and 0.814 ml (5.79 mM) of triethylamine, 2.059 g (3.86 mM) of 2-(2-benzoyloxypropan-1-yl)-3-octadecylcarbamoyloxypropanol m7 in dichloromethane is converted to the crude titled compound m7a by the same procedure as described in (50).

NMR: δppm (CDCl₃) 0.88 (t, J=6.4 Hz, 3H), 1.14-1.35 (m, 30H), 1.39 (d, J=6.2 Hz, 3H), 1.36-1.56 (m, 2H), 1.59-2.01 (m, 2H), 2.15-2.37 (m, 1H), 3.02 (s, 3H), 3.05-3.22 (m, 2H), 3.99-4.37 (m, 4H), 4.63-4.84 (m, 1H), 5.20-5.45 (m, 1H), 7.35-7.66 (m, 3H), 8.04 (d, J=6.8 Hz, 2H).

(128) Preparation of 1-azido-2-(2-benzoyloxypropan-1-yl)-3-n-octadecylcarbamoyloxypropane m7b

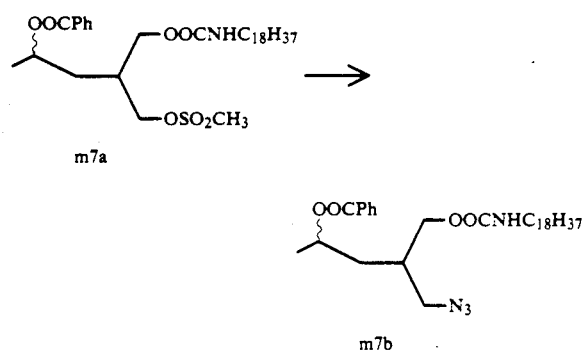

Using 1.889 g (38.6 mM) of lithium azide, the prevoiusly obtained crude 2-(2-benzoyloxypropan-1-yl)-3-octadecylcarbamoyloxypropyl methanesulfonate m7a in 50 ml of dimethylformamide is converted to 1.986 g (92.0% yield) of the titled compound m7b by the same procedure as described in (52).

NMR: δppm (CDCl₃) 0.88 (t, J=6.4 Hz, 3H), 1.17-1.36 (m, 30H), 1.38 (d, J=6.2 Hz, 3 Hz), 1.39-1.53 (m, 2H), 1.55-1.98 (m, 2H), 1.99-2.17 (m, 1H), 3.02-3.03 (m, 2H), 3.32-3.53 (m, 2H), 3.93-4.22 (m, 2H), 4.60-4.80 (br., 1H), 5.20-5.42 (m, 1H), 7.39-7.64 (m, 3H), 8.04 (d, J=6.8 Hz, 2H).

(129) Preparation of 2-(2-benzoyloxypropan-1-yl)-3-octadecylcarbamoyloxypropylamine m8

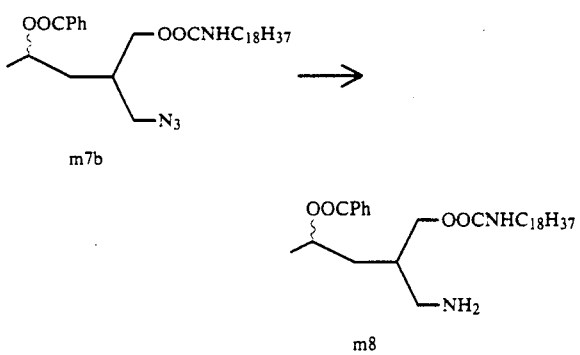

A suspension of 1.617 g (2.89 mM) of 1-azido-2-(2-benzoyloxypropan-1-yl)-3-octadecylcarbamoyloxypropane m7b and 170 mg of 10% palladium on charcoal in 150 ml of methanol is hydrogenated under hydrogen atmosphere for 1 hour. The mixture is filtered and the solvent of the filtrate is evaporated to obtained crude titled compound m8.

NMR: δppm (CDCl$_3$) 0.88 (t, J=6.4 Hz, 3H), 1.17–1.36 (m, 30H), 1.37 (d, J=6.2 Hz, 3H), 1.39–1.53 (m, 2H), 1.55–1.96 (m, 5H), 2.59–2.85 (m, 2H), 2.98–3.27 (m, 2H), 4.00–4.27 (m, 2H), 4.65–4.87 (br., 1H), 5.20–5.46 (m, 1H), 7.36–7.65 (m, 3H), 8.04 (d, J=6.8 Hz, 2H).

(130) Preparation of 2-(2-benzoyloxypropan-1-yl)-1-(3-chloropropylsulfonylamino)-3-n-octadecylcarbamoyloxypropane m9

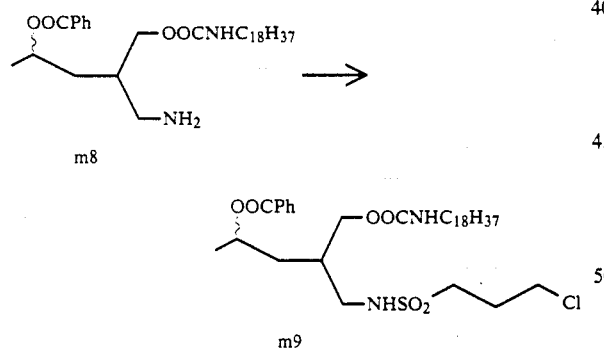

Using 0.33 ml (2.71 mM) of 3-chloropropanesulfonyl chloride and 0.495 ml (3.52 mM) of triethylamine, the previously obtained crude product of 2-(2-benzoyloxypropan-1-yl)-3-octadecylcarbamoyloxypropylamine m8 in 60 ml of dichloromethane is converted to 1.56 g (80.2% yield from the azide m7b) of the titled compound m9 as a wax.

NMR: δppm (CDCl$_3$) 0.88 (t, J=6.4 Hz, 3H), 1.17–1.36 (m, 30H), 1.39 (d, J=6.2 Hz, 3H), 1.37–1.53 (m, 2H), 1.57–1.88 (m, 2H), 1.90–2.11 (m, 1H), 2.17–2.36 (m, 2H), 2.92–3.29 (m, 6H), 3.65 (t, J=6.2 Hz, 2H), 3.97–4.35 (m, 2H), 4.70–4.86 (br., 1H), 5.20–5.50 (m, 2H), 7.39–7.64 (m, 3H), 8.04 (d, J=6.8 Hz, 2H).

(131) Preparation of 1-(3-chloropropylsulfonylamino)-2-(2-hydroxypropan-1-yl)-3-octadecylcarbamoyloxypropane m10

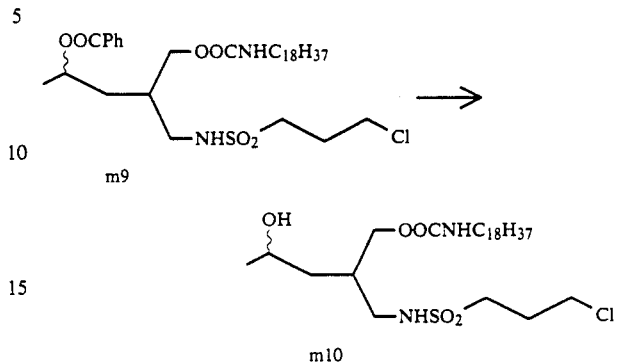

To an ice cooled solution of 941 mg (1.41 mM) of 2-(2-benzoyloxypropan-1-yl)-1-(3-chloropropylsulfonylamino)-3-octadecylcarbamoyloxypropane m9 in 50 ml of methanol is added 0.539 ml (2.80 mM) of 5.18 M/L sodium methoxide in methanol. After stirring at room temperature for 15 hours, the solvent is evaporated. The product is isolated by ethyl acetate extraction. The ethyl acetate layer is washed with saturated aqueous sodium chloride, dried over anhydrous magnesium sulfate and evaporated. Purification of the product by column silica gel chromatography using n-hexane-ethyl acetate (1:2) mixture as an eluent gives 491 mg (61.7% yield) of the titled compound m10.

NMR: δppm (CDCl$_3$) 0.88 (t, J=6.4 Hz, 3H), 1.12–1.36 (m, 33H), 1.36–1.60 (m, 4H), 1.80–2.20 (m, 2H), 2.18–2.37 (m, 2H), 2.99–3.27 (m, 6H), 3.68 (t, J=6.2 Hz, 2H), 3.83–4.27 (m, 3H), 4.67–4.96 (br., 1H), 5.27–5.85 (br., 1H).

(132) Preparation of 1-(3-chloropropylsulfonylamino)-3-octadecylcarbamoyloxy-2-(2-oxopropan-1-yl)propane IIIm1

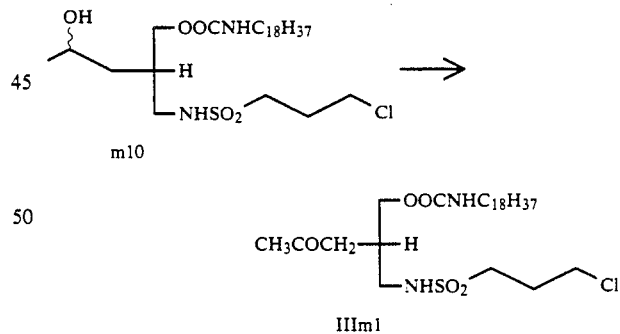

To a cooled solution of 0.0645 ml (0.75 mM) of oxalyl chloride in 50 ml of dichloromethane at −78° C., is added 0.106 ml (1.5 mM) of dimethylsulfoxide dropwise and the mixture is stirred for another 5 minutes. To this mixture is added a solution of 285 mg (0.5 mM) of 1-(3-chloropropylsulfonylamino)-2-(2-hydroxypropan-1-yl)-3-octadecylcarbamoyloxypropane m10 in 2 ml of dichloromethane at −70° C. with vigorous stirring. The mixture is allowed to react at −70° C. for 15 minutes and 0.836 ml (6 mM) of triethylamine is added. After allowing the temperature of the reaction mixture to rise to room temperature, the product is isolated with dichloromethane extraction. The dichloromethane layer is washed with 2N aqueous hydrochloric acid, water and saturated aqueous sodium bicarbonate, dried over anhydrous magnesium sulfate and evaporated to obtain crude product of the titled compound IIIm1.

NMR: δppm (CDCl$_3$) 0.88 (t, J=6.4 Hz, 3H), 1.14–1.41 (m, 30H), 1.37–1.61 (m, 2H), 2.12–2.77 (m, 5H), 2.18 (s, 3H), 2.97–3.28 (m, 6H), 3.68 (t, J=6.2 Hz, 2H), 3.86–4.25 (m, 2H), 4.65–4.86 (br, 1H), 5.26–5.42 (br., 1H).

(133) Preparation of 1-(3-iodopropylsulfonylamino)-3-octadecylcarbamoyloxy-2-(2-oxopropan-1-yl)propane IIm1

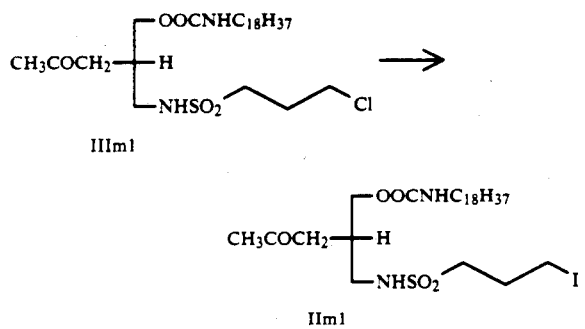

1-(3-Chloropropylsulfonylamino)-3-octadecylcarbamoyloxy-2-(2-oxopropan-1-yl)propane IIIm1 is allowed to react by the same procedure as described in (5). The summary of the experimental condition and the physical data of the product are listed in Table 8.

As a starting material the crude product prepared in (132) is used without further purification. The yield calculated from the compound m10 is 66%.

EXAMPLE 66

Preparation of 3-n-octadecylcarbamoyloxy-2-(2-oxopropan-1-yl)-1-(3-quinoliniopropylsulfonylamino)propane iodide Im1

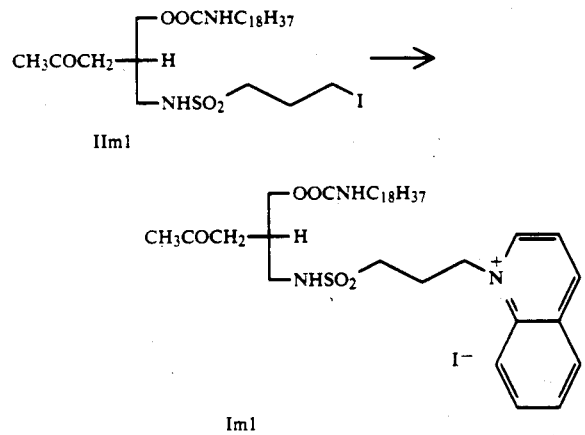

1-(3-iodopropylsulfonylamino)-3-octadecylcarbamoyloxy-2-(2-oxopropan-1-yl)propane IIm1 is allowed to react by the same procedure as described in Example 25. The summary of the experimental condition and the physical data of the product are listed in Table 10.

(134) Preparation of 5-hexadecyloxymethyl-2-phenyl-1,3-dioxane n2

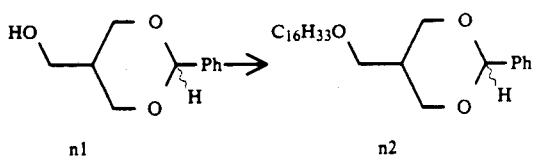

A suspension of 7.769 g (40 mM) of 5-hydroxymethyl-2-phenyl-1,3-dioxane n1 and 2.08 g (52 mM) of 60% sodium hydride in oil in 150 ml of anhydrous benzene is heated at 50° C. for 1 hour then a solution of 17.28 g (54 mM) of n-hexadecyl methanesulfonate in 50 ml of anhydrous benzene is added. The reaction mixture is heated under refluxing for 7 hours. The product is isolated by ethyl acetate extraction. The ethyl acetate layer is washed with saturated aqueous sodium chloride, dried over anhydrous magnesium sulfate and evaporated. Crystallization of the residue from n-pentane-methanol affords 16.203 g (97% yield) of the titled compound n2.

(135) Preparation of 2-bromomethyl-3-hexadecyloxypropanol benzoate n3

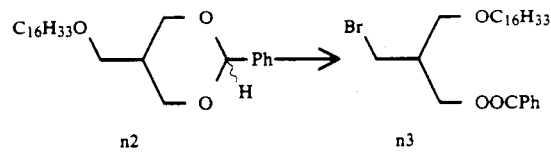

A mixture of 14.703 g (35.2 mM) of 5-n-hexadecyloxymethyl-2-phenyl-1,3-dioxane n2, 6.90 g (38.4 mM) of N-bromosuccinimide and 700 mg of barium carbonate in 200 ml of dichloromethane is heated under refluxing for 1 hour. After cooling, the mixture is poured into an ice cooled saturated aqueous sodium bicarbonate and the product is isolated by dichloromethane extraction. The dichloromethane layer is washed with 10% aqueous sodium thiosulfate and saturated aqueous sodium chloride, dried over anhydrous magnesium sulfate and evaporated. Purification of the residue by column silica gel chromatography using n-hexane-ethyl acetate (9:1) mixture as an eluent affords 13.843 g (79.3% yield) of the titled compound n3.

(136) Preparation of 2-cyanomethyl-3-hexadecyloxypropyl benzoate n3'

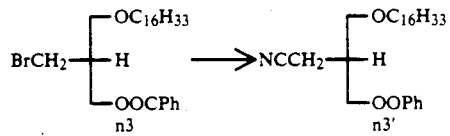

A mixture of 13.845 g (27.9 mM) of 2-bromomethyl-3-n-hexadecyloxypropyl benzoate n3 and 1.439 g (27.9 mM) of sodium cyanide (95% purity) in 150 ml of dimethylsulfoxide is heated at 90° C. for 1 hour. The product is isolated by ethyl acetate extraction. The ethyl acetate layer is washed with water (four times) and saturated aqueous sodium chloride, dried over anhydrous magnesium sulfate and evaporated to obtain 12.42 g of the crude product of the titled compound n3'.

NMR: δppm (CDCl$_3$) 0.88 (t, J=6.4 Hz, 3H), 1.15-1.43 (m, 26H), 1.45-1.70 (m, 2H), 2.39-2.67 (m, 3H), 3.45 (t, J=4.8 Hz, 2H), 3.50-3.67 (m, 2H), 4.26-4.52 (m, 2H), 7.40-7.65 (m, 3H), 8.05 (dd, J=6.4 & 1.6 Hz, 2H.

(137) Preparation of 2-cyanomethyl-3-hexadecyloxypropanol Vn1

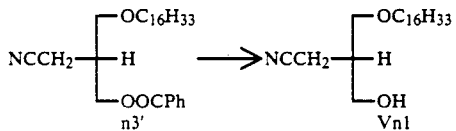

A mixture of 12.42 g of 2-cyanomethyl-3-hexadexyloxypropyl benzoate n3' and 15.5 ml (31.0 mM) of 2N aqueous sodium hydroxide in 60 ml of methanol and 100 ml of tetrahydrofuran is stirred at room temperature for 1 hour and solvents are evaporated. The product is isolated by ethyl acetate extraction. The ethyl acetate layer is washed with water, dried over anhydrous magnesium sulfate and evaporated. Purification by column silica gel chromatography using n-hexane-ethyl acetate (4:1) affords 6.430 g (67.8% yield) of the titled compound Vn1.

NMR: δppm (CDCl$_3$) 0.88 (t, J=6.4 Hz, 3H), 1.15-1.43 (m, 26H), 1.45-1.70 (m, 2H), 1.96-2.27 (m, 2H), 2.45-2.69 (m, 2H), 3.45 (t, J=6.6 Hz, 2H), 3.59 (d, J=4.8 Hz, 2H), 3.67-3.88 (m, 2H).

(138) Preparation of 2-cyanomethyl-3-hexadecyloxypropyl methanesulfonate Vn1a

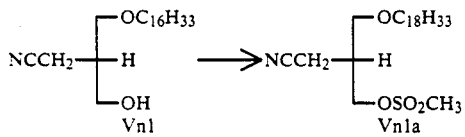

Using 1.08 ml (14 mM) of methanesulfonyl chloride and 2.39 ml (17 mM) of triethylamine, 3.40 g (10 mM) of 2-cyamomethyl-3-n-hexadecyloxypropanol Vn1 in 60 ml of dichloromethane is converted by the same procedure as described in (50) and the crude product of the titled compound Vn1a is obtained.

NMR: δppm (CDCl$_3$) 0.88 (t, J=6.4 Hz, 3H), 1.15-1.43 (m, 26H), 1.45-1.64 (m, 2H), 2.33-2.57 (m, 1H), 2.50-2.62 (m, 2H), 3.06 (s, 3H), 3.43 (t, J=6.6 Hz, 2H), 3.43-3.59 (m, 2H), 4.19-4.42 (m, 2H).

(139) Preparation of 1-azido-2-cyanomethyl-3-hexadecyloxypropane Vn1b

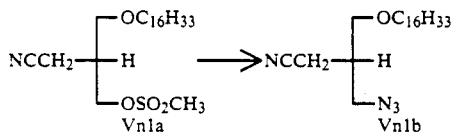

Using 4.9 g (100 mM) of lithium azide, crude product of 2-cyanomethyl-3-hexadecyloxypropyl methanesulfonate Vn1a obtained in the previous reaction in 30 ml of dimethylformamide is converted by the same procedure as described in the (52) and 3.504 g (96.1% yield) of the titled compound Vn1a is obtained.

NMR: δppm (CDCl$_3$) 0.88 (t, J=6.4 Hz, 3H), 1.15-1.43 (m, 26H), 1.45-1.64 (m, 2H), 2.10-2.30 (m, 1H), 2.50 (d, J=6.8 Hz, 2H), 3.37-3.59 (m, 6H).

(140) Preparation of 2-cyanomethyl-3-hexadecyloxypropylamine IVn1

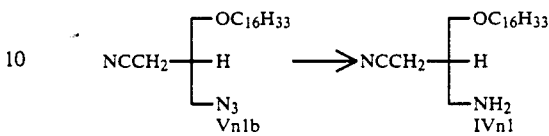

A suspension of 3.00 g (23 mM) of 1-azido-2-cyanomethyl-3-hexadecyloxypropane Vn1b and 300 mg of 10% palladium on charcoal in 100 ml of methanol is hydrogenated as described in (129) and the crude product of the titled compound IVn1 is obtained.

NMR: δppm (CDCl$_3$) 0.88 (t, J=6.4 Hz, 3H), 1.15-1.43 (m, 28H), 1.45-1.64 (m, 2H), 1.88-2.11 (m, 1H), 2.53 (d, J=6.4 Hz, 2H), 2.70-2.93 (m, 2H), 3.31-3.50 (m, 4H).

(141) Preparation of 1-(3-chloropropylsulfonylamino)-2-cyanomethyl-3-hexadecyloxypropane IIIn1

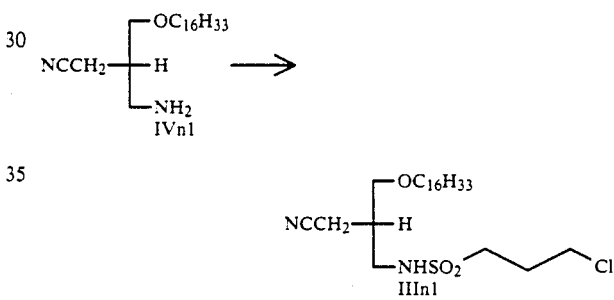

The crude 2-cyanomethyl-3-hexadecyloxypropylamine IVn1 prepared above is allowed to react by the same procedure as described in (4). The summary of the experimental condition and the physical data of the product are listed in Table 7.

(142) Preparation of 2-cyanomethyl-3-hexadecyloxy-1-(3-iodopropylsulfonylamino)propane IIn1

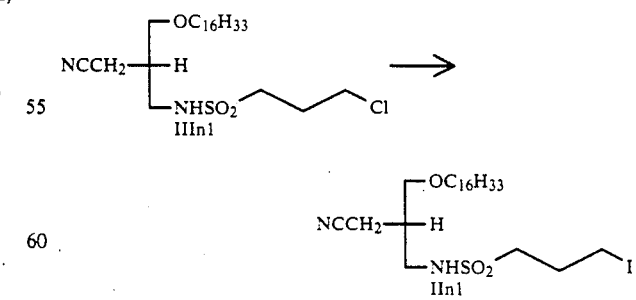

1-(3-Chloropropylsulfonylamino)-2-cyanomethyl-3-hexadecyloxypropane IIIn1 is allowed to react by the same procedure as described in (5). The summary of the experimental condition and the physical data of the product are listed in Table 8.

EXAMPLE 67

Preparation of
2-cyanomethyl-3-hexadecyloxy-1-(3-trimethylammoniopropylsulfonylamino)propane iodide In1

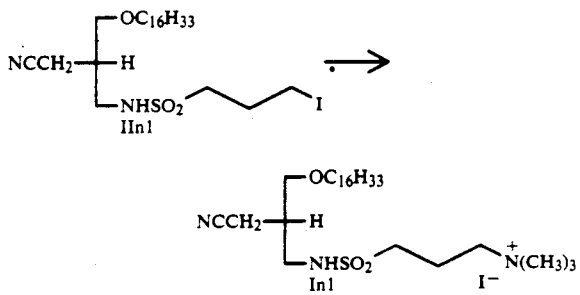

2-Cyanomethyl-3-hexadecyloxy-1-(3-iodopropylsulfonylamino)propane IIn1 is allowed to react by the same procedure as described in Example 8. The summary of the experimental condition and the physical data of the product are listed in Table 9.

EXAMPLE 68

Preparation of
2-cyanomethyl-3-hexadecyloxy-1-(3-quinoliniopropylsulfonylamino)propane iodide In2

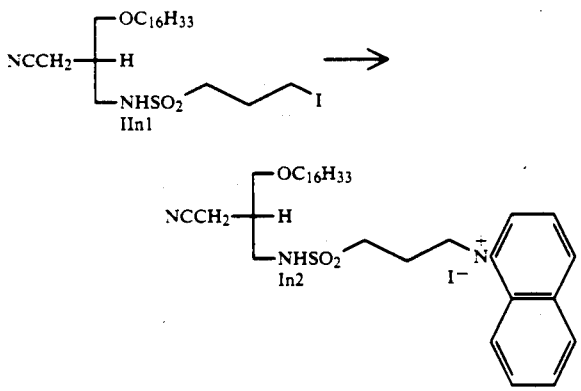

2-Cyanomethyl-3-hexadecyloxy-1-(3-iodopropylsulfonylamino)propane IIn1 is allowed to react by the same procedure as described in Example 25. The summary of the experimental condition and the physical data of the product are listed in Table 10.

(143) Preparation of
5-octadecylcarbamoyloxy-2-phenyl-1,3-dioxane n4

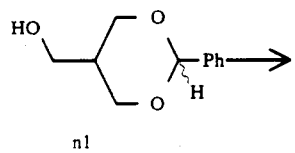

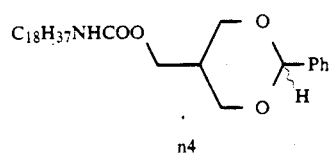

A solution of 7.769 g (40 mM) of 5-hydroxymethyl-2-phenyl-1,3-dioxane n1, 21.991 ml (64 mM) of octadecyl isocyanate and 100 mg of 4-dimethyaminopyridine in 100 ml of pyridine is allowed to react by the same procedure as described in (122) and crystallization of the product from ethanol affords 15.861 g (81.0% yield) of the titled compound n4.

IR: νmax (CHCl₃) 3440, 1705 cm⁻¹.

(144) Preparation of
2-bromemethyl-3-octadecylcarbamoyloxypropyl benzoate n5

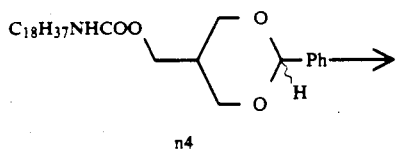

A mixture of 2.55 g (5.22 mM) of 5-n-octadecylcarbamoyloxy-2-phenyl-1,3-dioxane n4, 938 mg (5.22 mM) of N-bromosuccinimide and 100 mg of barium carbonate in 50 ml of dichloromethane is allowed to react by the same procedure as described in (135) and 1.86 g (62.6% yield) of the titled compound n5 is obtained.

NMR: δppm (CDCl₃) 0.88 (t, J=6.4 Hz, 3H), 1.17–1.41 (m, 30H), 1.36–1.57 (m, 2H), 2.46–2.68 (m, 1H), 3.16 (q, J=6.2 Hz, 2H), 3.57 (d, J=5.6 Hz, 2H), 4.26 (d, J=6.4 Hz, 2H), 4.44 (d, J=6.0 Hz, 2H), 4.59–4.77 (br. 1H), 7.40–7.60 (m, 3H), 8.03 (d, J=7.0 Hz, 2H).

(145) Preparation of
2-cyanomethyl-3-octadecylcarbamoyloxypropyl benzoate n5'

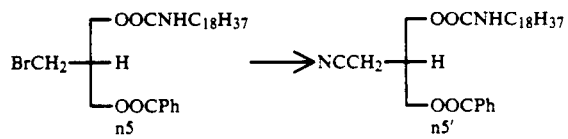

A mixture of 1.76 g (3.10 mM) of 2-bromomethyl-3-n-octadecylcarbamoyloxypropyl benzoate, 185 mg (3.26 mM) of 95% sodium cyanide in 30 ml of dimethylsulfoxide is allowed to react by the same procedure as described in the (136) and 1.49 g (95.5% yield) of the titled compound n5' is obtained.

NMR: δppm (CDCl₃) 0.88 (t, J=6.4 Hz, 3H), 1.17–1.41 (m, 30H), 1.36–1.57 (m, 2H), 2.61 (s, 3H), 3.17 (q, J=6.2 Hz, 2H), 4.16–4.53 (m, 4H), 4.65–4.81 (m, 1H), 7.41–7.67 (m, 3H), 8.05 (d, J=7.0 Hz, 2H).

(146) Preparation of 2-cyanomethyl-3-octadecylcarbamoyloxypropanol Vn2

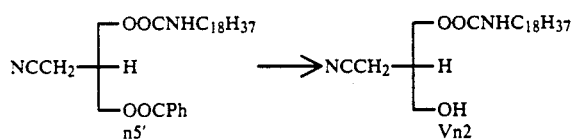

A mixture of 1.49 g (2.96 mM) of 2-cyanomethyl-3-n-octadecylcarbamoyloxypropyl benzoate n5′, 1.66 ml (3.32 mM) of 2N aqueous sodium hydroxide in 15 ml of methanol and 15 ml of tetrahydrofuran is allowed to react by the same procedure as described in (137) and 966 mg (76.8% yield) of the titled compound Vn2 is obtained.

NMR: δppm (CDCl$_3$) 0.88 (t, J=6.4 Hz, 3H), 1.17–1.40 (m, 30H), 1.37–1.57 (m, 2H), 2.11–2.32 (m, 1H), 2.47 (d, J=7.2 Hz, 2H), 2.56–2.77 (br, 1H), 3.18 (q, J=6.4 Hz, 2H), 3.65 (d, J=4.8 Hz, 2H), 4.22 (d, J=5.4 Hz, 2H), 4.70–4.87 (br., 1H).

(147) Preparation of 2-cyanomethyl-3-octadecylcarbamoyloxypropyl methanesulfonate Vn2a

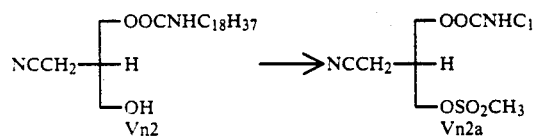

A mixture of 940 mg (2.29 mM) of 2-cyanomethyl-3-octadecylcarbamoyloxypropanol Vn2, 0.231 ml (2.98 mM) of methanesulfonyl chloride and 0.483 ml (3.44 mM) of triethylamine in 10 ml of dichloromethane is allowed to react by the same procedure as described in (52) and crude product of the titled compound Vn2a is obtained.

NMR: δppm (CDCl$_3$) 0.88 (t, J=6.4 Hz, 3H), 1.16–1.38 (m, 30H), 1.40–1.58 (m, 1H), 2.45–2.63 (m, 3H), 3.80 (s, 3H), 3.16 (q, J=6.4 Hz, 2H), 4.09–4.45 (m, 4H), 4.73–4.87 (br., 1H).

(148) Preparation of 1-azido-2-cyanomethyl-3-octadecylcarbamoyloxypropane Vn2b

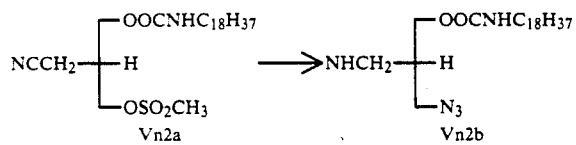

A mixture of the previously obtained crude 2-cyanomethyl-3-n-octadecylcarbamoyloxypropyl methanesulfonate Vn2a, 1.121 g (22.9 mM) of lithium azide in 15 ml of dimethylformamide is allowed to react by the same procedure as described in (53) and 854 mg (85.6% yield) of titled compound Vn2b is obtained.

NMR: δppm (CDCl$_3$) 0.88 (t, J=6.4 Hz, 3H), 1.16–1.40 (m, 30H), 1.40–1.58 (m, 2H), 2.20–2.40 (m, 1H), 2.51 (d, J=6.6 Hz, 2H), 3.18 (q, J=6.4 Hz, 2H), 3.40–3.66 (m, 2H), 4.00–4.23 (m, 2H), 4.60–4.84 (br., 1H).

(149) Preparation of 2-cyanomethyl-3-octadecylcarbamoyloxypropylamine IVn2

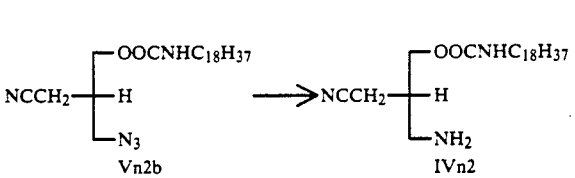

A mixture of 1-azido-2-cyanomethyl-3-octadecylcarbamoyloxypropane Vn2b, 80 mg of 10% palladium on charcoal in 40 ml of methanol is hydrogenated by the same procedure as described in (129) and crude product of the titled compound IVn2 is obtained.

NMR: δppm (CDCl$_3$) 0.88 (t, J=6.4 Hz, 3H), 1.16–1.40 (m, 30H), 1.40–1.58 (m, 2H), 1.96–2.97 (m, 7H), 3.00–3.29 (m, 2H), 3.96–4.27 (m, 2H), 4.60–4.90 (br., 1H).

(150) Preparation of 1-(3-chloropropylsulfonylamino)-2-cyanomethyl-3-octadecylcarbamoyloxypropane IIIn2

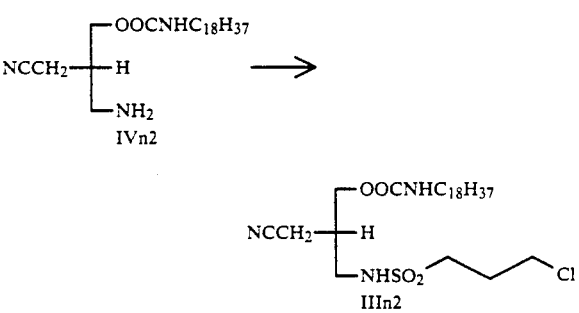

The crude 2-cyanomethyl-3-n-octadecylcarbamoyloxypropylamine IVn2 which was prepared above is allowed to react by the same procedure as described in (4). The summary of the experimental condition and the physical data of the product are listed in Table 7.

(151) Preparation of 2-cyanomethyl-3-octadecylcarbamoyloxy-1-(3-iodopropylsulfonylamino)propane IIn2

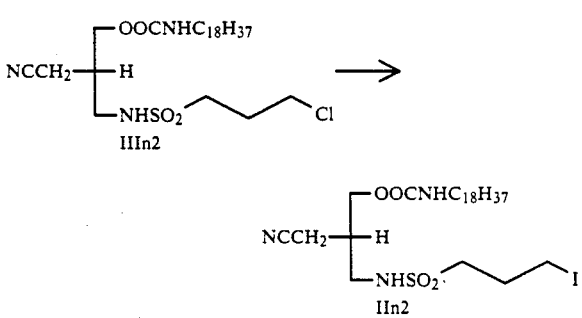

1-(3-Chloropropylsulfonylamino)-2-cyanomethyl-3-octadecylcarbamoyloxypropane IIIn2 is allowed to react by the same procedure as described in (5). The summary of the experimental condition and the physical data of the product are listed in Table 8.

EXAMPLE 69

Preparation of 2-cyanomethyl-3-octadecylcarbamoyloxy-1-(3-quinoliniopropylsulfonylamino)propane In3

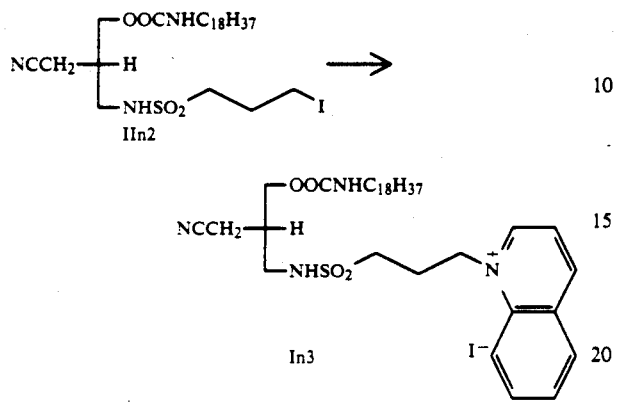

2-Cyanomethyl-3-octadecylcarbamoyloxy-1-(3-iodopropylsulfonylamino)propane IIn2 is allowed to react by the same procedure as described in Example 25. The summary of the experimental condition and the physical data of the product are listed in Table 10.

(152) Preparation of 2-(2-benzoyloxypropan-1-yl)-3-hexadecylthiopropanol methanesulfonate m12a

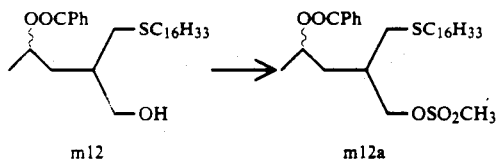

A mixture of 1.268 g (2.65 mM) of 2-(2-benzoyloxypropan-1-yl)-3-n-hexadecylthiopropanol m12, 0.270 ml (3.45 mM) of methanesulfonyl chloride and 0.56 ml (3.98 mM) of triethylamine in 30 ml of dichloromethane is allowed to react by the same procedure as described in (52) and the crude product of the titled compound m12a is obtained.

NMR: δppm (CDCl$_3$) 0.88 (t, J=6.4 Hz, 3H), 1.15-1.37 (m, 26H), 1.39 (d, J=6.4 Hz, 3 Hz), 1.41-1.62 (m, 2H), 1.68-1.86 (m, 1H), 1.88-2.21 (m, 2H), 3.02 (s, 3H), 4.24-4.43 (m, 2H), 5.19-5.42 (m, 1H), 7.38-7.63 (m, 3H), 8.03 (d, J=7.2 Hz, 2H).

(153) Preparation of 1-azido-2-(2-benzoyloxypropan-1-yl)-3-hexadecylthiopropane m12b

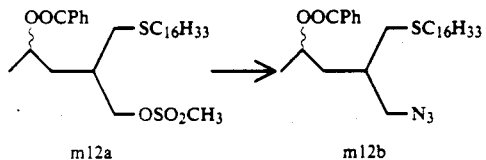

A mixture of the previously obtained 2-(2-benzoyloxypropan-1-yl)-3-n-hexadecylthiopropyl methanesulfonate m12a and 1.297 g (26.5 mM) of lithium azide in 50 ml of dimethylformamide is allowed to react by the same procedure as described in (53) and 1.291 g (96.6% yield) of the titled compound m12b is obtained.

NMR: δppm (CDCl$_3$) 0.88 (t, J=6.4 Hz, 3H), 1.16~1.37 (m, 26H), 1.38 (d, J=6.0 Hz, 3H), 1.44-1.62 (m, 2H), 1.63-1.78 (m, 1H), 1.80-2.03 (m, 2H), 2.38-2.50 (m, 2H), 2.49-2.72 (m, 2H), 3.41-3.62 (m, 2H), 5.17-5.37 (m, 1H), 7.39-7.62 (m, 3H), 8.03 (d, J=7.2 Hz, 2H).

Preparation of 2-(2-benzoyloxypropan-1-yl)-3-hexadecylthiopropylamine m13

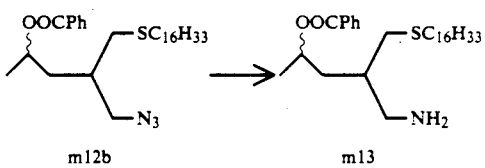

A mixture of 1.291 g (2.56 mM) of 1-azido-2-(2-benzoyloxypropan-1-yl)-3-n-hexadecylthiopropane m12b, 130 mg of 10% palladium on charcoal in 130 ml of methanol is hydrogenated by the same procedure as described in (129) and crude product of the titled compound m13 is obtained.

NMR: δppm (CDCl$_3$) 0.88 (t, J=6.4 Hz, 3H), 1.12-2.00 (m, 36H), 2.34-2.91 (m, 6H), 5.19-5.38 (m, 1H), 7.39-7.62 (m, 3H), 8.03 (d, J=7.2 Hz, 2H).

(155) Preparation of 2-(2-benzoyloxypropan-1-yl)-1-(3-chloropropylsulfonylamino)-3-hexadecylthiopropane m14

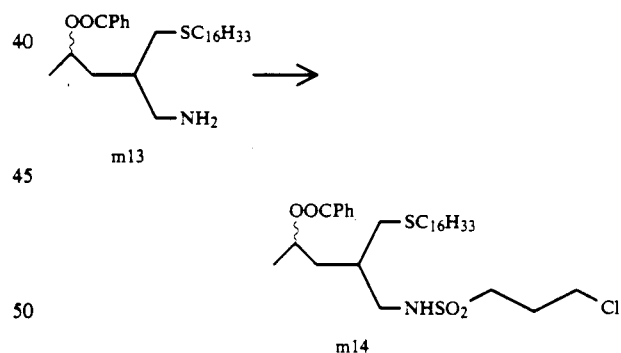

A solution of the previously obtained crude 2-(benzoyloxypropan-1-yl)-3-n-hexadecylthiopropylamine m13, 0.54 ml (3.84 mM) of triethylamine and 0.37 ml (3.07 mM) of 3-chloropropanesulfonyl chloride in 30 ml of dichloromethane is allowed to react by the same procedure as described in (4) and 1.295 g (81.6% yield) of the titled compound m14 is obtained.

NMR: δppm (CDCl$_3$) 0.88 (t, J=6.4 Hz, 3H), 1.14-1.45 (m, 29H), 1.41-1.61 (m, 2H), 1.63-1.81 (m, 1H), 1.82-2.01 (m, 2H), 2.15-2.37 (m, 2H), 2.37-2.77 (m, 4H), 3.09-3.34 (m, 4H), 3.65 (t, J=6.4 Hz, 2H), 4.65-5.08 (br., 1H), 5.10-5.46 (m, 1H), 7.39-7.62 (m, 3H), 8.03 (d, J=7.2 Hz, 2H).

(156) Preparation of 1-(3-chloropropylsulfonylamino)-3-hexadecylthio-2-(2-hydroxypropan-1-yl)propane m15

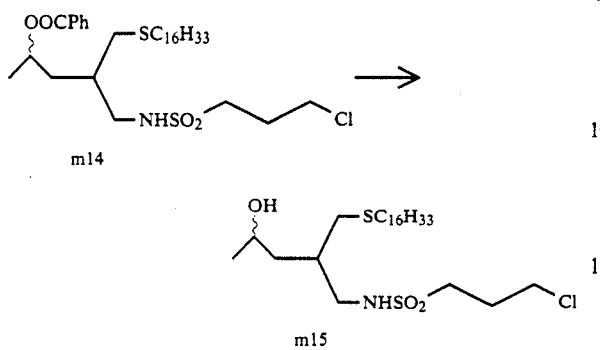

A mixture of 1.24 g (2.0 mM) of 2-(benzoyloxypropan-1-yl)-1-(3-chloropropylsulfonylamino)-3-n-hexadecylthiopropane m14 and 0.77 ml (2 mM) of 5.18 M/L sodium methoxide in methanol solution in 50 ml of methanol is allowed to react by the same procedure as described in (131) and 562 mg (54.5% yield) of the titled compound m15 is obtained.

NMR: $\delta$ppm (CDCl$_3$) 0.88 (t, J=6.4 Hz, 3H), 1.17–1.42 (m, 29H), 1.43–1.77 (m, 5H), 1.91–2.18 (m, 1H), 2.20–2.37 (m, 2H), 2.42–2.65 (m, 4H), 3.02–3.38 (m, 4H), 3.69 (t, J=6.0 Hz, 2H), 3.80–4.13 (m, 1H), 5.10–5.45 (broad, 1H).

(157) Preparation of 1-(3-chloropropylsulfonylamino)-3-hexadecylthio-2-(2-oxopropan-1-yl)propane IIIm2

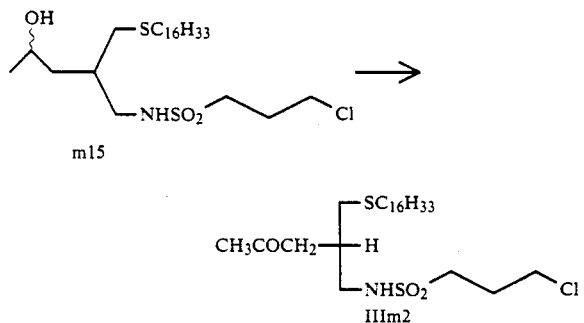

To a cooled solution of 0.19 ml (1.33 mM) of trifluoroacetic anhydride in 20 ml of dichloromethane at −78° C. is added 0.19 ml (2.66 mM) of dimethylsulfoxide and the mixture is stirred at −78° C. for 5 minutes. To the reaction mixture is added a solution of 428 mg (0.83 mM) of 1-(3-chloropropylsulfonylamino)-2-(2-hydroxypropan-1-yl)-3-n-hexadecylthiopropane m15 in 2 ml of dichloromethane with stirring and the mixture is stirred at −70° C. for an additional 15 minutes. 3.50 ml (24.9 mM) of triethylamine is added and the mixture is allowed to react by the same procedure as described in (132) and 213 mg (41.6% yield) of the titled compound IIIm2 is obtained.

NMR: $\delta$ppm (CDCl$_3$) 0.88 (t, J=6.4 Hz, 3H), 1.10–1.43 (m, 26H), 1.46–1.66 (m, 2H), 2.22–2.44 (m, 3H), 2.44–2.59 (m, 4H), 2.65 (d, J=6.0 Hz, 2H), 3.09–3.29 (m, 4H), 3.68 (t, J=6.4 Hz, 2H), 4.80 (t, J=6.4 Hz, 1H).

(158) Preparation of 3-n-hexadecylthio-1-(3-iodopropylsulfonylamino)-2-(2-oxopropan-1-yl)propane IIm2

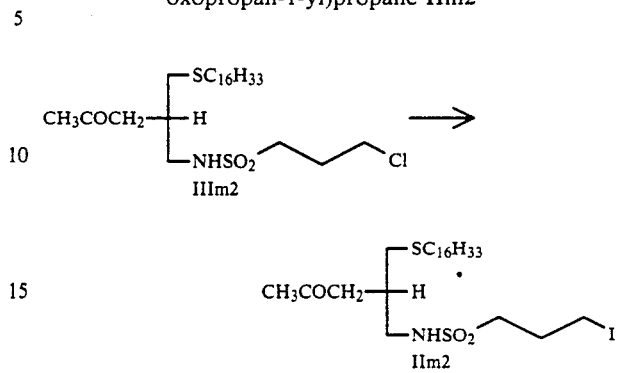

1-(3-Chloropropylsulfonylamino)-3-hexadecylthio-2-(2-oxopropan-1-yl)propane IIIm2 is allowed to react by the same procedure as described in (5). The summary of the experimental condition and the physical data of the product are listed in Table 8.

EXAMPLE 70

Preparation of 3-hexadecylthio-2-(2-oxopropan-1-yl)-1-(3-trimethylammoniopropylsulfonylamino)propane iodide Im2

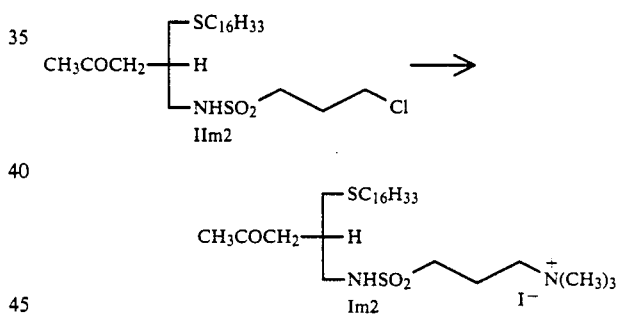

3-n-Hexadecylthio-1-(3-iodopropylsulfonylamino)-2-(2-oxopropan-1-yl)propane IIm2 is allowed to react by the same procedure as described in Example 8. The summary of the experimental condition and the physical data of the product are listed in Table 9.

EXAMPLE 71

Preparation of 1-hexadecylthio-2-(3-methyl-2H-1,2,4-triazoli-2-yl)-3-(3-trimethylammoniopropylsulfonylamino)propane iodide Io1

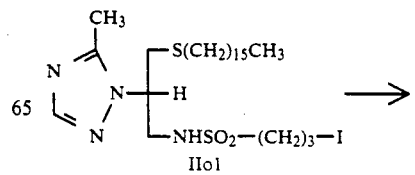

-continued

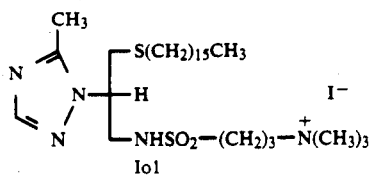
Io1

1-Hexadecylthio-3-(3-iodopropylsulfonylamino)-2-(3-methyl-2H-1,2,4-triazol-2-yl)propane IIo2 is allowed to react and worked up by the same procedure as described in Example 8. The summary of the experimental condition and the physical data of the product are listed in Table 9.

The said starting material is prepared by the same procedure as described in (77), (79), (80), (81), (3), (4), and (5) using 3-methyl-2H-1,2,4-triazole instead of 5-methyltetrazole in (77).

EXAMPLE 72

Preparation of 2-(3-methyl-2H-1,2,4-triazol-2-yl)-1-octadecyl-carbamoyloxy-3-(3-quinoliniopropylsuflonylamino)propane iodide Io2

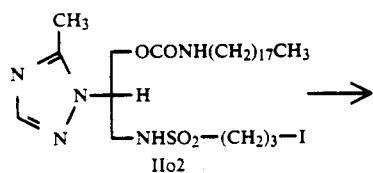
IIo2

-continued

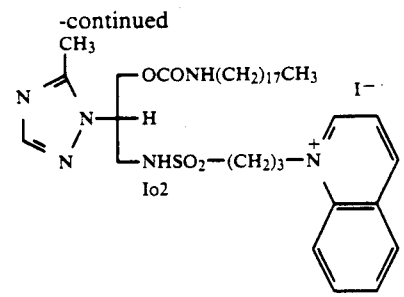
Io2

3-(3-Iodopropylsulfonylamino)-2-(3-methyl-2H-1,2,4-triazol-2-yl)-1-octadecylcarbamoyloxypropane IIo2 is allowed to react and worked up by the same procedure as described in Example 25. The summary of the experimental condition and the physical data of the product are listed in Table 10.

The said starting material is prepared by the same procedure as described in (77), (79), (80), (82), (3), (4), and (5) using 3-methyl-2H-1,2,4-triazole instead of 5-methyltetrazole in (77).

EXAMPLE 73

Preparation of 2-(3-methyl-1H-1,2,4-triazol-1-yl)-1-octadecyl-carbamoyloxy-3-(3-quinoliniopropylsuflonylamino)propane iodide Io3

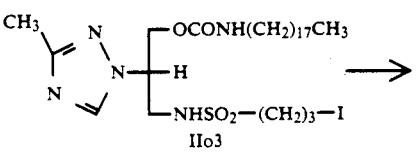
IIo3

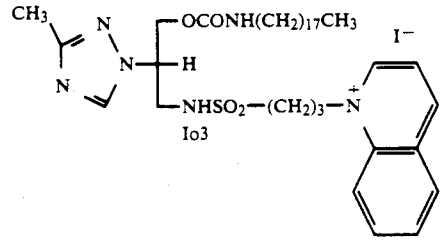
Io3

3-(3-Iodopropylsulfonylamino)-2-(3-methyl-1H-1,2,4-triazol-1-yl)-1-octadecylcarbamoyloxypropane IIo3 is allowed to react and worked up by the same procedure as described in Example 25. The summary of the experimental condition and the physical data of the product are listed in Table 10.

The said starting material is prepared by the same procedure as described in (77), (79), (80), (82), (3), (4), and (5) using 3-methyl-2H-1,2,4-triazole instead of 3-methyltetrazole in (77).

TABLE 5

$$R_2\underset{R_2'}{\underset{|}{\overset{CH_2-Y-R_1}{\overset{|}{C}}}}CH_2OH \longrightarrow R_2\underset{R_2'}{\underset{|}{\overset{CH_2-Y-R_1}{\overset{|}{C}}}}CH_2-N\begin{pmatrix}\text{phthalimide}\end{pmatrix}$$

VI

| (Ref. Ex. No.) | R$_1$ | R$_2$ | R$_2'$ | Y | S.M. [g] ([mM]) | Imide [g] ([mM]) | PPh$_3$ [g] ([mM]) | DEAD [ml] ([mM]) | THF [ml] | Yield [g] (%) | NMR δ ppm |
|---|---|---|---|---|---|---|---|---|---|---|---|
| (23) | —C$_{16}$H$_{33}$ | —O—(CH$_2$)$_3$— | | S | 2.26 (6.05) | 1.34 (9.08) | 2.38 (9.08) | 1.43 (9.08) | 60 | 2.66 (88) | (CDCl$_3$) 0.88(t, 3H), 1.25(s, 26H), 1.45-1.65(m, 2H), 1.90-2.10(m, 4H), 2.59(t, 2H, J=7.2Hz), 2.71, 2.84(ABq, 2H, J=13.3Hz), 3.83(s, 2H), 3.80-4.00(m, 2H), 7.68-7.80(m, 2H), 7.80-7.92 (m, 2H). |
| (26) | —CONHC$_{18}$H$_{37}$ | —O—(CH$_2$)$_3$— | | O | 1.71 (4) | 0.907 (6.16) | 1.61 (6.16) | 0.972 (6.16) | 30 | 2.08 (94) | (CDCl$_3$) 0.88(t, 3H), 1.25(s, 30H), 1.40-1.60(m, 2H), 1.75-2.10(m, 4H), 3.16(q, 2H, J=6.4Hz), 3.84 (s, 2H), 3.80-4.00(m, 2H), 4.03(s, 2H), 4.70-4.85(br, 1H), 7.70-7.80(m, 2H), 7.80-7.90 (m, 2H). |
| (30) | —C$_{16}$H$_{33}$ | —OOCNHCH$_3$ | H | S | 1.362 (3.5) | 1.029 (7.0) | 1.834 (7.0) | 1.218 (7.7) | 55 | 1.9 | (CDCl$_3$) 0.80-1.80(m, 31H), 2.50-2.80(m, 4H), 2.68 (d, J=5Hz, 3H), 4.00(m, 2H), 4.65(br, 1H), 5.15(m, 1H), 7.65-7.95(m, 4H). |
| (35) | —CONHC$_{18}$H$_{37}$ | —OOCNHCH$_3$ | H | O | 2.0 (4.5) | 1.32 (9.0) | 2.36 (9.0) | 1.57 (9.0) | 45 | 2.54 | (CDCl$_3$) 0.86(t, J=6Hz, 3H), 1.26(br.s, 32H), 2.68(d, J=6Hz, 3H), 3.20(m, 2H), 3.80(m, 2H), 4.22 (d, J=6Hz, 2H), 4.80(m, 2H), 5.35(m, 1H), 7.65-8.05(m, 4H). |
| (43) | —CONHC$_{18}$H$_{37}$ | —NHCOOCH$_3$ | H | O | 0.224 (0.504) | 0.100 (0.680) | 0.176 (0.671) | 0.117 (0.672) | 4 | 0.237 (82) | (CDCl$_3$) 0.87(3H, t, J=4Hz), 1.27(30H, s), 1.50(2H, br.s), 3.18(2H, m), 3.56(3H, s), 3.87(2H, d, J=7Hz), 4.19(2H, m), 4.26(1H, m), 4.78 (1H, m), 5.26(1H, m), 7.7-7.8(2H, m), 7.8-7.95(2H, m). |
| (44) | —CONHC$_{18}$H$_{37}$ | —NHCOOiBu | H | O | 0.109 (0.224) | 0.040 (0.272) | 0.071 (0.271) | 0.047 (0.263) | 6 | 0.134 (97.2) | (CDCl$_3$) 0.89(3H, t, J=5Hz), 1.26(30H, s), 1.51(2H, m), 3.18(2H, m), 3.7-4.0(2H), 4.1-4.3(3H), 4.79(1H, t, J=5Hz), 5.01(1H, d, J=5Hz), 7.7-7.9(4H, m). |
| (86) | —C$_{16}$H$_{33}$ | 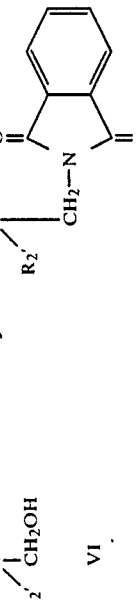 | H | S | 1.13 (2.8) | 1.25 (8.4) | 1.12 (4.2) | 0.74 (4.2) | 50 | — | (CDCl$_3$) 0.88(t, J=7Hz, 3H), 1.35-1.55(m, 2H), 2.27 (t, J=7Hz, 2H), 2.56(s, 3H), 3.16(ABX, J=13.8 & 1.6Hz, 1H), 3.19(ABX, J=13.8 & 11.4Hz, 1H), 4.24(d, J=7Hz, 2H), 4.8-5.0(m, 1H), 8.7-8.95 (m, 4H). |

TABLE 5-continued $$\underset{\text{VI}}{\overset{R_2}{\underset{R_2'}{\bigg\rangle}}\text{C}\overset{CH_2-Y-R_1}{\underset{CH_2OH}{\bigg\langle}}} \longrightarrow \underset{R_2'}{\overset{R_2}{\bigg\rangle}}\text{C}\overset{CH_2-Y-R_1}{\underset{CH_2-N\underset{O}{\overset{O}{\bigg\langle}}\text{Ph}}{\bigg\langle}}$$

| (Ref. Ex. No.) | R₁ | R₂ | R₂' | Y | S.M. [g] ([mM]) | Imide [g] ([mM]) | PPh₃ [g] ([mM]) | DEAD [ml] ([mM]) | THF [ml] | Yield [g] (%) | NMR δ ppm |
|---|---|---|---|---|---|---|---|---|---|---|---|
| (92) | —C₁₆H₃₃ | CH₃, triazolyl | H | S | 2.65 (6.6) | 2.93 (19.8) | 2.62 (9.9) | 1.77 (9.9) | 100 | 2.61 (74) | (CDCl₃) 0.88(t, J=7Hz, 3H), 1.45-1.65(m, 2H), 2.50 (t, J=7Hz, 2H), 2.53(s, 3H), 3.18(ABX, J=14.2 & 6.3Hz, 1H), 3.26(ABX, J=14.2 & 8.7Hz, 1H), 4.21(ABX, J=14 & 9.0Hz, 1H), 4.26(ABX, J=14 & 3.6Hz, 1H), 5.2-5.4(m, 1H), 7.7-7.9(m, 4H). |
| (102) | —C₁₆H₃₃ | isoxazolyl-OMe | H | S | 2.25 (5.6) | 1.24 (8.4) | 2.22 (8.4) | 1.44 (8.4) | 60 | 2.98 quant. | (CDCl₃) 0.88(t, J=7Hz, 3H), 1.5-1.7(m, 2H), 2.63(t, J=7.4Hz, 2H), 2.86(ABX, J=14.4 & 6.74Hz, 1H), 2.96(ABX, J=14.4 & 5.66Hz, 1H), 4.13(ABX, J=14.4 & 7.26Hz, 1H), 4.19(ABX, J=14.4 & 3.54Hz, 1H), 5.1-5.25(m, 1H), 5.93(d, J=1.8Hz, 1H), 7.65-7.8(m, 2H), 7.8-7.95(m, 2H), 8.05(d, J=1.8Hz, 1H). |
| (107) | —C₁₆H₃₃ | CH₃OCH₂— | H | O | 7.77 (22.5) | 6.63 (45) | 11.8 (45) | 7.84 (45) | 200 | 10.64 quant. | (CDCl₃) 0.88(t, J=6Hz, 3H), 2.4(septet, J=5Hz, 1H), 3.25-3.55(m, 6H), 3.27(s, 3H), 3.78(d, J=7Hz, 2H), 7.65-7.8(m, 2H), 7.8-7.95(m, 2H). |
| (111) | —C₁₆H₃₃ | CH₃OCH₂— | H | S | 3.6 (10) | 2.21 (15) | 3.93 (15) | 2.36 (15) | 50 | 3.60 (74) | (CDCl₃) 0.88(t, 3H), 1.25(s, 26H), 1.40-1.65(m, 2H), 2.22-2.42(m, 1H), 2.42-2.72(m, 4H), 3.29(s, 3H), 3.36-3.52(m, 2H), 3.80(d, 2H, J=7.0Hz), 7.68-7.80(m, 2H), 7.80-7.95(m, 2H). |
| (114) | —CONHC₁₈H₃₇ | CH₃OCH₂— | H | O | 6.0 (14) | 4.25 (29) | 7.57 (29) | 4.98 (29) | 200 | 6.51 (83) | (CDCl₃) 0.88(t, J=6Hz, 3H), 1.4-1.6(m, 2H), 2.35-2.6 (m, 1H), 3.12(q, J=7Hz, 2H), 3.28(s, 3H), 3.41 (d, J=5.6Hz, 2H), 3.79(d, J=7Hz, 2H), 4.12(d, J=5Hz, 2H), 4.67(broad, 1H), 7.2-7.8(m, 2H), 7.8-7.95(m, 2H). |

S.M.: starting material,
Imide: phthalimide,
Ph: phenyl,
DEAD: diethyl azocarboxylate,
THF: tetrahydrofuran,
tBu: tert-butyl.

TABLE 6

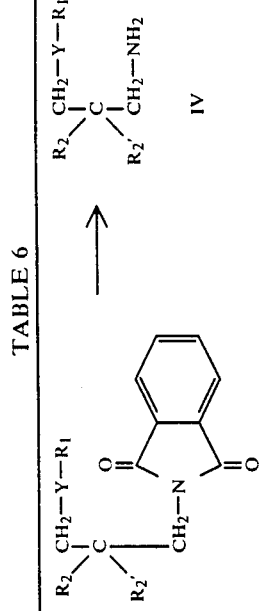

| (Ref. Ex. No.) | R₁ | R₂ | R₂' | Y | S.M. [g] ([mM]) | NH₂NH₂·H₂O [g] ([mM]) | CH₃OH [ml] | Yield [g] (%) | NMR δ ppm |
|---|---|---|---|---|---|---|---|---|---|
| (23) | —C₁₆H₃₃ | —O—(CH₂)₃— | | S | 1.58 (3.17) | 0.19 (3.8) | 30 | 1.054 (89) | (CDCl₃) 0.88(t, 3H), 1.26(s, 26H), 1.48-1.70(m, 2H), 1.70-2.10 (m, 4H), 2.56(t, 2H, J=7.4Hz), 2.64-2.86(m, 4H), 3.76-3.98 (m, 2H). |
| (26) | —CONHC₁₈H₃₇ | —O—(CH₂)₃— | | O | 2.08 (3.74) | 0.281 (5.61) | 50 | 1.52 (95) | (CDCl₃) 0.88(t, 3H), 1.26(s, 30H), 1.40-1.60(m, 2H), 1.72(s, 2H), 1.70-1.85(m, 2H), 1.85-2.05(m, 2H), 2.70, 2.78(ABq, 2H, J=1 3.3Hz), 3.16(q, 2H, J=6.6Hz), 3.87(t, 2H, J=6.4Hz), 4.04(s, 2H), 4.75-4.92(br.1H). |
| (30) | —C₁₆H₃₃ | —OOCNHCH₃ | H | S | 1.6 | 0.34 (6.6) | 60 | 0.929 | (CDCl₃) 0.75-1.75(m, 33H), 2.46-3.03(m, 9H), 4.80(m, 2H). |
| (35) | —CONHC₁₈H₃₇ | —OOCNHCH₃ | H | O | 2.54 (4.42) | 0.336 (6.64) | 25 | 1.208 | (CDCl₃) 0.86(t, J=6Hz, 3H), 1.26(br.s, 32H), 2.80(d, J=6Hz, 3H), 2.92(m, 2H), 3.16(m, 2H), 4.22(d, J=6Hz, 2H), 4.86(m, 3H). |
| (43) | —CONHC₁₈H₃₇ | —NHCOOCH₃ | H | O | 1.47 (2.56) | 1.0 (20) | 30 | 0.872 (76.7) | (CDCl₃) 0.89(3H, t, J=5Hz), 1.27(30H, s), 1.49(4H), 2.80(2H, s), 3.18(2H, m), 3.69(3H, s), 3.79(1H, s), 4.17(2H, s), 4.76 (1H, s), 5.25(1H, s). |
| (44) | —CONHC₁₈H₃₇ | —NHCOOtBu | H | O | 0.840 (1.36) | 2 (40) | 20 | 0.540 (64.4) | (CDCl₃) 0.88(3H, t, J=6Hz), 1.26(30H, s), 1.45(11H, 1.87(2H, s), 2.81(2H, br.s), 3.16(2H, m), 3.79(1H, br.s), 4.15(2H, m), 4.83(1H, t, J=4Hz), 5.79(1H, d, J=4Hz). |
| (86) | —C₁₆H₃₃ | (5-methyl-1,2,3,4-tetrazol-1-yl) | H | S | — | 0.35 (7.0) | 70 | 1.47 | (CDCl₃) 0.89(t, J=6Hz, 3H), 1.4-1.65(m, 2H), 2.31(t, J=7.3Hz, 2H), 2.64(s, 3H), 2.93(ABX, J=14 & 11Hz, 1H), 3.02(ABX, J=14 & 5.4Hz, 1H), 3.2-3.45(m, 2H), 4.25-4.45(m, 1H). |
| (92) | —C₁₆H₃₃ | (5-methyl-1,2,3,4-tetrazol-2-yl) | H | S | 2.61 (4.9) | 0.49 (9.8) | 100 | 1.63 (83) | (CDCl₃) 0.88(t, J=7Hz, 3H), 2.46(t, J=7Hz, 2H), 2.56(s, 3H), 3.07 (d, J=7.2Hz, 2H), 3.34(d, J=6.2Hz, 2H), 4.8-4.95(m, 1H). |
| (102) | —C₁₆H₃₃ | (isoxazol-3-yloxy) | H | S | 2.94 (5.6) | 0.56 (11.1) | 100 | 1.36 (62) | (CDCl₃) 0.88(t, J=7Hz, 3H), 1.45-1.7(m, 2H), 2.55-2.7(m, 2H), 2.81 (ABX, J=13.8 & 7.8Hz, 1H), 2.94(ABX, J=13.8 & 4.8Hz, 1H), 3.16(sextet, J=16 & 5Hz, 2H), 4.7-4.9(m, 1H), 5.98(d, J=1.8Hz, 1H), 8.14(d, J=1.8Hz, 1H). |

TABLE 6-continued
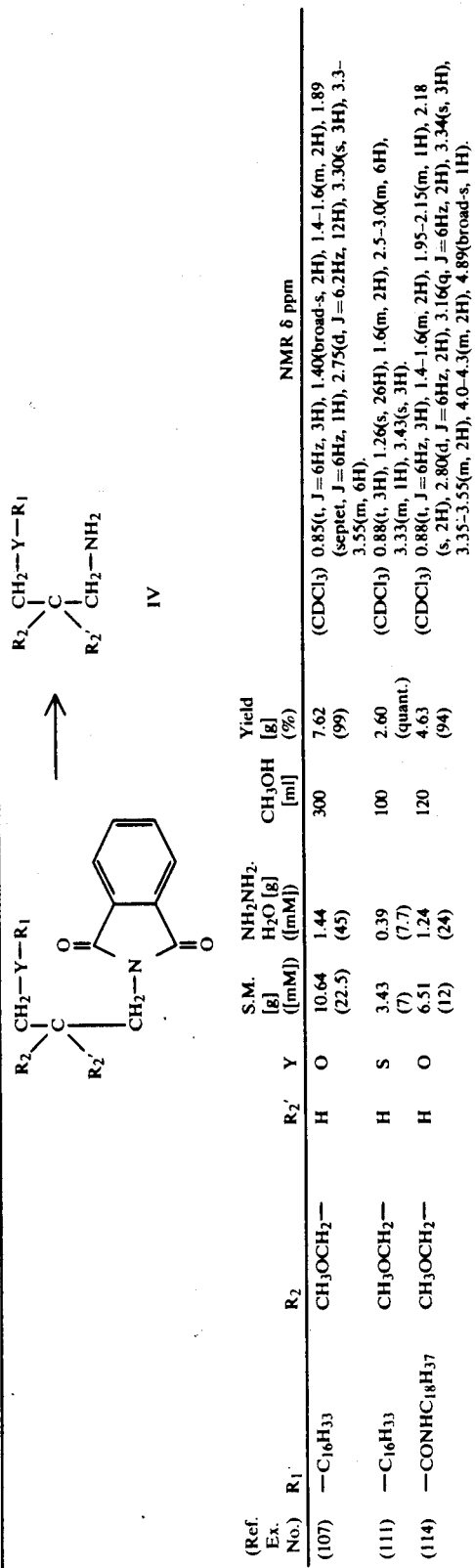
| (Ref. Ex. No.) | R₁ | R₂ | R₂' | Y | S.M. [g] ([mM]) | NH₂NH₂·H₂O [g] ([mM]) | CH₃OH [ml] | Yield [g] (%) | NMR δ ppm |
|---|---|---|---|---|---|---|---|---|---|
| (107) | —C₁₆H₃₃ | CH₃OCH₂— | H | O | 10.64 (22.5) | 1.44 (45) | 300 | 7.62 (99) | (CDCl₃) 0.85(t, J=6Hz, 3H), 1.40(broad-s, 2H), 1.4–1.6(m, 2H), 1.89 (septet, J=6Hz, 1H), 2.75(d, J=6.2Hz, 12H), 3.30(s, 3H), 3.3–3.55(m, 6H). |
| (111) | —C₁₆H₃₃ | CH₃OCH₂— | H | S | 3.43 (7) | 0.39 (7.7) | 100 | 2.60 (quant.) | (CDCl₃) 0.88(t, 3H), 1.26(s, 26H), 1.6(m, 2H), 2.5–3.0(m, 6H), 3.33(m, 1H), 3.43(s, 3H). |
| (114) | —CONHC₁₈H₃₇ | CH₃OCH₂— | H | O | 6.51 (12) | 1.24 (24) | 120 | 4.63 (94) | (CDCl₃) 0.88(t, J=6Hz, 3H), 1.4–1.6(m, 2H), 1.95–2.15(m, 1H), 2.18 (s, 2H), 2.80(d, J=6Hz, 2H), 3.16(q, J=6Hz, 2H), 3.34(s, 3H), 3.35–3.55(m, 2H), 4.0–4.3(m, 2H), 4.89(broad-s, 1H). |

TABLE 7

$$\underset{IV}{\overset{R_2\text{—}CH_2\text{—}Y\text{—}R_1}{\underset{R_2'\text{—}CH_2\text{—}NH_2}{C}}} \quad \xrightarrow[CH_2Cl_2]{ClSO_2\diagup\diagdown\diagup\diagdown Cl} \quad \underset{III}{\overset{R_2\text{—}CH_2\text{—}Y\text{—}R_1}{\underset{R_2'\text{—}CH_2NSO_2\diagup\diagdown\diagup\diagdown Cl}{C}}_{R_6}}$$

| (Ref. Ex. No.) | $R_1$ | $R_2$ | $R_2'$ | $R_6$ | Y | S.M. [g] ([mM]) | NEt$_3$ [ml] ([mM]) | Chloride [g] ([mM]) | CH$_2$Cl$_2$ [ml] | Yield [g] (%) | NMR δ ppm |
|---|---|---|---|---|---|---|---|---|---|---|---|
| (24) | —C$_{16}$H$_{33}$ | —O—(CH$_2$)$_3$— | | H | S | 1.0 (2.7) | 0.488 (3.51) | 0.526 (2.97) | 20 | 1.194 (86) | (CDCl$_3$) 0.88(t, 3H), 1.26(s, 26H), 1.45-1.67(m, 2H), 1.80-2.08(m, 4H), 2.22-2.38(m, 2H), 2.57(t, 2H, J=7.3Hz), 2.69, 2.72(ABq, 2H, J=12.5Hz), 3.14-3.38 (m, 4H), 3.69(t, 2H, J=6.2Hz), 3.82-3.94(m, 2H), 4.65(t, 1H, J=6.4Hz). |
| (27) | —CONHC$_{18}$H$_{37}$ | —O—(CH$_2$)$_3$— | | H | O | 1.513 (3.55) | 0.593 (4.26) | 0.69 (3.90) | 20 | 1.693 (84) | (CDCl$_3$) 0.88(t, 3H), 1.26(s, 30H), 1.40-1.60(m, 2H), 1.70-2.10(m, 4H), 2.20-2.38(m, 2H), 3.08-3.28(m, 6H), 3.68(t, 2H, J=6.2Hz), 3.80-4.16(m, 4H), 4.78-4.90 (br, 1H), 5.14(t, 1H, J=6.5Hz). |
| (31) | —C$_{16}$H$_{33}$ | —OOCNHCH$_3$ | | H | S | 1.161 (3.0) | 0.501 (3.6) | 0.636 (3.6) | 40 | 1.459 (92) | (CDCl$_3$) 0.80-1.80(m, 31H), 2.15-2.80(m, 6H), 2.81(d, J=5Hz, 3H), 3.15-3.35(m, 2H), 3.35-3.55(m, 2H), 3.68(t, J=6Hz, 2H), 4.75-5.20(br.m, 3H). |
| (36) | —CONHC$_{18}$H$_{37}$ | —OOCNHCH$_3$ | | H | O | 1.10 (2.48) | 0.301 (2.98) | 0.527 (2.98) | 110 | 1.225 (85) | (CDCl$_3$) 0.84(t, J=6Hz, 3H), 1.24(br.s, 32H), 2.24(m, 2H), 2.74(d, J=6Hz, 3H), 2.95-3.50(m, 6H), 3.65(t, J=6Hz, 2H), 4.20(d, J=6Hz, 2H), 4.50(br.s, 1H), 4.95 (m, 3H). |
| (56) | —CONHC$_{18}$H$_{37}$ | —NHCOOCH$_3$ | | H | O | 0.836 (1.88) | 1 (7.17) | 0.750 (4.24) | 22 | 0.745 (67.6) | (CDCl$_3$) 0.88(t, J=5Hz), 1.27(30H, s), 1.50(2H, m), 2.27 (2H, m), 3.1-3.4(6H), 3.70(3H, s), 3.6-3.8(2H, m), 3.95(1H, m), 4.19(2H, d, J=5Hz), 4.86(1H, t, J=5Hz), 5.45(1H, t, J=5Hz). |
| (57) | —CONHC$_{18}$H$_{37}$ | —NHCOOiBu | | H | O | 0.501 (1.03) | 1.5 (21) | 0.365 (2.06) | 13 | 0.500 (77.4) | (CDCl$_3$) 0.89(3H, t, J=5Hz), 1.26(30H, m), 1.45(9H, s), 1.50(2H, m), 2.29(2H, m), 3.20(6H), 3.69(2H, t, J=6Hz), 3.88(1H, br.s), 4.17(2H, d, J=5Hz), 4.80 (1H, t, J=4Hz), 5.14(1H, br.s), 5.43(1H, br.s). |
| (58) | —C$_{16}$H$_{33}$ | —NHCOOCH$_3$ | | H | S | 3.470 (8.928) | 1.5 (10.9) | 1.77 g (10) | 45 | 4.603 (97.4) | (CDCl$_3$) 0.88(3H, t, J=6.5Hz), 1.26(26H, s), 1.58(2H, m), 2.29(2H, m), 2.54(2H, t, J=7.3Hz), 2.65(1H, dd, J=7.2, 13.2Hz), 2.76(1H, dd, J=6.0, 13.2Hz), 3.18-3.46(4H), 3.69(2H, t, J=6.2Hz), 3.69(3H, s), 3.88 (1H, m), 4.97(1H, t, J=6.5Hz), 5.25(1H, d, J=7.3Hz). |
| (59) | —C$_{16}$H$_{33}$ | —NHCOOiBu | | H | S | 3.69 (8.567) | 1.5 (10.9) | 1.77 (10) | 50 | 4.74 (96.8) | (CDCl$_3$) 0.88(3H, t, J=6.5Hz), 1.26(26H, s), 1.46(9H, s), 1.58(2H, m), 2.29(2H, m), 2.54(2H, t, J=7.2Hz), 2.65(1H, dd, J=6.3, 13.7Hz), 2.74(1H, dd, J=5.9, 13.7Hz), 3.18-3.45(4H), 3.69(2H, t, J=6.2Hz), 3.84(1H, m), 4.90-5.10(2H). |

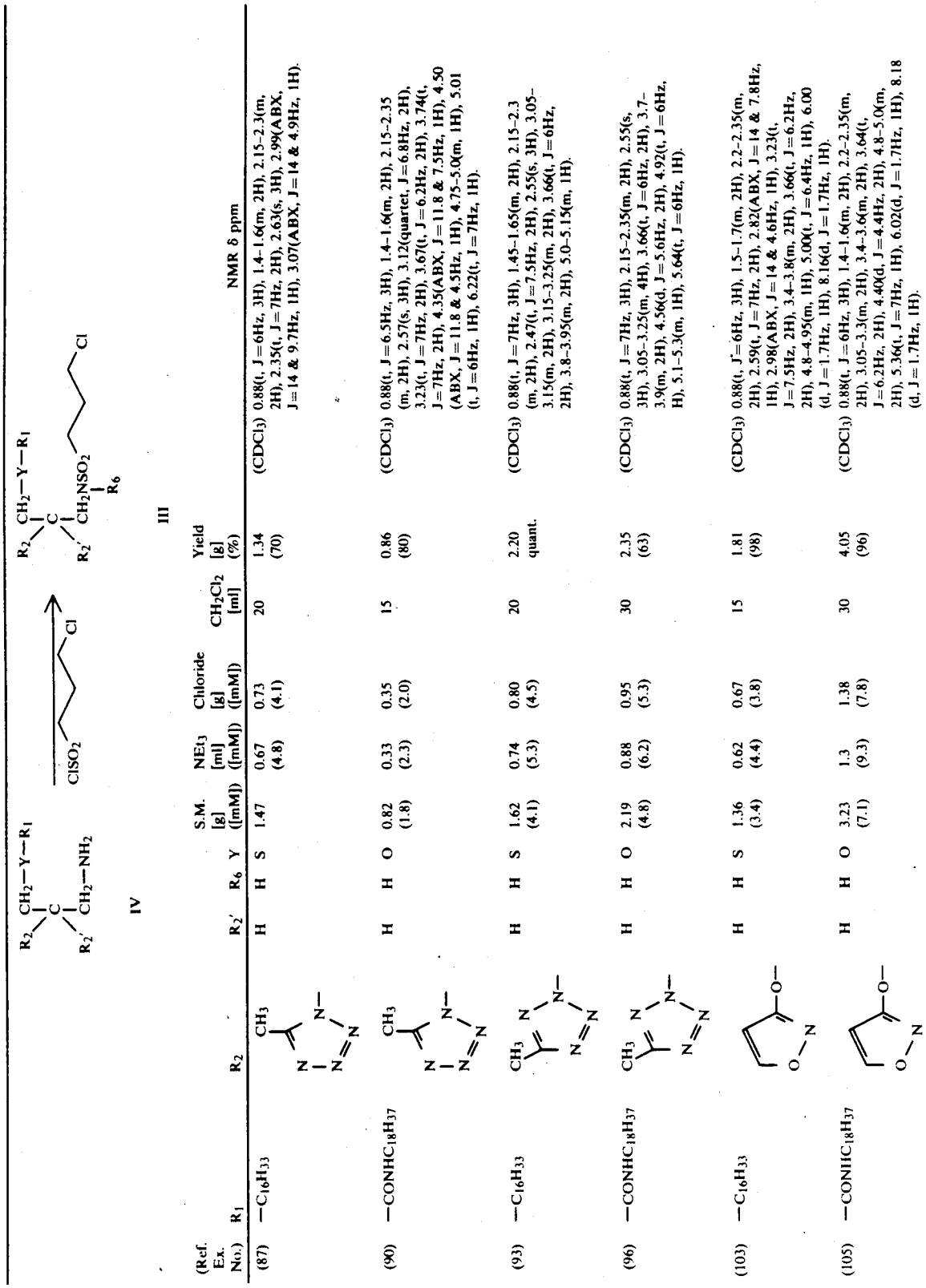

TABLE 7-continued $$\underset{IV}{\overset{R_2}{\underset{R_2'}{>}}}C\overset{CH_2-Y-R_1}{\underset{CH_2-NH_2}{<}} \xrightarrow[CH_2Cl_2]{\underset{Cl}{\overset{ClSO_2}{\nearrow}}\nearrow} \underset{III}{\overset{R_2}{\underset{R_2'}{>}}}C\overset{CH_2-Y-R_1}{\underset{CH_2NSO_2}{<}}\overset{Cl}{\underset{R_6}{\searrow}}$$

| (Ref. Ex. No.) | R₁ | R₂ | R₂' | R₆ | Y | S.M. [g] ([mM]) | NEt₃ [ml] ([mM]) | Chloride [g] ([mM]) | CH₂Cl₂ [ml] | Yield [g] (%) | NMR δ ppm |
|---|---|---|---|---|---|---|---|---|---|---|---|
| (108) | —C₁₆H₃₃ | CH₃OCH₂— | H | H | O | 2.0 (5.8) | 1.06 (7.6) | 1.14 (6.4) | 20 | 2.63 (93) | (CDCl₃) 0.88(t, J=6Hz, 3H), 1.35-1.65(m, 2H), 2.05-2.3 (m, 1H), 2.15-2.45(m, 2H), 3.34(s, 3H), 3.69(t, J=6.5Hz, 2H), 5.26(t, J=6Hz, 1H). |
| (112) | —C₁₆H₃₃ | CH₃OCH₂— | H | H | S | 1.44 (4) | 0.67 (4.8) | 0.78 (4.4) | 20 | 1.374 (69) | (CDCl₃) 0.88(t, 3H), 1.26(s, 26H), 1.50-1.65(m, 2H), 1.96-2.16(m, 1H), 2.22-2.36(m, 2H), 2.44-2.66 (m, 4H), 3.15-3.32(m, 4H), 3.35(s, 3H), 3.38-3.60 (m, 2H), 3.69(t, 2H, J=6.2Hz), 5.06(t, 1H, J=5.8Hz). |
| (115) | —CONHC₁₈H₃₇ | CH₃OCH₂— | H | H | O | 2.0 (4.8) | 0.88 (6.3) | 0.95 (5.3) | 60 | 2.52 (94) | (CDCl₃) 0.88(t, J=6Hz, 3H), 1.4-1.6(m, 2H), 2.1-2.4(m, 3H), 3.0-3.3(m, 6H), 3.34(s, 3H), 3.35-3.55(m, 2H), 3.69(t, J=6.2Hz, 2H), 4.06(ABX, J=14 & 7.3Hz, 1H), 4.18(ABX, J=14 & 6.7Hz, 1H), 4.81(t, J=6Hz, 1H), 5.36(t, J=7Hz, 1H). |
| (141) | —C₁₆H₃₃ | NCCH₂— | H | H | O | — | 1.51 (10.76) | 1.456 (8.28) | 30 | 3.233 (87.8) | (CDCl₃) 0.88(t, J=6.4Hz, 3H), 1.15-1.43(m, 26H), 1.46-1.67(m, 2H), 2.17-2.37(m, 3H), 2.45-2.69(m, 2H), 3.13-3.36(m, 4H), 3.45(t, J=6.6Hz, 2H), 3.48-3.63 (m, 2H), 3.69(t, J=6.4Hz, 2H), 4.92(t, J=6.3Hz, 1H). |
| (150) | —CONHC₁₈H₃₇ | NCCH₂— | H | H | O | — | 0.36 (2.58) | 0.335 (1.89) | 10 | 0.965 (95.6) | (CDCl₃) 0.88(t, J=6.4Hz, 3H), 1.16-1.38(m, 30H), 1.40-1.58(m, 2H), 2.20-2.40(m, 3H), 2.50(d, J=6.8Hz, 2H), 3.01-3.33(m, 6H), 3.69(t, J=6.2Hz, 2H), 4.32 (dd, J=9.2 & 3.3Hz, 1H), 4.15(dd, J=9.2 & 4.2Hz, 1H), 4.84(t, J=4.4Hz, 1H), 5.44(t, J=5.4Hz, 1H). |

TABLE 8

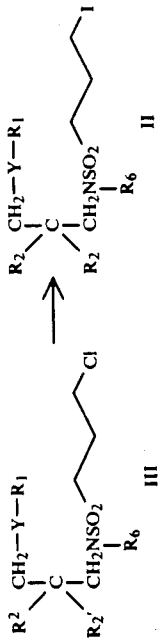

| (Ref. Ex. No.) | R1 | R2 | R2' | R6 | Y | S.M. [g] ([mM]) | NaI [mg] ([mM]) | MEK [ml] | Yield [g] (%) | NMR δ ppm |
|---|---|---|---|---|---|---|---|---|---|---|
| (25) | —C16H33 | —O—(CH2)3— | | H | S | 1.0 (1.95) | 1100 (7.33) | 20 | 1.063 (90) | (CDCl3) 0.88(t, 3H), 1.26(s, 26H), 1.45–1.70(m, 2H), 1.85–2.10(m, 4H), 2.25–2.42(m, 2H), 2.58(t, 2H, J=7.3Hz), 2.69, 2.72 (ABq, 2H, J=12.9Hz), 3.14–3.26(m, 4H), 3.30(t, 2H, J=6.7Hz), 3.82–3.96(m, 2H), 4.67(t, 1H, J=6.3Hz). |
| (28) | —CONHC18H37 | —O—(CH2)3— | | H | O | 1.50 (2.64) | 1500 (10) | 30 | 1.325 (76) | (CDCl3) 0.88(t, 3H), 1.26(s, 30H), 1.40–1.60(m, 2H), 1.70–2.10(m, 4H), 2.25–2.40(m, 2H), 3.10–3.24(m, 6H), 3.30(t, 2H, J=6.6Hz), 3.84–4.14(m, 4H), 4.78–4.92(br, 1H), 5.14(t, 1H, J=6.4Hz). |
| (32) | —C16H33 | —OOCNHCH3 | H | H | S | 0.528 (1.0) | 450 (3.0) | 10 | 0.593 (96) | (CDCl3) 0.75–1.75(m, 31H), 2.13–2.80(m, 6H), 2.80(d, J=5Hz, 3H), 3.05–3.55(m, 6H), 4.75–5.23(br.m, 3H). |
| (37) | —CONHC18H37 | —OOCNHCH3 | H | H | O | 1.22 (2.09) | 626 (4.18) | 60 | 1.151 (82) | (CDCl3) 0.90(t, J=6Hz, 3H), 1.26(br.s, 32H), 2.30(m, 2H), 2.80 (d, J=6Hz, 3H), 3.00–3.45(m, 8H), 4.22(d, J=6Hz, 2H), 4.96 (m, 3H), 5.52(m, 1H). |
| (67) | —CONHC18H37 | —NHCOOCH3 | H | H | O | 0.340 (0.582) | 170 (1.13) | 5 | 0.375 (95.4) | (CDCl3) 0.90(3H, t, J=4Hz), 1.28(30H, s), 1.51(2H, m), 2.34(2H, m), 3.1–3.4(8H), 3.71(3H, s), 3.97(1H, m), 4.19(2H, s), 4.85 (1H, s), 5.43(1H, s). |
| (68) | —CONHC18H37 | —NHCOOtBu | H | H | O | 0.402 (0.642) | 180 (1.20) | 5 | 0.409 (88.8) | (CDCl3) 0.88(3H, t, J=6Hz), 1.26(30H, s), 1.45(11H, s), 2.32(2H, m), 3.1–3.3(6H), 3.31(2H, t, J=7Hz), 3.89(1H, br.s), 4.17(2H, br.s), 4.82(1H, br.s), 5.15(1H, br.s), 5.44(1H, br.s). |
| (69) | —CONHC18H37 | —NHCOCH3 | H | H | O | 0.427 (0.751) | 180 (1.20) | 5 | 0.457 (92.2) | (CDCl3) 0.88(3H, t, J=6Hz), 1.26(30H, s), 1.50(2H, m), 2.02(3H, s), 2.31(2H, m), 3.1–3.3(4H), 3.15(2H, t, J=7Hz), 3.30(2H, t, J=7Hz), 4.17(3H), 4.93(1H, t, J=5Hz), 5.74(1H, t, J=5Hz), 6.49(1H, s). |
| (70) | —CONHC18H37 | —NHCONHCH3 | H | H | O | 0.460 (0.789) | 180 (1.20) | 5 | 0.508 (95.5) | (CDCl3) 0.88(3H, t, J=6Hz), 1.26(30H, s), 1.50(2H, m), 1.69(1H, br. s), 2.31(2H, m), 2.77(3H, s), 3.1–3.3(4H), 3.14(2H, t, J=7Hz), 3.30(2H, t, J=7Hz), 4.05(1H, m), 4.14(2H, d, J=4Hz), 5.01(1H, t, J=5Hz), 5.45(1H, s), 6.06(1H, s). |
| (71) | —C16H33 | —NHCOOCH3 | H | H | S | 4.500 (8.503) | 2548 (16.999) | 50 | 4.771 (90.4) | (CDCl3) 0.88(3H, t, J=6.5Hz), 1.26(26H, s), 1.58(2H, m), 2.32(2H, m), 2.54(2H, t, J=7.3Hz), 2.66(1H, dd, J=6.8, 13.5Hz), 2.77 (1H, dd, J=6.1, 13.5Hz), 3.12–3.47(6H), 3.70(3H, s), 3.58 (1H, m), 4.95(1H, t, J=6.0Hz), 5.25(1H, d, J=7.5Hz). |
| (72) | —C16H33 | —NHCOOtBu | H | H | S | 1.518 (2.657) | 800 (5.337) | 15 | 1.671 (94.9) | (CDCl3) 0.88(3H, t, J=6.4Hz), 1.26(26H, s), 1.46(9H, s), 1.58(2H, m), 2.32(2H, m), 2.54(2H, t, J=7.0Hz), 2.70(2H, m), 3.12–3.45(4H), 3.30(2H, t, J=6.6Hz), 3.83(1H, m), 4.9–5.1(2H). |
| (73) | —C16H33 | —NHCOCH3 | H | H | S | 0.914 (1.781) | 550 (3.669) | 12 | 1.002 (93.0) | (CDCl3) 0.88(3H, t, J=6.5Hz), 1.26(26H, s), 1.58(2H, m), 2.03(3H, s), 2.31(2H, m), 2.54(2H, t, J=7.3Hz), 2.65(1H, dd, J=7.1, 13.3Hz), 2.77(1H, dd, J=5.9, 13.3Hz), 3.12–3.37(4H), 3.30 (2H, t, J=6.6Hz), 4.12(1H.m), 5.24(1H, t, J=6.2Hz), 6.24 (1H, d, J=7.5Hz). |
| (74) | —C16H33 | —NHCONHCH3 | H | H | S | 1.039 (1.967) | 600 (4.003) | 17 | 1.156 (94.8) | (CDCl3) 0.88(3H, t, J=6.5Hz), 1.26(26H, s), 1.58(2H, m), 1.70(1H, br.s), 2.31(2H, m), 2.54(2H, t, J=7.2Hz), 2.66(1H, dd, |

TABLE 8-continued $$\begin{array}{c}R_2\\ \diagup\\ R_2'\end{array}\!\!C\!\!\begin{array}{c}CH_2-Y-R_1\\ \diagdown\\ CH_2NSO_2\\ |\\ R_6\end{array}\quad\longrightarrow\quad\begin{array}{c}R_2\\ \diagup\\ R_2'\end{array}\!\!C\!\!\begin{array}{c}CH_2-Y-R_1\\ \diagdown\\ CH_2NSO_2\\ |\\ R_6\end{array}$$

III                                                                                    II

| (Ref. Ex. No.) | $R_1$ | $R_2$ | $R_2'$ | $R_6$ | Y | S.M. [g] ([mM]) | NaI [mg] ([mM]) | MEK [ml] | Yield [g] (%) | NMR δ ppm |
|---|---|---|---|---|---|---|---|---|---|---|
| (75) | —CONHC$_{18}$H$_{37}$ | —NHCOCH$_3$ | H | Ac | O | 0.335 (0.549) | 180 (1.20) | 5 | 0.351 (91.1) | (CDCl$_3$) 0.88(t, J=6Hz), 1.26(30H, s), 1.50(2H, s), 1.99(3H, s), 2.35(2H, m), 2.47(3H, s), 3.18(2H, m), 3.30(2H, t, J=7Hz), 3.53(2H, t, J=7Hz), 3.90(2H, m), 4.15(2H, m), 4.48(1H, m), 4.81(1H, t, J=6Hz), 6.09(1H, d, J=6Hz), J=6.8, 13.5Hz), 2.75(1H, dd, J=6.1, 13.5Hz), 2.78(3H, s), 3.12-3.44(4H), 3.30(2H, t, J=6.6Hz), 4.00(1H, br.s), 5.09 (1H, br.s), 5.75(1H, br.s). |
| (88) | —C$_{16}$H$_{37}$ | CH$_3$-triazole | H | H | S | 1.29 (2.4) | 540 (3.6) | 20 | 1.33 (88) | (CDCl$_3$) 0.88(t, J=6.5Hz, 3H), 1.4-1.6(m, 2H), 2.2-1.4(m, 4H), 2.61 (s, 3H), 2.95-3.1(m, 2H), 3.1-3.3(m, 2H), 3.28(t, J=6.6Hz, 2H), 3.6-3.85(m, 2H), 4.55-4.7(m, 1H), 4.6-4.75(m, 1H), 3.15-3.3(m, 2H), 3.55-3.8(m, 4H), 4.6-4.75(m, 1H). |
| (91) | —CONHC$_{18}$H$_{37}$ | CH$_3$-triazole | H | H | O | 0.83 (1.4) | 475 (3.2) | 10 | 0.905 (94) | (CDCl$_3$) 0.88(t, J=5Hz, 3H), 1.4-1.6(m, 2H), 2.15-2.35(m, 2H), 2.58(s, 3H), 3.05-3.25(m, 4H), 3.29(t, J=7Hz, 3H), 3.74 (t, J=6Hz, 2H), 4.35(ABX, J=11.0 & 7.7Hz, 1H), 4.51(ABX, J=11.0 & 5.3Hz, 1H), 4.75-4.95(m, 1H), 5.02(t, J=6Hz, 1H), 6.26(t, J=6Hz, 1H). |
| (94) | —C$_{16}$H$_{33}$ | H$_3$C-triazole | H | H | S | 2.2 (4.1) | 920 (6.2) | 30 | 2.27 (88) | (CDCl$_3$) 0.88(t, J=7Hz, 3H), 1.45-1.55(m, 2H), 2.15-2.3(m, 2H), 2.45(t, J=7Hz, 2H), 2.56(s, 3H), 3.07(d, J=6.5Hz, 2H), 3.09(t, J=7Hz, 2H), 3.27(t, J=6.7Hz, 2H), 4.7-4.9(m, 2H), 5.0-5.15(m, 1H). |
| (97) | —CONHC$_{18}$H$_{37}$ | H$_3$C-triazole | H | H | O | 2.29 (3.9) | 1170 (7.8) | 30 | 2.42 (92) | (CDCl$_3$) 0.88(t, J=7Hz, 3H), 2.26(quintet, J=6Hz, 2H), 2.56(s, 3H), 3.05-3.20(m, 4H), 3.27(t, J=6.7Hz, 2H), 3.73(ABX, J=15.4 & 5.7Hz, 1H), 3.85(ABX, J=15.4 & 7.3Hz, 1H), 4.56(d, J=5.4Hz, 2H), 4.91(t, J=6Hz, 1H), 5.1-5.3(m, 1H), 5.6(t, J=6Hz, 1H). |
| (104) | —C$_{16}$H$_{33}$ | isoxazole-OMe | H | H | S | 1.76 (3.3) | 833 (5.6) | 25 | 1.78 (86) | (CDCl$_3$) 0.88(t, J=7Hz, 3H), 1.5-1.7(m, 2H), 2.2-2.4(m, 2H), 2.59 (t, J=7Hz, 2H), 2.82(ABX, J=13.6 & 7.8Hz, 1H), 2.98(ABX, J=13.6 & 4.2Hz, 1H), 3.18(t, J=7.5Hz, 2H), 3.28(t, J=6.7Hz, 2H), 3.4-3.8(m, 2H), 4.8-5.0(m, 1H), 5.09(t, J=6Hz, 1H), 6.01(d, J=1.8 Hz, 1H), 8.16(d, J=1.8Hz, 1H). |

TABLE 8-continued $$\begin{array}{c} R_2 \\ R_2' \end{array} \!\!\! \begin{array}{c} CH_2-Y-R_1 \\ C \\ CH_2NSO_2 \\ R_6 \end{array} \quad \text{III} \quad \longrightarrow \quad \begin{array}{c} Cl \\ \end{array} \quad \longrightarrow \quad \begin{array}{c} R_2 \\ R_2' \end{array} \!\!\! \begin{array}{c} CH_2-Y-R_1 \\ C \\ CH_2NSO_2 \\ R_6 \end{array} \quad \text{II} \quad \begin{array}{c} I \\ \end{array}$$

| (Ref. Ex. No.) | R₁ | R₂ | R₂' | R₆ | Y | S.M. [g] ([mM]) | NaI [mg] ([mM]) | MEK [ml] | Yield [g] (%) | NMR δ ppm |
|---|---|---|---|---|---|---|---|---|---|---|
| (107) | —CONHC₁₈H₃₇ | 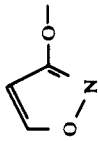 | H | H | O | 4.05 (6.8) | 1740 (11.6) | 50 | 3.96 (85) | (CDCl₃) 0.88(t, J=6Hz, 3H), 1.4–1.6(m, 2H), 2.2–2.4(m, 2H), 3.05–3.3(m, 4H), 3.28(t, J=6.6Hz, 2H), 3.4–3.6(m, 2H), 4.40 (d, J=5Hz, 2H), 4.85–5.0(m, 2H), 5.40(t, J=7Hz, 1H), 6.06 (d, J=1.8Hz, 1H), 8.18(d, J=1.8Hz, 1H). |
| (109) | —C₁₆H₃₃ | CH₃OCH₂— | H | H | O | 2.63 (5.4) | 1380 (9.2) | 30 | 3.09 (99) | (CDCl₃) 0.88(t, J=6Hz, 3H), 2.2–2.4(m, 1H), 2.05–2.25(m, 2H), 3.12 (t, J=7Hz, 2H), 3.34(s, 3H), 5.27(t, J=6Hz, 1H). |
| (113) | —C₁₆H₃₃ | CH₃OCH₂— | H | H | S | 1.37 (2.75) | 3000 (20) | 70 | 1.06 (65) | (CDCl₃) 0.88(t, 3H), 1.26(s, 26H), 1.48–1.65(m, 2H), 1.98–2.16(m, 1H), 2.24–2.40(m, 2H), 2.45–2.60(m, 4H), 3.10–3.34(m, 4H), 3.31(t, 2H, J=6.7Hz), 3.35(s, 3H), 3.40–3.60(m, 2H), 5.10 (t, 1H, J=6.5Hz). |
| (116) | —CONHC₁₈H₃₇ | CH₃OCH₂— | H | H | O | 2.52 (4.6) | 1160 (7.7) | 30 | 2.41 (82) | (CDCl₃) 0.88(s, 3H), 1.4–1.6(m, 2H), 2.1–2.4(m, 3H), 3.05–3.3(m, 4H), 3.31(t, J=7Hz, 2H), 3.35–3.55(m, 2H), 3.35(s, 3H), 4.06(ABX, J=12 & 6.8Hz, 1H), 4.18(ABX, J=12 & 5.2Hz, 1H), 4.86(t, J=6Hz, 1H), 5.40(t, J=6Hz, 1H). |
| (133) | —CONHC₁₈H₃₇ | CH₃COCH₂— | H | H | O | — | 750 (5) | 10 | 0.218 | (CDCl₃) 0.88(t, J=6.4Hz, 3H), 1.18–1.38(m, 30H), 1.40–1.57(m, 2H), 2.19(s, 3H), 2.20–2.77(m, 5H), 3.03–3.24(m, 6H), 3.29(t, J=6.4Hz, 2H), 3.95–4.20(m, 2H), 4.67–4.82(br, 1H), 5.22–5.36(br, 1H). |
| (142) | —C₁₆H₃₃ | NCCH₂— | H | H | O | 0.447 (1.0) | 1490 (10.0) | 20 | 0.493 (86.4) | (CDCl₃) 0.88(t, J=6.4Hz, 3H), 1.15–1.43(m, 26H), 1.46–1.67(m, 2H), 2.17–2.40(m, 3H), 2.44–2.68(m, 2H), 3.08–3.12(m, 2H), 3.23–3.37(m, 4H), 3.45(t, J=6.6Hz, 2H), 3.49–3.63(m, 2H), 4.96 (t, J=6.3Hz, 1H). |
| (151) | —CONHC₁₈H₃₇ | NCCH₂— | H | H | O | 0.6 (1.09) | 1633 (10.9) | 30 | 0.622 (88.9) | (CDCl₃) 0.88(t, J=6.4Hz, 3H), 1.18–1.40(m, 30H), 1.40–1.58(m, 2H), 2.20–2.44(m, 3H), 2.50(d, J=6.6Hz, 2H), 3.04–3.29(m, 6H), 3.30(t, J=6.4Hz, 2H), 4.15(dd, J=9.2 & 4.2Hz, 1H), 4.32(dd, J=9.2 & 3.3 Hz, 1H), 4.84(t, J=4.4Hz, 1H), 5.44(t, J=5.4Hz, 1H). |
| (158) | —C₁₆H₃₃ | CH₃COCH₂— | H | H | S | 0.213 (0.42) | 630 (4.2) | 20 | 0.186 (73.8) | (CDCl₃) 0.88(t, J=6.4Hz, 3H), 1.13–1.47(m, 26H), 1.47–1.67(m, 2H), 2.19(s, 3H), 2.23–2.44(m, 3H), 2.44–2.60(m, 4H), 2.65(d, J=6.0Hz, 2H), 3.07–3.27(m, 4H), 3.30(t, J=6.4Hz, 2H), 4.69 (t, J=6.4Hz, 1H). |

MEK: methyl ethyl ketone

TABLE 9

$$R_2 \quad CH_2-Y-R_1$$
$$\underset{R_2'}{\overset{|}{C}}-CH_2NSO_2-R_6 \quad \rightarrow \quad \underset{R_2'}{\overset{R_2}{\underset{|}{C}}}-\underset{\underset{R_6}{|}}{\overset{CH_2-Y-R_1}{\underset{|}{C}}}-CH_2NSO_2 \quad \overset{I^-}{\underset{}{N(CH_3)_3}}$$

II → I

| Ex. No. | R₁ | R₂ | R₂' | R₆ | Y | S.M. [mg] ([mM]) | 4.2M/L-toluene [ml] | Yield [mg] (%) | NMR δ ppm | IR νmax [cm⁻¹] | m.p. [°C] |
|---|---|---|---|---|---|---|---|---|---|---|---|
| 29 | —C₁₆H₃₃ | —O—(CH₂)₃— | | H | S | 500 (0.828) | 15 | 510 (93) | (CDCl₃) 0.88(t, 3H), 1.26(s, 26H), 1.45-1.65(m, 2H), 1.90-2.10(m, 4H), 2.30-2.52(m, 2H), 2.58(t, 2H, J=7.3Hz), 2.72, 2.84(ABq, 2H, J=13.2Hz), 3.20-3.54(m, 6H), 3.43(s, 9H), 3.68-4.00(m, 2H), 5.99(t, 1H, J=6.4Hz). | (CHCl₃) 3380, 2910, 2840, 1465, 1320, 1210, 1140, 1030 | 79~84 |
| 32 | —C₁₆H₃₃ | —OOCNHCH₃ | H | H | S | 340 (0.548) | 7 | 330 (89) | (CDCl₃) 0.75-1.75(m, 31H), 2.30-3.00(m, 9H), 3.39 (br.s, 13H), 3.80(m, 2H), 4.88(m, 1H), 5.70 (m, 1H), 6.50(m, 1H). | (CHCl₃) 3400, 1720, 1330, 1150 | 95~96 |
| 34 | —CONHC₁₈H₃₇ | —OOCNHCH₃ | H | H | O | 338 (0.5) | 10 | 220 (60) | (CDCl₃–CD₃OD) 0.85(t, J=6Hz, 3H), 1.24(br.s, 32H), 2.72(s, 3H), 2.85-3.25(m, 11H), 3.34 (s, 9H), 3.55-3.85(m, 2H), 4.16(d, J=6Hz, 2H), 4.94(m, 1H). | (Nujol) 3320, 1695, 1540, 1380, 1260, 1140 | 91~93 |
| 35 | —CONHC₁₈H₃₇ | —NHCOOCH₃ | H | H | O | 561 (0.830) | 7 | 323 (52.9) | (CDCl₃) 0.87(3H, t, J=5Hz), 1.25(30H, s), 1.50(2H, m), 2.43(2H, br.s), 3.12(2H, m), 3.35(2H, m), 3.39(9H, s), 3.66(3H, s), 3.87(2H, m), 4.05(1H, m), 4.16(2H, br.s), 5.42(1H, br.s), 5.92(1H, br.s), 6.35(1H, br.s). | (Nujol) 3320, 1705, 1144 | 57~59 |
| 36 | —CONHC₁₈H₃₇ | —NHCOOtBu | H | H | O | 167 (0.233) | 10 | 93 (50.1) | (CDCl₃) 0.88(3H, t, J=6Hz), 1.26(30H, s), 1.44 (11H), 2.43(2H, br.s), 3.12(2H, m), 3.30 (4H), 3.39(9H, s), 3.90(3H), 4.17(2H, br. s), 5.43(2H, br.s), 6.52(1H, br.s). | (Nujol) 3360, 1691, 1323, 1311, 1145 | 80~81 |
| 37 | —CONHC₁₈H₃₇ | —NHCOCH₃ | H | H | O | 212 (0.321) | 10 | 217 (93.9) | (CD₃OD) 0.90(3H, t, J=6Hz), 1.28(30H, s), 1.48(2H, m), 1.97(3H, s), 2.28(2H, m), 3.08(2H, t, J=6Hz), 3.18(9H, s), 3.1~3.4(4H), 3.52 (2H, m), 4.0-4.2(3H). | (Nujol) 3330, 3270, 1690, 1646, 1294, 1270, | 94~97 |
| 38 | —CONHC₁₈H₃₇ | —NHCONHCH₃ | H | H | O | 242 (0.359) | 10 | 192 (72.9) | (CDCl₃) 0.88(3H, t, J=5Hz), 1.25(30H, s), 1.48(2H, m), 2.32(2H, br.s), 2.71(3H, d, J=3Hz), 3.09(2H, m), 3.2-3.5(2H), 3.36(9H, s), 3.80(2H, br.s), 4.10(3H, s), 5.75(1H, s), 5.85(1H, s), 6.03(1H, s), 6.71(1H, s). | (Nujol) 3320, 1703, 1647, 1310, 1144 | 75~80 |
| 39 | —C₁₆H₃₃ | —NHCOOCH₃ | H | H | S | 621 (1) | 10 | 446 (65.6) | (CDCl₃) 0.89(3H, t, J=6.5Hz), 1.26(26H, s), 1.57 (2H, m), 2.42(2H, m), 2.55(2H, t, J=7.3Hz), 2.75(2H, d, J=6.1Hz), 3.24-3.45(4H), 3.41 (9H, s), 3.69(3H, s), 3.86(3H, m), 5.89 (1H, d, J=7.4Hz), 6.60(1H, t, J=6.2Hz). | (KBr) 3380, 3310, 3150, 1702, 1322, 1142 | 68~72 |
| 40 | —C₁₆H₃₃ | —NHCOOtBu | H | H | S | 663 (1) | 5 | 555 (76.9) | (CDCl₃) 0.88(3H, t, J=6.5Hz), 1.26(26H, s), 1.45 (9H, s), 1.57(2H, m), 2.43(2H, m), 2.55 (2H, t, J=7.3Hz), 2.74(2H, d, J=6.2Hz), 3.23-3.50(4H), 3.40(9H, s), 3.87(3H, m), 5.37 (1H, d, J=6.5Hz), 6.46(1H, t, J=5.8Hz). | (KBr) 3320, 1676, 1323, 1145 | 60~67 |
| 41 | —C₁₆H₃₃ | —NHCOCH₃ | H | H | S | 478 | 5 | 462 | (CDCl₃+CD₃OD) 0.88(3H, t, J=6.3Hz), 1.26(26H, s), | (KBr) | 103~ |

TABLE 9-continued $$\begin{array}{c} R_2\ \ CH_2-Y-R_1 \\ | \\ C \\ | \\ R_2'\ \ CH_2NSO_2 \\ \quad\quad\quad | \\ \quad\quad\quad R_6 \\ II \end{array} \longrightarrow \begin{array}{c} R_2\ \ CH_2-Y-R_1 \\ | \\ C \\ | \\ R_2'\ \ CH_2NSO_2 \\ \quad\quad\quad | \\ \quad\quad\quad R_6 \\ \quad\quad\quad\quad\quad N(CH_3)_3\ \ I^- \\ I \end{array}$$

| Ex. No. | R₁ | R₂ | R₂' | R₆ | Y | S.M. [mg] ([mM]) | 4.2M/L-toluene [ml] | Yield [mg] (%) | NMR δ ppm | IR νmax [cm⁻¹] | m.p. [°C.] |
|---|---|---|---|---|---|---|---|---|---|---|---|
|  |  |  |  |  |  | (0.791) |  | (88.0) | 1.57(2H, m), 2.06(3H, s), 2.37(2H, m), 2.54(2H, t, J=7.3Hz), 2.68(2H, d, J=6.7Hz), 3.18–3.50(4H), 3.29(9H, s), 3.75(2H, m), 4.14(1H, m). | 3360, 3285, 3190, 1673, 1631, 1325, 1142 | 106 |
| 42 | —C₁₆H₃₃ | —NHCONHCH₃ | H | H | S | 546 (0.881) | 5 | 555 (92.8) | (CDCl₃+CD₃OD) 0.88(3H, t, J=6.5Hz), 1.26(26H, s), 1.57(2H, m), 2.22–2.46(2H), 2.55(2H, t, J=7.2Hz), 2.62(1H, dd, J=6.6, 13.0Hz), 2.70 (1H, dd, J=5.2, 13.2Hz), 2.73(3H, s), 3.12–3.30(3H), 3.27(9H, s), 3.43(1H, dd, J=3.3, 13.1Hz), 3.76(2H, m), 3.99(1H, m). | (KBr) 3315, 3165, 1652, 1319, 1140 | 111~115 |
| 43 | —CONHC₁₈H₃₇ | —NHCOCH₃ | H | H | Ac O | 132 (0.188) | 10 | 106 (72) | (CDCl₃) 0.88(3H, t, J=6Hz), 1.26(30H, s), 1.50(2H, m), 2.02(3H, s), 2.46(2H, br.s), 2.50(3H, s), 3.12(2H, m), 3.35(2H, m), 3.41(9H, s), 3.7–4.05(4H), 4.14(2H, m), 4.48(1H, m), 5.56(1H, t, J=5Hz), 6.91(1H, t, J=5Hz). | (Nujol) 3330, 1690, 1658, 1270, 1152 | 90~93 |
| 53 | —C₁₆H₃₃ | ![CH3-tetrazolyl] | H | H | S | 600 (0.95) | 13 | 590 (90) | (CDCl₃) 0.88(t, J=6Hz, 3H), 1.4–1.6(m, 2H), 2.1–2.35(m, 2H), 2.41(t, J=7Hz, 2H), 2.72(s, 3H), 3.0–3.4(m, 4H), 3.30(s, 9H), 3.5–3.9 (m, 4H), 4.75–4.95(m, 1H), 6.9–7.15 (m, 1H). | 1340 | 104~107.5 |
| 55 | —C₁₆H₃₃ | ![H3C-triazolyl] | H | H | S | 700 (1.1) | 13 | 650 (85) | (CDCl₃) 0.88(t, J=7Hz, 3H), 1.4–1.6(m, 2H), 2.2–2.4 (broad, 2H), 2.40(t, J=7Hz, 2H), 2.55(s, 3H), 3.0–3.3(m, 4H), 3.35(s, 9H), 3.6–3.9 (m, 4H), 5.1–5.25(m, 1H), 6.75–6.9(m, 1H). | 1340 | Amorphous powder |
| 57 | —C₁₆H₃₃ | ![isoxazolyl] | H | H | S | 700 (1.1) | 15 | 670 (87) | (CDCl₃) 0.88(t, J=7Hz, 3H), 1.45–1.65(m, 2H), 2.25–2.7(m, 2H), 2.58(t, J=7Hz, 2H), 2.92(d, J=5Hz, 2H), 3.2–3.45(m, 2H), 3.35(s, 9H), 3.5–3.9(m, 4H), 4.95–5.05(m, 1H), 6.18(d, J=1.8Hz, 1H), 6.55–6.75(m, 1H), 8.24(d, J=1.8Hz, 1H). | 1336 | Amorphous powder |

TABLE 9-continued

| Ex. No. | $R_1$ | $R_2$ | $R_2'$ | $R_6$ | Y | S.M. [mg] ([mM]) | 4.2M/L-toluene [ml] | Yield [mg] (%) | NMR δ ppm | IRνmax [cm$^{-1}$] | m.p. [°C.] |
|---|---|---|---|---|---|---|---|---|---|---|---|
| 58 | —CONHC$_{18}$H$_{37}$ | isoxazolyl-O— | H | H | O | 700 (1.0) | 30 | 710 (93) | (CDCl$_3$) 0.88(t, J=6Hz, 3H), 1.35-1.55(m, 2H), 2.2-2.5(m, 2H), 2.95-3.2(m, 2H), 3.2-3.45(m, 2H), 3.35(s, 9H), 3.4-3.65(m, 2H), 3.55-3.9(m, 2H), 4.2-4.45(m, 2H), 4.9-5.05(m, 1H), 5.35-5.55(m, 1H), 6.17(s, 1H), 6.7-6.9(m, 1H), 8.28(s, 1H). | 1719, 1336 | 90~99 |
| 60 | —C$_{16}$H$_{33}$ | CH$_3$OCH$_2$— | H | Ac | O | 810 (1.3) | 19 | 800 (90) | (CDCl$_3$) 0.88(t, J=6Hz, 3H), 1.4-1.6(m, 2H), 2.2-2.4(m, 1H), 2.35-2.6(m, 2H), 2.40(s, 3H), 3.47(s, 3H), 3.73(t, J=7Hz, 2H), 3.86(d, J=7Hz, 2H), 3.9-4.05(m, 2H). | 1698 | Amorphous powder |
| 61 | —C$_{16}$H$_{33}$ | CH$_3$OCH$_2$— | H | H | O | 1000 (1.7) | 25 | 950 (86) | (CDCl$_3$) 0.88(t, J=6Hz, 3H), 1.4-1.6(m, 2H), 2.05-2.25(m, 2H), 2.25-2.5(m, 2H), 3.44(s, 3H), 3.8-4.0(m, 2H), 6.02(t, J=6Hz, 1H). | 1330 | 79~80 |
| 63 | —C$_{16}$H$_{33}$ | —CH$_3$OCH$_2$— | H | H | S | 874 (1.48) | 10 | 468 (49) | (CDCl$_3$) 0.88(t, 3H), 1.26(s, 26H), 1.45-1.65(m, 2H), 1.98-2.20(m, 1H), 2.28-2.52(m, 2H), 2.51(t, 2H, J=7.3Hz), 2.62(d, 2H, J=7.0Hz), 3.10-3.50(m, 4H), 3.36(s, 3H), 3.43(s, 9H), 3.52(d, 2H, J=5.2Hz), 3.76-3.94(m, 2H), 6.20(t, 1H, J=6.0Hz). | 3400, 2930, 2855, 1475, 1330, 1200, 1150 | 65~70 |
| 67 | —C$_{16}$H$_{33}$ | NCCH$_2$— | H | H | O | 300 (0.53) | 5.0 | 328 (98.1) | (CDCl$_3$) 0.88(t, J=6.4Hz, 3H), 1.15-1.43(m, 26H), 1.45-1.60(m, 2H), 2.27-2.57(m, 3H), 2.68(d, J=6.4Hz, 2H), 3.08-3.63(m, 8H), 3.39(s, 9H), 3.76-3.97(m, 2H), 6.63(t, J=6.3Hz, 1H). | 2230, 1320, 1140 | — |
| 70 | —C$_{16}$H$_{33}$ | CH$_3$COCH$_2$— | H | H | S | 160 | 3.0 | 175 (98.0) | (CDCl$_3$) 0.88(t, J=6.4Hz, 3H), 1.13-1.45(m, 26H), 1.45-1.65(m, 2H), 2.21(s, 3H), 2.29-2.80(m, 9H), 3.04-3.37(m, 4H), 3.41(s, 9H), 3.78-3.95(m, 2H), 6.42(t, J=6.4Hz, 1H). | 1700, 1320, 1140 | — |
| 71 | —C$_{16}$H$_{33}$ | methylimidazolyl | H | H | S | 600 (0.96) | 13 | 490 (82) | (CDCl$_3$) 0.88(t, J=6.4Hz, 3H), 1.35-1.6(m, 2H), 2.05-2.3(m, 2H), 2.30(t, J=7.4Hz, 2H), 2.62(s, 3H), 2.9-3.25(m, 4H), 3.30(s, 9H), 3.5-3.85(m, 4H), 4.55-4.75(m, 1H), 7.0-7.2(m, 1H), 7.89(s, 1H). | 1327 | Amorphous powder |

TABLE 10

$$\begin{array}{c} R_2\phantom{xx}CH_2-Y-R_1 \\ \diagdown\phantom{x}| \\ C \\ \diagup\phantom{x}| \\ R_2'\phantom{xx}CH_2NSO_2 \\ \phantom{xxxxxx}|\phantom{xx}\\ \phantom{xxxxxx}R_6 \end{array} \quad \xrightarrow{\phantom{xxx}} \quad \begin{array}{c} R_2\phantom{xx}CH_2-Y-R_1 \\ \diagdown\phantom{x}| \\ C \\ \diagup\phantom{x}| \\ R_2'\phantom{xx}CH_2NSO_2 \\ \phantom{xxxxxx}|\phantom{xx}\\ \phantom{xxxxxx}R_6 \end{array}$$

II → I (with quinolinium group)

| Ex. No. | $R_1$ | $R_2$ | $R_2'$ | $R_6$ | Y | S.M. [mg] ([mM]) | Quino-line [ml] | Yield [mg] (%) | NMR δ ppm | IRνmax [cm$^{-1}$] | m.p. [°C] |
|---|---|---|---|---|---|---|---|---|---|---|---|
| 30 | —CONHC$_{18}$H$_{37}$ | —O—(CH$_2$)$_3$— | | H | O | 500 (0.76) | 0.95 | 150 (25) | (CDCl$_3$) 0.88(t, 3H), 1.25(s, 30H), 1.40-1.60(m, 2H), 1.68-2.00(m, 4H), 2.60-2.82(m, 2H), 3.11(q, 2H, J=6.6Hz), 3.18-3.40(m, 2H), 3.50-3.70(m, 2H), 3.70-3.94(m, 2H), 3.99(s, 2H), 5.48(t, 1H, J=5.7Hz), 5.54-5.72(m, 2H), 5.91(t, 1H, J=6.5Hz), 7.98(t, 1H, J=7.5Hz), 8.15-8.37(m, 3H), 8.70(d, 1H, J=9.2Hz), 9.25(d, 1H, J=8.2Hz), 10.34(d, 1H, J=5.0Hz). | (CHCl$_3$) 3400, 2930, 2850, 1710, 1460, 1430, 1325, 1230, 1140, 1040 | 57~62 |
| 31 | —C$_{16}$H$_{33}$ | —OOCNHCH$_3$ | H | H | S | 376 (0.6) | 1.5 | 295 (66) | (CDCl$_3$) 0.75-1.75(m, 31H), 2.35-2.90(m, 9H), 3.30-3.70 (m, 4H), 4.85(m, 1H), 5.65(m, 3H), 6.32(m, 1H), 7.85-9.13(m, 6H), 10.15(d, J=6Hz, 1H). | (CHCl$_3$) 3450, 3300, 1630, 1600, 1320, 1140 | 49~54 |
| 33 | —CONHC$_{18}$H$_{37}$ | —OOCNHCH$_3$ | H | H | O | 338 (0.5) | 3 | 255 (63) | (CDCl$_3$-CD$_3$OD) 0.90(t, J=6Hz, 3H), 1.30(br.s, 32H), 2.76 (s, 3H), 2.95-3.60(m, 11H), 4.20(m, 2H), 4.96 (m, 1H), 5.48(m, 2H), 7.90-8.40(m, 4H), 8.65 (d, J=9Hz, 1H), 9.05(d, J=8Hz, 1H), 10.02 (d, J=5Hz, 1H). | (Nujol) 3360, 1690, 1390, 1260, 1160 | 137~139 (dec.) |
| 44 | —CONHC$_{18}$H$_{37}$ | —NHCOOCH$_3$ | H | H | O | 361 (0.534) | 3 | 301 (70.0) | (CDCl$_3$) 0.88(3H, t, J=5Hz), 1.25 (30H, s), 1.50(2H, m), 2.72(2H, br.s), 3.12(2H, m), 3.35(2H, br.s), 3.59(5H, s), 4.00(1H, br.s), 4.15(2H, s), 5.86(1H, br. s), 6.25(1H, br.s), 5.55(2H, br.s), 8.00(1H, t, J=8Hz), 8.20 (1H, m), 8.29(2H, m), 8.69(1H, d, J=8Hz), 9.01 (1H, d, J=8Hz), 10.19(1H, s). | (Nujol) 3320, 1702, 1143 | 70~74 |
| 45 | —CONHC$_{18}$H$_{37}$ | —NHCOOtBu | H | H | O | 206 (0.287) | 2 | 168 (69.1) | (CDCl$_3$) 0.88(3H, t, J=6Hz), 1.25(30H, s), 1.39(9H, s), 1.50(2H, m), 2.74(2H, m), 3.13(2H, m), 3.32 (2H, t, J=7Hz), 3.58(2H, t, J=7Hz), 3.94(1H, m), 4.15(2H, s), 5.45(1H, s), 5.59(1H, t, J=8Hz), 6.19(1H, s), 7.99(1H, t, J=9Hz), 8.17(1H, dd, J=5, 10Hz), 8.23(2H, m), 8.65(1H, d, J=5Hz), 8.97(1H, d, J=5Hz), 10.33(1H, d, J=5Hz). | (Nujol) 3360, 1693, 1323, 1148 | 78~82 |
| 46 | —CONHC$_{18}$H$_{37}$ | —NHCOCH$_3$ | H | H | O | 215 (0.326) | 2 | 211 (82.1) | (CDCl$_3$) 0.88(3H, t, J=6Hz), 1.25(30H, s), 1.48(2H, m), 2.01(3H, s), 2.68(2H, m), 3.10(2H, m), 3.33 (2H, m), 3.56(2H, m), 4.12(2H, m), 4.28(1H, m), 5.54(4H, m), 6.56(1H, m), 7.19(1H, d, J=7Hz), 7.99(1H, t, J=7Hz), 8.17(1H, dd, J=7, 6Hz), 8.25-8.42(2H), 8.70(1H, d, J=9Hz), 8.99(1H, d, J=5Hz), 10.13(1H, d, J=6Hz). | (Nujol) 3335, 1692, 1660, 1310, 1272, 1142 | 77~82 |

TABLE 10-continued $$\begin{array}{c} R_2 \quad CH_2-Y-R_1 \\ \diagdown \diagup \\ C \\ \diagup \diagdown \\ R_2' \quad CH_2NSO_2 \\ \qquad\qquad R_6 \end{array} \longrightarrow \text{I}$$

(Structure II on left with I substituent; product I shown with quinolinium N+ attached to butyl chain linked to central C bearing R_2, R_2', CH_2-Y-R_1, CH_2NSO_2R_6)

| Ex. No. | R_1 | R_2 | R_2' | R_6 | Y | S.M. [mg] ([mM]) | Quinoline [ml] | Yield [mg] (%) | NMR δ ppm | IR νmax [cm⁻¹] | m.p. [°C] |
|---|---|---|---|---|---|---|---|---|---|---|---|
| 47 | —CONHC_18H_37 | —NHCONHCH_3 | H | H | O | 242 (0.359) | 2 | 230 (79.8) | (CDCl_3) 0.88(3H, t, J=5Hz), 1.25(30H, s), 1.48(2H, m), 2.61(2H, d, J=4Hz), 2.65(2H, m), 3.08(2H, m), 3.28(2H, m), 3.54(2H, m), 4.11(3H), 5.4-5.7 (3H), 6.18(1H, d, J=7Hz), 6.30(1H, br.s), 8.01 (1H, t, J=7Hz), 8.16(1H, d, J=7, 5Hz), 8.25-8.45 (2H), 8.68(1H, d, J=7Hz), 8.99(1H, d, J=7Hz), 10.06(1H, d, J=5Hz). | (Nujol) 3220, 1694, 1634, 1257, 1144 | 83~86 |
| 48 | —C_16H_33 | —NHCOOCH_3 | H | H | S | 627 (1.01) | 3 | 556 (73.7) | (CDCl_3) 0.87(3H, t, J=6.5Hz), 1.25(26H, s), 1.54(2H, m), 2.52(2H, t, J=7.3Hz), 2.73(4H, d, J=6.7Hz), 3.40(2H, t, J=5.8Hz), 3.50-3.69(2H), 3.60(3H, s), 3.88(2H, m), 5.56(2H, m), 5.86(1H, d, J=8.0Hz), 6.37(1H, t, J=6.3Hz), 7.98(1H, dd, J=7.1, 8.0Hz), 8.19(1H, d, J=5.9, 8.4Hz), 8.12–8.38(2H), 8.68(1H, d, J=8.9Hz), 8.99(1H, d, J=8.9Hz), 10.23(1H, dd, J=1.5, 5.9Hz). | (KBr) 3380, 3300, 3065, 1700, 1625, 1319, 1137 | — |
| 49 | —C_16H_33 | —NHCOOtBu | H | H | S | 663 (1) | 4 | 490 (61.9) | (CDCl_3) 0.88(3H, t, J=6.4Hz), 1.25(26H, s), 1.40(9H, s), 1.58(2H, m), 2.53(2H, t, J=7.3Hz), 2.73 (4H, m), 3.38(2H, m), 3.57(2H, m), 3.85(1H, br. s), 5.34(1H, d, J=8.0Hz), 5.58(2H, m), 6.21 (1H, t, J=6.0Hz), 7.99(1H, t, J=7.5Hz), 8.13–8.36 (3H, m), 8.65(1H, d, J=9.0Hz), 8.98(1H, d, J=8.4Hz), 10.31(1H, d, J=5.2Hz). | (KBr) 3360, 3280, 3095, 1700, 1319, 1138 | — |
| 50 | —C_16H_33 | —NHCOCH_3 | H | H | S | 478 (0.791) | 2.5 | 326 (56.2) | (CDCl_3) 0.88(3H, t, J=6.4Hz), 1.25(26H, s), 1.54(2H, m), 2.03(3H, s), 2.51(2H, t, J=7.3Hz), 2.59-2.81(4H), 3.40(2H, m), 3.55(2H, t, J=6.3Hz), 4.18(1H, m), 5.53(2H, m), 6.48(1H, t, J=6.0Hz), 6.99(1H, d, J=8.4Hz), 8.00(1H, dd, J=6.6, 7.3Hz), 8.19(1H, dd, J=5.9, 8.4Hz), 8.24–8.38 (2H), 8.67(1H, d, J=8.7Hz), 8.98(1H, d, J=8.4Hz), 10.15(1H, dd, J=1.2, 5.9Hz). | (KBr) 3280, 3075, 1648, 1311, 1139. | — |
| 51 | —C_16H_33 | —NHCONHCH_3 | H | H | S | 551 (0.889) | 3 | 413 (62.0) | (CDCl_3) 0.88(3H, t, J=6.4Hz), 1.25(26H, s), 1.53(2H, m), 2.45–2.80(4H), 2.52(2H, t, J=7.2Hz), 2.64 (3H, d, J=4.5Hz), 3.15–3.59(4H), 4.04(1H, br. s), 5.49(3H, m), 6.01(1H, d, J=8.0Hz), 6.27 (1H, t, J=5.7Hz), 8.01(1H, t, J=7.5Hz), 8.13–8.40 (3H), 8.66(1H, d, J=8.7Hz), 8.98 (1H, d, J=8.4Hz), 10.09(1H, d, J=5.8Hz). | (KBr) 3310, 3100, 1641, 1317, 1138. | — |
| 52 | —CONHC_18H_37 | —NHCOOH_3 | H | Ac | O | 132 | 2 | 102 | (CDCl_3) 0.88(3H, t, J=6Hz), 1.25(30H, s), 1.50(2H, m), | (Nujol) | 83~85 |

TABLE 10-continued $$\begin{array}{c}\text{R}_2\diagdown\phantom{xx}\text{CH}_2-\text{Y}-\text{R}_1\\ \phantom{xxxx}\text{C}\\ \text{R}_2'\diagup\phantom{xx}\text{CH}_2\text{NSO}_2\\ \phantom{xxxxxxx}|\\ \phantom{xxxxxxx}\text{R}_6\end{array}\quad\xrightarrow{\phantom{xxx}}\quad\begin{array}{c}\text{R}_2\diagdown\phantom{xx}\text{CH}_2-\text{Y}-\text{R}_1\\ \phantom{xxxx}\text{C}\\ \text{R}_2'\diagup\phantom{xx}\text{CH}_2\text{NSO}_2\\ \phantom{xxxxxxx}|\\ \phantom{xxxxxxx}\text{R}_6\end{array}$$

II → I (with N-substituted quinolinium)

| Ex. No. | R$_1$ | R$_2$ | R$_2'$ | R$_6$ | Y | S.M. [mg] ([mM]) | Quinoline [ml] | Yield [mg] (%) | NMR δ ppm | IRνmax [cm$^{-1}$] | m.p. [°C] |
|---|---|---|---|---|---|---|---|---|---|---|---|
|  |  |  |  |  |  |  |  | (65.3) | 2.04(3H, s), 2.48(3H, s), 2.79(2H, m), 3.13 (2H, m), 3.8–4.3(8H), 4.45(1H, m), 5.47(1H, br.s), 5.68(1H, t, J=7Hz), 6.81(1H, d, J=7Hz), 8.03(1H, t, J=7Hz), 8.16(1H, dd, J=5, 7Hz), 8.30 (2H, d, J=7Hz), 8.68(1H, d, J=7Hz), 9.00 (1H, dd, J=7Hz), 10.33(1H, d, J=5Hz). | 3330, 1690, 1659, 1150 |  |
| 54 | —CONHC$_{18}$H$_{37}$ | CH$_3$, 1-methyl-tetrazolyl | H | H | O | 500 (0.73) | 0.6 | 510 (86) | (CDCl$_3$) 0.90(t, J=6Hz, 3H), 2.4–2.75(m, 2H), 2.58(s, 3H), 2.95–3.15(m, 2H), 3.4–3.8(m, 2H), 3.6–3.95(m, 2H), 4.25–4.6(m, 2H), 4.25–4.6(m, 2H), 4.85–5.1(m, 1H), 5.25–5.55(m, 3H), 6.9–7.15(m, 1H), 7.94(t, J=7.6Hz, 1H), 8.1–8.4(m, 3H), 8.68(d, J=9Hz, 1H), 9.05(d, J=8.4Hz, 1H), 9.88(d, J=5.8Hz, 1H). | (CHCl$_3$) 1729, 1334. | 77~87 |
| 56 | —CONHC$_{18}$H$_{37}$ | H$_3$C-tetrazolyl | H | H | O | 500 (0.73) | 0.6 | 440 (74) | (CDCl$_3$) 0.88(t, J=6.4Hz, 3H), 2.46(s, 3H), 2.45–2.8(m, 2H), 2.96–3.2(m, 2H), 3.5–3.75(m, 2H), 3.65–3.95(m, 2H), 4.35–4.7(m, 2H), 5.15–5.45(m, 2H), 5.35–5.7(m, 2H), 6.7–6.95(m, 1H), 7.99 (t, J=8Hz, 1H), 8.1–8.4(m, 3H), 8.70(d, J=9.4Hz, 1H), 9.04(d, J=8.2Hz, 1H), 10.04 (d, J=5.6Hz, 1H). | (CHCl$_3$) 1726, 1340. | Amorphous powder |
| 59 | —CONHC$_{18}$H$_{37}$ | isoxazolyl | H | H | O | 500 (0.73) | 0.6 | 440 (74) | (CDCl$_3$) 0.90(t, J=6Hz, 3H), 1.35–1.55(m, 2H), 2.6–2.7 (m, 2H), 3.10(qualet, J=6Hz, 2H), 3.4–3.7(m, 4H), 4.28(ABX, J=12 & 6.4Hz, 1H), 4.38(ABX, J=12 & 4.4Hz, 1H), 4.85–5.00(m, 1H), 5.35(t, J=5Hz, 1H), 5.54(t, J=7Hz, 2H), 6.08(d, J=2Hz, 1H), 6.45(t, J=6Hz, 1H), 7.96(t, J=8Hz, 1H), 8.10(d, J=2H, 1H), 8.1–8.35(m, 3H), 8.70(d, J=10Hz, 1H), 9.01(d, J=10Hz, 1H). | (CHCl$_3$) 1721, 1330 | Amphorous powder |
| 62 | —C$_{16}$H$_{33}$ | CH$_3$OCH$_2$— | H | H | O | 500 (0.87) | 1 | 370 (60) | (CDCl$_3$) 0.88(t, J=6Hz, 3H), 1.4–1.6(m, 2H), 2.1–2.3(m, 1H), 2.65–2.85(m, 2H), 3.32(s, 3H), 5.65(t, J=8.4Hz, 2H), 5.87(t, J=5Hz, 3H), 8.0(t, J=7Hz, 1H), 8.15–8.4(m, 3H), 8.68(d, J=8Hz, 1H), 9.03 (d, J=9Hz, 1H), 10.39(d, J=5.6Hz, 1H). | 1320 | 81~84 |
| 64 | —CON$\mid$C$_{18}$H$_{37}$ | CH$_3$OCH$_2$— | H | H | O | 500 | 0.8 | 460 | (CDCl$_3$) 0.88(t, J=6Hz, 3H), 1.4–1.6(m, 2H), 2.1–2.35 | 1710, | 55~60 |

TABLE 10-continued $$\underset{R_6}{\overset{R_2}{\underset{R_2'}{C}}}\overset{CH_2-Y-R_1}{\underset{CH_2NSO_2}{}} \quad II \quad \longrightarrow \quad \underset{R_6}{\overset{R_2}{\underset{R_2'}{C}}}\overset{CH_2-Y-R_1}{\underset{CH_2NSO_2}{}} \quad I$$

| Ex. No. | R₁ | R₂ | R₂' | R₆ | Y | S.M. [mg] ([mM]) | Quinoline [ml] | Yield [mg] (%) | NMR δ ppm | IR νmax [cm⁻¹] | m.p. [°C.] |
|---|---|---|---|---|---|---|---|---|---|---|---|
| | | | | | | | | (77) | (m, 1H), 2.6–2.85(m, 2H), 3.05–3.2(m, 2H), 3.15–3.35(m, 2H), 3.30(s, 3H), 3.44(d, J=6Hz, 2H), 3.58(t, J=6Hz, 2H), 3.95–4.25(m, 2H), 5.34(t, J=6Hz, 1H), 5.61(t, J=8Hz, 2H), 6.08(t, J=6Hz, 1H), 7.98(t, J=9Hz, 1H), 8.15–8.4(m, 3H), 8.71 (d, J=9Hz, 1H), 9.03(d, J=8.6Hz, 1H), 10.31(d, J=5.8Hz, 1H). | 1322 | |
| 65 | —CONHC₁₈H₃₇ | CH₃OCH₃— | H | Ac | O | 650 (0.95) | 0.8 | 540 (70) | (CDCl₃) 0.88(t, J=6Hz, 3H), 1.4–1.6(m, 2H), 2.25–2.5 (m, 1H), 2.42(s, 3H), 2.65–2.9(m, 1H), 3.13(q, J=7Hz, 2H), 3.30(s, 3H), 3.41(d, J=4Hz, 2H), 3.87(d, J=6.8Hz, 2H), 3.95–4.2(m, 4H), 5.10(t, J=7Hz, 1H), 5.68(t, J=6.5Hz, 2H), 8.01(t, J=7.4Hz, 1H), 8.15–8.4(m, 3H), 8.71(d, J=8.8Hz, 1H), 9.07(d, J=8.6Hz, 1H), 10.42(d, J=5.6Hz, 1H). | 1710 | 55~65 |
| 66 | —CONHC₁₈H₃₇ | CH₃COCH₃— | H | H | O | 182 (0.276) | 0.26 | 204 (93.8) | (CDCl₃) 0.88(t, J=6.4Hz, 3H), 1.17–1.36(m, 30H), 1.38–1.59(m, 2H), 2.16(s, 3H), 2.36–2.58(m, 2H), 2.60–2.84(m, 3H), 3.02–3.24(m, 4H), 3.47–3.64 (m, 2H), 4.04(d, J=4.8Hz, 2H), 5.21–5.33(m, 1H), 5.58(t, J=7.2Hz, 2H), 6.16–6.30(m, 1H), 8.10 (t, J=7.6Hz, 1H), 8.14–8.37(m, 3H), 8.70(d, J=9.0Hz, 1H), 9.02(d, J=8.6Hz, 1H), 10.30(d, J=6.0Hz, 1H). | 1703, 1320, 1140 | — |
| 68 | —C₁₆H₃₃ | NOCH₂— | H | H | O | 132 (0.23) | 0.27 | 134 (82.6) | (CDCl₃) 0.88(t, J=6.4Hz, 3H), 1.15–1.43(m, 26H), 1.43–1.62(m, 2H), 2.19–2.42(m, 1H), 2.42–2.87(m, 4H), 3.09–3.68(m, 8H), 5.58(t, J=7.8Hz, 2H), 6.54(t, J=6.3Hz, 1H), 7.99(t, J=7.2Hz, 1H), 8.14–8.36(m, 3H), 8.69(d, J=9.0Hz, 1H), 8.99(d, J=8.2Hz, 1H), 10.23(d, J=5.6Hz, 1H). | 2230, 1320 | — |
| 69 | —CONHC₁₈H₃₇ | NCCH₂— | H | H | O | 140 (0.22) | 0.26 | 152 (91) | (CDCl₃) 0.88(t, J=6.4Hz, 3H), 1.16–1.40(m, 30H), 1.39–1.57(m, 2H), 2.23–2.54(m, 1H), 2.51–2.65(m, 2H), 2.65–2.86(m, 2H), 3.02–3.20(m, 2H), 3.52–3.72(m, 2H), 4.14(d, J=4.8Hz, 2H), 5.13–5.28 (br., 1H), 5.56(t, J=7.8Hz, 2H), 6.56–6.74(br., 1H), 7.99(t, J=7.2Hz, 1H), 8.12–8.39(m, 3H), 8.69(d, J=9.2Hz, 1H), 8.99(d, J=9.2Hz, 1H), 10.18(d, J=6.0Hz, 1H). | 2230, 1710, 1320, 1140 | — |

TABLE 10-continued

| Ex. No. | R₁ | R₂ | R₂' | R₆ | Y | S.M. [mg] ([mM]) | Quinoline [ml] | Yield [mg] (%) | NMR δ ppm | IRνmax [cm⁻¹] | m.p. [°C.] |
|---|---|---|---|---|---|---|---|---|---|---|---|
| 72 | —CONHC₁₈H₃₇ | CH₃ / imidazole | H | H | O | 500 (0.73) | 0.6 | 450 (76) | (CDCl₃) 0.88(t, J=6Hz, 3H), 2.49(s, 3H), 2.45–2.7(m, 2H), 2.9–3.2(m, 2H), 3.4–3.8(m, 4H), 4.15–4.55(m, 2H), 4.7–4.9(m, 1H), 5.35–5.6(m, 3H), 6.9–7.1(m, 1H), 7.71(s, 1H), 7.97(d, J=7.7Hz, 1H), 8.1–8.3(m, 1H), 8.29(d, J=8Hz, 1H), 8.67(d, J=9.2Hz, 1H), 9.03 (d, J=9.6Hz, 1H), 10.07(d, J=6.4Hz, 1H) | 1719, 1330 | Amorphous powder |
| 73 | —CONHC₁₈H₃₇ | CH₃ / imidazole | H | H | O | 389 (0.57) | 0.68 | 393 (85) | (CDCl₃) 0.88(t, J=6.4Hz, 3H), 1.12–1.38(m, 30H), 1.35–1.68(m, 2H), 2.28(s, 3H), 2.46–2.84(m, 2H), 2.97–3.20(m, 2H), 3.33–3.79(m, 4H), 4.24–4.49(m, 2H), 4.72–4.94(m, 1H), 5.34–5.60(m, 3H), 6.90–7.09(m, 1H), 7.97(t, J=7.6Hz, 1H), 8.11–8.40(m, 4H), 8.67(d, J=9.0Hz, 1H), 8.99 (d, J=8.6Hz, 1H), 10.16(d, J=5.0Hz, 1H) | 1718, 1320, 1140 | |

EFFECT OF THE INVENTION

The compounds of the present invention are PAF analogues which serve as PAF receptor antagonist and/or antitumor agent. The compounds of the present invention inhibit the platelet from aggregation induced by PAF and may be useful agents for the treatment of physiological and pathological disorders in which PAF may participate, for example, endotoxic shock, asthma, inflammation, acute tissue transplant rejection, hypotension, gastric ulcer, and nephritis. The platelet aggregation inhibitory activities (in vitro) of the representative compounds of the present invention are shown below.

Materials Tested and Methods

Mature male rabbits (NIBS-JW, RABITON Institute Inc., weighing 2.2-2.5 kg) were used. Under sodium pentobarbital anesthesia (Somnopentyl, Pitmab Moore, about 25 mg/Kg, i.v.), blood (7.2 ml each) was successively collected from the carotid artery by cannulation and put into centrifuge tubes containing 0.8 ml each of 3.8% sodium citrate solution. (The total volume of blood sample in each tube was adjusted to 8 ml.)

The blood sample in each tube was gently shaken and then centrifuged for 10 minutes at 200 g at 22° C. to give platelet rich plasma (PRP). The remaining blood was further centrifuged at 3,000 rpm (about 1,900 g) for 10 minutes at 22° C. to give platelet-poor plasma (PPP).

PRP was diluted with PPP to prepare a blood sample whose platelet number was $50-55 \times 10^4/\mu l$. The sample was subjected to a platelet aggregation test.

The platelet aggregation was examined by the method of Born [Born, G. V. R., Nature, 194, 927-929 (1962)], using a Type AUTO RAM-61 aggregometer, (Rika Denki Co., Ltd., Tokyo). A volume of 230 $\mu l$ of PRP, whose platelet number was adjusted to $50-55 \times 10^4/\mu l$, was placed in a measuring cuvette and set in the aggregometer. PRP was warmed at 37° C. for 1 minute with stirring at 1,200 rpm, and then a solution of the test compound [dimethylsulfoxide solution (1 $\mu l$) of the compound+saline (9 $\mu l$)] was added thereto. Exactly 2 minutes later, 10 $\mu l$ of platelet activating factor (PAF, $C_{16}$) (final concetration: 20 nM) was added as a platelet aggregating agent, and the change in light transmission caused by platelet aggregation was recorded.

The light transmissions of PRP and PPP were taken as 0% and 100% aggregation, respectively, and the maximum light transmission after addition of an aggregating agent was made the maximum aggregation. The inhibition rate of the platelet aggregation was expressed as the percentage of the maximum aggregation by a test compound to that by a control (Vehicle added group).

The results of the test are shown as follows. The results are shown as the concentration of the test compounds which inhibit 50% platelet aggregation, i.e., $IC_{50}$ ($\mu M$).

| Compound Number* | $IC_{50}$ ($\mu M$) | Compound Number* | $IC_{50}$ ($\mu M$) | Compound Number* | $IC_{50}$ ($\mu M$) |
|---|---|---|---|---|---|
| Ia1 | 48.10 | Ia2 | 1.89 | Ia3 | 5.20 |
| Ia4 | 64.2 | Ia5 | 1.89 | Ia6 | 45.4 |
| Ia7 | 0.65 | Ia8 | 82.1 | Ia9 | 3.64 |
| Ia10 | 79.9 | Ia11 | 2.97 | Ia12 | 5.95 |
| Ia13 | 1.77 | Ia14 | 1.29 | Ia16 | 13.5 |
| Ia20 | 16.0 | Ia25 | 0.36 | Ia26 | 1.93 |
| Ia27 | 0.74 | Ib2 | 0.385 | Ic1 | 0.92 |

-continued

| Compound Number* | $IC_{50}$ ($\mu M$) | Compound Number* | $IC_{50}$ ($\mu M$) | Compound Number* | $IC_{50}$ ($\mu M$) |
|---|---|---|---|---|---|
| Ic3 | 0.33 | Ie5 | 0.533 | Ie6 | 3.09 |
| Ie7 | 0.85 | Ie8 | 1.97 | If3 | 0.965 |
| If4 | 0.873 | Ig2 | 14.3 | Ig4 | 1.83 |
| If5 | 0.558 | Ig6 | 1.32 | Ih1 | 23.2 |
| Ih2 | 0.125 | Ii2 | 0.63 | Ij3 | 0.25 |
| Ik3 | 0.60 | Ik4 | 80.3 | Ik5 | 0.40 |
| Ik6 | 0.34 | $PGE_1$ | 0.259 | | |

*Compound Number corresponds to the number in the examples.

The reason why $PGE_1$ is chosen as a reference compound is that the activity level of the prepared novel compounds are aimed at that of $PGE_1$, since $PGE_1$ is known to potently inhibit the PAF-induced platelet aggregation. As a result, the compounds of the present invention can mostly inhibit the platelet aggregation as potent as $PGE_1$ can.

Antitumor activity is proven by various methods, e.g., the inhibition of Meth A fibrosarcama growth in Balb-c mouse (Slc), the survival effect of C3H/HeN mouse injected into MH134 (mouse hepatoma) and DS mouse injected into Ehrlich (Ehrlich Ascites carinoma).

The compound (I) of the present invention can be orally or parenterally administered to humans or animals. For example, the compound (I) which is dissolved or suspended in a solvent for injection (e.g., distilled water for injection, ethanol, glycerol, propylene glycol, olive oil, peanut oil) can be administered intravenously, intramuscularly, or subcutaneously. For an injectable use, the compound (I) may be a solution or suspension which is sealed in an ampule or, preferably, may be crystals, a powder, fine crystals, or lyophilizate which are preserved in an ampule or vial. The latter formulation may be used by dissolving them with a solvent for injection. The stabilizer may be further added thereto. The compound (I) may be also formulated into powder, tablets, granules, capsules, troches, or dry syrups for oral use, together with pharmaceutical additives such as a diluent (e.g., starch, sucrose, lactose, calcium carbonate, kaolin), lubricant (e.g., stearic acid, sodium benzoate, boric acid, silica, polyethylene glycol) or the like.

The compound (I) can be administered, for example, for the treatment of endotoxic shock, asthma, inflammation, acute tissue transplant rejection, hypotension, gastric ulcer, nephritis, or tumor, at a usual dosage for an adult of about 1 mg to 5 g per day in 1 to 3 divided doses. The compound (I) should be, however, used by increasing or decreasing the recommended dosage, taking into consideration the age, body weight, severity of disease, clinical history of a patient, or the like.

What we claim is:

1. A compound represented by the formula:

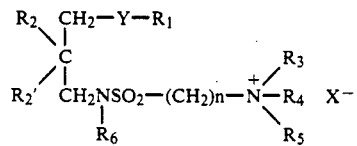

wherein $R_1$ is alkyl or alkylcarbamoyl; $R_2$ is lower alkyloxy, lower alkylcarbamoyloxy, lower alkylcarbonylamino, lower alkyloxycarbonylamino, lower alkylureido, lower alkyloxymethyl, lower alkylcarbonylmethyl, cyanomethyl, a 5-membered heterocyclic group, or a 5-membered heterocyclyloxy group, wherein one or more N, O or S heteroatoms are present; $R_2'$ is hydrogen or taken together with $R_2$ forms $-O(CH_2)_m-$ wherein m is an integer of 1 to 5; $R_3$, $R_4$, and $R_5$ taken together with the adjacent nitrogen atom form quinolinio or isoquinolinio which are unsubstituted or substituted by a member selected from the group consisting of lower alkyl, carboxyl, lower alyloxycarbonyl, hydroxy, lower alkyloxy, acyloxy, lower alkylamino, amino, carbamoyl and ureido; $R_6$ is hydrogen or lower alkylcarbonyl; $X^-$ is a pharmaceutically acceptable anion; Y is oxygen or sulfur; and n is an integer of 1 to 10.

2. A compound claimed in claim 1 wherein $R_1$ is $C_{12}$ to $C_{20}$ alkyl; and n is an integer of 1 to 5.

3. A compound claimed in claim 1 wherein $R_1$ is $C_{12}$ to $C_{20}$ alylcarbamoyl; and n is an integer of 1 to 5.

4. A compound claimed in claims 2 or 3 wherein $R_2'$ is hydrogen; $R_6$ is hydrogen; and $X^-$ is halogen anion.

5. A compound claimed in any of claims 1 to 3 wherein $R_2$ is lower alkyloxy; and $R_3$, $R_4$ and $R_5$ taken together with the adjacent nitrogen atom form quinolinio.

6. A compound claimed in any of claims 1 to 3 wherein $R_2$ is lower alkyloxymethyl; and $R_3$, $R_4$ and $R_5$ taken together with the adjacent nitrogen atom form quinolinio.

7. A compound claimed in any of claims 1 to 3 wherein $R_2$ is N-containing 5-membered heterocyclic group which may contain oxygen or sulfur and optionally may be substituted; and $R_3$, $R_4$ and $R_5$ taken together with the adjacent nitrogen atom form quinolinio.

8. A compound claimed in any of claims 1 to 3 wherein $R_2$ is lower alkylcarbamoyloxy; and $R_3$, $R_4$ and $R_5$ taken together with the adjacent nitrogen atom form quinolinio.

9. A compound claimed in claim 1, namely, 2-methoxy-1-octadecylcarbamoyloxy-3-(3-quinoliniopropylsulfonylamino)propane iodide.

10. A compound claimed in claim 1, namely, 2-methoxy-1-octadecylcarbamoylthio-3-(3-quinoliniopropylsulfonylamino)propane iodide.

11. A compound claimed in claim 1, namely, 2-methoxymethyl-1-octadecylcarbamoyloxy-3-(3-quinoliniopropylsulfonylamino)propane iodide.

12. A compound claimed in claim 1, namely, 2-(5-methyl-1H-tetrazol-1-yl)-1-octadecylcarbamoyloxy-3-(3-quinoliniopropylsulfonylamino)propane iodide.

13. A compound claimed in claim 1, namely, 2-(5-methyl-2H-tetrazol-2-yl)-1-octadecylcarbamoyloxy-3-(3-quinoliniopropylsulfonylamino)propane iodide.

14. A compound claimed in claim 1, namely, 2-(3-methyl-2H-1,2,4-triazol-2-yl)-1-octadecylcarbamoyloxy-3-(3-quinoliniopropylsulfonylamino)propane iodide.

15. A compound claimed in claim 1, namely, 2-methylcarbamoyloxy-1-octadecylcarbamoyloxy-3-(3-quinoliniopropylsulfonylamino)propane iodide.

16. A compound claimed in claim 4 wherein $R_2$ is lower alkyloxy; and $R_3$, $R_4$ and $R_5$ taken together with the adjacent nitrogen atom form quinolinio.

17. A compound claimed in claim 4 wherein $R_2$ is lower alkyloxymethyl; and $R_3$, $R_4$ and $R_5$ taken together with the adjacent nitrogen atom form quinolinio.

18. A compound claimed in claim 4 wherein $R_2$ is N-containing 5-membered heterocyclic group which may contain oxygen or sulfur and optionally may be substituted; and $R_3$, $R_4$ and $R_5$ taken together with the adjacent nitrogen atom form quinolinio.

19. A compound claimed in claim 4 wherein $R_2$ is lower alkylcarbamoyloxy; and $R_3$, $R_4$ and $R_5$ taken together with the adjacent nitrogen atom form quinolinio.

* * * * *